United States Patent
Bouaboula et al.

(10) Patent No.: US 9,714,221 B1
(45) Date of Patent: Jul. 25, 2017

(54) SUBSTITUTED 6,7-DIHYDRO-5H-BENZO[7]ANNULENE COMPOUNDS, PROCESSES FOR THEIR PREPARATION AND THERAPEUTIC USES THEREOF

(71) Applicant: Sanofi, Paris (FR)

(72) Inventors: Monsif Bouaboula, Paris (FR); Maurice Brollo, Paris (FR); Victor Certal, Paris (FR); Youssef El-Ahmad, Paris (FR); Bruno Filoche-Romme, Paris (FR); Frank Halley, Paris (FR); Gary McCort, Paris (FR); Laurent Schio, Paris (FR); Michel Tabart, Paris (FR); Corinne Terrier, Paris (FR); Fabienne Thompson, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/432,470

(22) Filed: Feb. 14, 2017

(30) Foreign Application Priority Data

Feb. 15, 2016 (EP) .................................. 16305174

(51) Int. Cl.
| | |
|---|---|
| *C07D 207/12* | (2006.01) |
| *C07D 401/12* | (2006.01) |
| *C07D 403/12* | (2006.01) |
| *C07D 405/12* | (2006.01) |
| *A61K 31/4025* | (2006.01) |
| *A61K 31/341* | (2006.01) |
| *A61K 31/351* | (2006.01) |
| *C07D 471/04* | (2006.01) |
| *C07D 413/12* | (2006.01) |
| *C07F 7/08* | (2006.01) |
| *C07D 417/12* | (2006.01) |

(52) U.S. Cl.
CPC ......... *C07D 207/12* (2013.01); *C07D 401/12* (2013.01); *C07D 403/12* (2013.01); *C07D 405/12* (2013.01); *C07D 413/12* (2013.01); *C07D 417/12* (2013.01); *C07D 471/04* (2013.01); *C07F 7/0812* (2013.01)

(58) Field of Classification Search
CPC ................ C07D 207/12; C07D 401/12; C07D 403/12; C07D 405/12; A61K 31/4025; A61K 31/341; A61K 31/351
USPC ............ 548/541; 570/129, 130; 514/424, 63
See application file for complete search history.

(56) References Cited

U.S. PATENT DOCUMENTS 9,309,211 B2  4/2016  Xiao et al.

FOREIGN PATENT DOCUMENTS

WO    WO 2013/097773     7/2013

OTHER PUBLICATIONS

Anstead G.M., et al., 2,3-Diarylindenes and 2,3-diarylindenones: Synthesis, Molecular Structure, Photochemistry, Estrogen Receptor Binding Affinity, and Comparisons with Related Triarylethylenes, Journal of Medicinal Chemistry, 1988, vol. 31 (7), pp. 1316-1326.
McCague R., et al., Nonisomerizable Analogues of (Z)-and (E)-4-Hydroxytamoxifen, Synthesis and Endocrinological Properties of Substituted Diphenylbenzocycloheptenes, Journal of Medicinal Chemistry, 1988, vol. 31 (7), pp. 1285-1290.

*Primary Examiner* — Matthew Coughlin
*Assistant Examiner* — Sagar Patel
(74) *Attorney, Agent, or Firm* — Kelly L. Bender

(57) ABSTRACT

Compounds of formula (I):

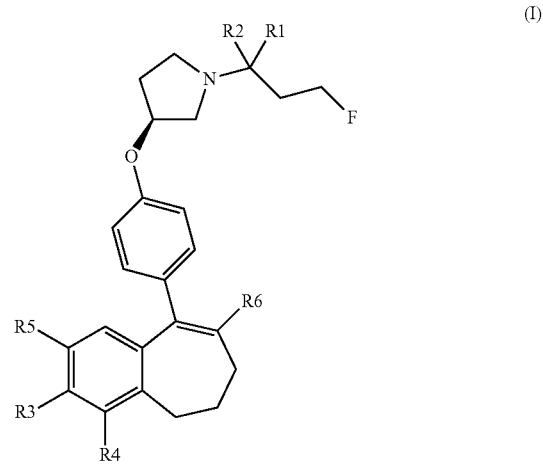

wherein R1 and R2 represent hydrogen or deuterium atoms; R3 represents a hydrogen atom or a —COOH, a —OH or a —OPO(OH)$_2$ group; R4 represents a hydrogen atom or a fluorine atom; R5 represents a hydrogen atom or a —OH group; wherein at least one of R3 or R5 is different from a hydrogen atom; when R3 represents a —COOH, —OH or —OPO(OH)$_2$ group, then R5 represents a hydrogen atom; when R5 represents a —OH group, then R3 and R4 represent hydrogen atoms; and R6 is selected from an optionally substituted phenyl, heteroaryl, cycloalkyl and heterocycloalkyl group;

and the preparation and the therapeutic uses of the compounds of formula (I) as inhibitors and degraders of estrogen receptors, useful especially in the treatment of cancer.

17 Claims, No Drawings

SUBSTITUTED 6,7-DIHYDRO-5H-BENZO[7]ANNULENE COMPOUNDS, PROCESSES FOR THEIR PREPARATION AND THERAPEUTIC USES THEREOF

Provided herein are novel substituted 6,7-dihydro-5H-benzo[7]annulene compounds, the processes for their preparation, as well as the therapeutic uses thereof, in particular as anticancer agents via selective antagonism and degradation of estrogen receptors.

The Estrogen Receptors (ER) belong to the steroid/nuclear receptor superfamily involved in the regulation of eukaryotic gene expression, cellular proliferation and differentiation in target tissues. ERs are in two forms: the estrogen receptor alpha (ERα) and the estrogen receptor beta (ERβ) respectively encoded by the ESR1 and the ESR2 genes. ERα and ERβ are ligand-activated transcription factors which are activated by the hormone estrogen (the most potent estrogen produced in the body is 17β-estradiol). In the absence of hormone, ERs are largely located in the cytosol of the cell. When the hormone estrogen binds to ERs, ERs migrate from the cytosol to the nucleus of the cell, form dimers and then bind to specific genomic sequences called Estrogen Response Elements (ERE). The DNA/ER complex interacts with co-regulators to modulate the transcription of target genes.

ERα is mainly expressed in reproductive tissues such as uterus, ovary, breast, bone and white adipose tissue. Abnormal ERα signaling leads to development of a variety of diseases, such as cancers, metabolic and cardiovascular diseases, neurodegenerative diseases, inflammation diseases and osteoporosis.

ERα is expressed in not more than 10% of normal breast epithelium but approximately 50-80% of breast tumors. Such breast tumors with high level of ERα are classified as ERα-positive breast tumors. The etiological role of estrogen in breast cancer is well established and modulation of ERα signaling remains the mainstay of breast cancer treatment for the majority ERα-positive breast tumors. Currently, several strategies for inhibiting the estrogen axis in breast cancer exist, including: 1-blocking estrogen synthesis by aromatase inhibitors that are used to treat early and advanced ERα-positive breast cancer patients; 2-antagonizing estrogen ligand binding to ERα by tamoxifen which is used to treat ERα-positive breast cancer patients in both pre- and post-menopausal setting; 3-antagonizing and downregulating ERα levels by fulvestrant, which is used to treat breast cancer in patients that have progressed despite endocrine therapies such as tamoxifen or aromatase inhibitors.

Although these endocrine therapies have contributed enormously to reduction in breast cancer development, about more than one-third of ERα-positive patients display de-novo resistance or develop resistance over time to such existing therapies. Several mechanisms have been described to explain resistance to such hormone therapies. For example, hypersensitivity of ERα to low estrogen level in treatment with aromatase inhibitors, the switch of tamoxifen effects from antagonist to agonist effects in tamoxifen treatments or multiple growth factor receptor signaling pathways. More recently, acquired mutations in ERα occurring after initiation of hormone therapies may play a role in treatment failure and cancer progression. Certain mutations in ERα, particularly those identified in the Ligand Binding Domain (LBD), result in the ability to bind to DNA in the absence of ligand and confer hormone independence in cells harboring such mutant receptors.

Most of the endocrine therapy resistance mechanisms identified rely on ERα-dependent activity. One of the new strategies to counterforce such resistance is to shut down the ERα signaling by removing ERα from the tumor cells using Selective Estrogen Receptors degraders (SERDs). Clinical and preclinical data showed that a significant number of the resistance pathways can be circumvented by the use SERDs.

There is still a need to provide SERDs with good degradation efficacy.

G. M. Anstead et al. have described 2,3-diarylindenes and 2,3-diarylindenones as binders of estrogen receptors (Journal of Medicinal Chemistry, 1988, Vol. 31, No. 7, p. 1316-1326).

R. McCague et al. have described analogues of (Z)- and (E)-4-hydroxytamoxifen and have tested their binding affinities to estrogen receptors (Journal of Medicinal Chemistry, 1998, Vol. 31, No. 7, p. 1285-1290).

Provided herein are novel compounds able to selectively antagonize and degrade the estrogen receptors (SERDs compounds), for use in cancer treatment.

Provided herein are compounds of the formula (I):

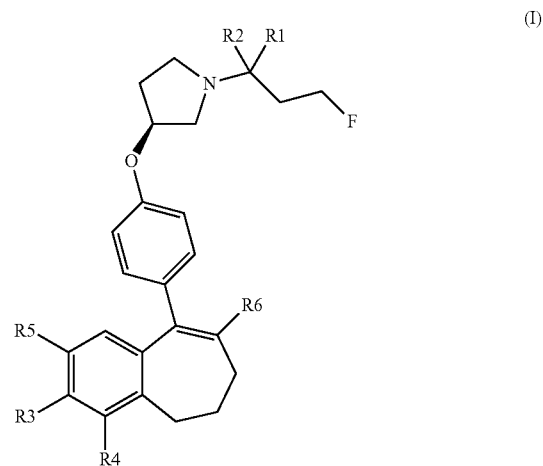

wherein:
R1 and R2 represent independently a hydrogen atom or a deuterium atom;
R3 represents a hydrogen atom, a —COOH group, a —OH group or a —OPO(OH)$_2$ group;
R4 represents a hydrogen atom or a fluorine atom;
R5 represents a hydrogen atom or a —OH group;
wherein:
  at least one of R3 or R5 is different from a hydrogen atom;
  when R3 represents a —COOH group, a —OH group or a —OPO(OH)$_2$ group, then R5 represents a hydrogen atom;
  when R5 represents a —OH group, then R3 and R4 represent hydrogen atoms;
R6 is selected from:
  a phenyl group or a heteroaryl group comprising 3 to 9 carbon atoms and comprising from 1 to 3 heteroatoms independently selected from oxygen, nitrogen and sulphur, said phenyl and heteroaryl groups being unsubstituted or substituted with 1 to 3 substituents independently selected from: a ($C_1$-$C_6$)-alkyl group unsubstituted or substituted with one or more (such as 1, 2 or 3) fluorine atoms; a halogen atom; a —OH group; a ($C_1$-$C_6$)-alkoxy group unsubstituted or substituted with one or more (such as 1, 2 or 3) fluorine atoms; a cyano group; a sulphur group substituted with 5 fluorine atoms or ($C_1$-$C_6$)-alkyl groups substituted with two or more (such as 2 or 3) fluorine atoms; a sulfonyl-($C_1$-$C_6$)-alkyl group wherein said ($C_1$-$C_6$)-alkyl group are unsubstituted or substituted with two or more (such as 2 or 3) fluorine atoms; a silane group substituted with 3 ($C_1$-$C_6$)-alkyl groups; an amine group unsubstituted or substituted with one or more (such as 1 or 2) ($C_1$-$C_6$)-alkyl groups; an amide group unsubstituted or substituted with one or more (such as 1 or 2) ($C_1$-$C_6$)-alkyl groups; a heterocycloalkyl group saturated or partially saturated, comprising 3 to 5 carbon atoms and comprising 1 or 2 heteroatoms independently selected from oxygen, nitrogen and sulphur; or a heteroaryl group comprising 2 to 4 carbon atoms and comprising 1 to 3 heteroatoms selected from oxygen, nitrogen and sulphur and being unsubstituted or substituted with an oxo group;

a cycloalkyl group or a heterocycloalkyl group comprising 4 to 9 carbon atoms and comprising 1 or 2 heteroatoms independently selected from oxygen, nitrogen and sulphur, said cycloalkyl or heterocycloalkyl groups being saturated or partially saturated and being unsubstituted or substituted with 1 to 4 substituents independently selected from:

a fluorine atom; a —OH group; a ($C_1$-$C_6$)-alkyl group; a —COOR7 group wherein R7 is a ($C_1$-$C_6$)-alkyl group; and an oxo group.

The compounds of formula (I) contain one or more asymmetric carbon atoms, more particularly one asymmetric carbon atom on the pyrrolydinyl group. They may therefore exist in the form of enantiomers. The compounds of formula (I) include enantiomers, racemates, and mixtures thereof. (In particular, the carbon 3 of the pyrrolidinyl group linked to the oxygen atom of the formula (I) may be in the absolute configuration (R) or (S). The carbon 3 of the pyrrolidinyl group is advantageously in the absolute configuration (S).

The compounds of formula (I) also include tautomer forms thereof.

The compounds of formula (I) may exist in the form of bases, acids, or zwitterions.

The compounds of formula (I) can be in the form of addition salts with acids or bases. Hence, provided herein inter alia, are compounds of formula (I) or to pharmaceutically acceptable salts thereof.

These salts may be prepared with pharmaceutically acceptable acids or bases, although the salts of other acids or bases useful, for example, for purifying or isolating the compounds of formula (I) are provided.

As used herein, the terms below have the following definitions unless otherwise mentioned throughout the instant specification:

a halogen atom: a fluorine, a chlorine, a bromine or an iodine atom;

an oxo: a "=O" group;

a cyano group: a "—C≡N" group;

an amine group: a nitrogen atom unsubstituted or substituted with one or more ($C_1$-$C_6$)-alkyl groups;

an amide group: a —C(O)NH$_2$ group wherein the nitrogen atom can be unsubstituted or substituted with one or more ($C_1$-$C_6$)-alkyl groups;

a silane group: a silicon atom substituted with 3 ($C_1$-$C_6$)-alkyl groups;

an alkyl group: a linear or branched saturated hydrocarbon-based aliphatic group comprising, unless otherwise mentioned, from 1 to 6 carbon atoms (noted "($C_1$-$C_6$)-alkyl"). By way of examples, mention may be made of, but not limited to: methyl, ethyl, propyl, n-propyl, isopropyl, butyl, isobutyl, sec-butyl, tert-butyl, pentyl, isopentyl, hexyl and isohexyl groups, and the like;

an alkoxy group: an —O-alkyl group where the alkyl group is as previously defined. By way of examples, mention may be made of, but not limited to: methoxy, ethoxy, propoxy, isopropoxy, linear, secondary or tertiary butoxy, isobutoxy, pentoxy or hexoxy groups, and the like;

a cycloalkyl group: a cyclic alkyl group comprising, unless otherwise mentioned, from 3 to 6 carbon atoms, saturated or partially unsaturated and unsubstituted or substituted. By way of examples, mention may be made of, but not limited to: cyclopropyl, cyclobutyl, cyclopentyl, cyclohexyl, cyclohexenyl groups, and the like;

a heterocycloalkyl group: a cyclic alkyl group comprising, unless otherwise mentioned, from 3 to 6 carbon atoms and containing 1 or 2 heteroatoms such as oxygen, nitrogen or sulphur. Such nitrogen atom may be substituted by an oxygen atom in order to form a —N—O bond. Such —N—O bond can be in a form of a N-oxide (—N$^+$—O$^-$). Such heterocycloalkyl group may be saturated or partially saturated and unsubstituted or substituted and may be monocyclic or bicyclic.

By way of examples of monocyclic heterocycloalkyl groups, mention may be made of, but not limited to: tetrahydropyridinyl, dihydropyridinyl, dihydropyranyl, tetrahydropyranyl groups, and the like.

A bicyclic heterocycloalkyl group means: a phenyl group fused to a monocyclic heterocycloalkyl group as defined above. By way of examples of bicyclic heterocycloalkyl groups, mention may be made of, but not limited to: tetrahydroquinolinyl, indolinyl, benzodioxolyl, dihydrobenzodioxinyl, dihydrobenzoxazinyl, benzofuranyl groups, all optionally substituted as above indicated, and the like.

A heteroaryl group: a cyclic aromatic group containing between 4 and 9 carbon atoms and containing between 1 and 3 heteroatoms, such as nitrogen, oxygen or sulphur. Such nitrogen atom may be substituted by an oxygen atom in order to form a —N—O bond. Such —N—O bond can be in a form of a N-oxide (—N$^+$—O$^-$). Said heteroaryl group may be monocyclic or bicyclic. By way of examples of heteroaryl groups, mention may be made of, but not limited to: isoxazole, pyridine, pyrimidine, benzotriazole, benzoxazole, pyrrolo[2,3-b]pyridine, benzimidazole, benzoxadiazole, benzothiazole, benzothiadiazole, benzofuran, indole, quinolyl, indazole, benzisoxazole, benzisothiazole groups and the like;

A zwitterion: a globally neutral molecule with a positive and a negative electrical charge and having an acid group and a basic group. By way of examples, mention may be made of, but not limited to compounds of formula (I) having R3 which represents a —COOH group or an —OPO(OH)$_2$ group.

In an embodiment, in the compounds of formula (I), R1 and R2 represent hydrogen atoms.

In another embodiment, in the compounds of formula (I), R1 and R2 represent deuterium atoms.

In another embodiment, in the compounds of formula (I), R3 represents a hydrogen atom.

In another embodiment, in the compounds of formula (I), R3 represents a —COOH group.

In another embodiment, in the compounds of formula (I), R3 represents a —OH group.

In another embodiment, in the compound of formula (I), R3 represents a —COOH group or a —OH group.

In another embodiment, in the compounds of formula (I), R3 represents a —OPO(OH)$_2$ group.

In another embodiment, in the compounds of formula (I), R4 represents a hydrogen atom.

In another embodiment, in the compounds of formula (I), R4 represents a fluorine atom.

In another embodiment, in the compounds of formula (I), R5 represents a hydrogen atom.

In another embodiment, in the compounds of formula (I), R5 represents a —OH group.

In another embodiment, in the compounds of formula (I) R6 is selected from a phenyl group unsubstituted or substituted with 1 to 3 substituents independently selected from: a (C$_1$-C$_6$)-alkyl group unsubstituted or substituted with one or more (such as 1, 2 or 3) fluorine atoms; a halogen atom; a —OH group; a (C$_1$-C$_6$)-alkoxy group unsubstituted or substituted with one or more (such as 1, 2 or 3) fluorine atoms; a cyano group; a sulphur group substituted with 5 fluorine atoms or (C$_1$-C$_6$)-alkyl groups substituted with two or more (such as 2 or 3) fluorine atoms; a sulfonyl-(C$_1$-C$_6$)-alkyl group wherein said (C$_1$-C$_6$)-alkyl group are unsubstituted or substituted with two or more (such as 2 or 3) fluorine atoms; a silane group substituted with 3 (C$_1$-C$_6$)-alkyl groups; an amine group unsubstituted or substituted with one or more (such as 1 or 2) (C$_1$-C$_6$)-alkyl groups; an amide group unsubstituted or substituted with one or more (such as 1 or 2) (C$_1$-C$_6$)-alkyl groups; a heterocycloalkyl group saturated or partially saturated, comprising 3 to 5 carbon atoms and comprising 1 or 2 heteroatoms independently selected from oxygen, nitrogen and sulphur; and a heteroaryl group comprising 2 to 4 carbon atoms and comprising 1 to 3 heteroatoms selected from oxygen, nitrogen and sulphur and being unsubstituted or substituted with an oxo group.

In another embodiment, in the compounds of formula (I), R6 is selected from a phenyl group unsubstituted or substituted with 1 to 3 substituents independently selected from: a (C$_1$-C$_6$)-alkyl group unsubstituted or substituted with one or more (such as 1, 2 or 3) fluorine atoms; a halogen atom; a —OH group; a (C$_1$-C$_6$)-alkoxy group unsubstituted or substituted with one or more (such as 1, 2 or 3) fluorine atoms; a cyano group; a sulphur group substituted with 5 fluorine atoms or (C$_1$-C$_6$)-alkyl groups substituted with two or more (such as 2 or 3) fluorine atoms; a sulfonyl-(C$_1$-C$_6$)-alkyl group wherein said (C$_1$-C$_6$)-alkyl group are unsubstituted or substituted with two or more (such as 2 or 3) fluorine atoms; a silane group substituted with 3 (C$_1$-C$_6$)-alkyl groups; an amide group unsubstituted or substituted with one or more (such as 1 or 2) (C$_1$-C$_6$)-alkyl groups; a heterocycloalkyl group saturated or partially saturated, comprising 3 to 5 carbon atoms and comprising 1 or 2 heteroatoms independently selected from oxygen, nitrogen and sulphur, and a heteroaryl group comprising 2 to 4 carbon atoms and comprising 1 to 3 heteroatoms selected from oxygen, nitrogen and sulphur and being unsubstituted or substituted with an oxo group.

In another embodiment, in the compounds of formula (I), R6 is selected from a phenyl group unsubstituted or substituted with 1 to 3 substituents independently selected from: a (C$_1$-C$_3$)-alkyl group unsubstituted or substituted with one or more (such as 1, 2 or 3) fluorine atoms; a halogen atom; a —OH group; a (C$_1$-C$_3$)-alkoxy group unsubstituted or substituted with one or more (such as 1, 2 or 3) fluorine atoms; a cyano group; a sulphur group substituted with 5 fluorine atoms or (C$_1$-C$_3$)-alkyl groups substituted with two or more (such as 2 or 3) fluorine atoms; a sulfonyl-(C$_1$-C$_3$)-alkyl group wherein said (C$_1$-C$_3$)-alkyl group are unsubstituted or substituted with two or more (such as 2 or 3) fluorine atoms; a silane group substituted with 3 (C$_1$-C$_3$)-alkyl groups; an amide group unsubstituted or substituted with one or more (such as 1 or 2) (C$_1$-C$_3$)-alkyl groups; a heterocycloalkyl group saturated or partially saturated, comprising 3 to 5 carbon atoms and comprising 1 or 2 heteroatoms independently selected from oxygen, nitrogen and sulphur, and a heteroaryl group comprising 2 to 4 carbon atoms and comprising 1 to 3 heteroatoms selected from oxygen, nitrogen and sulphur and being unsubstituted or substituted with an oxo group.

In another embodiment, in the compounds of formula (I), R6 is selected from a phenyl group unsubstituted or substituted with 1 to 3 substituents independently selected from: a methyl group; an ethyl group; an isopropyl group; a tert-butyl group; a —CHF$_2$ group; a —CF$_3$ group; a —CF$_2$CH$_3$ group; a chlorine atom; a fluorine atom; a —OH group; a —OCH$_3$ group; a —OCH$_2$CH$_3$ group; a —OCH$_2$CH$_2$F group; a —OCHF$_2$ group; a —OCH$_2$CHF$_2$ group; a —OCF$_3$ group; a —OCH$_2$CF$_3$ group; a cyano group; a —SCHF$_2$ group; a —SCF$_3$ group; a —SF$_5$ group; a —SO$_2$CH$_3$ group; a —SO$_2$CF$_3$ group; a —Si(CH$_3$)$_3$ group; an oxetane group; a piperidine group; a morpholine group; a pyrrolidine group and a triazolone group.

In another embodiment, in the compounds of formula (I), R6 is selected from an unsubstituted or substituted phenyl group selected from the following list:

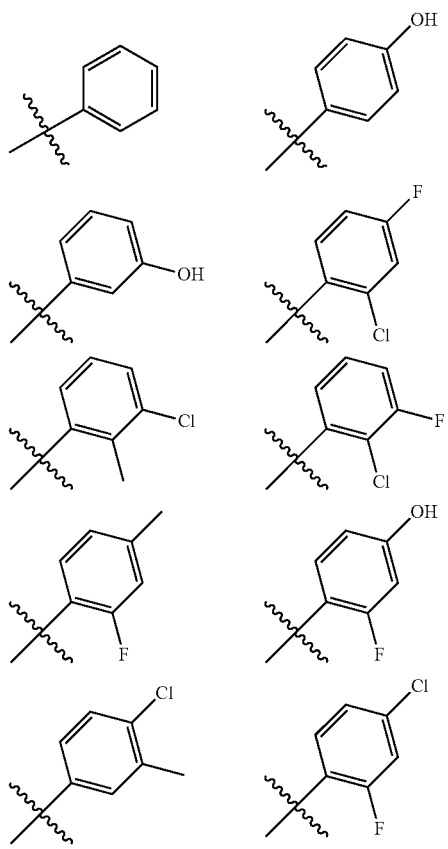

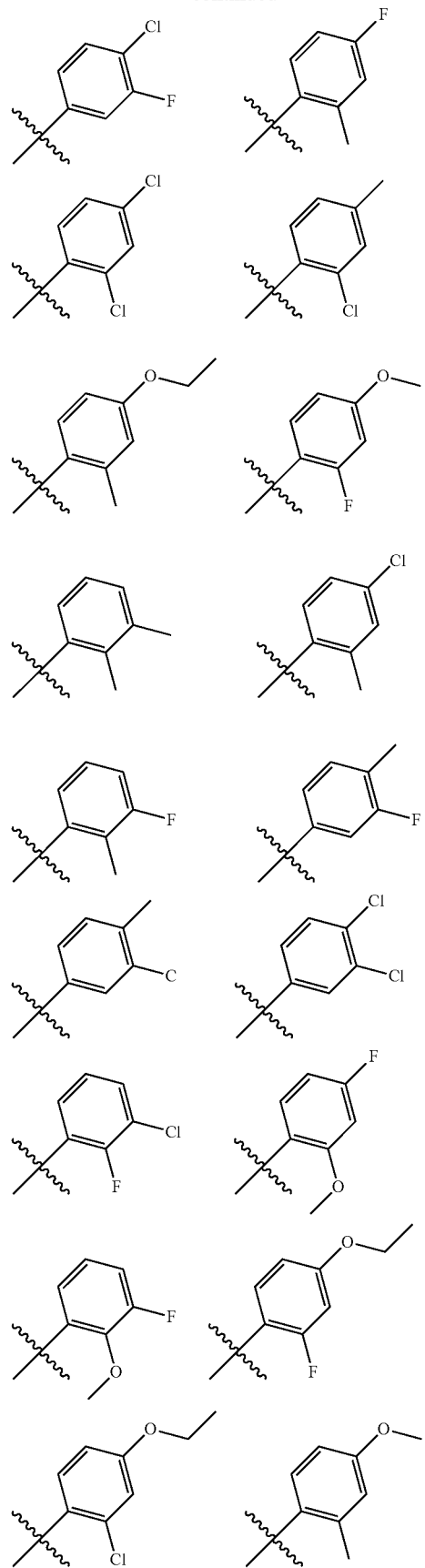
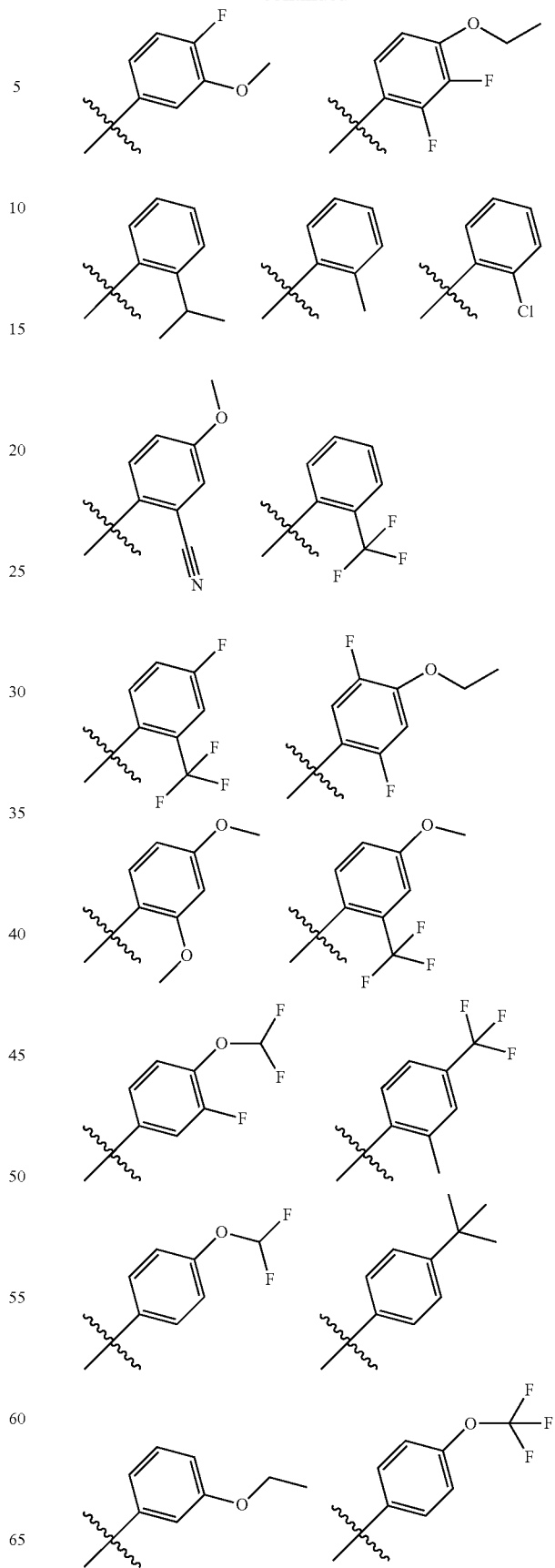

-continued
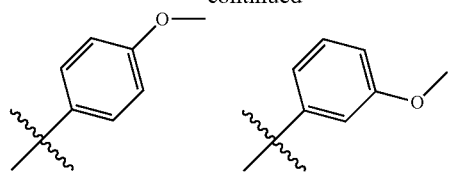
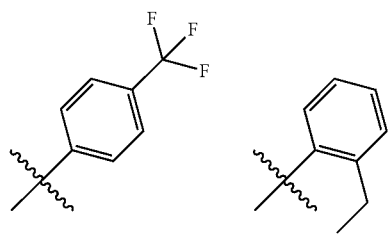
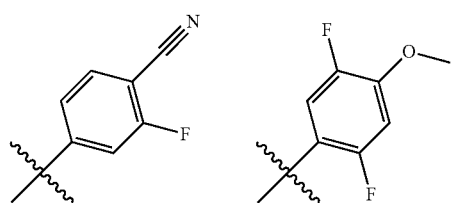
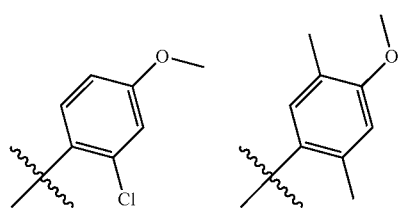
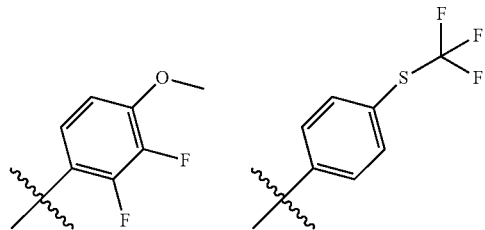
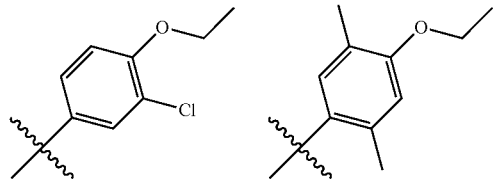
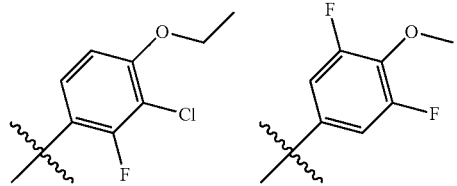
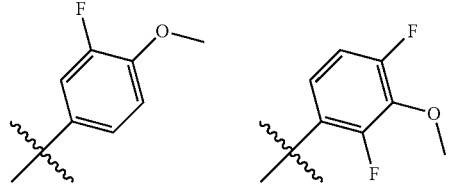
-continued
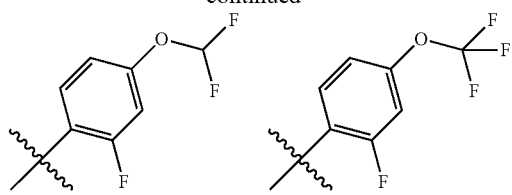
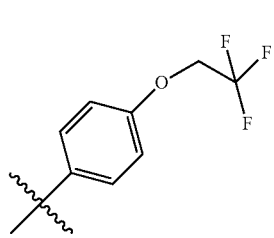
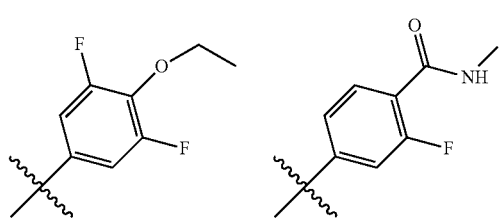
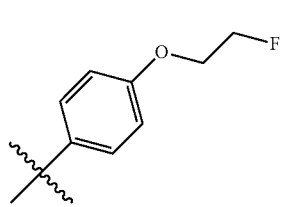
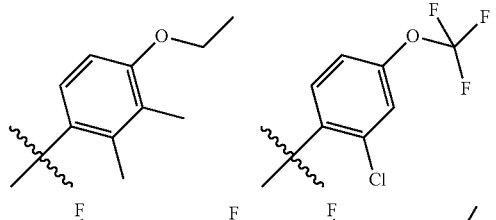
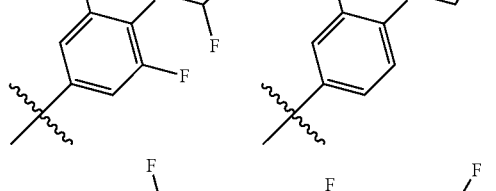
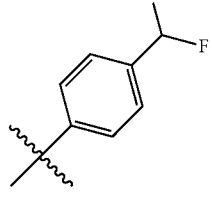
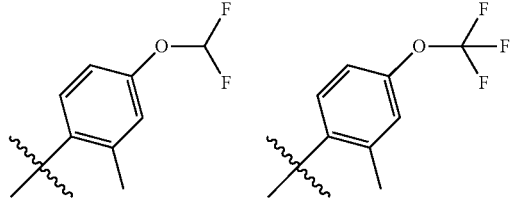

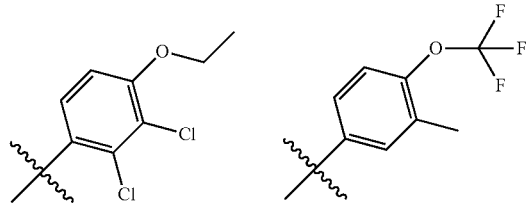
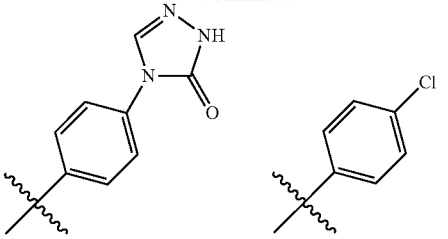
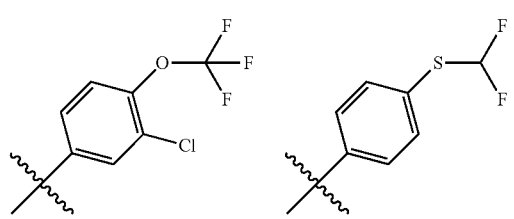
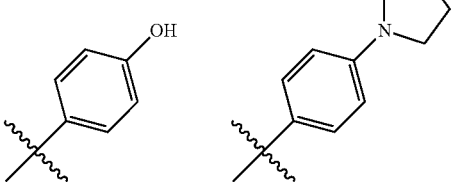
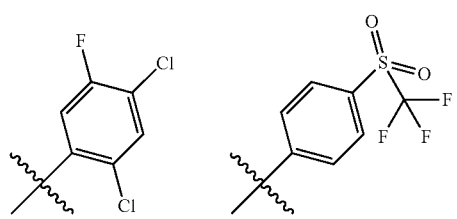
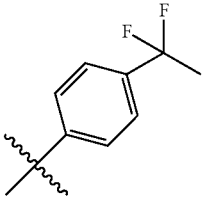
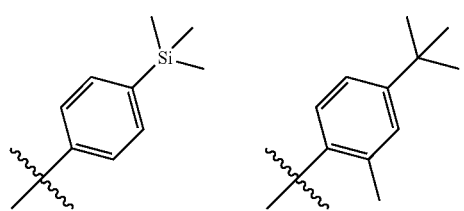
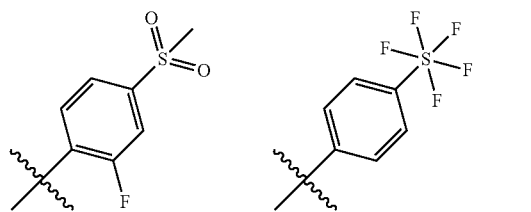
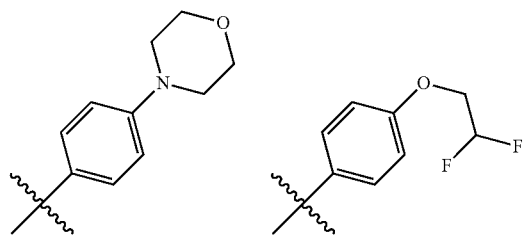
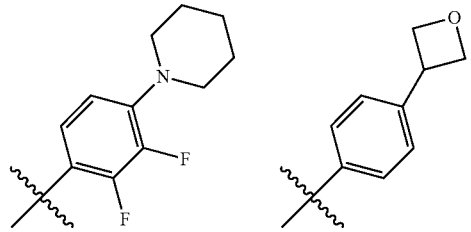

In another embodiment, in the compounds of formula (I), R6 is selected from a heteroaryl group comprising 3 to 9 carbon atoms and comprising from 1 to 3 heteroatoms independently selected from oxygen, nitrogen and sulphur, said heteroaryl group being unsubstituted or substituted with 1 to 3 substituents independently selected from: a ($C_1$-$C_6$)-alkyl group unsubstituted or substituted with one or more (such as 1, 2 or 3) fluorine atoms; a halogen atom; a —OH group; a N-oxide (—$N^+$—$O^-$), a ($C_1$-$C_6$)-alkoxy group unsubstituted or substituted with one or more (such as 1, 2 or 3) fluorine atoms; a cyano group; a sulphur group substituted with 5 fluorine atoms or ($C_1$-$C_6$)-alkyl groups substituted with two or more (such as 2 or 3) fluorine atoms; a sulfonyl-($C_1$-$C_6$)-alkyl group wherein said ($C_1$-$C_6$)-alkyl group being unsubstituted or substituted with two or more (such as 2 or 3) fluorine atoms; a silane group substituted with 3 ($C_1$-$C_6$)-alkyl groups; an amine group unsubstituted or substituted with one or more (such as 1 or 2) ($C_1$-$C_6$)-alkyl groups; an amide group unsubstituted or substituted with one or more (such as 1 or 2) ($C_1$-$C_6$)-alkyl groups; a heterocycloalkyl group saturated or partially saturated, comprising 3 to 5 carbon atoms and comprising 1 or 2 heteroatoms independently selected from oxygen, nitrogen and sulphur; and a heteroaryl group comprising 2 to 4 carbon atoms and comprising 1 to 3 heteroatoms selected from oxygen, nitrogen and sulphur and being unsubstituted or substituted with an oxo group.

In another embodiment, in the compounds of formula (I), R6 is selected from a heteroaryl group comprising 3 to 9 carbon atoms and comprising from 1 to 3 heteroatoms independently selected from oxygen, nitrogen and sulphur, said heteroaryl group being unsubstituted or substituted with 1 to 3 substituents independently selected from: a ($C_1$-$C_6$)-alkyl group unsubstituted or substituted with one or more (such as 1, 2 or 3) fluorine atoms; a halogen atom; a —OH group; a ($C_1$-$C_6$)-alkoxy group unsubstituted or substituted with one or more (such as 1, 2 or 3) fluorine atoms; and an amine group unsubstituted or substituted with one or more (such as 1 or 2) ($C_1$-$C_6$)-alkyl groups.

In another embodiment, the compounds of formula (I), R6 is selected from a heteroaryl group comprising 3 to 9 carbon atoms and comprising from 1 to 3 heteroatoms independently selected from oxygen, nitrogen and sulphur, said heteroaryl group being unsubstituted or substituted with 1 to 3 substituents independently selected from: a $(C_1$-$C_3)$-alkyl group unsubstituted or substituted with one or more (such as 1, 2 or 3) fluorine atoms; a halogen atom; a —OH group; a $(C_1$-$C_3)$-alkoxy group unsubstituted or substituted with one or more (such as 1, 2 or 3) fluorine atoms; and an amine group unsubstituted or substituted with one or more (such as 1 or 2) $(C_1$-$C_3)$-alkyl groups.

In another embodiment, in the compounds of formula (I), R6 is selected from a heteroaryl group comprising 3 to 9 carbon atoms and comprising from 1 to 3 heteroatoms independently selected from oxygen, nitrogen and sulphur, said heteroaryl group being unsubstituted or substituted with 1 to 3 substituents independently selected from: a methyl group; a —$CF_3$ group; a chlorine atom; a fluorine atom; a —OH group; a —$OCH_3$ group; a —$OCH_2CH_3$ group; a —$OCHF_2$ group; and a —$NH_2$ group.

In another embodiment, in the compounds of formula (I), R6 is selected from an unsubstituted or substituted heteroaryl group selected from the following list:

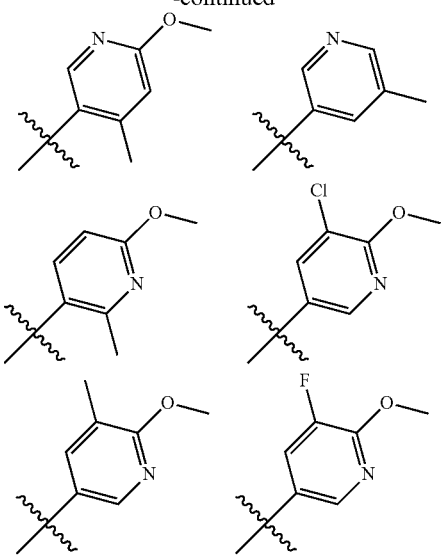

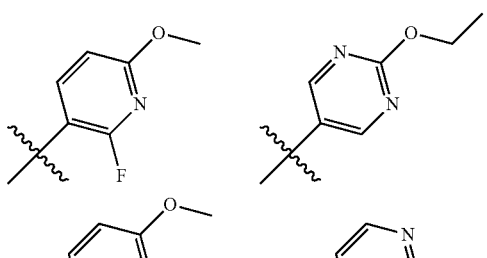

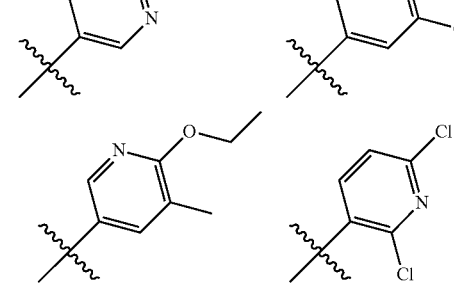

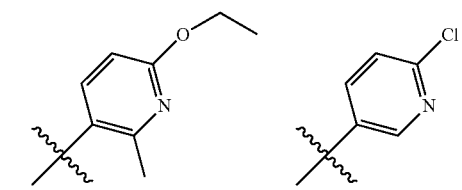

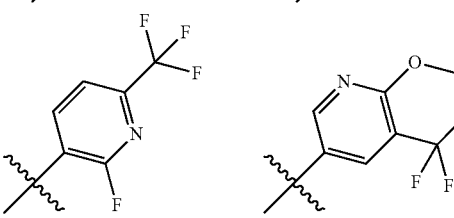

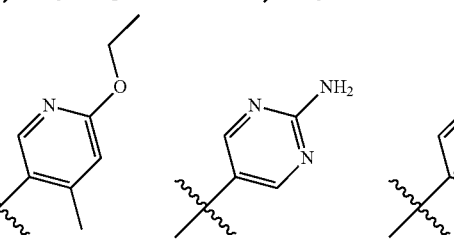

-continued

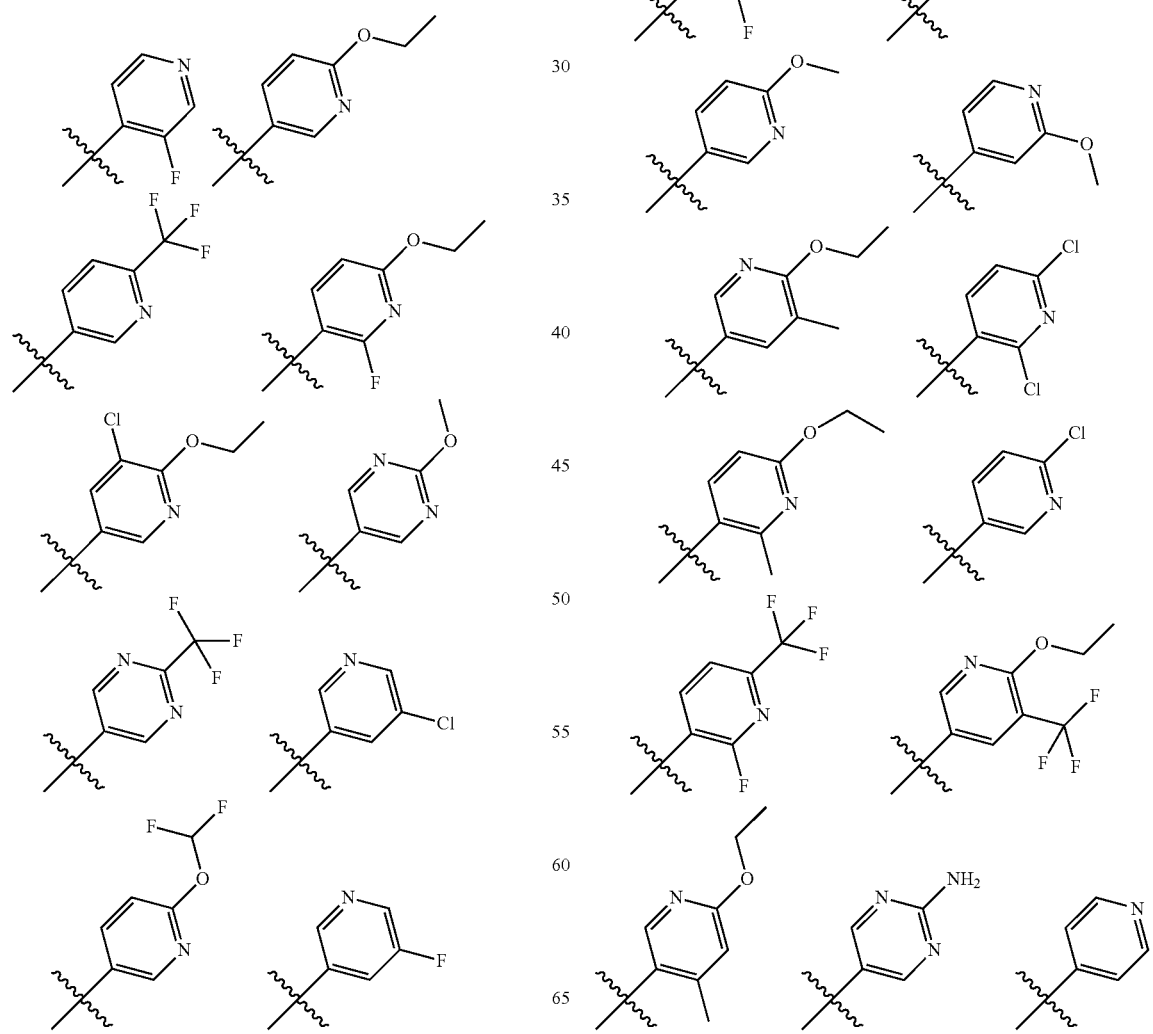

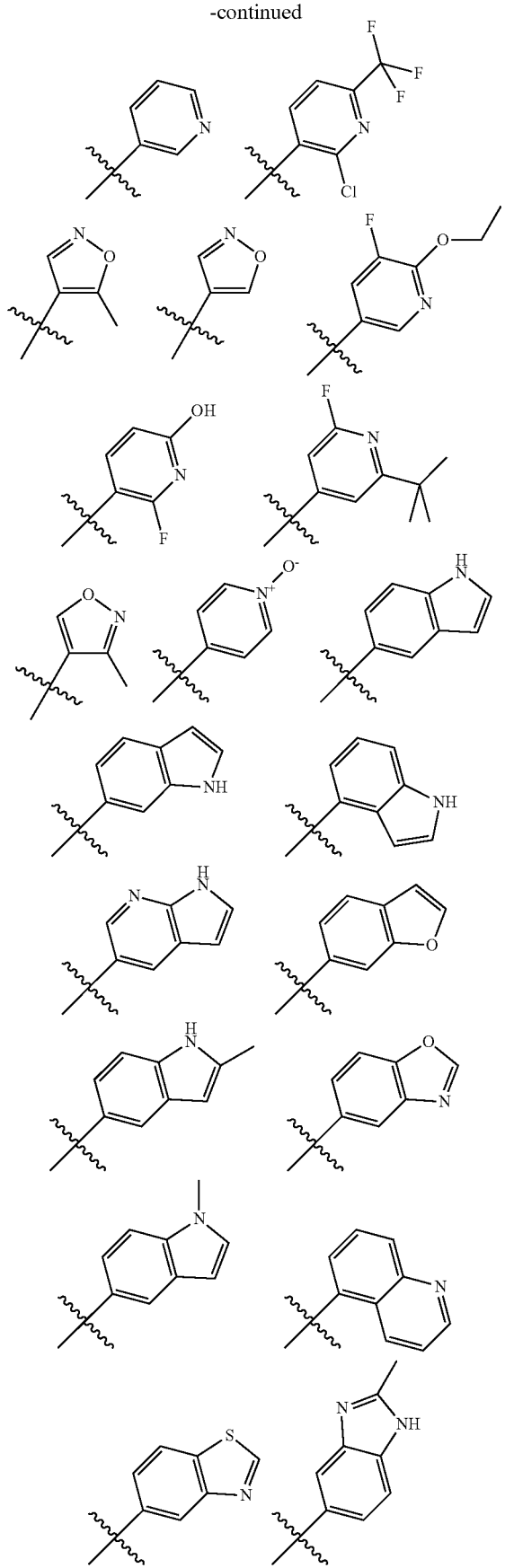
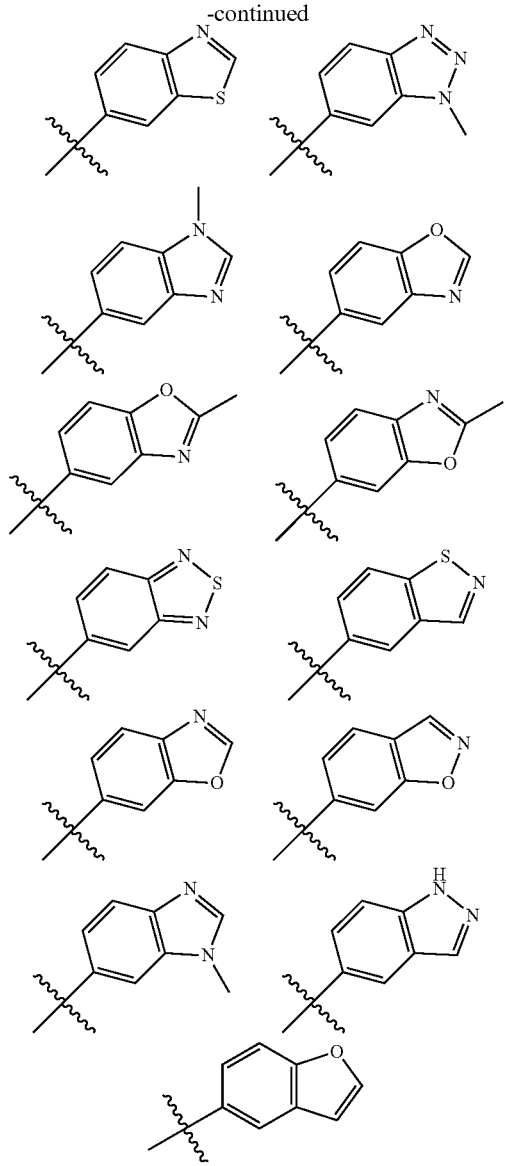

In another embodiment, in the compounds of formula (I), R6 is selected from a $(C_1-C_6)$-cycloalkyl group saturated or partially saturated and unsubstituted or substituted with 1 or 2 substituents independently selected from: a fluorine atom; a —OH group; a $(C_1-C_6)$-alkyl group; a —COOR7 group wherein R7 is a $(C_1-C_6)$-alkyl group; and an oxo group.

In another embodiment, in the compounds of formula (I), R6 is selected from a $(C_1-C_6)$-cycloalkyl group saturated or partially saturated and unsubstituted or substituted with 1 or 2 substituents independently selected from: a fluorine atom; a —OH group; a $(C_1-C_3)$-alkyl group; a —COOR7 group wherein R7 is a $(C_1-C_3)$-alkyl group; and an oxo group.

In another embodiment, in the compounds of formula (I), R6 is selected from a $(C_1-C_6)$-cycloalkyl group saturated or partially saturated, unsubstituted or substituted with 1 or 2 substituents independently selected from: a fluorine atom or a —OH group.

In another embodiment, in the compounds of formula (I), R6 is selected from a substituted $(C_1-C_6)$-cycloalkyl group selected from the following list:

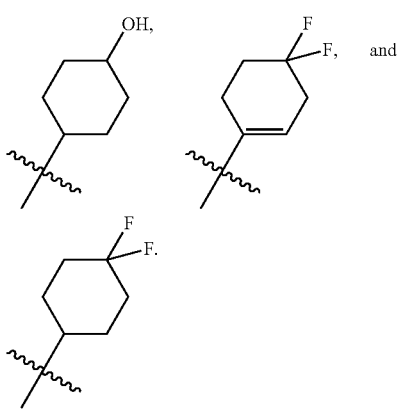

In another embodiment, in the compounds of formula (I), R6 is selected from a heterocycloalkyl group comprising 4 to 9 carbon atoms and comprising 1 or 2 heteroatoms independently selected from oxygen, nitrogen and sulphur, said heterocycloalkyl group being saturated or partially saturated and being unsubstituted or substituted with 1 to 4 substituents independently selected from: a fluorine atom; a —OH group; a ($C_1$-$C_6$)-alkyl group; a —COOR7 group wherein R7 is an ($C_1$-$C_6$)-alkyl group; and an oxo group.

In another embodiment, in the compounds of formula (I), R6 is selected from:
- a monocyclic-($C_1$-$C_6$)-heterocycloalkyl group comprising one heteroatom selected from oxygen, nitrogen and sulphur, said monocyclic heterocycloalkyl group being saturated or partially saturated and being unsubstituted or substituted with 1 or 2 substituents independently selected from: a ($C_1$-$C_6$)-alkyl group and a —COOR7 group wherein R7 is an ($C_1$-$C_6$)-alkyl group or
- a bicyclic heterocycloalkyl group comprising 8 to 9 carbon atoms and comprising 1 or 2 heteroatoms independently selected from oxygen, nitrogen and sulphur, said bicyclic heterocycloalkyl group being saturated or partially saturated and being unsubstituted or substituted with 1 to 4 substituents independently selected from: a fluorine atom; a ($C_1$-$C_6$)-alkyl group; a —COOR7 group wherein R7 is an ($C_1$-$C_6$)-alkyl group; and an oxo group.

In another embodiment, in the compounds of formula (I), R6 is selected from:
- a monocyclic-($C_1$-$C_6$)-heterocycloalkyl group comprising one heteroatom selected from oxygen, nitrogen and sulphur, said monocyclic heterocycloalkyl group being saturated or partially saturated and being unsubstituted or substituted with 1 or 2 substituents independently selected from: a ($C_1$-$C_3$)-alkyl group and a —COOR7 group wherein R7 is an ($C_1$-$C_4$)-alkyl group or
- a bicyclic heterocycloalkyl group comprising 8 to 9 carbon atoms and comprising 1 or 2 heteroatoms independently selected from oxygen, nitrogen and sulphur, said bicyclic heterocycloalkyl group being saturated or partially saturated and being unsubstituted or substituted with 1 to 4 substituents independently selected from: a fluorine atom; a ($C_1$-$C_3$)-alkyl group; a —COOR7 group wherein R7 is an ($C_1$-$C_4$)-alkyl group; and an oxo group.

In another embodiment, in the compounds of formula (I), R6 is selected from:
- a monocyclic ($C_1$-$C_6$)-heterocycloalkyl group comprising one heteroatom selected from oxygen, nitrogen and sulphur, said monocyclic heterocycloalkyl group being saturated or partially saturated and being unsubstituted or substituted with 1 or 2 substituents independently selected from: a methyl group and a —COO-tert butyl group or
- a bicyclic heterocycloalkyl group comprising 8 to 9 carbon atoms and comprising 1 or 2 heteroatoms independently selected from oxygen, nitrogen and sulphur, said bicyclic heterocycloalkyl group being saturated or partially saturated and being unsubstituted or substituted with 1 to 4 substituents independently selected from: a fluorine atom; a methyl group; an ethyl group; a —COO-tert butyl group; and an oxo group.

In another embodiment, in the compounds of formula (I), R6 is selected from a monocyclic ($C_1$-$C_6$)-heterocycloalkyl group comprising one heteroatom selected from oxygen, nitrogen and sulphur, said monocyclic ($C_1$-$C_6$)-heterocycloalkyl group being saturated or partially saturated and being unsubstituted or substituted with 1 or 2 substituents independently selected from: a methyl group and a —COO-tert butyl group.

In another embodiment, in the compounds of formula (I), R6 is selected from an unsubstituted or substituted monocyclic ($C_1$-$C_6$)-heterocycloalkyl group selected from the following list:

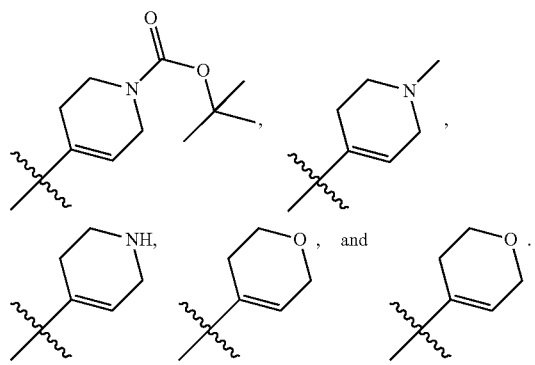

In another embodiment, in the compounds of formula (I), R6 is selected from a bicyclic heterocycloalkyl group comprising 8 to 9 carbon atoms and comprising 1 or 2 heteroatoms independently selected from oxygen, nitrogen and sulphur, said bicyclic heterocycloalkyl group being saturated or partially saturated and being unsubstituted or substituted with 1 to 4 substituents independently selected from: a fluorine atom; a methyl group; an ethyl group; a —COO-tert butyl group; and an oxo group.

In another embodiment, in the compounds of formula (I), R6 is selected from an unsubstituted or substituted bicyclic heterocycloalkyl group selected from the following list:

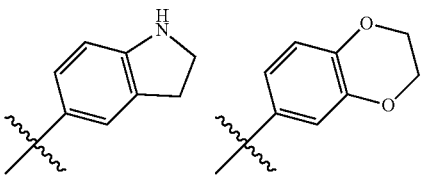

-continued

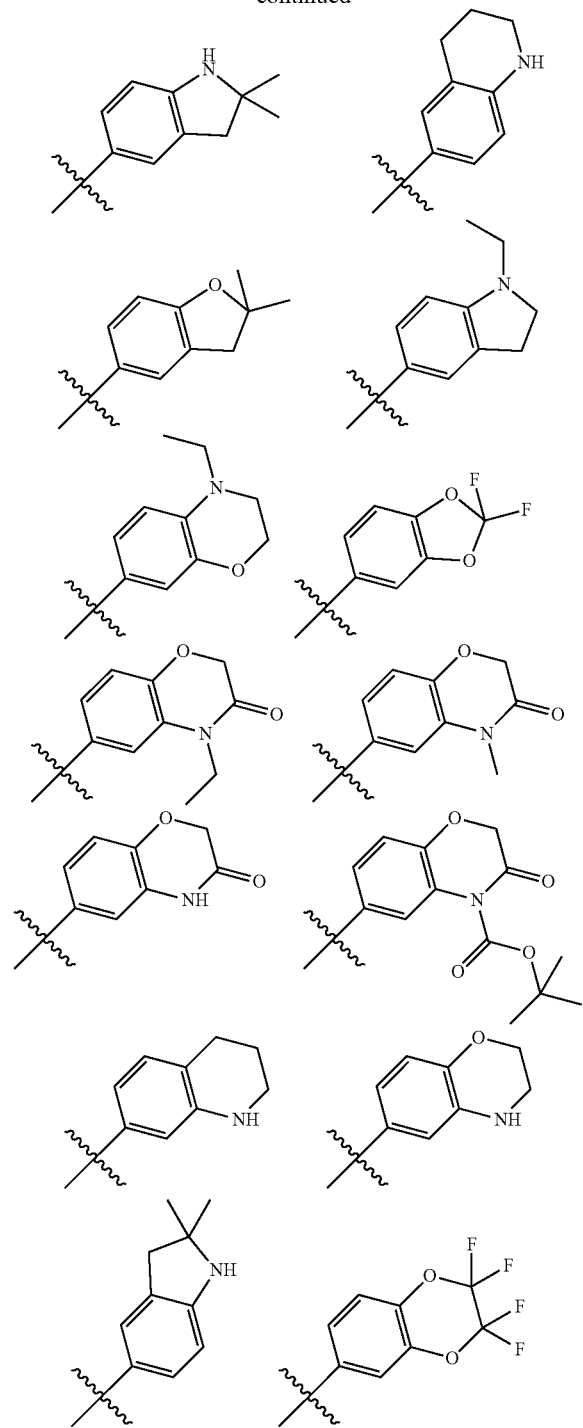

The compounds of formula (I) include the compounds having any combination of the above-defined embodiments for R1, R2, R3, R4, R5 and R6 with each other.

Among the compounds of formula (I), mention may be made in particular of the following compounds:

5-[4-[(3S)-1-(3-fluoropropyl)pyrrolidin-3-yl]oxyphenyl]-6-(4-hydroxyphenyl)-8,9-dihydro-7H-benzo[7]annulen-3-ol;

5-[4-[(3S)-1-(3-fluoropropyl)pyrrolidin-3-yl]oxyphenyl]-6-(3-hydroxyphenyl)-8,9-dihydro-7H-benzo[7]annulen-3-ol;

5-[4-[(3S)-1-(3-fluoropropyl)pyrrolidin-3-yl]oxyphenyl]-6-(1H-indol-5-yl)-8,9-dihydro-7H-benzo[7]annulen-3-ol;

6-(2-chloro-4-fluoro-phenyl)-5-[4-[(3S)-1-(3-fluoropropyl)pyrrolidin-3-yl]oxyphenyl]-8,9-dihydro-7H-benzo[7]annulen-3-ol;

6-(2-chloro-4-fluoro-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(3-hydroxyphenyl)-8,9-dihydro-7H-benzo[7]annulen-2-ol;

6-(3-chloro-2-methyl-phenyl)-5-[4-[(3S)-1-(3-fluoropropyl)pyrrolidin-3-yl]oxyphenyl]-8,9-dihydro-7H-benzo[7]annulen-2-ol;

6-(2-chloro-3-fluoro-phenyl)-5-[4-[(3S)-1-(3-fluoropropyl)pyrrolidin-3-yl]oxyphenyl]-8,9-dihydro-7H-benzo[7]annulen-2-ol;

6-(2-fluoro-4-methyl-phenyl)-5-[4-[(3S)-1-(3-fluoropropyl)pyrrolidin-3-yl]oxyphenyl]-8,9-dihydro-7H-benzo[7]annulen-2-ol;

6-(2-fluoro-4-hydroxy-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(4-hydroxyphenyl)-8,9-dihydro-7H-benzo[7]annulen-2-ol;

5-[4-[(3S)-1-(3-fluoropropyl)pyrrolidin-3-yl]oxyphenyl]-6-(1H-indol-5-yl)-8,9-dihydro-7H-benzo[7]annulen-2-ol;

6-(4-chloro-3-methyl-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(3-fluoro-4-pyridyl)-8,9-dihydro-7H-benzo[7]annulen-2-ol;

6-(4-chloro-2-fluoro-phenyl)-5-[4-[(3S)-1-(3-fluoropropyl)pyrrolidin-3-yl]oxyphenyl]-8,9-dihydro-7H-benzo[7]annulen-2-ol;

6-(4-chloro-3-fluoro-phenyl)-5-[4-[(3S)-1-(3-fluoropropyl)pyrrolidin-3-yl]oxyphenyl]-8,9-dihydro-7H-benzo[7]annulen-2-ol;

6-(4-fluoro-2-methyl-phenyl)-5-[4-[(3S)-1-(3-fluoropropyl)pyrrolidin-3-yl]oxyphenyl]-8,9-dihydro-7H-benzo[7]annulen-2-ol;

6-(2,4-dichlorophenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(1H-indol-6-yl)-8,9-dihydro-7H-benzo[7]annulen-2-ol;

5-[4-[(3S)-1-(3-fluoropropyl)pyrrolidin-3-yl]oxyphenyl]-6-(1H-indol-4-yl)-8,9-dihydro-7H-benzo[7]annulen-2-ol;

5-[4-[(3S)-1-(3-fluoropropyl)pyrrolidin-3-yl]oxyphenyl]-6-indolin-5-yl-8,9-dihydro-7H-benzo[7]annulen-2-ol;

5-[4-[(3S)-1-(3-fluoropropyl)pyrrolidin-3-yl]oxyphenyl]-6-(1H-pyrrolo[2,3-b]pyridin-5-yl)-8,9-dihydro-7H-benzo[7]annulen-2-ol;

6-(2-chloro-4-methyl-phenyl)-5-[4-[(3S)-1-(3-fluoropropyl)pyrrolidin-3-yl]oxyphenyl]-8,9-dihydro-7H-benzo[7]annulen-2-ol;

tert-butyl 4-[5-[4-[(3S)-1-(3-fluoropropyl)pyrrolidin-3-yl]oxyphenyl]-2-hydroxy-8,9-dihydro-7H-benzo[7]annulen-6-yl]-3,6-dihydro-2H-pyridine-1-carboxylate;

5-[4-[(3S)-1-(3-fluoropropyl)pyrrolidin-3-yl]oxyphenyl]-6-(1-methyl-3,6-dihydro-2H-pyridin-4-yl)-8,9-dihydro-7H-benzo[7]annulen-2-ol;

5-[4-[(3S)-1-(3-fluoropropyl)pyrrolidin-3-yl]oxyphenyl]-6-(1,2,3,6-tetrahydropyridin-4-yl)-8,9-dihydro-7H-benzo[7]annulen-2-ol;

6-(4-ethoxy-2-methyl-phenyl)-5-[4-[(3S)-1-(3-fluoropropyl)pyrrolidin-3-yl]oxyphenyl]-8,9-dihydro-7H-benzo[7]annulen-2-ol;

6-(benzofuran-5-yl)-5-[4-[(3S)-1-(3-fluoropropyl)pyrrolidin-3-yl]oxyphenyl]-8,9-dihydro-7H-benzo[7]annulen-2-ol;

6-(2-fluoro-4-methoxy-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(2-methyl-1H-indol-5-yl)-8,9-dihydro-7H-benzo[7]annulen-2-ol;

6-(2,3-dimethylphenyl)-5-[4-[(3S)-1-(3-fluoropropyl)pyrrolidin-3-yl]oxyphenyl]-8,9-dihydro-7H-benzo[7]annulen-2-ol;

6-(4-chloro-2-methyl-phenyl)-5-[4-[(3S)-1-(3-fluoropropyl)pyrrolidin-3-yl]oxyphenyl]-8,9-dihydro-7H-benzo[7]annulen-2-ol;

6-(3-fluoro-2-methyl-phenyl)-5-[4-[(3S)-1-(3-fluoropropyl)pyrrolidin-3-yl]oxyphenyl]-8,9-dihydro-7H-benzo[7]annulen-2-ol;

6-(6-ethoxy-3-pyridyl)-5-[4-[(3S)-1-(3-fluoropropyl)pyrrolidin-3-yl]oxyphenyl]-8,9-dihydro-7H-benzo[7]annulen-2-ol;

6-(3-fluoro-4-methyl-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(1,1-dideuterio-3-fluoro-propyl)pyrrolidin-3-yl]oxyphenyl]-6-(2-fluoro-4-methyl-phenyl)-8,9-dihydro-7H-benzo[7]annulen-2-ol;

6-(3-chloro-4-methyl-phenyl)-5-[4-[(3S)-1-(3-fluoropropyl)pyrrolidin-3-yl]oxyphenyl]-8,9-dihydro-7H-benzo[7]annulen-2-ol;

6-(3,4-dichlorophenyl)-5-[4-[(3S)-1-(3-fluoropropyl)pyrrolidin-3-yl]oxyphenyl]-8,9-dihydro-7H-benzo[7]annulen-2-ol;

6-(3-chloro-2-fluoro-phenyl)-5-[4-[(3S)-1-(3-fluoropropyl)pyrrolidin-3-yl]oxyphenyl]-8,9-dihydro-7H-benzo[7]annulen-2-ol;

6-(4-fluoro-2-methoxy-phenyl)-5-[4-[(3S)-1-(3-fluoropropyl)pyrrolidin-3-yl]oxyphenyl]-8,9-dihydro-7H-benzo[7]annulen-2-ol;

6-(3-fluoro-2-methoxy-phenyl)-5-[4-[(3S)-1-(3-fluoropropyl)pyrrolidin-3-yl]oxyphenyl]-8,9-dihydro-7H-benzo[7]annulen-2-ol;

6-(4-ethoxy-2-fluoro-phenyl)-5-[4-[(3S)-1-(3-fluoropropyl)pyrrolidin-3-yl]oxyphenyl]-8,9-dihydro-7H-benzo[7]annulen-2-ol;

6-(2-chloro-4-ethoxy-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(4-methoxy-2-methyl-phenyl)-8,9-dihydro-7H-benzo[7]annulen-2-ol;

1-fluoro-6-(2-fluoro-4-methyl-phenyl)-5-[4-[(3S)-1-(3-fluoropropyl)pyrrolidin-3-yl]oxyphenyl]-8,9-dihydro-7H-benzo[7]annulen-2-ol;

6-(4-ethoxy-2-methyl-phenyl)-1-fluoro-5-[4-[(3S)-1-(3-fluoropropyl)pyrrolidin-3-yl]oxyphenyl]-8,9-dihydro-7H-benzo[7]annulen-2-ol;

6-(2,4-dichlorophenyl)-1-fluoro-5-[4-[(3S)-1-(3-fluoropropyl)pyrrolidin-3-yl]oxyphenyl]-8,9-dihydro-7H-benzo[7]annulen-2-ol;

6-(2-fluoro-4-methyl-phenyl)-5-[4-[(3S)-1-(3-fluoropropyl)pyrrolidin-3-yl]oxyphenyl]-8,9-dihydro-7H-benzo[7]annulene-2-carboxylic acid;

6-(2,3-dihydro-1,4-benzodioxin-6-yl)-5-[4-[(3S)-1-(3-fluoropropyl)pyrrolidin-3-yl]oxyphenyl]-8,9-dihydro-7H-benzo[7]annulen-2-ol;

6-(4-fluoro-3-methoxy-phenyl)-5-[4-[(3S)-1-(3-fluoropropyl)pyrrolidin-3-yl]oxyphenyl]-8,9-dihydro-7H-benzo[7]annulen-2-ol;

6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid;

6-(4-ethoxy-2,3-difluoro-phenyl)-5-[4-[(3S)-1-(3-fluoropropyl)pyrrolidin-3-yl]oxyphenyl]-8,9-dihydro-7H-benzo[7]annulen-2-ol;

6-(4-chloro-3-fluoro-phenyl)-5-[4-[(3S)-1-(3-fluoropropyl)pyrrolidin-3-yl]oxyphenyl]-8,9-dihydro-7H-benzo[7]annulene-2-carboxylic acid;

6-(1,3-benzoxazol-5-yl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(4-hydroxyphenyl)-8,9-dihydro-7H-benzo[7]annulene-2-carboxylic acid;

5-[4-[(3S)-1-(3-fluoropropyl)pyrrolidin-3-yl]oxyphenyl]-6-(2-isopropylphenyl)-8,9-dihydro-7H-benzo[7]annulen-2-ol;

5-[4-[(3S)-1-(3-fluoropropyl)pyrrolidin-3-yl]oxyphenyl]-6-(o-tolyl)-8,9-dihydro-7H-benzo[7]annulen-2-ol;

6-(2-chlorophenyl)-5-[4-[(3S)-1-(3-fluoropropyl)pyrrolidin-3-yl]oxyphenyl]-8,9-dihydro-7H-benzo[7]annulen-2-ol;

2-[5-[4-[(3S)-1-(3-fluoropropyl)pyrrolidin-3-yl]oxyphenyl]-2-hydroxy-8,9-dihydro-7H-benzo[7]annulen-6-yl]-5-methoxy-benzonitrile;

5-[4-[(3S)-1-(3-fluoropropyl)pyrrolidin-3-yl]oxyphenyl]-6-[2(trifluoromethyl)phenyl]-8,9-dihydro-7H-benzo[7]annulen-2-ol;

5-[4-[(3S)-1-(3-fluoropropyl)pyrrolidin-3-yl]oxyphenyl]-6-[4-fluoro-2-(trifluoromethyl)phenyl]-8,9-dihydro-7H-benzo[7]annulen-2-ol;

6-(4-ethoxy-2,5-difluoro-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(4-methoxy-2-methyl-phenyl)-8,9-dihydro-7H-benzo[7]annulene-2-carboxylic acid hydrochloride;

6-(2,4-dimethoxyphenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-[4-methoxy-2-(trifluoromethyl)phenyl]-8,9-dihydro-7H-benzo[7]annulen-2-ol;

6-[4-(difluoromethoxy)-3-fluoro-phenyl]-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-[2-methyl-4-(trifluoromethyl)phenyl]-8,9-dihydro-7H-benzo[7]annulen-2-ol;

5-[4-[(3S)-1-(3-fluoropropyl)pyrrolidin-3-yl]oxyphenyl]-6-[6-(trifluoromethyl)-3-pyridyl]-8,9-dihydro-7H-benzo[7]annulen-2-ol;

6-[4-(difluoromethoxy)phenyl]-5-[4-[(3S)-1-(3-fluoropropyl)pyrrolidin-3-yl]oxyphenyl]-8,9-dihydro-7H-benzo[7]annulen-2-ol;

6-(2,2-dimethylindolin-5-yl)-5-[4-[(3S)-1-(3-fluoropropyl)pyrrolidin-3-yl]oxyphenyl]-8,9-dihydro-7H-benzo[7]annulen-2-ol;

6-(6-ethoxy-2-fluoro-3-pyridyl)-5-[4-[(3S)-1-(3-fluoropropyl)pyrrolidin-3-yl]oxyphenyl]-8,9-dihydro-7H-benzo[7]annulen-2-ol;

6-(4-tert-butylphenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(1,2,3,4-tetrahydroquinolin-6-yl)-8,9-dihydro-7H-benzo[7]annulen-2-ol;

6-(3-ethoxyphenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-ol;

5-[4-[(3S)-1-(3-fluoropropyl)pyrrolidin-3-yl]oxyphenyl]-6-(4-methoxyphenyl)-8,9-dihydro-7H-benzo[7]annulen-2-ol;

5-[4-[(3S)-1-(3-fluoropropyl)pyrrolidin-3-yl]oxyphenyl]-6-(3-methoxyphenyl)-8,9-dihydro-7H-benzo[7]annulen-2-ol;

5-[4-[(3S)-1-(3-fluoropropyl)pyrrolidin-3-yl]oxyphenyl]-6-[4-(trifluoromethyl)phenyl]-8,9-dihydro-7H-benzo[7]annulen-2-ol;

6-[4-(difluoromethoxy)-3-fluoro-phenyl]-1-fluoro-5-[4-[(3S)-1-(3-fluoropropyl)pyrrolidin-3-yl]oxyphenyl]-8,9-dihydro-7H-benzo[7]annulen-2-ol;

6-(5-chloro-6-ethoxy-3-pyridyl)-5-[4-[(3S)-1-(3-fluoropropyl)pyrrolidin-3-yl]oxyphenyl]-8,9-dihydro-7H-benzo[7]annulen-2-ol;

6-(2-ethylphenyl)-5-[4-[(3S)-1-(3-fluoropropyl)pyrrolidin-3-yl]oxyphenyl]-8,9-dihydro-7H-benzo[7]annulen-2-ol;

6-(6-ethoxy-2-fluoro-3-pyridyl)-1-fluoro-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(2-methoxypyrimidin-5-yl)-8,9-dihydro-7H-benzo[7]annulen-2-ol;

5-[4-[(3S)-1-(3-fluoropropyl)pyrrolidin-3-yl]oxyphenyl]-6-[2-(trifluoromethyl)pyrimidin-5-yl]-8,9-dihydro-7H-benzo[7]annulen-2-ol;

2-fluoro-4-[5-[4-[(3S)-1-(3-fluoropropyl)pyrrolidin-3-yl]oxyphenyl]-2-hydroxy-8,9-dihydro-7H-benzo[7]annulen-6-yl]benzonitrile;

6-(5-chloro-3-pyridyl)-5-[4-[(3S)-1-(3-fluoropropyl)pyrrolidin-3-yl]oxyphenyl]-8,9-dihydro-7H-benzo[7]annulen-2-ol;

6-[6-(difluoromethoxy)-3-pyridyl]-5-[4-[(3S)-1-(3-fluoropropyl)pyrrolidin-3-yl]oxyphenyl]-8,9-dihydro-7H-benzo[7]annulen-2-ol;

6-(2,5-difluoro-4-methoxy-phenyl)-5-[4-[(3S)-1-(3-fluoropropyl)pyrrolidin-3-yl]oxyphenyl]-8,9-dihydro-7H-benzo[7]annulen-2-ol;

6-(2-chloro-4-methoxy-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(5-fluoro-3-pyridyl)-8,9-dihydro-7H-benzo[7]annulen-2-ol;

5-[4-[(3S)-1-(3-fluoropropyl)pyrrolidin-3-yl]oxyphenyl]-6-(6-methoxy-4-methyl-3-pyridyl)-8,9-dihydro-7H-benzo[7]annulen-2-ol;

5-[4-[(3S)-1-(3-fluoropropyl)pyrrolidin-3-yl]oxyphenyl]-6-(4-methoxy-2,5-dimethyl-phenyl)-8,9-dihydro-7H-benzo[7]annulen-2-ol;

6-(2,3-difluoro-4-methoxy-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-[4-(trifluoromethylsulfanyl)phenyl]-8,9-dihydro-7H-benzo[7]annulen-2-ol;

6-(3-chloro-4-ethoxy-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(5-methyl-3-pyridyl)-8,9-dihydro-7H-benzo[7]annulen-2-ol;

5-[4-[(3S)-1-(3-fluoropropyl)pyrrolidin-3-yl]oxyphenyl]-6-(6-methoxy-2-methyl-3-pyridyl)-8,9-dihydro-7H-benzo[7]annulen-2-ol;

6-(2,2-dimethyl-3H-benzofuran-5-yl)-5-[4-[(3S)-1-(3-fluoropropyl)pyrrolidin-3-yl]oxyphenyl]-8,9-dihydro-7H-benzo[7]annulen-2-ol;

6-(5-chloro-6-methoxy-3-pyridyl)-5-[4-[(3S)-1-(3-fluoropropyl)pyrrolidin-3-yl]oxyphenyl]-8,9-dihydro-7H-benzo[7]annulen-2-ol;

6-(4-ethoxy-2,5-dimethyl-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(6-methoxy-5-methyl-3-pyridyl)-8,9-dihydro-7H-benzo[7]annulen-2-ol 6-(5-fluoro-6-methoxy-3-pyridyl)-5-[4-[(3S)-1-(3-fluoropropyl)pyrrolidin-3-yl]oxyphenyl]-8,9-dihydro-7H-benzo[7]annulen-2-ol;

6-(3-chloro-4-ethoxy-2-fluoro-phenyl)-5-[4-[(3S)-1-(3-fluoropropyl)pyrrolidin-3-yl]oxyphenyl]-8,9-dihydro-7H-benzo[7]annulen-2-ol;

6-(2-fluoro-6-methoxy-3-pyridyl)-5-[4-[(3S)-1-(3-fluoropropyl)pyrrolidin-3-yl]oxyphenyl]-8,9-dihydro-7H-benzo[7]annulen-2-ol;

6-(3,5-difluoro-4-methoxy-phenyl)-5-[4-[(3S)-1-(3-fluoropropyl)pyrrolidin-3-yl]oxyphenyl]-8,9-dihydro-7H-benzo[7]annulen-2-ol;

6-(1-ethylindolin-5-yl)-5-[4-[(3S)-1-(3-fluoropropyl)pyrrolidin-3-yl]oxyphenyl]-8,9-dihydro-7H-benzo[7]annulen-2-ol;

6-(2-ethoxypyrimidin-5-yl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(6-methoxy-3-pyridyl)-8,9-dihydro-7H-benzo[7]annulen-2-ol;

5-[4-[(3S)-1-(3-fluoropropyl)pyrrolidin-3-yl]oxyphenyl]-6-(2-methoxy-4-pyridyl)-8,9-dihydro-7H-benzo[7]annulen-2-ol;

6-(6-ethoxy-5-methyl-3-pyridyl)-5-[4-[(3S)-1-(3-fluoropropyl)pyrrolidin-3-yl]oxyphenyl]-8,9-dihydro-7H-benzo[7]annulen-2-ol;

6-(3-fluoro-4-methoxy-phenyl)-5-[4-[(3S)-1-(3-fluoropropyl)pyrrolidin-3-yl]oxyphenyl]-8,9-dihydro-7H-benzo[7]annulen-2-ol;

6-(2,4-difluoro-3-methoxy-phenyl)-5-[4-[(3S)-1-(3-fluoropropyl)pyrrolidin-3-yl]oxyphenyl]-8,9-dihydro-7H-benzo[7]annulen-2-ol;

6-(4-chloro-3-methyl-phenyl)-1-fluoro-5-[4-[(3S)-1-(3-fluoropropyl)pyrrolidin-3-yl]oxyphenyl]-8,9-dihydro-7H-benzo[7]annulen-2-ol;

1-fluoro-5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-ol;

1-fluoro-5-[4-[(3S)-1-(3-fluoropropyl)pyrrolidin-3-yl]oxyphenyl]-6-[4-fluoro-2-(trifluoromethyl)phenyl]-8,9-dihydro-7H-benzo[7]annulen-2-ol;

6-[4-(difluoromethoxy)-2-fluoro-phenyl]-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-[2-fluoro-4-(trifluoromethoxy)phenyl]-8,9-dihydro-7H-benzo[7]annulen-2-ol;

6-(2,6-dichloro-3-pyridyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-[4-(2,2,2-trifluoroethoxy)phenyl]-8,9-dihydro-7H-benzo[7]annulen-2-ol;

6-(4-ethoxy-3,5-difluoro-phenyl)-5-[4-[(3S)-1-(3-fluoropropyl)pyrrolidin-3-yl]oxyphenyl]-8,9-dihydro-7H-benzo[7]annulen-2-ol;

6-(4-chloro-2-fluoro-phenyl)-1-fluoro-5-[4-[(3S)-1-(3-fluoropropyl)pyrrolidin-3-yl]oxyphenyl]-8,9-dihydro-7H-benzo[7]annulen-2-ol;

6-(2-chloro-3-fluoro-phenyl)-1-fluoro-5-[4-[(3S)-1-(3-fluoropropyl)pyrrolidin-3-yl]oxyphenyl]-8,9-dihydro-7H-benzo[7]annulen-2-ol;

1-fluoro-5-[4-[(3S)-1-(3-fluoropropyl)pyrrolidin-3-yl]oxyphenyl]-6-[2-methyl-4-(trifluoromethyl)phenyl]-8,9-dihydro-7H-benzo[7]annulen-2-ol;

1-fluoro-5-[4-[(3S)-1-(3-fluoropropyl)pyrrolidin-3-yl]oxyphenyl]-6-[4-(trifluoromethyl)phenyl]-8,9-dihydro-7H-benzo[7]annulen-2-ol;

6-(6-ethoxy-2-methyl-3-pyridyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(1-methylindol-5-yl)-8,9-dihydro-7H-benzo[7]annulen-2-ol;

6-(6-chloro-3-pyridyl)-5-[4-[(3S)-1-(3-fluoropropyl)pyrrolidin-3-yl]oxyphenyl]-8,9-dihydro-7H-benzo[7]annulen-2-ol;

2-fluoro-4-[5-[4-[(3S)-1-(3-fluoropropyl)pyrrolidin-3-yl]oxyphenyl]-2-hydroxy-8,9-dihydro-7H-benzo[7]annulen-6-yl]-N-methyl-benzamide;

5-[4-[(3S)-1-(3-fluoropropyl)pyrrolidin-3-yl]oxyphenyl]-6-[2-fluoro-6-(trifluoromethyl)-3-pyridyl]-8,9-dihydro-7H-benzo[7]annulen-2-ol;

6-[4-(2-fluoroethoxy)phenyl]-5-[4-[(3S)-1-(3-fluoropropyl)pyrrolidin-3-yl]oxyphenyl]-8,9-dihydro-7H-benzo[7]annulen-2-ol;

6-(4-ethoxy-2,3-dimethyl-phenyl)-5-[4-[(3S)-1-(3-fluoropropyl)pyrrolidin-3-yl]oxyphenyl]-8,9-dihydro-7H-benzo[7]annulen-2-ol;

6-(6-ethoxy-5-(trifluoromethyl)-3-pyridyl]-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(4-methyl-2,3-dihydro-1,4-benzoxazin-7-yl)-8,9-dihydro-7H-benzo[7]annulen-2-ol;

6-(2,2-difluoro-1,3-benzodioxol-5-yl)-5-[4-[(3S)-1-(3-fluoropropyl)pyrrolidin-3-yl]oxyphenyl]-8,9-dihydro-7H-benzo[7]annulen-2-ol;

4-ethyl-6-[5-[4-[(3S)-1-(3-fluoropropyl)pyrrolidin-3-yl]oxyphenyl]-2-hydroxy-8,9-dihydro-7H-benzo[7]annulen-6-yl]-1,4-benzoxazin-3-one;

6-[2-chloro-4-(trifluoromethoxy)phenyl]-5-[4-[(3S)-1-(3-fluoropropyl)pyrrolidin-3-yl]oxyphenyl]-8,9-dihydro-7H-benzo[7]annulen-2-ol;

6-[4-(difluoromethoxy)-3,5-difluoro-phenyl]-5-[4-[(3S)-1-(3-fluoropropyl)pyrrolidin-3-yl]oxyphenyl]-8,9-dihydro-7H-benzo[7]annulen-2-ol;

6-(4-tert-butylphenyl)-1-fluoro-5-[4-[(3S)-1-(3-fluoropropyl)pyrrolidin-3-yl]oxyphenyl]-8,9-dihydro-7H-benzo[7]annulen-2-ol;

6-(6-ethoxy-4-methyl-3-pyridyl)-5-[4-[(3S)-1-(3-fluoropropyl)pyrrolidin-3-yl]oxyphenyl]-8,9-dihydro-7H-benzo[7]annulen-2-ol;

6-(3-chloro-4-ethoxy-5-fluoro-phenyl)-5-[4-[(3S)-1-(3-fluoropropyl)pyrrolidin-3-yl]oxyphenyl]-8,9-dihydro-7H-benzo[7]annulen-2-ol;

6-(2-aminopyrimidin-5-yl)-5-[4-[(3S)-1-(3-fluoropropyl)pyrrolidin-3-yl]oxyphenyl]-8,9-dihydro-7H-benzo[7]annulen-2-ol;

6-[4-(difluoromethyl)phenyl]-5-[4-[(3S)-1-(3-fluoropropyl)pyrrolidin-3-yl]oxyphenyl]-8,9-dihydro-7H-benzo[7]annulen-2-ol;

6-[4-(difluoromethoxy)phenyl]-1-fluoro-5-[4-[(3S)-1-(3-fluoropropyl)pyrrolidin-3-yl]oxyphenyl]-8,9-dihydro-7H-benzo[7]annulen-2-ol;

6-[3,5-difluoro-4-(trifluoromethoxy)phenyl]-5-[4-[(3S)-1-(3-fluoropropyl)pyrrolidin-3-yl]oxyphenyl]-8,9-dihydro-7H-benzo[7]annulen-2-ol;

6-[4-(difluoromethoxy)-2-methyl-phenyl]-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-[2-methyl-4-(trifluoromethoxy)phenyl]-8,9-dihydro-7H-benzo[7]annulen-2-ol;

6-[5-[4-[(3S)-1-(3-fluoropropyl)pyrrolidin-3-yl]oxyphenyl]-2-hydroxy-8,9-dihydro-7H-benzo[7]annulen-6-yl]-4-methyl-1,4-benzoxazin-3-one;

6-[5-[4-[(3S)-1-(3-fluoropropyl)pyrrolidin-3-yl]oxyphenyl]-2-hydroxy-8,9-dihydro-7H-benzo[7]annulen-6-yl]-4H-1,4-benzoxazin-3-one;

6-(2,3-dichloro-4-ethoxy-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-[3-methyl-4-(trifluoromethoxy)phenyl]-8,9-dihydro-7H-benzo[7]annulen-2-ol;

6-[3-chloro-4-(trifluoromethoxy)phenyl]-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(5-quinolyl)-8,9-dihydro-7H-benzo[7]annulen-2-ol;

5-[4-[(3S)-1-(3-fluoropropyl)pyrrolidin-3-yl]oxyphenyl]-6-(4-pyridyl)-8,9-dihydro-7H-benzo[7]annulen-2-ol;

5-[4-[(3S)-1-(3-fluoropropyl)pyrrolidin-3-yl]oxyphenyl]-6-(3-pyridyl)-8,9-dihydro-7H-benzo[7]annulen-2-ol;

6-[2-chloro-6-(trifluoromethyl)-3-pyridyl]-5-[4-[(3S)-1-(3-fluoropropyl)pyrrolidin-3-yl]oxyphenyl]-8,9-dihydro-7H-benzo[7]annulen-2-ol;

tert-butyl 6-[5-[4-[(3S)-1-(3-fluoropropyl)pyrrolidin-3-yl]oxyphenyl]-2-hydroxy-8,9-dihydro-7H-benzo[7]annulen-6-yl]-2, 3-dihydro-1,4-benzoxazine-4-carboxylate;

6-[4-(difluoromethylsulfanyl)phenyl]-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(1,2,3,4-tetrahydroquinolin-7-yl)-8,9-dihydro-7H-benzo[7]annulen-2-ol;

5-[4-[(3S)-1-(3-fluoropropyl)pyrrolidin-3-yl]oxyphenyl]-6-[4-(trifluoromethoxy)phenyl]-8,9-dihydro-7H-benzo[7]annulene-2-carboxylic acid;

1-fluoro-5-[4-[(3S)-1-(3-fluoropropyl)pyrrolidin-3-yl]oxyphenyl]-6-[2-fluoro-4-(trifluoromethoxy)phenyl]-8,9-dihydro-7H-benzo[7]annulen-2-ol;

1-fluoro-5-[4-[(3S)-1-(3-fluoropropyl)pyrrolidin-3-yl]oxyphenyl]-6-[4-(trifluoromethylsulfanyl)phenyl]-8,9-dihydro-7H-benzo[7]annulen-2-ol;

6-(2,4-dichloro-5-fluoro-phenyl)-5-[4-[(3S)-1-(3-fluoropropyl)pyrrolidin-3-yl]oxyphenyl]-8,9-dihydro-7H-benzo[7]annulen-2-ol;

[5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-yl] dihydrogen phosphate;

5-[4-[(3S)-1-(3-fluoropropyl)pyrrolidin-3-yl]oxyphenyl]-6-(5-methylisoxazol-4-yl)-8,9-dihydro-7H-benzo[7]annulen-2-ol;

6-[4-(difluoromethoxy)-2-fluoro-phenyl]-1-fluoro-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-[4-(trifluoromethylsulfonyl)phenyl]-8,9-dihydro-7H-benzo[7]annulen-2-ol;

6-(3,4-dihydro-2H-1,4-benzoxazin-6-yl)-5-[4-[(3S)-1-(3-fluoropropyl)pyrrolidin-3-yl]oxyphenyl]-8,9-dihydro-7H-benzo[7]annulen-2-ol hydrochloride;

5-[4-[(3S)-1-(3-fluoropropyl)pyrrolidin-3-yl]oxyphenyl]-6-[2-fluoro-4-(trifluoromethoxy)phenyl]-8,9-dihydro-7H-benzo[7]annulene-2-carboxylic acid;

5-[4-[(3S)-1-(3-fluoropropyl)pyrrolidin-3-yl]oxyphenyl]-6-isoxazol-4-yl-8,9-dihydro-7H-benzo[7]annulen-2-ol;

6-(6-ethoxy-5-fluoro-3-pyridyl)-5-[4-[(3S)-1-(3-fluoropropyl)pyrrolidin-3-yl]oxyphenyl]-8,9-dihydro-7H-benzo[7]annulen-2-ol;

6-fluoro-5-[5-[4-[(3S)-1-(3-fluoropropyl)pyrrolidin-3-yl]oxyphenyl]-2-hydroxy-8,9-dihydro-7H-benzo[7]annulen-6-yl]pyridin-2-ol;

6-(6-tert-butyl-2-fluoro-4-pyridyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(4-trimethylsilylphenyl)-8,9-dihydro-7H-benzo[7]annulen-2-ol;

6-(2,2-dimethylindolin-5-yl)-5-[4-[(3S)-1-(3-fluoropropyl)pyrrolidin-3-yl]oxyphenyl]-8,9-dihydro-7H-benzo[7]annulene-2-carboxylic acid hydrochloride;

6-(1,3-benzothiazol-5-yl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(2-methyl-1H-benzimidazol-5-yl)-8,9-dihydro-7H-benzo[7]annulen-2-ol;

5-[4-[(3S)-1-(3-fluoropropyl)pyrrolidin-3-yl]oxyphenyl]-6-[4-(trifluoromethylsulfanyl)phenyl]-8,9-dihydro-7H-benzo[7]annulene-2-carboxylic acid;

6-(1,3-benzothiazol-6-yl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(3-methylbenzotriazol-5-yl)-8,9-dihydro-7H-benzo[7]annulen-2-ol;

6-[2-chloro-4-(trifluoromethoxy)phenyl]-1-fluoro-5-[4-[(3S)-1-(3-fluoropropyl)pyrrolidin-3-yl]oxyphenyl]-8,9-dihydro-7H-benzo[7]annulen-2-ol;

6-(4-tert-butyl-2-methyl-phenyl)-5-[4-[(3S)-1-(3-fluoropropyl)pyrrolidin-3-yl]oxyphenyl]-8,9-dihydro-7H-benzo[7]annulen-2-ol;

6-(2-fluoro-4-methylsulfonyl-phenyl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(3-methylisoxazol-4-yl)-8,9-dihydro-7H-benzo[7]annulen-2-ol;

5-[4-[(3S)-1-(3-fluoropropyl)pyrrolidin-3-yl]oxyphenyl]-6-[4-(pentafluoro-sulfanyl)phenyl]-8,9-dihydro-7H-benzo[7]annulen-2-ol;

5-[4-[(3S)-1-(3-fluoropropyl)pyrrolidin-3-yl]oxyphenyl]-6-(4-morpholinophenyl)-8,9-dihydro-7H-benzo[7]annulen-2-ol;

6-[4-(2,2-difluoroethoxy)-2-fluoro-phenyl]-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(1-methylbenzimidazol-5-yl)-8,9-dihydro-7H-benzo[7]annulen-2-ol;

6-(1,2-benzoxazol-5-yl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-(1-oxidopyridin-1-ium-4-yl)-8,9-dihydro-7H-benzo[7]annulen-2-ol;

5-[4-[(3S)-1-(3-fluoropropyl)pyrrolidin-3-yl]oxyphenyl]-6-(4-pyrrolidin-1-ylphenyl)-8,9-dihydro-7H-benzo[7]annulen-2-ol;

5-[4-[(3S)-1-(3-fluoropropyl)pyrrolidin-3-yl]oxyphenyl]-6-(2-methyl-1,3-benzoxazol-5-yl)-8,9-dihydro-7H-benzo[7]annulen-2-ol;

5-[4-[(3S)-1-(3-fluoropropyl)pyrrolidin-3-yl]oxyphenyl]-6-(2-methyl-1,3-benzoxazol-6-yl)-8,9-dihydro-7H-benzo[7]annulen-2-ol;

6-(2,1,3-benzoxadiazol-5-yl)-5-[4-[(3S)-1-(3-fluoropropyl)pyrrolidin-3-yl]oxyphenyl]-8,9-dihydro-7H-benzo[7]annulen-2-ol;

6-(2,1,3-benzothiadiazol-5-yl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-[4-(oxetan-3-yl)phenyl]-8,9-dihydro-7H-benzo[7]annulen-2-ol;

5-[4-[(3S)-1-(3-fluoropropyl)pyrrolidin-3-yl]oxyphenyl]-6-(2,2,3,3-tetrafluoro-1,4-benzodioxin-6-yl)-8,9-dihydro-7H-benzo[7]annulen-2-ol;

6-(1,2-benzothiazol-5-yl)-5-[4-[(3S)-1-(3-fluoropropyl)pyrrolidin-3-yl]oxyphenyl]-8,9-dihydro-7H-benzo[7]annulen-2-ol;

6-[2,3-difluoro-4-(1-piperidyl)phenyl]-5-[4-[(3S)-1-(3-fluoropropyl)pyrrolidin-3-yl]oxyphenyl]-8,9-dihydro-7H-benzo[7]annulen-2-ol;

6-(1,3-benzoxazol-6-yl)-5-[4-[(3S)-1-(3-fluoropropyl)pyrrolidin-3-yl]oxyphenyl]-8,9-dihydro-7H-benzo[7]annulen-2-ol;

6-(1,2-benzoxazol-6-yl)-5-[4-[(3S)-1-(3-fluoropropyl)pyrrolidin-3-yl]oxyphenyl]-8,9-dihydro-7H-benzo[7]annulen-2-ol;

6-[4-(1,1-difluoroethyl)phenyl]-5-[4-[(3S)-1-(3-fluoropropyl)pyrrolidin-3-yl]oxyphenyl]-8,9-dihydro-7H-benzo[7]annulen-2-ol;

6-(3,6-dihydro-2H-pyran-4-yl)-5-[4-[(3S)-1-(3-fluoropropyl)pyrrolidin-3-yl]oxyphenyl]-8,9-dihydro-7H-benzo[7]annulen-2-ol;

5-[4-[(3S)-1-(3-fluoropropyl)pyrrolidin-3-yl]oxyphenyl]-6-tetrahydropyran-4-yl-8,9-dihydro-7H-benzo[7]annulen-2-ol;

5-[4-[(3S)-1-(3-fluoropropyl)pyrrolidin-3-yl]oxyphenyl]-6-(4-hydroxycyclohexyl)-8,9-dihydro-7H-benzo[7]annulen-2-ol;

5-[4-[(3S)-1-(3-fluoropropyl)pyrrolidin-3-yl]oxyphenyl]-6-(3-methylbenzimidazol-5-yl)-8,9-dihydro-7H-benzo[7]annulen-2-ol;

4-[4-[5-[4-[(3S)-1-(3-fluoropropyl)pyrrolidin-3-yl]oxyphenyl]-2-hydroxy-8,9-dihydro-7H-benzo[7]annulen-6-yl]phenyl]-1H-1,2,4-triazol-5-one;

6-(4,4-difluorocyclohexen-1-yl)-5-[4-[(3S)-1-(3-fluoropropyl)pyrrolidin-3-yl]oxyphenyl]-8,9-dihydro-7H-benzo[7]annulen-2-ol;

6-(4,4-difluorocyclohexyl)-5-[4-[(3S)-1-(3-fluoropropyl)pyrrolidin-3-yl]oxyphenyl]-8,9-dihydro-7H-benzo[7]annulen-2-ol;

6-(4-chlorophenyl)-5-[4-[(3S)-1-(3-fluoropropyl)pyrrolidin-3-yl]oxyphenyl]-8,9-dihydro-7H-benzo[7]annulene-2-carboxylic acid;

6-(2-chlorophenyl)-5-[4-[(3S)-1-(3-fluoropropyl)pyrrolidin-3-yl]oxyphenyl]-8,9-dihydro-7H-benzo[7]annulene-2-carboxylic acid;

6-(2,4-dichlorophenyl)-1-fluoro-5-[4-[(3S)-1-(3-fluoropropyl)pyrrolidin-3-yl]oxyphenyl]-8,9-dihydro-7H-benzo[7]annulene-2-carboxylic acid;

6-(4-chloro-2-fluoro-phenyl)-1-fluoro-5-[4-[(3S)-1-(3-fluoropropyl)pyrrolidin-3-yl]oxyphenyl]-8,9-dihydro-7H-benzo[7]annulene-2-carboxylic acid;

6-(2-chloro-4-fluoro-phenyl)-1-fluoro-5-[4-[(3S)-1-(3-fluoropropyl)pyrrolidin-3-yl]oxyphenyl]-8,9-dihydro-7H-benzo[7]annulene-2-carboxylic acid;

9-(4-{[(3S)-1-(3-fluoropropyl)pyrrolidin-3-yl]oxy}phenyl)-8-phenyl-6,7-dihydro-5H-benzo[7]annulen-3-ol;

5-[4-[(3S)-1-(3-fluoropropyl)pyrrolidin-3-yl]oxyphenyl]-6-(1H-indazol-5-yl)-8,9-dihydro-7H-benzo[7]annulen-2-ol;

6-(2-Chloro-3-fluoro-phenyl)-5-{4-[(S)-1-(3-fluoro-propyl)-pyrrolidin-3-yloxy]-phenyl}-8,9-dihydro-7H-benzocycloheptene-2-carboxylic acid;

5-{4-[(S)-1-(3-Fluoro-propyl)-pyrrolidin-3-yloxy]-phenyl}-6-phenyl-8,9-dihydro-7H-benzocycloheptene-2-carboxylic acid;

6-Benzooxazol-5-yl-5-{4-[(S)-1-(3-fluoro-propyl)-pyrrolidin-3-yloxy]-phenyl}-8,9-dihydro-7H-benzocycloheptene-2-carboxylic acid; and 6-[4-(1,1-Difluoro-ethyl)-phenyl]-5-{4-[(S)-1-(3-fluoro-propyl)-pyrrolidin-3-yloxy]-phenyl}-8,9-dihydro-7H-benzocycloheptene-2-carboxylic acid;

or a pharmaceutically acceptable salt thereof.

Another embodiment is a compound selected from the above list, or a pharmaceutically acceptable salt thereof, for use in therapy, especially as an inhibitor and degrader of estrogen receptors.

Another embodiment is a compound selected from the above list, or a pharmaceutically acceptable salt thereof, for use in the treatment of cancer, especially breast cancer.

Another embodiment is a method of treating cancer, comprising administering to a subject in need thereof, in particular a human, a therapeutically effective amount of a compound selected from the above list, or a pharmaceutically acceptable salt thereof.

Another embodiment is a pharmaceutical composition comprising as active principle an effective dose of a compound selected from the above list, or a pharmaceutically acceptable salt thereof, and also at least one pharmaceutically acceptable excipient.

The compounds of the formula (I) can be prepared by the following processes.

The compounds of the formula (I) and other related compounds having different substituents are synthesized using techniques and materials described below or otherwise known by the skilled person in the art. In addition, solvents, temperatures and other reaction conditions presented below may vary as deemed appropriate to the skilled person in the art.

General below methods for the preparation of compounds of formula (I) are optionally modified by the use of appropriate reagents and conditions for the introduction of the various moieties found in the compound of formula (I) as described below.

The following abbreviations and empirical formulae are used:

AcOEt ethyl acetate
$AlCl_3$ aluminium trichloride
Boc tert-butyloxycarbonyl
$P(Ph)_2$-$(CH_2)_3$—$P(Ph)_2$ 1,3-bis(diphenylphosphino)propane
$Ph_3P$=O triphenylphosphine oxide
$Cs_2CO_3$ cesium carbonate
CO carbon monoxide
DCM dichloromethane
DMF N,N-dimethylformamide
DMSO dimethyl sulfoxide
EDCl 1-Ethyl-3-(3-dimethylaminopropyl)carbodiimide
$Et_3N$ triethylamine
EtOH ethanol
$Et_2O$ diethyl ether
Hal halogen atom
HCl hydrogen chloride
HPLC high-performance liquid chromatography
$K_2CO_3$ potassium carbonate
LCMS liquid chromatography/mass spectrometry
$LiAlD_4$ lithium aluminum deuteride
Lutidine 2,6-dimethyl-pyridine
MeOH methanol
$MgSO_4$ magnesium sulfate
NaOH sodium hydroxide
NaCl sodium chloride
$NaHCO_3$ sodium bicarbonate
$Na_2SO_4$ sodium sulfate
$NH_4H_2PO_4$ ammonium dihydrogen phosphate
$NH_4Cl$ ammonium chloride
$NH_4OH$ ammonium hydroxide
$Pd(OAc)_2$ palladium acetate
$Pd(dppf)Cl_2$ 1,1'bis(diphenylphosphino)ferrocene]dichloropalladium(II)
$Tf_2O$ triflic anhydride
THF tetrahydrofuran
° C. degrees Celsius
RT room temperature
min minute(s)
mL milliliter(s)
mmol millimole(s)
µmol micromole(s)

µM micromolar
nM nanomolar
ppm parts per million
SCX strong cation exchange
HIC hydrophobic interaction column converted in STEP 1 into the corresponding enol triflate intermediate (B) by treatment for example with triflic anhydride (Tf₂O) in solution in dichloromethane (DCM) in the presence of a base, for example pyridine, at room temperature. This intermediate (B) is subjected in STEP 2 to a SCHEME 1: Preparation of compounds of the formula (I) - General process

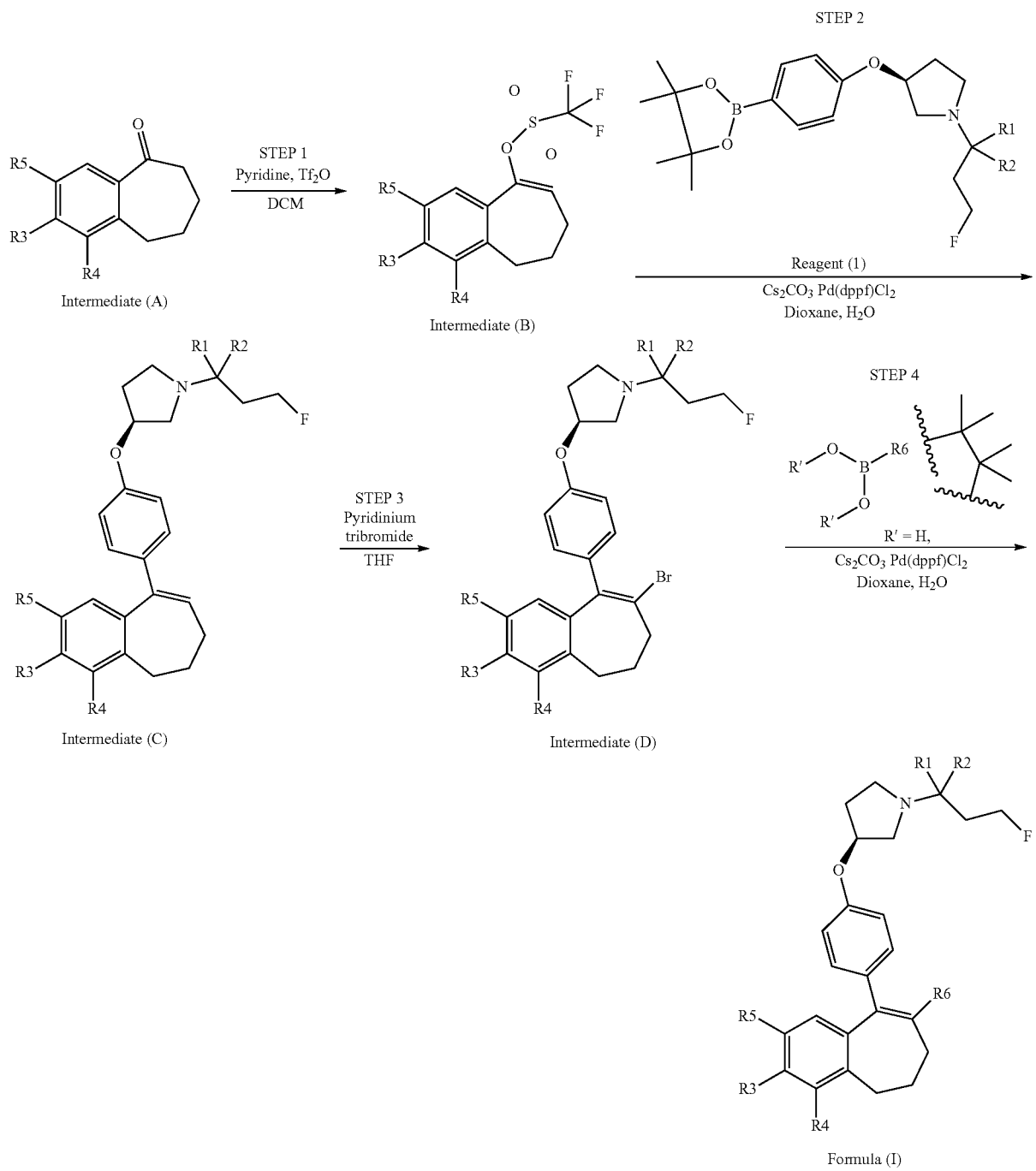

According to SCHEME 1, in which R1, R2, R3, R4, R5 and R6 are defined as described above, a substituted 5-oxo-6,7,8,9-tetrahydro-5H-benzo[7]annulene intermediate (A) is Suzuki coupling with reagent (1) ((S)-1-(3-fluoropropyl)-3-(4-(4,4,5,5-tetramethyl-1,3,2dioxaborolan2yl)phenoxy)pyrrolidine) using for example [1,1'-bis(diphenylphosphino)

ferrocene]dichloropalladium(II) (Pd(dppf)Cl₂), complex with DCM, as catalyst, in a mixture of dioxane and water and in the presence of a base, for example cesium carbonate (Cs₂CO₃), at room temperature or by heating up to reflux. The preparation of reagent (1) is described hereunder in SCHEME 2.

The intermediate (C) obtained is brominated in STEP 3 using for example pyridinium tribromide in DCM or tetrahydrofuran (THF) at room temperature. This bromo derivative intermediate (D) is then subjected in STEP 4 to a second Suzuki coupling with a suitable boronic reagent R6B(OR')₂, wherein —B(OR')₂ is a boronic acid or a pinacolate ester and R6 is as above defined, using for example Pd(dppf)Cl₂, complex with DCM, as catalyst, in a mixture of dioxane and water as solvent and in the presence of a base, for example Cs₂CO₃, at room temperature or by heating up to reflux.

In the above-described reactions, it can be necessary to protect reactive functional groups, for example hydroxy, amino, thio or carboxy groups, where these groups are desired in the final product, to avoid their unwanted participation in the reactions. Conventional protecting groups can be used in accordance with standard practice, for example, see T.W. Greene and P.G.M. Wuts in "Protective Groups in Organic Chemistry", John Wiley and Sons, 2006.

When R3 or R5 represents a —OH group, this —OH group is protected, for example as a pivaloyl ester. Deprotection can be performed just after STEP 3 or after STEP 4 by treating, with an aqueous solution of sodium hydroxide 2N (NaOH), a solution of the pivaloyl ester in methanol (MeOH) at room temperature, followed by acidification with an aqueous solution of hydrogen chloride 2N (HCl).

When R3 represents a —COOH group, this —COOH group is protected, for example as a methyl ester. Deprotection is performed just after STEP 4 by treating, with an aqueous solution of sodium hydroxide (NaOH) 2N, a solution of the methyl ester in MeOH at room temperature, followed by acidification with an aqueous solution of HCl 2N.

In an embodiment, it can be advantageous to use a variation of SCHEME 1, called SCHEME 1a depicted below, that consists in transforming intermediate (D) into a boronate derivative which is engaged in a Suzuki coupling with an halogenated derivative R6-Hal, wherein R6 is as above defined and Hal represents a halogen atom selected from a chlorine, a bromine or an iodine atom. Deprotection of the —OH group or —COOH group of R3 or R5 can be performed before or after STEP 1 or STEP 2 of SCHEME 1a, as explained above.

SCHEME 1a:

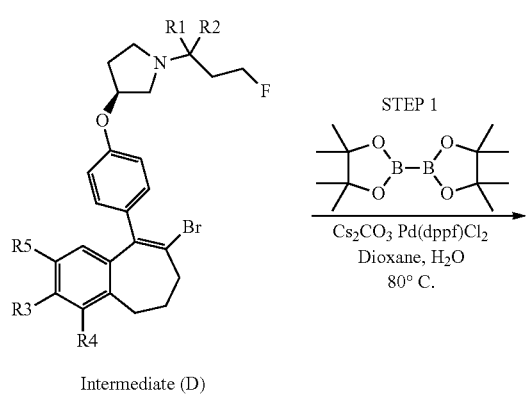

Intermediate (D)

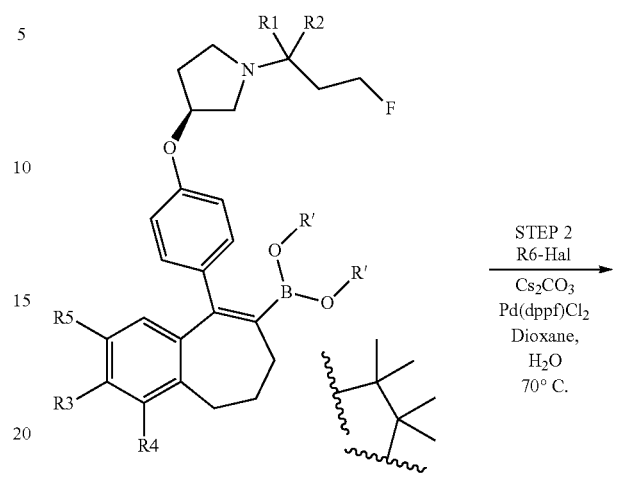

R' = H,
Intermediate (D')

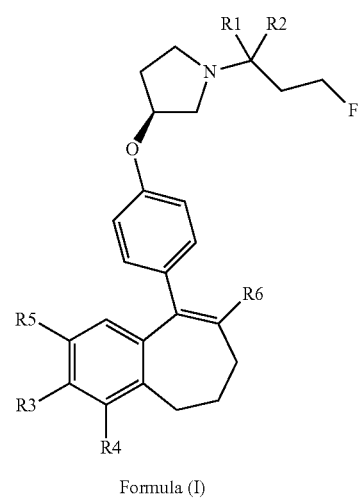

Formula (I)

STEP 1 of the above SCHEME 1a consists of reacting intermediate (D) with 4,4,4',4',5,5,5',5'-octamethyl-2,2'-bi(1, 3,2-dioxaborolane) using for example Pd(dppf)Cl₂, complex with DCM, as catalyst, in a mixture of dioxane and water and in the presence of a base, for example Cs₂CO₃, at about 80° C. Intermediate (D') obtained is engaged in STEP 2 of the above SCHEME 1a in a Suzuki coupling with R6-Hal, wherein R6 and Hal are as above defined, using for example Pd(dppf)Cl₂, complex with DCM, as catalyst, in a mixture of dioxane and water as solvent and in the presence of a base, for example Cs₂CO₃, at about 70° C.

In another embodiment, it can be advantageous, when the compounds of formula (I) are such that R3 is a —COOH group, to use a variation of SCHEME 1, called SCHEME 1b depicted below.

SCHEME 1b: When R3 represents a —COOH group

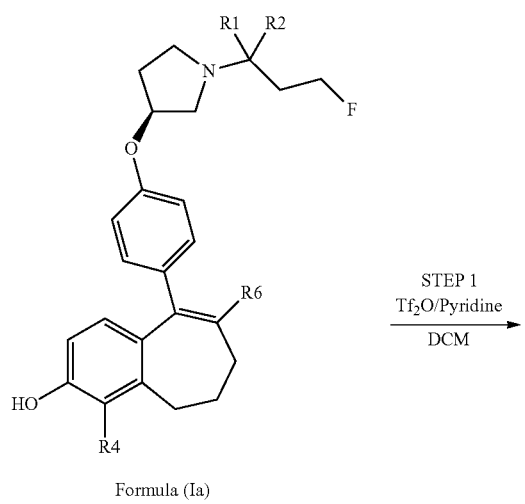

wherein R1, R2, R4 and R6 are as above defined in formula (I). In STEP 1 of SCHEME 1b the —OH group of R3 in the compounds of formula (Ia) is transformed into a triflate group with, for example Tf₂O in DCM with a base, for example pyridine, at room temperature.

The intermediate (K) obtained is then carbonylated in STEP 2 of SCHEME 1b under 2 to 10 bars of carbon monoxide (CO) at about 70° C. in a mixture of MeOH and N,N-dimethylformamide (DMF) using for example palladium acetate (Pd(OAc)₂) and 1,3-bis(diphenylphosphino) propane (P(Ph)₂-(CH₂)₃—P(Ph)₂) as catalytic system.

The methyl ester of formula (Ib) then obtained is deprotected as defined above, so as to obtain compounds of formula (I) wherein R1, R2, R4 and R6 are as above defined in formula (I) and R3 is a —COOH group.

In another embodiment, it can be advantageous as well, when R3 represents a —COOH group, to use a variation of SCHEME 1, called SCHEME 1c depicted below. This SCHEME 1c is an alternative process to the above SCHEME 1b.

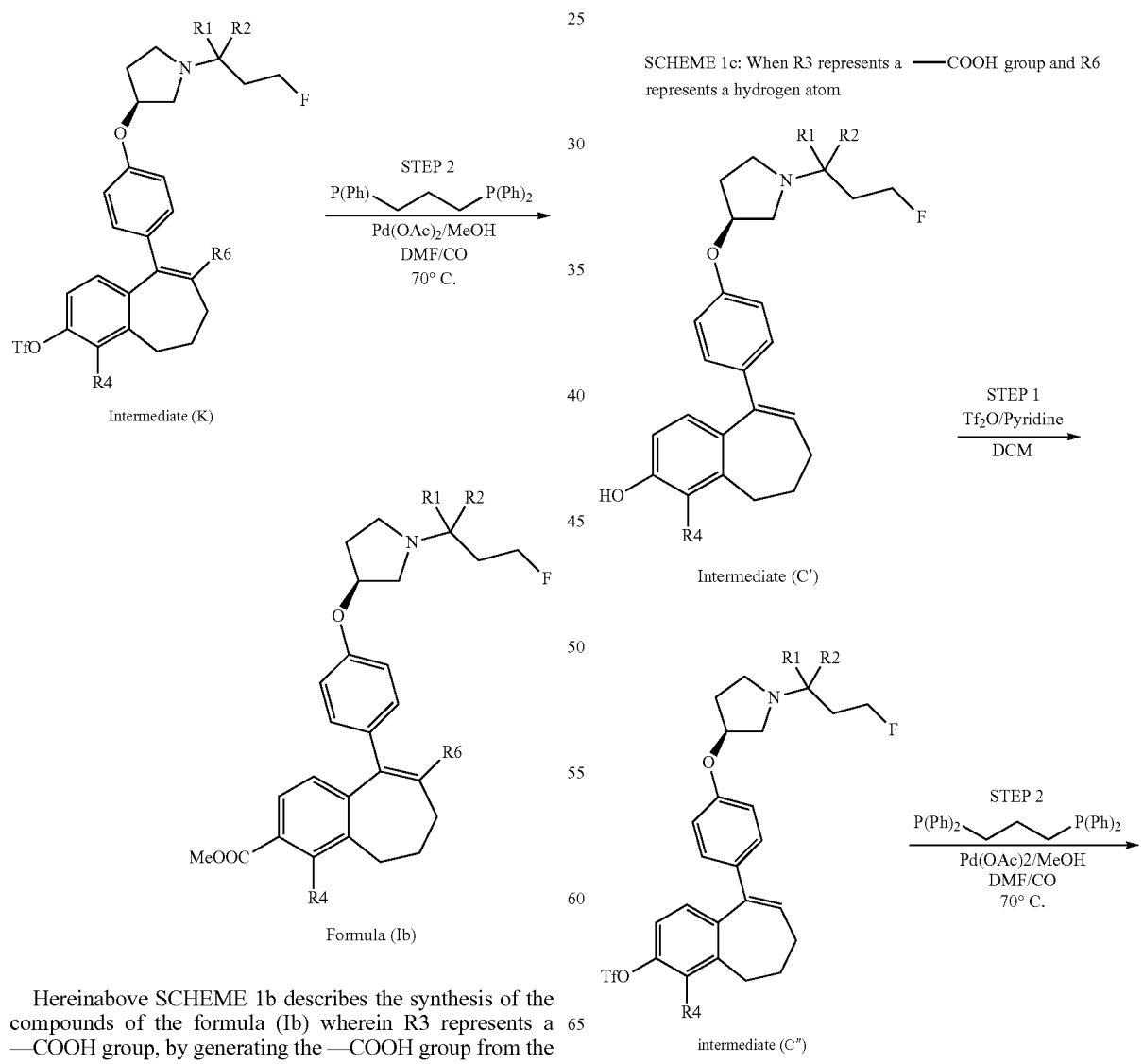

Hereinabove SCHEME 1b describes the synthesis of the compounds of the formula (Ib) wherein R3 represents a —COOH group, by generating the —COOH group from the —OH group of R3 of the compounds of formula (Ia)

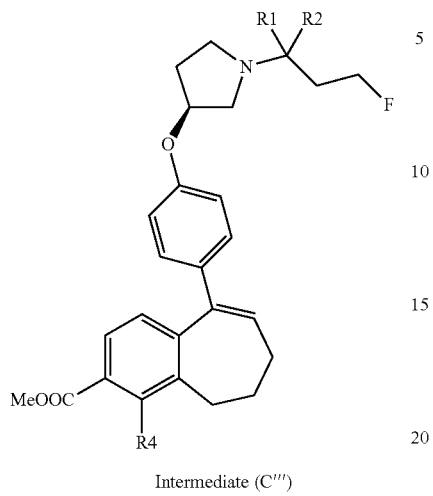

Intermediate (C''')

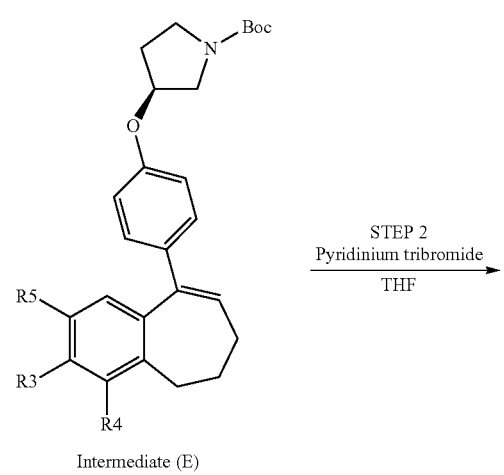

Intermediate (E)

Hereinabove SCHEME 1c describes the synthesis of the intermediates (C''') as defined above by generating the —COOMe group from the —OH group of intermediates (C') wherein R1, R2 and R4 are as above defined in formula (I). In STEP 1 of SCHEME 1c, the —OH group is transformed into a triflate group with, for example, Tf$_2$O in DCM with a base, for example pyridine, at room temperature.

The intermediate (C'') then obtained is carbonylated in STEP 2 of SCHEME 1c under 2 to 10 bars of CO at about 70° C. in a mixture of MeOH and DMF using for example Pd(dppf)Cl$_2$ or Pd(OAc)$_2$ and P(Ph)$_2$-(CH$_2$)$_3$—P(Ph)$_2$ as catalytic system.

In another embodiment, when R1 and R2 represent simultaneously a deuterium atom and R3 is other than a —COOH group, a process of synthesis of compounds of formula (Ic) is described below in SCHEME 1d which is a variation of the general SCHEME 1.

SCHEME 1d: When R1 and R2 are both deuterium atoms and R3 is different from a —COOH group.

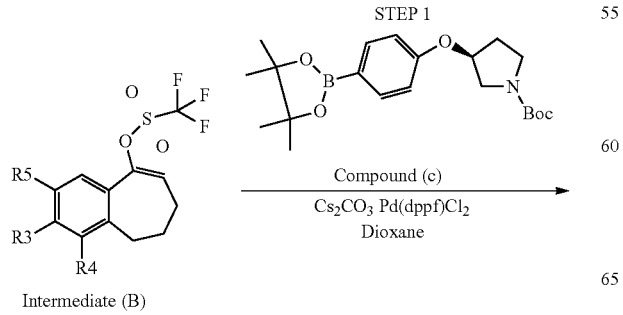

Intermediate (B)

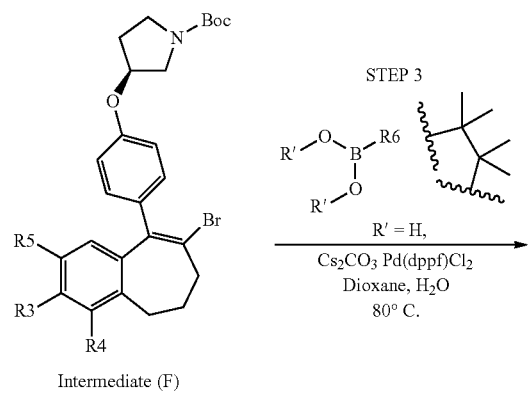

Intermediate (F)

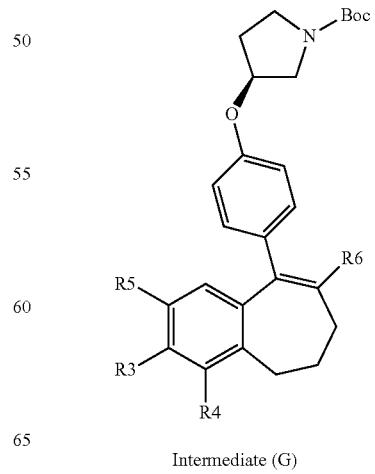

Intermediate (G)

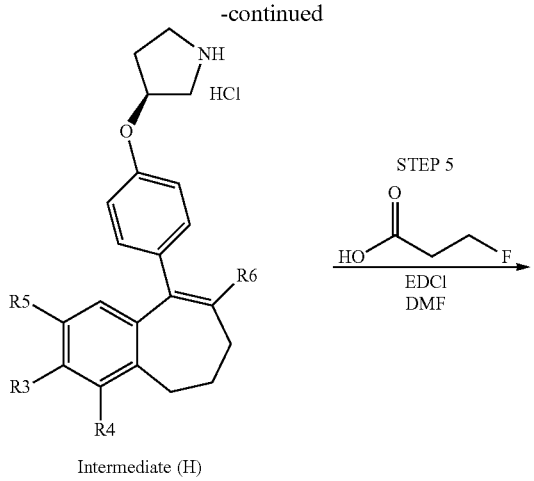

Intermediate (H)

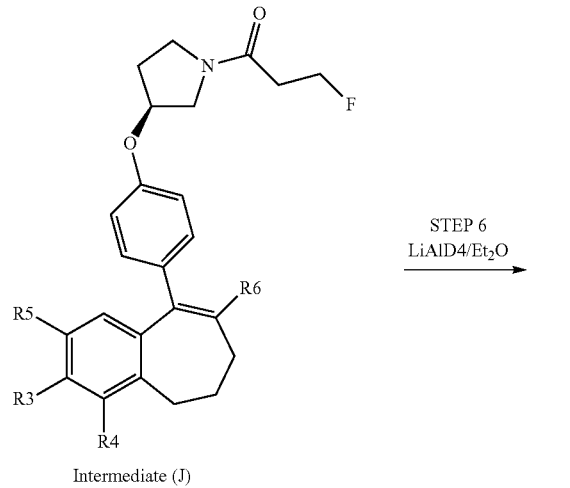

Intermediate (J)

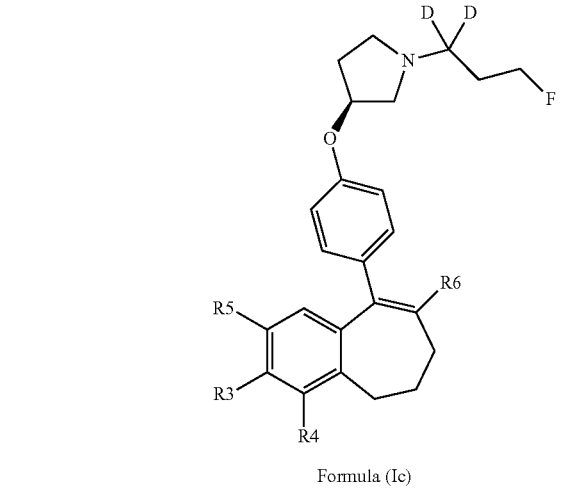

Formula (Ic)

According to SCHEME 1d, a substituted enol triflate intermediate (B), obtained in accordance to STEP 1 of SCHEME 1, is subjected in STEP 1 of SCHEME 1d to a Suzuki coupling with compound (c) (tert-butyl (3S)-3-[4-(tetramethyl-1,3,2-dioxaborolan-2-yl)phenoxy]pyrrolidine-1-carboxylate) using for example Pd(dppf)Cl$_2$, complex with DCM, as catalyst, in dioxane and in the presence of a base, for example Cs$_2$CO$_3$, at room temperature.

The intermediate (E) then obtained is brominated in STEP 2 of SCHEME 1d using for example pyridinium tribromide in DCM or THF at room temperature.

This bromo derivative intermediate (F) obtained is then subjected in STEP 3 of SCHEME 1d to a second Suzuki coupling with a suitable boronic reagent R6B(OR')$_2$, wherein the —B(OR')$_2$ group is a boronic acid or a pinacolate ester, and R6 is as above defined, using for example Pd(dppf)Cl$_2$, complex with DCM, as catalyst, in a mixture of dioxane and water and in the presence of a base, for example Cs$_2$CO$_3$, at room temperature or by heating up to reflux.

This intermediate (G) obtained is N-deprotected in STEP 4 of SCHEME 1d using for example a 4N solution of HCl in dioxane, at room temperature.

The NH-pyrrolidine intermediate (H) obtained is amidified in STEP 5 of SCHEME 1d using for example 3-fluoropropionic acid in DMF at room temperature using for example 1-ethyl-3-(3-dimethylaminopropyl)carbodiimide (EDCl) as coupling agent.

Finally, the carbonyl of the amide intermediate (J) then obtained is reduced in STEP 6 of SCHEME 1d into the deuteriated amine of formula (Ic) by for example lithium aluminum deuteride (LiAlD$_4$) in ether (Et$_2$O) at room temperature.

When R3 or R5 is a —OH group, this —OH group is protected, for example as a pivaloyl ester. Deprotection is done at the final STEP 6 for example by reduction with LiAlD$_4$.

SCHEME 2: Preparation of reagent (1) of SCHEME 1

STEP 1

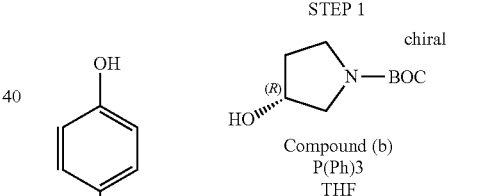

Compound (a)

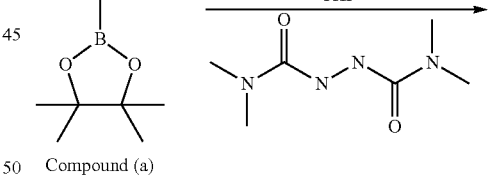

Compound (c)

STEP 2
HCl/dioxane
MeOH

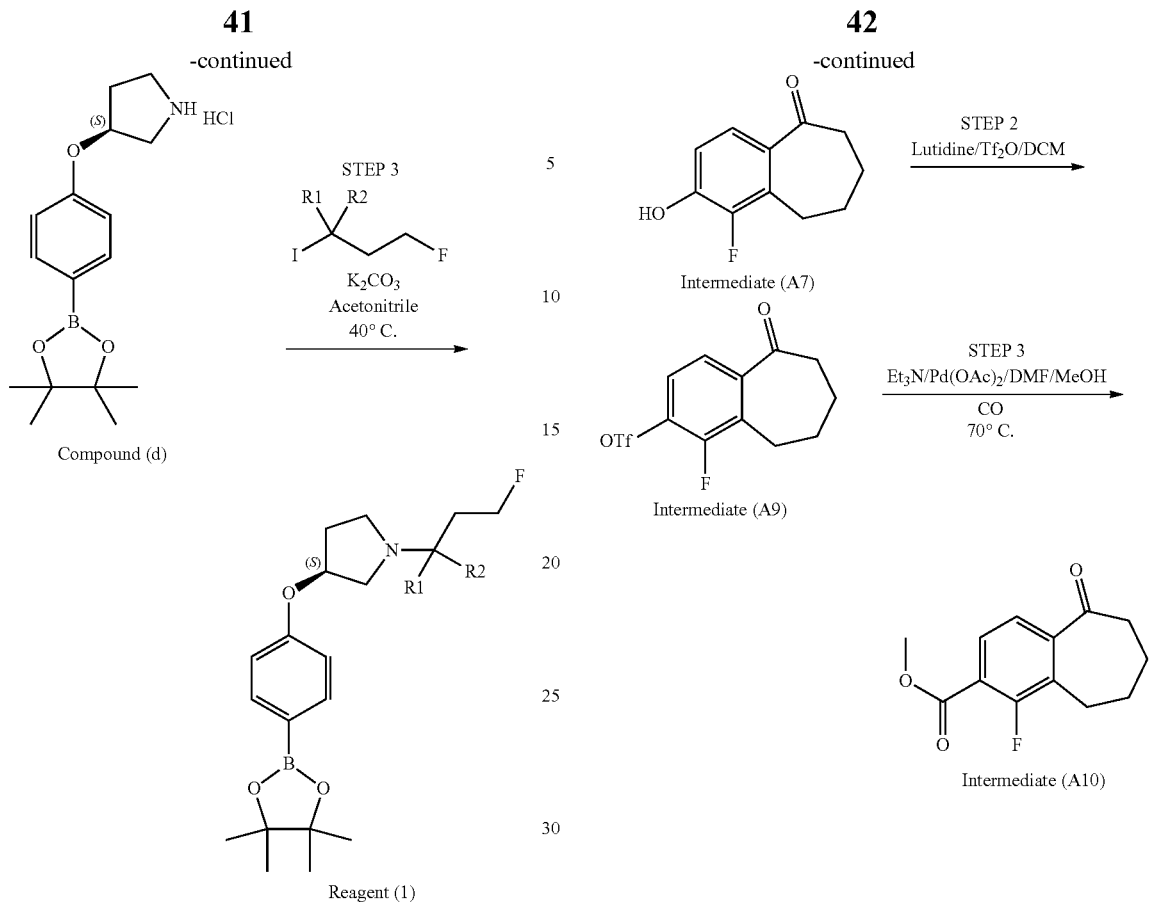

Compound (d)

Reagent (1)

According to the above SCHEME 2, commercially available compound (a) (4-(4,4,5,5-tetramethyl-1,3,2-dioxaborolan-2-yl)phenol) is condensed in STEP 1 of SCHEME 2 in THF at room temperature on (R)-1-N-Boc-3-hydroxypyrrolidine using N,N,N',N'-tetramethylazodicarboxamide as coupling agent.

Compound (c) thus obtained is N-deprotected in STEP 2 of SCHEME 2 in MeOH at room temperature using an acidic agent for example a solution of HCl 4N in dioxane.

Alkylation of the pyrrolidine nitrogen is then performed in STEP 3 of SCHEME 2 by reacting compound (d) with the corresponding 1,1-disubstituted 1-halogeno-3-fluoro propane, for example 1-iodo-3-fluoropropane in acetonitrile in presence of potassium carbonate ($K_2CO_3$) at about 40° C.

The new intermediate (A10) wherein R3 represents a —COOMe group, R4 represents a fluorine atom and R5 represents a hydrogen atom can be prepared according to reaction SCHEME 3 highlighted below:

SCHEME 3: Preparation of the Intermediate (A10)

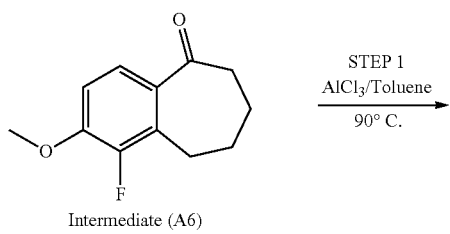

Intermediate (A6)

According to SCHEME 3, intermediate (A6) (1-fluoro 2-methoxy 5-oxo-6,7,8,9-tetrahydro-5H-benzo[7]annulene) is converted in STEP 1 into the corresponding phenol intermediate (A7) by treatment for example with aluminum trichloride ($AlCl_3$) in toluene at about 90° C.

The —OH group is then transformed in STEP 2 of SCHEME 3 into a triflate group by treatment with a base, for example 2,6-dimethyl-pyridine (lutidine), using for example $Tf_2O$ in DCM at room temperature to obtain intermediate (A9).

The intermediate (A9) then obtained is finally carbonylated in STEP 3 of SCHEME 3 in the presence of a base, for example triethylamine ($Et_3N$) and a catalyst, for example $Pd(OAc)_2$, under 2 to 10 bars of CO in a mixture of DMF and MeOH at about 70° C. to produce intermediate (A10) (1-fluoro 5-oxo-6,7,8,9-tetrahydro-5H-benzo[7]annulene 2-carboxylic acid, methyl ester).

In the above SCHEMES 1, 1a, 1b, 1c, 1d, 2 and 3 the starting compounds and the reactants, when their preparation is not herein described, are commercially available, for example by Sigma-Aldrich, Fluka, Acros Organics, Alfa Aesar, and the like, or are described in the literature, or may be prepared by methods which are known to a person skilled in the art.

In another aspect, provided are the compounds as defined below, wherein R1, R2, R3, R4, R5 and R6 are as defined in formula (I) above, which are useful as intermediates or reagents in the synthesis of the compounds of the formula (I) as above defined, or salts thereof:

(A10)
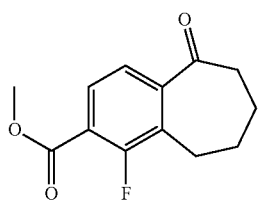
(A7)
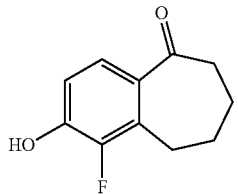
(1)
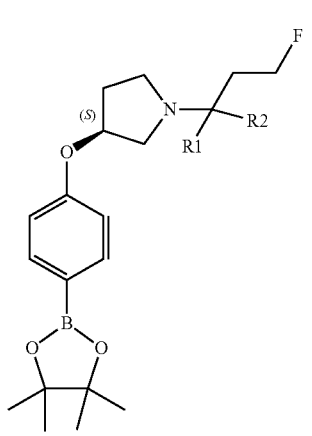
(C)
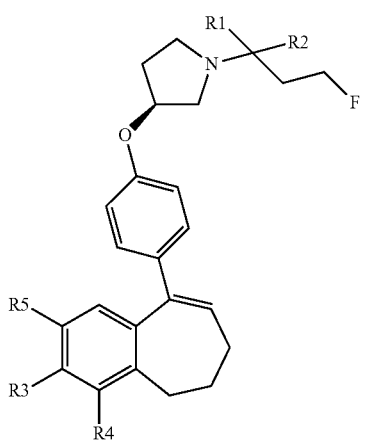
(D)
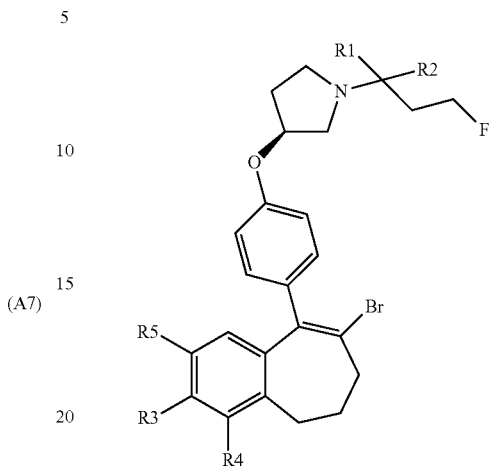
(E)
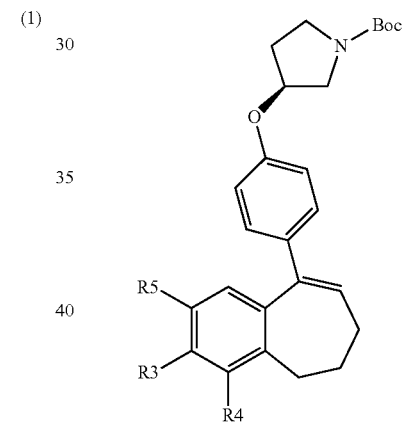
(F)
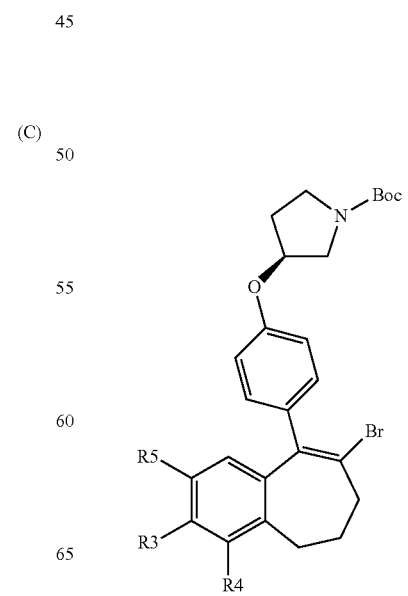

-continued (G)

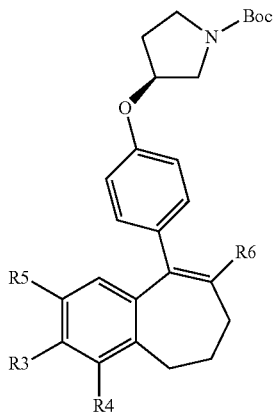

(H)

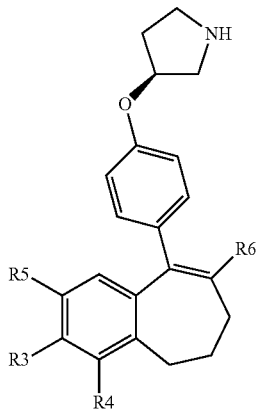

-continued (J)

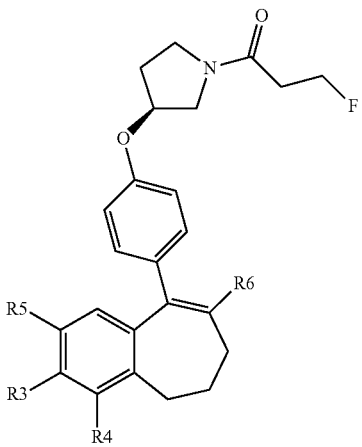

Some compounds of formula (I) are described, with their structure, name, method of preparation and analytical data, in the below Table 1, which is merely illustrative and does not limit the scope of the present invention.

The methods of preparation A, B and C mentioned in table 1 are respectively described in examples 1, 51 and 48 below.

The examples with numbers underlined in Table 1 are further detailed hereafter.

The 1H NMR spectra at 400 and 500 MHz were performed on a Bruker Avance DRX-400 and Bruker Avance DPX-500 spectrometer, respectively, with the chemical shifts (δ in ppm) in the solvent dimethyl sulfoxide-d6 (d6-DMSO) referenced at 2.5 ppm at a temperature of 303 K. Coupling constants (J) are given in Hertz.

The liquid chromatography/mass spectra (LC/MS) were obtained on a UPLC Acquity Waters instrument, light scattering detector Sedere and SQD Waters mass spectrometer using UV detection DAD 210<l<400 nm and column Acquity UPLC CSH C18 1.7 μm, dimension 2.1×30 mm, mobile phase $H_2O+0.1\%$ $HCO_2H/CH_3CN+0.1\%$ $HCO_2H$.

TABLE 1

| Examples | Structure | Name | Method | NMR | MASS: LC/MS (m/z, MH+): |
|---|---|---|---|---|---|
| 1 | 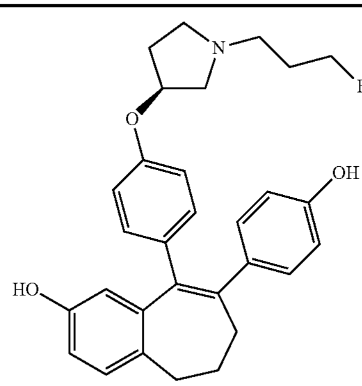 | 5-[4-[(3S)-1-(3-fluoropropyl)pyrrolidin-3-yl]oxyphenyl]-6-(4-hydroxyphenyl)-8,9-dihydro-7H-benzo[7]-annulen-3-ol | A | 1H NMR (400 MHz, DMSO-d6, δ ppm): 1.69 (m, 1 H); 1.80 (dm, J = 25.3 Hz, 2 H); 1.98 (m, 2 H); 2.20 (m, 3 H); 2.39 (m, 1 H); 2.48 (m, 2 H); 2.54 (m, 1 H); 2.63 (m, 3 H); 2.80 (dd, J = 6.4 and 10.4 Hz, 1 H); 4.48 (td, J = 6.1 and 47.5 Hz, 2 H); 4.75 (m, 1 H); 6.19 (d, J = 2.6 Hz, 1 H); 6.55 (m, 3 H); 6.62 (d, J = 8.8 Hz, 2 H); 6.72 (d, J = 8.8 Hz, 2 H); 6.92 (d, J = 8.6 Hz, 2 H); 7.04 (d, J = 8.6 Hz, 1 H); 8.98 (s, 1 H); 9.28 (s, 1 H) | 474 |

TABLE 1-continued

| Examples | Structure | Name | Method | NMR | MASS: LC/MS (m/z, MH+): |
|---|---|---|---|---|---|
| 2 | 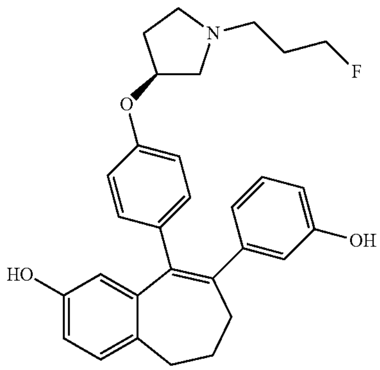 [SMILES: Oc1cccc(C2=C(c3ccc(O[C@H]4CCN(CCCF)C4)cc3)c3cc(O)ccc3CCC2)c1] | 5-[4-[(3S)-1-(3-fluoro-propyl)pyrrolidin-3-yl]oxyphenyl]-6-(3-hydroxy-phenyl)-8,9-dihydro-7H-benzo[7]-annulen-3-ol | A | 1H NMR (400 MHz, DMSO-d6, δ ppm): 1.69 (m, 1 H); 1.79 (dm, J = 25.3 Hz, 2 H); 1.99 (m, 2 H); 2.19 (m, 3 H); 2.35 to 2.68 (m, 7 H); 2.80 (m, 1 H); 4.47 (td, J = 6.0 and 47.5 Hz, 2 H); 4.72 (m, 1 H); 6.20 (d, J = 2.5 Hz, 1 H); 6.48 to 6.55 (m, 3 H); 6.58 (dd, J = 2.5 and 8.6 Hz, 1 H); 6.62 (d, J = 8.6 Hz, 2 H); 6.74 (d, J = 8.6 Hz, 2 H); 6.96 (t, J = 8.2 Hz, 1 H); 7.06 (d, J = 8.2 Hz, 1 H); 9.00 (s, 1 H); 9.19 (s, 1 H) | 474 |
| 3 | 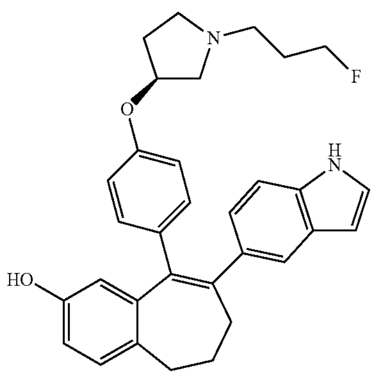 [SMILES: Oc1ccc2c(c1)C(c1ccc(O[C@H]3CCN(CCCF)C3)cc1)=C(c1ccc3[nH]ccc3c1)CCC2] | 5-[4-[(3S)-1-(3-fluoro-propyl)pyrrolidin-3-yl]oxyphenyl]-6-(1H-indol-5-yl)-8,9-dihydro-7H-benzo[7]-annulen-3-ol | A | 1H NMR (400 MHz, DMSO-d6, δ ppm): 1.67 (m, 1 H); 1.78 (dm, J = 25.3 Hz, 2 H); 2.00 (m, 2 H); 2.17 (m, 1 H); 2.30 (t, J = 7.0 Hz, 2 H); 2.37 (m, 1 H); 2.44 (t, J = 7.2 Hz, 2 H); 2.53 (m, 1 H); 2.61 (m, 1 H); 2.69 (m, 2 H); 2.78 (dd, =6.4 and 10.4 Hz, 1 H); 4.47 (td, J = 6.1 and 47.5 Hz, 2 H); 4.70 (m, 1 H); 6.21 (d, J = 2.9 Hz, 1 H); 6.29 (t, J = 2.9 Hz, 1 H); 6.58 (m, 3 H); 6.74 (d, J = 8.8 Hz, 2 H); 6.85 (dd, J = 1.7 and 8.5 Hz, 1 H); 7.07 (d, J = 8.3 Hz, 1 H); 7.16 (d, J = 8.5 Hz, 1 H); 7.25 (t, J = 2.9 Hz, 1 H); 7.34 (s, 1 H); 8.99 (s, 1 H); 10.97 (m, 1 H) | 497 |
| 4 | 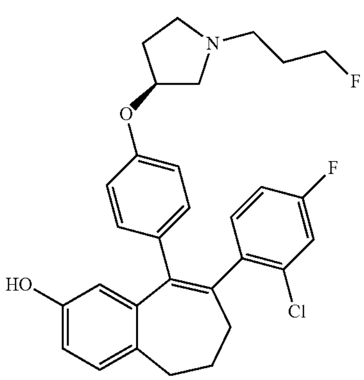 [SMILES: Oc1ccc2c(c1)C(c1ccc(O[C@H]3CCN(CCCF)C3)cc1)=C(c1ccc(F)cc1Cl)CCC2] | 6-(2-chloro-4-fluoro-phenyl)-5-[4-[(3S)-1-(3-fluoro-propyl)-pyrrolidin-3-yl]oxy-phenyl]-8,9-dihydro-7H-benzo[7]-annulen-3-ol | A | 1H NMR (400 MHz, DMSO-d6, δ ppm): 1.67 (m, 1 H); 1.79 (dm, J = 25.3 Hz, 2 H); 2.03 (m, 2 H); 2.15 (t, J = 7.0 Hz, 2 H); 2.20 (m, 1 H); 2.38 (m, 1 H); 2.46 (t, J = 7.2 Hz, 2 H); 2.52 (dd, J = 3.2 and 10.4 Hz, 1 H); 2.62 (m, 1 H); 2.69 to 2.82 (m, 3 H); 4.47 (td, J = 6.1 and 47.5 Hz, 2 H); 4.72 (m, 1 H); 6.20 (d, J = 2.7 Hz, 1 H); 6.62 (dd, J = 2.7 and 8.3 Hz, 1 H; 6.64 (d, J = 8.8 Hz, 2 H); 6.72 (d, J = 8.8 Hz, 2 H); 7.04 (dt, J = 2.7 and 9.0 Hz, 1 H); 7.10 (d, J = 8.3 Hz, 1 H); 7.17 (dd, J = 6.4 and 8.9 Hz, 1 H); 7.40 (dd J = 2.7 and 8.9 Hz, 1 H); 9.07 (s, 1 H) | 510 |

TABLE 1-continued

| Examples | Structure | Name | Method | NMR | MASS: LC/MS (m/z, MH+): |
|---|---|---|---|---|---|
| 5 | 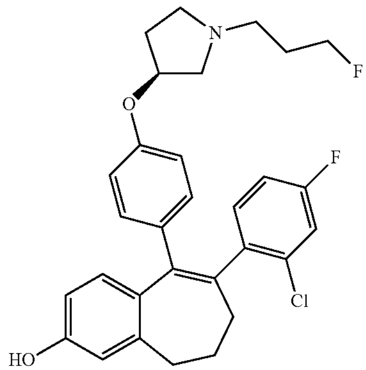 [SMILES: Oc1ccc2c(c1)CCCC(c1ccc(F)cc1Cl)=C2c1ccc(O[C@H]2CCN(CCCF)C2)cc1] | 6-(2-chloro-4-fluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.67 (m, 1 H); 1.79 (dm, J = 25.3 Hz, 2 H); 2.08 (m, 2 H); 2.19 (m, 3 H); 2.37 (m, 1 H); 2.46 (t, J = 7.2 Hz, 2 H); 2.53 (m, 1 H); 2.61 to 2.83 (m, 4 H); 4.47 (td, J = 6.2 and 47.6 Hz, 2 H); 4.72 (m, 1 H); 6.57 (s, 2 H); 6.60 (d, J = 8.8 Hz, 2 H); 6.71 (m, 3 H); 7.02 (dt, J = 2.6 and 9.0 Hz, 1 H); 7.17 (dd, J = 6.4 and 9.0 Hz, 1 H); 7.39 (dd, J = 2.6 and 9.0 Hz, 1 H); 9.43 (s, 1 H) | 508 |
| 6 | 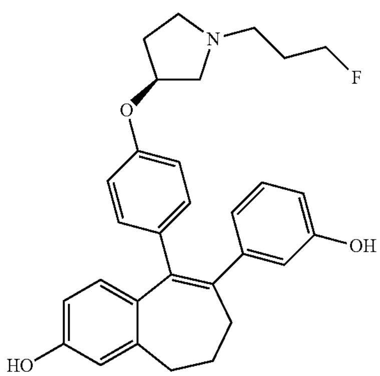 [SMILES: Oc1cccc(C2=C(c3ccc(O[C@H]4CCN(CCCF)C4)cc3)c3ccc(O)cc3CCC2)c1] | 5-[4-[(3S)-1-(3-fluoropropyl)-pyrrolidin-3-yl]oxy-phenyl]-6-(3-hydroxy-phenyl)-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.03 (m, 2 H); 2.20 (m, 3 H); 2.38 (m, 1 H); 2.47 (t, J = 7.2 Hz, 2 H); 2.55 (dd, J = 3.2 and 10.4 Hz, 1 H); 2.66 (m, 3 H); 2.80 (dd, J = 6.3 and 10.4 Hz, 1 H); 4.48 (td, J = 6.1 and 47.5 Hz, 2 H); 4.73 (m, 1 H); 6.48 to 6.55 (m, 5 H); 6.60 (d, J = 8.8 Hz, 2 H); 6.69 (s, 1 H); 6.72 (d, J = 8.8 Hz, 2 H); 6.94 (t, J = 8.0 Hz, 1 H); 9.15 (s, 1 H); 9.39 (s, 1 H) | 474 |
| 7 | 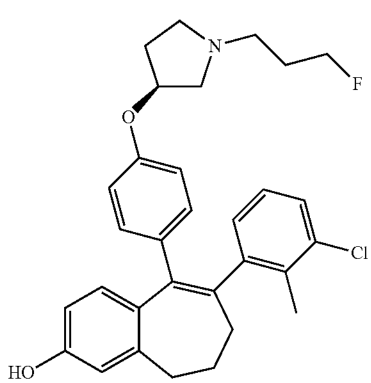 [SMILES: Cc1c(Cl)cccc1C1=C(c2ccc(O[C@H]3CCN(CCCF)C3)cc2)c2ccc(O)cc2CCC1] | 6-(3-chloro-2-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.66 (m, 1 H); 1.79 (dm, J = 25.3 Hz, 2 H); 2.01 to 2.23 (m, 5 H); 2.20 (s, 3 H); 2.35 (m, 1 H); 2.45 (t, J = 7.2 Hz, 2 H); 2.52 (m, 1 H); 2.60 to 2.82 (m, 4 H); 4.47 (td, J = 6.1 and 47.5 Hz, 2 H); 4.72 (m, 1 H); 6.57 (d, J = 1.5 Hz, 2 H); 6.59 (d, J = 8.9 Hz, 2 H); 6.66 (d, J = 8.9 Hz, 2 H); 6.71 (t, J = 1.5 Hz, 1 H); 6.97 (d, J = 8.0 Hz, 1 H); 7.03 (t, J = 8.0 Hz, 1 H); 7.21 (d, J = 8.0 Hz, 1 H); 9.41 (s, 1 H) | 506 |

TABLE 1-continued

| Examples | Structure | Name | Method | NMR | MASS: LC/MS (m/z, MH+): |
|---|---|---|---|---|---|
| 8 | 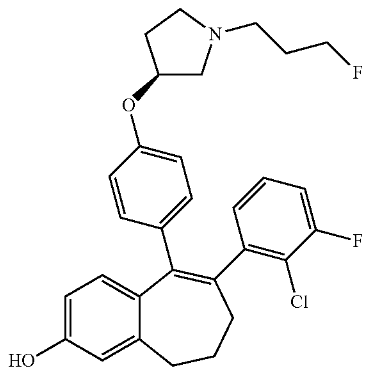 [SMILES: Oc1ccc2c(c1)CCCC(c1cccc(F)c1Cl)=C2c1ccc(O[C@H]2CCN(CCCF)C2)cc1] | 6-(2-chloro-3-fluoro-phenyl)-5-[4-[(3S)-1-(3-fluoro-propyl)-pyrrolidin-3-yl]oxyphenyl]-8,9-dihydro-7H-benzo[7]-annulen-2-ol | A | 1H NMR (400 MHz, DMSO-d6, δ ppm): 1.66 (m, 1 H); 1.79 (dm, J = 25.3 Hz, 2 H); 2.08 (m, 2 H); 2.18 (m, 3 H); 2.37 (m, 1 H); 2.43 (t, J = 7.2 Hz, 2 H); 2.52 (m, 1 H); 2.62 (m, 1 H); 2.78 (m, 3 H); 4.47 (td, J = 6.1 and 47.5 Hz, 2 H); 4.71 (m, 1 H); 6.58 (s, 2 H); 6.60 (d, J = 8.9 Hz, 2 H); 6.70 (s, 1 H); 6.72 (d, J = 8.9 Hz, 2 H); 6.99 (m, 1 H); 7.20 (m, 2 H); 9.46 (s, 1 H) | 510 |
| 9 | 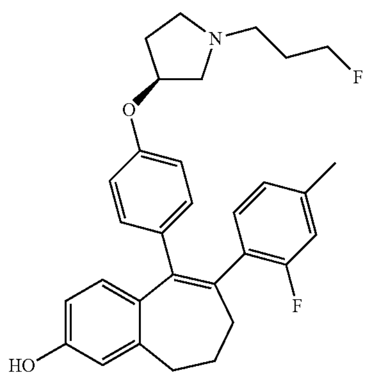 [SMILES: Cc1ccc(C2=C(c3ccc(O[C@H]4CCN(CCCF)C4)cc3)c3ccc(O)cc3CCC2)c(F)c1] | 6-(2-fluoro-4-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.03 (m, 2 H); 2.12 to 2.22 (m, 3 H); 2.23 (s, 3 H); 2.38 (m, 1 H); 2.47 (t, J = 7.2 Hz, 2 H); 2.52 (m, 1 H); 2.63 (m, 1 H); 2.49 (t, J = 7.2 Hz, 2 H); 2.79 (dd, J = 6.3 and 10.4 Hz, 1 H); 4.47 (td, J = 6.3 and 47.5 Hz, 2 H); 4.71 (m, 1 H); 6.56 (s, 2 H); 6.59 (d, J = 8.8 Hz, 2 H); 6.69 (s, 1 H); 6.71 (d, J = 8.8 Hz, 2 H); 6.82 (d, J = 8.0 Hz, 1 H); 6.87 (d, J = 11.3 Hz, 1 H); 7.00 (t, J = 8.0 Hz, 1 H); 9.41 (s, 1 H) | 490 |
| 10 | 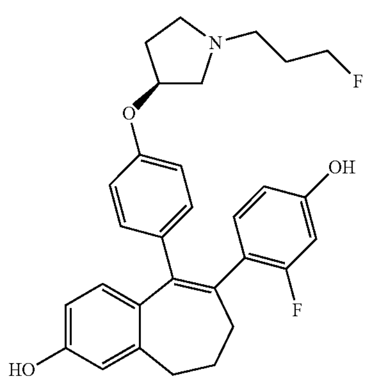 [SMILES: Oc1ccc(C2=C(c3ccc(O[C@H]4CCN(CCCF)C4)cc3)c3ccc(O)cc3CCC2)c(F)c1] | 6-(2-fluoro-4-hydroxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.04 (m, 2 H); 2.13 (t, J = 7.0 Hz, 2 H); 2.20 (m, 1 H); 2.38 (m, 1 H); 2.46 (t, J = 7.2 Hz, 2 H); 2.53 (dd, J = 3.0 and 10.4 Hz, 1 H); 2.60 to 2.70 (m, 3 H); 2.79 (dd, J = 6.4 and 10.4 Hz, 1 H); 4.47 (td, J = 6.1 and 47.5 Hz, 2 H); 4.73 (m, 1 H); 6.40 (dd, J = 2.6 and 11.9 Hz, 1H); 6.42 (dd, J = 2.6 and 8.7 Hz, 1H); 6.54 (m, 2 H); 6.60 (d, J = 8.8 Hz, 2 H); 6.69 (s, 1 H); 6.72 (d, J = 8.8 Hz, 2 H); 6.89 (t, J = 8.7 Hz, 1 H); 9.39 (s, 1 H); 9.70 (s, 1 H) | 492 |

TABLE 1-continued

| Examples | Structure | Name | Method | NMR | MASS: LC/MS (m/z, MH+): |
|---|---|---|---|---|---|
| 11 | 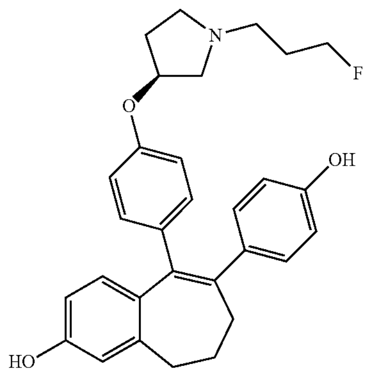 [SMILES: Oc1ccc(C2=C(c3ccc(O[C@H]4CCN(CCCF)C4)cc3)c3ccc(O)cc3CCC2)cc1] | 5-[4-[(3S)-1-(3-fluoropropyl)-pyrrolidin-3-yl]oxy-phenyl]-6-(4-hydroxy-phenyl)-8,9-dihydro-7H-benzo[7]-annulen-2-ol | A | 1H NMR (400 MHz, DMSO-d6, δ ppm): 1.69 (m, 1 H); 1.80 (dm, J = 25.3 Hz, 2 H); 2.02 (m, 2 H); 2.20 (m, 3 H); 2.39 (m, 1 H); 2.48 (t, J = 7.2 Hz, 2 H); 2.54 (dd, J = 3.2 and 10.4 Hz, 1 H); 2.63 (m, 3 H); 2.80 (dd, J = 6.4 and 10.4 Hz, 1 H); 4.48 (td, J = 6.1 and 47.5 Hz, 2 H); 4.73 (m, 1 H); 6.52 (m, 4 H); 6.60 (d, J = 8.8 Hz, 2 H); 6.68 (s, 1 H); 6.71 (d, J = 8.8 Hz, 2 H); 6.91 (d, J = 8.8 Hz, 2 H); 9.23 (s, 1 H); 9.32 (s, 1 H) | 474 |
| 12 | 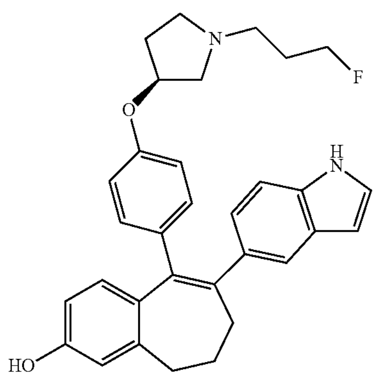 [SMILES: Oc1ccc2c(c1)CCCC(c1ccc3[nH]ccc3c1)=C2c1ccc(O[C@H]2CCN(CCCF)C2)cc1] | 5-[4-[(3S)-1-(3-fluoropropyl)-pyrrolidin-3-yl]oxy-phenyl]-6-(1H-indol-5-yl)-8,9-dihydro-7H-benzo[7]-annulen-2-ol | A | 1H NMR (400 MHz, DMSO-d6, δ ppm): 1.67 (m, 1 H); 1.78 (dm, J = 25.3 Hz, 2 H); 2.03 (m, 2 H); 2.15 (m, 1 H); 2.30 (t, J = 7.0 Hz, 2 H); 2.37 (m, 1 H); 2.45 (t, J = 7.2 Hz, 2 H); 2.51 (m, 1 H); 2.61 (m, 1 H); 2.70 (t, J = 7.0 Hz, 2 H); 2.77 (dd, J = 6.4 and 10.4 Hz, 1 H); 4.46 (td, J = 6.1 and 47.5 Hz, 2 H); 4.69 (m, 1 H); 6.28 (t, J = 2.8 Hz, 1 H); 6.53 (d, J = 8.8 Hz, 2 H); 6.55 (m, 2 H); 6.68 (d, J = 1.5 Hz, 1 H); 6.73 (d, J = 8.8 Hz, 2 H); 6.84 (dd, J = 1.8 and 8.5 Hz, 1 H); 7.13 (d, J = 8.5 Hz, 1 H); 7.23 (t, J = 2.8 Hz, 1 H); 7.32 (d, J = 1.8 Hz, 1 H); 9.38 (s, 1 H); 11.90 (t, J = 2.8 Hz, 1 H) | 497 |
| 13 | 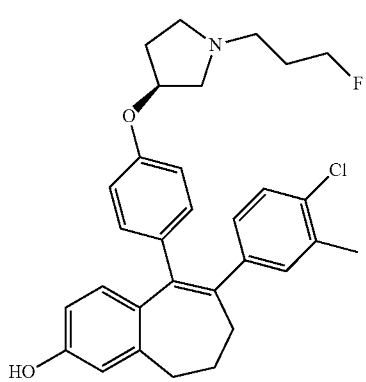 [SMILES: Cc1cc(C2=C(c3ccc(O[C@H]4CCN(CCCF)C4)cc3)c3ccc(O)cc3CCC2)ccc1Cl] | 6-(4-chloro-3-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.00 to 2.23 (m, 4 H); 2.12 (s, 3 H); 2.38 (m, 1 H); 2.46 (t, J = 7.2 Hz, 2 H); 2.53 (m, 1 H); 2.59 to 2.81 (m, 5 H); 4.47 (td, J = 6.1 and 47.5 Hz, 2 H); 4.72 (m, 1 H); 6.56 (s, 2 H); 6.59 (d, J = 8.8 Hz, 2 H); 6.65 (d, J = 8.8 Hz, 2 H); 6.70 (s, 1 H); 7.01 (d, J = 8.5 Hz, 1 H); 7.09 (dd, J = 2.4 and 8.5 Hz, 1 H); 7.18 (d, = 2.4 Hz, 1 H); 9.39 (s, 1 H) | 506 |

TABLE 1-continued

| Examples | Structure | Name | Method | NMR | MASS: LC/MS (m/z, MH+): |
|---|---|---|---|---|---|
| 14 | 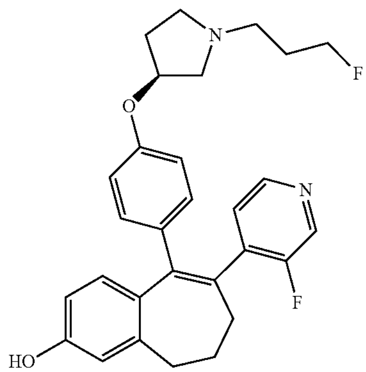 [SMILES: Oc1ccc2c(c1)CCCC(c1ccncc1F)=C2c1ccc(O[C@H]2CCN(CCCF)C2)cc1] | 5-[4-[(3S)-1-(3-fluoropropyl)-pyrrolidin-3-yl]oxy-phenyl]-6-(3-fluoro-4-pyridyl)-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.05 (m, 2 H); 2.20 (m, 3 H); 2.38 (m, 1 H); 2.45 (t, J = 7.3 Hz, 2 H); 2.53 (m, 1 H); 2.60 to 2.71 (m, 3 H); 2.79 (dd, J = 6.1 and 10.4 Hz, 1 H); 4.46 (td, J = 6.1 and 47.5 Hz, 2 H); 4.73 (m, 1 H); 6.59 (m, 2 H); 6.63 (d, J = 8.9 Hz, 2 H); 6.73 (m, 3 H); 7.25 (dd, J = 5.0 and 6.4 Hz, 1 H); 8.24 (dd, J = 1.7 and 5.0 Hz, 1 H); 8.37 (d, J = 1.7 Hz, 1 H); 9.50 (s, 1 H) | 477 |
| 15 | 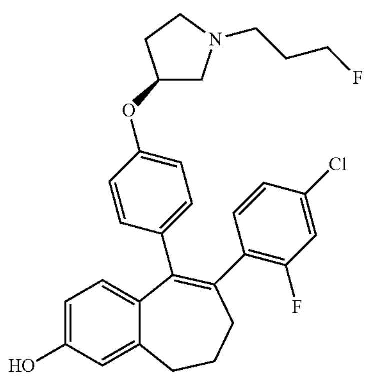 [SMILES: Oc1ccc2c(c1)CCCC(c1ccc(Cl)cc1F)=C2c1ccc(O[C@H]2CCN(CCCF)C2)cc1] | 6-(4-chloro-2-fluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.06 (m, 2 H); 2.13 to 2.24 (m, 3 H); 2.39 (m, 1 H); 2.47 (t, J = 7.2 Hz, 2 H); 2.53 (m, 1 H); 2.73 (m, 1 H); 2.70 (t, J = 7.2 Hz, 2 H); 2.80 (dd, J = 6.3 and 10.4 Hz, 1 H); 4.47 (td, J = 6.3 and 47.5 Hz, 2 H); 4.73 (m, 1 H); 6.58 (s, 2 H); 6.62 (d, J = 8.8 Hz, 2 H); 6.70 (s, 1 H); 6.72 (d, J = 8.8 Hz, 2 H); 7.11 (dd, J = 2.2 and 8.2 Hz, 1 H); 7.18 (t, J = 8.2 Hz, 1 H); 7.27 (dd, J = 2.2 and 9.9 Hz, 1 H); 9.41 (s, 1 H) | 510 |
| 16 | 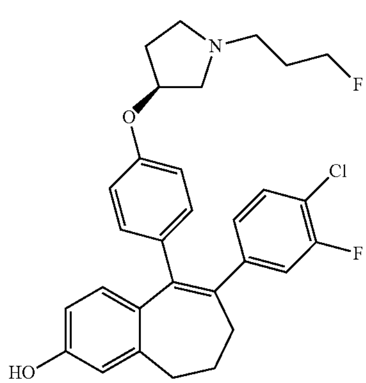 [SMILES: Oc1ccc2c(c1)CCCC(c1ccc(Cl)c(F)c1)=C2c1ccc(O[C@H]2CCN(CCCF)C2)cc1] | 6-(4-chloro-3-fluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.06 (m, 2 H); 2.15 to 2.19 (m, 3 H); 2.39 (m, 1 H); 2.48 (m, 2 H); 2.55 (m, 1 H); 2.68 (m, 3 H); 2.80 (dd, J = 6.3 and 10.4 Hz, 1 H); 4.47 (td, J = 6.1 and 47.5 Hz, 2 H); 4.78 (m, 1 H); 6.57 (s, 2 H); 6.67 (d, J = 8.8 Hz, 2 H); 6.69 (s, 1 H); 6.75 (d, J = 8.8 Hz, 2 H); 6.94 (dd, J = 2.0 and 8.5 Hz, 1 H); 7.13 (dd, J = 2.0 and 11.0 Hz, 1 H); 7.34 (t, J = 8.5 Hz, 1 H); 9.42 (s, 1 H) | 510 |

TABLE 1-continued

| Examples | Structure | Name | Method | NMR | MASS: LC/MS (m/z, MH+): |
|---|---|---|---|---|---|
| 17 | 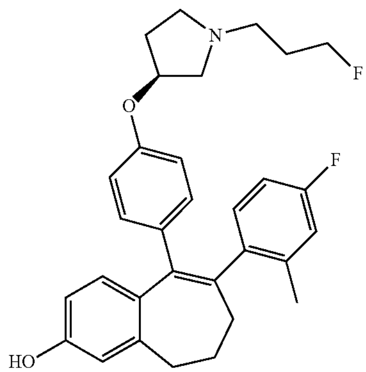 [SMILES: Cc1cc(F)ccc1C1=C(c2ccc(O[C@H]3CCN(CCCF)C3)cc2)c2ccc(O)cc2CCC1] | 6-(4-fluoro-2-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.02 to 2.24 (m, 5 H); 2.12 (s, 3 H); 2.38 (m, 1 H); 2.45 (t, J = 7.2 Hz, 2 H); 2.52 (dd, J = 3.0 and 10.4 Hz, 1 H); 2.59 to 2.82 (m, 4 H); 4.47 (td, J = 6.1 and 47.5 Hz, 2 H); 4.71 (m, 1 H); 6.55 (s, 2 H); 6.58 (d, J = 8.8 Hz, 2 H); 6.67 (d, J = 8.8 Hz, 2 H); 6.70 (s, 1 H); 6.74 (dt, J = 3.1 and 8.9 Hz, 1 H); 6.93 (dd, J = 3.1 and 10.4 Hz, 1 H); 7.02 (dd, J = 6.6 and 8.9 Hz, 1 H); 9.34 (s, 1 H) | 490 |
| 18 | 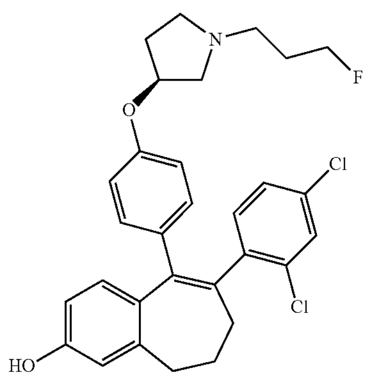 | 6-(2,4-dichloro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.06 (m, 2 H); 2.18 (m, 3 H); 2.38 (m, 1 H); 2.48 (t, J = 7.2 Hz, 2 H); 2.53 (m, 1 H); 2.62 (m, 1 H); 2.69 to 2.82 (m, 3 H); 4.47 (td, J = 6.1 and 47.5 Hz, 2 H); 4.72 (m, 1 H); 6.57 (s, 2 H); 6.61 (d, J = 8.8 Hz, 2 H); 6.70 (s, 1 H); 6.72 (d, J = 8.8 Hz, 2 H); 7.14 (d, J = 8.8 Hz, 1 H); 7.23 (dd, J = 2.5 and 8.8 Hz, 1 H); 7.54 (d, J = 2.5 Hz, 1 H); 9.42 (s, 1 H) | 526 |
| 19 | 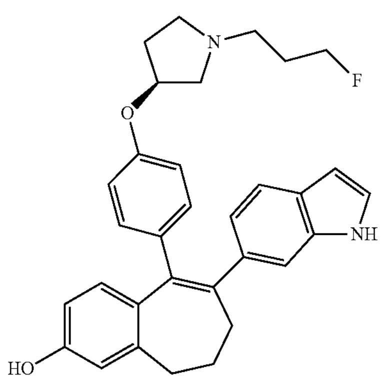 [SMILES: Oc1ccc2c(c1)CCCC(c1ccc3cc[nH]c3c1)=C2c1ccc(O[C@H]2CCN(CCCF)C2)cc1] | 5-[4-[(3S)-1-(3-fluoropropyl)-pyrrolidin-3-yl]oxy-phenyl]-6-(1H-indol-6-yl)-8,9-dihydro-7H-benzo[7]-annulen-2-ol | A | 1H NMR (400 MHz, DMSO-d6, δ ppm): 1.67 (m, 1 H); 1.78 (dm, J = 25.3 Hz, 2 H); 2.03 (m, 2 H); 2.15 (m, 1 H); 2.25 to 2.40 (m, 3 H); 2.43 (t, J = 7.2 Hz, 2 H); 2.52 (m, 1 H); 2.61 (m, 1 H); 2.69 (t, J = 7.0 Hz, 2 H); 2.77 (dd, J = 6.4 and 10.4 Hz, 1 H); 4.47 (td, J = 6.1 and 47.5 Hz, 2 H); 4.70 (m, 1 H); 6.30 (t, J = 2.8 Hz, 1 H); 6.53 (d, J = 8.8 Hz, 2 H); 6.55 (s, 2 H); 6.70 (s, 1 H); 6.73 (d, J = 8.8 Hz, 2 H); 6.79 (dd, J = 1.6 and 8.3 Hz, 1 H); 7.15 (s, 1 H); 7.24 (t, J = 2.8 Hz, 1 H); 7.31 (d, J = 8.3 Hz, 1 H); 9.35 (s, 1 H); 10.89 (t, J = 2.8 Hz, 1 H) | 497 |

TABLE 1-continued

| Examples | Structure | Name | Method | NMR | MASS: LC/MS (m/z, MH+): |
|---|---|---|---|---|---|
| 20 | 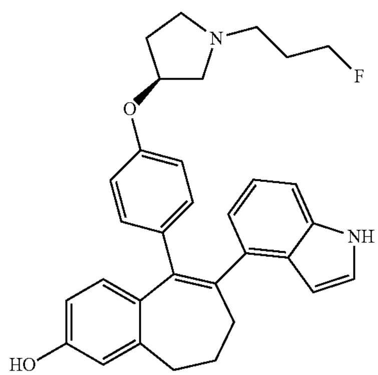 [SMILES: Oc1ccc2c(c1)CCCC(c1cccc3[nH]ccc13)=C2c1ccc(O[C@H]2CCN(CCCF)C2)cc1] | 5-[4-[(3S)-1-(3-fluoropropyl)-pyrrolidin-3-yl]oxy-phenyl]-6-(1H-indol-4-yl)-8,9-dihydro-7H-benzo[7]-annulen-2-ol | A | 1H NMR (400 MHz, DMSO-d6, δ ppm): 1.62 (m, 1 H); 1.77 (dm, J = 25.3 Hz, 2 H); 2.00 (m, 2 H); 2.13 (m, 1 H); 2.31 (m, 3 H); 2.41 (t, J = 7.2 Hz, 2 H); 2.57 (m, 2 H); 2.74 (m, 3 H); 4.46 (td, J = 6.1 and 47.5 Hz, 2 H); 4.65 (m, 1 H); 6.25 (d, J = 3.0 Hz, 1 H); 6.44 (d, J = 8.8 Hz, 2 H); 6.58 (s, 2 H); 6.72 (m, 3 H); 6.71 (s, 1 H); 6.89 (t, J = 8.3 Hz, 1 H); 7.15 (d, J = 8.3 Hz, 1 H); 7.22 (7, J = 3.0 Hz, 1 H); 9.38 (s, 1 H); 11.00 (m, 1 H) | 497 |
| 21 | 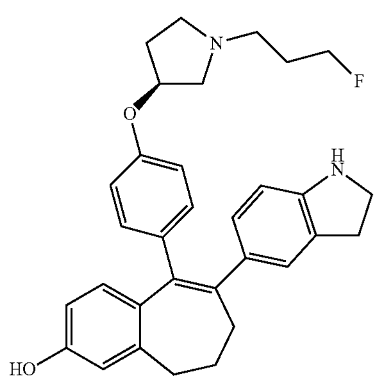 [SMILES: Oc1ccc2c(c1)CCCC(c1ccc3c(c1)CCN3)=C2c1ccc(O[C@H]2CCN(CCCF)C2)cc1] | 5-[4-[(3S)-1-(3-fluoropropyl)-pyrrolidin-3-yl]oxy-phenyl]-6-indolin-5-yl-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.01 (m, 2 H); 2.19 (m, 3 H); 2.39 (m, 1 H); 2.42 to 2.57 (m, 3 H); 2.61 (m, 3 H); 2.82 to 2.92 (m, 3 H); 3.38 (m, 2 H); 4.47 (td, J = 6.1 and 47.5 Hz, 2 H); 4.75 (m, 1 H); 5.39 (s, 1 H); 6.24 (d, J = 8.0 Hz, 1 H); 6.51 (s, 2 H); 6.60 (d, J = 8.8 Hz, 2 H); 6.64 (m, 2 H); 6.72 (d, J = 8.8 Hz, 2 H); 6.81 (s, 1 H); 9.30 (s, 1 H) | 499 |
| 22 | 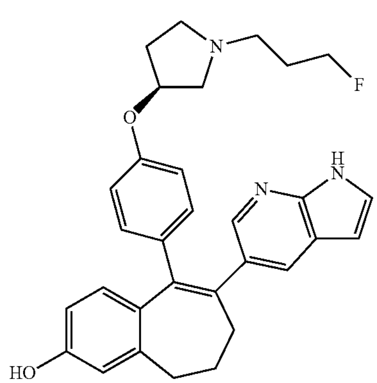 [SMILES: Oc1ccc2c(c1)CCCC(c1cnc3[nH]ccc3c1)=C2c1ccc(O[C@H]2CCN(CCCF)C2)cc1] | 5-[4-[(3S)-1-(3-fluoropropyl)-pyrrolidin-3-yl]oxy-phenyl]-6-(1H-pyrrolo[2,3-b]pyridin-5-yl)-8,9-dihydro-7H-benzo[7]-annulen-2-ol | A | 1H NMR (400 MHz, DMSO-d6, δ ppm): 1.67 (m, 1 H); 1.78 (dm, J = 25.3 Hz, 2 H); 2.07 (m, 2 H); 2.17 (m, 1 H); 2.29 to 2.40 (m, 3 H); 2.44 (t, J = 7.2 Hz, 2 H); 2.52 (m, 1 H); 2.61 (m, 1 H); 2.71 (t, J = 7.0 Hz, 2 H); 2.78 (dd, J = 6.4 and 10.4 Hz, 1 H); 4.46 (td, J = 6.1 and 47.5 Hz, 2 H); 4.71 (m, 1 H); 6.32 (dd, J = 2.0 and 2.9 Hz, 1 H); 6.57 (s, 2 H); 6.59 (d, J = 8.8 Hz, 2 H); 6.70 (s, 1 H); 6.74 (d, J = 8.8 Hz, 2 H); 7.38 (t, J = 2.9 Hz, 1 H); 7.77 (d, J = 2.9 Hz, 1 H); 7.89 (d, J = 2.9 Hz, 1 H); 9.39 (s, 1 H); 11.49 (t, J = 2.9 Hz, 1 H) | 498 |

TABLE 1-continued

| Examples | Structure | Name | Method | NMR | MASS: LC/MS (m/z, MH+): |
|---|---|---|---|---|---|
| 23 | 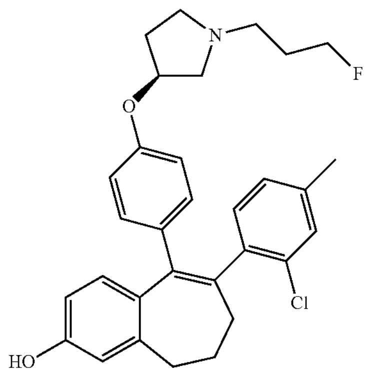 [SMILES: Cc1ccc(C2=C(c3ccc(O[C@H]4CCN(CCCF)C4)cc3)c3ccc(O)cc3CCC2)c(Cl)c1] | 6-(2-chloro-4-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.67 (m, 1 H); 1.79 (dm, J = 25.3 Hz, 2 H); 2.05 (m, 2 H); 2.11 to 2.22 (m, 3 H); 2.23 (s, 3 H); 2.38 (m, 1 H); 2.45 (t, J = 7.2 Hz, 2 H); 2.52 (m, 1 H); 2.58 to 2.83 (m, 4 H); 4.47 (td, J = 6.1 and 47.5 Hz, 2 H); 4.71 (m, 1 H); 6.56 (s, 2 H); 6.58 (d, J = 8.8 Hz, 2 H); 6.72 (s, 1 H); 6.72 (d, J = 8.8 Hz, 2 H); 6.92 (d, J = 8.3 Hz, 1 H); 6.99 (d, J = 8.3 Hz, 1 H); 7.21 (s, 1 H); 9.41 (s, 1 H) | 506 |
| 24 | 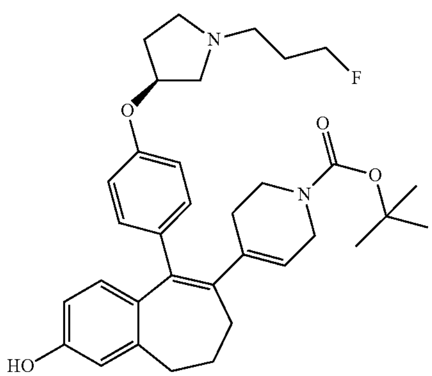 [SMILES: CC(C)(C)OC(=O)N1CC=C(C2=C(c3ccc(O[C@H]4CCN(CCCF)C4)cc3)c3ccc(O)cc3CCC2)CC1] | tert-butyl 4-[5-[4-[(3S)-1-(3-fluoropropyl)-pyrrolidin-3-yl]oxy-phenyl]-2-hydroxy-8,9-dihydro-7H-benzo[7]-annulen-6-yl]-3,6-dihydro-2H-pyridine-1-carboxylate | A | 1H NMR (400 MHz, DMSO-d6, δ ppm): 1.38 (s, 9 H); 1.70 to 2.08 (m, 9 H); 2.24 (m, 1 H); 2.40 (m, 1 H); 2.45 to 2.57 (m, 4 H); 2.60 (dd, J = 3.01 and 10.4 Hz, 1 H); 2.67 (m, 1 H); 2.83 (dd, J = 6.4 and 10.4 Hz, 1 H); 3.24 (m, 2 H); 3.71 (m, 2 H); 4.49 (td, J = 6.1 and 47.5 Hz, 2 H); 4.80 (m, 1 H); 5.48 (m, 1 H); 6.52 (m, 2 H); 6.64 (s, 1 H); 6.74 (d, J = 8.8 Hz, 2 H); 6.91 (d, J = 8.8 Hz, 2 H); 9.34 (s, 1 H) | 563 |
| 25 | 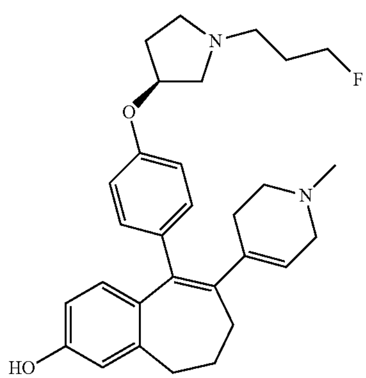 [SMILES: CN1CC=C(C2=C(c3ccc(O[C@H]4CCN(CCCF)C4)cc3)c3ccc(O)cc3CCC2)CC1] | 5-[4-[(3S)-1-(3-fluoropropyl)-pyrrolidin-3-yl]oxy-phenyl]-6-(1-methyl-3,6-dihydro-2H-pyridin-4-yl)-8,9-dihydro-7H-benzo[7]-annulen-2-ol | A | 1H NMR (400 MHz, DMSO-d6, δ ppm): 1.69 to 1.89 (m, 3 H); 1.93 to 2.08 (m, 6 H); 2.14 (s, 3 H); 2.20 to 2.32 (m, 3 H); 2.40 (m, 1 H); 2.46 to 2.55 (m, 4 H); 2.60 (dd, J = 3.0 and 10.4 Hz, 1 H); 2.69 (m, 1 H); 2.75 (m, 2 H); 2.84 (dd, J = 6.3 and 10.4 Hz, 1 H); 4.49 (td, J = 6.1 and 47.5 Hz, 2 H); 4.81 (m, 1 H); 5.42 (m, 1 H); 6.51 (s, 2 H); 6.63 (s, 1 H); 6.73 (d, J = 8.8 Hz, 2 H); 6.91 (d, J = 8.8 Hz, 2 H); 9.31 (s, 1 H) | 477 |

TABLE 1-continued

| Examples | Structure | Name | Method | NMR | MASS: LC/MS (m/z, MH+): |
|---|---|---|---|---|---|
| 26 | 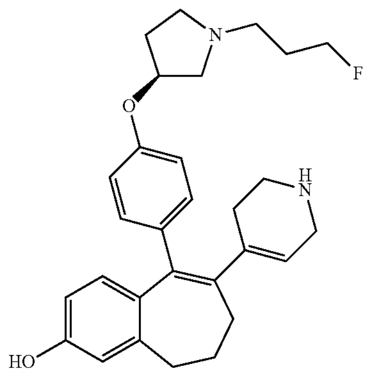 [SMILES: Oc1ccc2c(c1)CCCC(C1=CCNCC1)=C2c1ccc(O[C@H]2CCN(CCCF)C2)cc1] | 5-[4-[(3S)-1-(3-fluoropropyl)-pyrrolidin-3-yl]oxy-phenyl]-6-(1,2,3,6-tetrahydropyridin-4-yl)-8,9-dihydro-7H-benzo[7]-annulen-2-ol | A | 1H NMR (400 MHz, DMSO-d6, δ ppm): 1.70 to 1.89 (m, 5 H); 1.93 to 2.08 (m, 4 H); 2.15 (m, 1 H); 2.25 (m, 1 H); 2.40 (m, 1 H); 2.45 to 2.55 (m, 4 H); 2.60 (dd, J = 3.0 and 10.4 Hz, 1 H); 2.65 (m, 3 H); 2.83 (dd, J = 6.3 and 10.4 Hz, 1 H); 3.11 (m, 2 H); 4.48 (td, J = 6.1 and 47.5 Hz, 2 H); 4.81 (m, 1 H); 5.44 (m, 1 H); 6.51 (s, 2 H); 6.53 (s, 1 H); 6.73 (d, J = 8.8 Hz, 2 H); 6.92 (d, J = 8.8 Hz, 2 H); 9.31 (s, 1 H) | 434 |
| 27 | 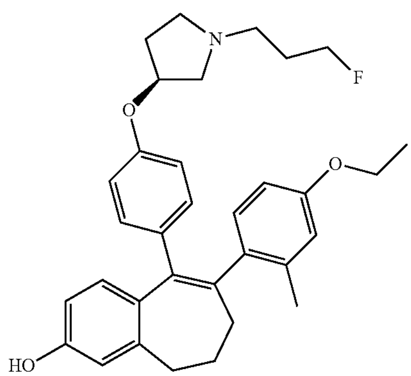 [SMILES: CCOc1ccc(C2=C(c3ccc(O[C@H]4CCN(CCCF)C4)cc3)c3ccc(O)cc3CCC2)c(C)c1] | 6-(4-ethoxy-2-methyl-phenyl)-5-[4-[(3S)-1-(3-fluoropropyl)-pyrrolidin-3-yl]oxyphenyl]-8,9-dihydro-7H-benzo[7]-annulen-2-ol | A | 1H NMR (400 MHz, DMSO-d6, δ ppm): 1.29 (t, J = 7.1 Hz, 3 H); 1.68 (m, 1 H); 1.79 (dm, J = 25.3 Hz, 2 H); 1.99 to 2.23 (m, 5 H); 2.08 (s, 3 H); 2.35 (m, 1 H); 2.46 (t, J = 7.2 Hz, 2 H); 2.53 (m, 1 H); 2.59 to 2.81 (m, 4 H); 3.94 (q, J = 7.1 Hz, 2 H); 4.47 (td, J = 6.1 and 47.5 Hz, 2 H); 4.70 (m, 1 H); 6.55 (m, 4 H); 6.59 (dd, J = 2.5 and 8.7 Hz, 1 H); 6.66 (m, 3 H); 6.70 (s, 1 H); 6.90 (d, J = 8.7 Hz, 1 H); 9.36 (s, 1 H) | 516 |
| 28 | 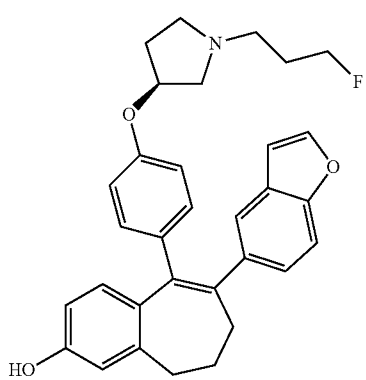 [SMILES: Oc1ccc2c(c1)CCCC(c1ccc3occc3c1)=C2c1ccc(O[C@H]2CCN(CCCF)C2)cc1] | 6-(benzofuran-5-yl)-5-[4-[(3S)-1-(3-fluoropropyl)-pyrrolidin-3-yl]oxyphenyl]-8,9-dihydro-7H-benzo[7]-annulen-2-ol | A | 1H NMR (400 MHz, DMSO-d6, δ ppm): 1.69 (m, 1 H); 1.80 (dm, J = 25.3 Hz, 2 H); 2.05 (m, 2 H); 2.19 (m, 1 H); 2.20 (t, J = 7.0 Hz, 2 H); 2.35 to 2.80 (m, 6 H); 2.70 (t, J = 7.0 Hz, 2 H); 4.46 (td, J = 6.1 and 47.5 Hz, 2 H); 4.73 (m, 1 H); 6.58 (m, 4 H); 6.70 (s, 1 H); 6.72 (d, J = 8.8 Hz, 2 H); 6.82 (dd, J = 1.1 and 2.5 Hz, 1 H); 7.05 (d, J = 2.0 and 8.7 Hz, 1 H); 7.37 (d, J = 8.7 Hz, 1 H); 7.42 (d, J = 2.0 Hz, 1 H); 7.91 (d, J = 2.5 Hz, 1 H); 9.39 (s, 1 H) | 498 |

TABLE 1-continued

| Examples | Structure | Name | Method | NMR | MASS: LC/MS (m/z, MH+): |
|---|---|---|---|---|---|
| 29 | 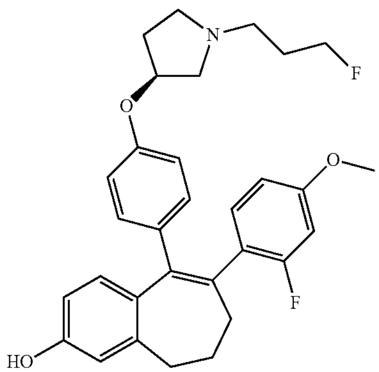 [SMILES: COc1ccc(C2=C(c3ccc(O[C@H]4CCN(CCCF)C4)cc3)c3ccc(O)cc3CCC2)c(F)c1] | 6-(2-fluoro-4-methoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.03 (m, 2 H); 2.15 (t, J = 7.0 Hz, 2 H); 2.20 (m, 1 H); 2.39 (m, 1 H); 2.47 (t, J = 7.2 Hz, 2 H); 2.53 (m, 1 H); 2.60 to 2.71 (m, 3 H); 2.79 (dd, J = 6.4 and 10.4 Hz, 1 H); 3.71 (s, 3 H); 4.48 (td, J = 6.1 and 47.5 Hz, 2 H); 4.72 (m, 1 H); 6.55 (s, 2 H); 6.60 (m, 3 H); 6.65 to 6.73 (m, 4 H); 7.02 (t, J = 8.9 Hz, 1 H); 9.40 (s, 1 H) | 506 |
| 30 | 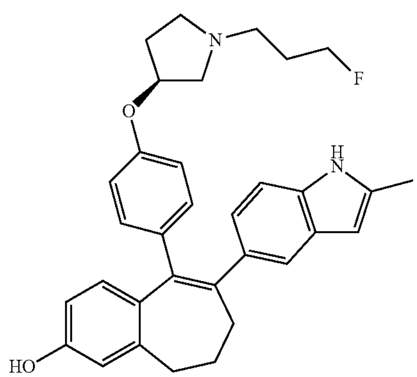 [SMILES: Cc1cc2cc(C3=C(c4ccc(O[C@H]5CCN(CCCF)C5)cc4)c4ccc(O)cc4CCC3)ccc2[nH]1] | 5-[4-[(3S)-1-(3-fluoropropyl)-pyrrolidin-3-yl]oxy-phenyl]-6-(2-methyl-1H-indol-5-yl)-8,9-dihydro-7H-benzo[7]-annulen-2-ol | A | 1H NMR (400 MHz, DMSO-d6, δ ppm): 1.61 to 1.87 (m, 3 H); 2.02 (m, 2 H); 2.15 (m, 1 H); 2.22 to 2.80 (m, 13 H); 4.47 (td, J = 6.1 and 47.5 Hz, 2 H); 4.70 (m, 1 H); 5.95 (s, 1 H); 6.52 (m, 4 H); 6.65 to 6.79 (m, 4 H); 7.02 (d, J = 8.5 Hz, 1 H); 7.16 (s, 1 H); 9.31 (s, 1 H); 10.76 (m, 1 H) | 511 |
| 31 | 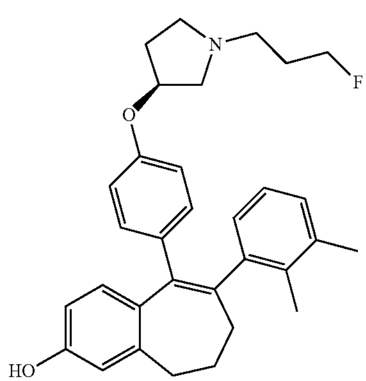 [SMILES: Cc1cccc(C2=C(c3ccc(O[C@H]4CCN(CCCF)C4)cc3)c3ccc(O)cc3CCC2)c1C] | 6-(2,3-dimethyl-phenyl)-5-[4-[(3S)-1-(3-fluoropropyl)-pyrrolidin-3-yl]oxy_phenyl]-8,9-dihydro-7H-benzo[7]-annulen-2-ol | A | 1H NMR (400 MHz, DMSO-d6, δ ppm): 1.65 (m, 1 H); 1.79 (dm, J = 25.3 Hz, 2 H); 1.98 to 2.22 (m, 5 H); 2.10 (s, 3 H); 2.19 (s, 3 H); 2.36 (m, 1 H); 2.45 (t, J = 7.2 Hz, 2 H); 2.52 (m, 1 H); 2.59 to 2.70 (m, 2 H); 2.72 (m, 2 H); 4.46 (td, J = 6.1 and 47.5 Hz, 2 H); 4.70 (m, 1 H); 6.54 (d, J = 8.8 Hz, 2 H); 6.57 (s, 2 H); 6.65 (d, J = 8.8 Hz, 2 H); 6.70 (s, 1 H); 6.79 (d, J = 7.8 Hz, 1 H); 6.77 (t, J = 7.8 Hz, 1 H); 6.92 (d, J = 7.8 Hz, 1 H); 9.38 (s, 1 H) | 486 |

TABLE 1-continued

| Examples | Structure | Name | Method | NMR | MASS: LC/MS (m/z, MH+): |
|---|---|---|---|---|---|
| 32 | 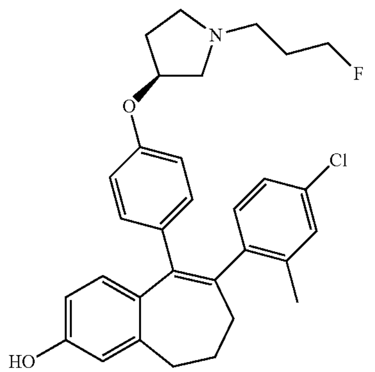 | 6-(4-chloro-2-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.67 (m, 1 H); 1.79 (dm, J = 25.3 Hz, 2 H); 2.00 to 2.24 (m, 5 H); 2.13 (s, 3 H); 2.36 (m, 1 H); 2.45 (t, J = 7.2 Hz, 2 H); 2.52 (m, 1 H); 2.59 to 2.81 (m, 4 H); 4.47 (td, J = 6.1 and 47.5 Hz, 2 H); 4.72 (m, 1 H); 6.55 (s, 2 H); 6.58 (d, J = 8.8 Hz, 2 H); 6.65 (d, J = 8.8 Hz, 2 H); 6.71 (s, 1 H); 7.02 (d, J = 8.2 Hz, 1 H); 7.10 (d, J = 8.2 Hz, 1 H); 7.19 (s, 1 H); 9.40 (s, 1 H) | 506 |
| 33 | 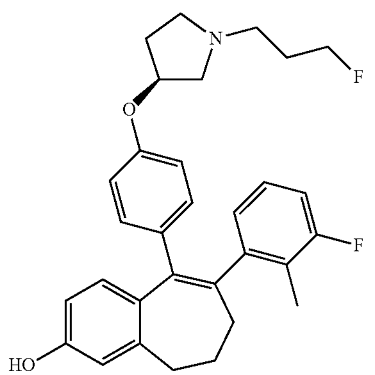 [SMILES: Cc1c(F)cccc1C1=C(c2ccc(O[C@H]3CCN(CCCF)C3)cc2)c2ccc(O)cc2CCC1] | 6-(3-fluoro-2-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.66 (m, 1 H); 1.79 (dm, J = 25.3 Hz, 2 H); 2.00 to 2.23 (m, 5 H); 2.03 (s, 3 H); 2.36 (m, 1 H); 2.44 (t, J = 7.2 Hz, 2 H); 2.53 (m, 1 H); 2.59 to 2.80 (m, 4 H); 4.47 (td, J = 6.1 and 47.5 Hz, 2 H); 4.71 (m, 1 H); 6.55 (s, 2 H); 6.58 (d, J = 8.8 Hz, 2 H); 6.65 (d, J = 8.8 Hz, 2 H); 6.71 (s, 1 H); 6.88 (d, J = 7.8 Hz, 1 H); 6.92 (m, 1 H); 7.16 (m, 1 H); 9.41 (s, 1 H) | 490 |
| 34 | 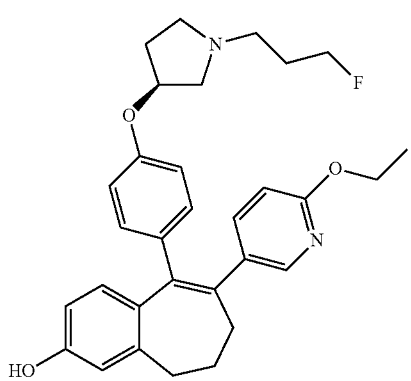 [SMILES: CCOc1ccc(C2=C(c3ccc(O[C@H]4CCN(CCCF)C4)cc3)c3ccc(O)cc3CCC2)cn1] | 6-(6-ethoxy-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.26 (t, J = 7.1 Hz, 3 H); 1.70 (m, 1 H); 1.80 (dm, J = 25.3 Hz, 2 H); 2.05 (m, 2 H); 2.15 to 2.28 (m, 3 H); 2.38 (m, 1 H); 2.47 (t, J = 7.1 Hz, 2 H); 2.55 (m, 1 H); 2.66 (m, 3 H); 2.80 (dd, J = 6.5 and 10.5 Hz, 1 H); 4.20 (q, J = 7.1 Hz, 2 H); 4.47 (td, J = 6.1 and 47.5 Hz, 2 H); 4.76 (m, 1 H); 6.55 (s, 2 H); 6.60 (d, J = 8.7 Hz, 1 H); 6.64 (d, J = 8.8 Hz, 2 H); 6.69 (s, 1 H); 6.76 (d, J = 8.8 Hz, 2 H); 7.43 (dd, J = 2.4 and 8.7 Hz, 1 H); 7.84 (d, J = 2.4 Hz, 1 H); 9.40 (s, 1 H) | 503 |

TABLE 1-continued

| Examples | Structure | Name | Method | NMR | MASS: LC/MS (m/z, MH+): |
|---|---|---|---|---|---|
| 35 | 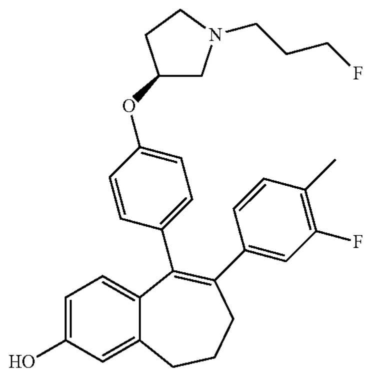 [SMILES: Cc1ccc(C2=C(c3ccc(O[C@H]4CCN(CCCF)C4)cc3)c3ccc(O)cc3CCC2)cc1F] | 6-(3-fluoro-4-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.02 (m, 2 H); 2.13 (s, 3 H); 2.17 to 2.27 (m, 3 H); 2.39 (m, 1 H); 2.47 (t, J = 7.2 Hz, 2 H); 2.54 (dd, J = 3.0 and 10.4 Hz, 1 H); 2.66 (m, 3 H); 2.80 (dd, J = 6.4 and 10.4 Hz, 1 H); 4.47 (td, J = 6.1 and 47.5 Hz, 2 H); 4.76 (m, 1 H); 6.54 (s, 2 H); 6.62 (d, J = 8.8 Hz, 2 H); 6.69 (s, 1 H); 6.74 (d, J = 8.8 Hz, 2 H); 6.84 (m, 2 H); 7.04 (t, J = 8.2 Hz, 1 H); 9.41 (s, 1 H) | 490 |
| 36 | 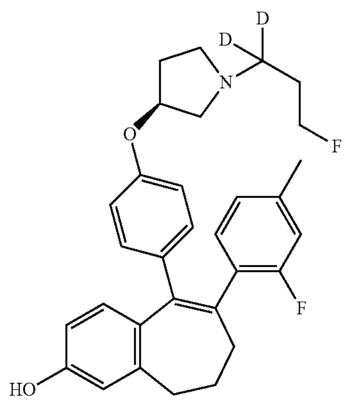 [SMILES: [2H]C([2H])(CCF)N1CC[C@H](Oc2ccc(C3=C(c4ccc(C)cc4F)CCCc4cc(O)ccc43)cc2)C1] | 5-[4-[(3S)-1-(1,1-dideuterio-3-fluoro-propyl)-pyrrolidin-3-yl]oxy-phenyl]-6-(2-fluoro-4-methyl-phenyl)-8,9-dihydro-7H-benzo[7]-annulen-2-ol | A | 1H NMR (400 MHz, DMSO-d6, δ ppm): 1.67 (m, 1 H); 1.77 (td, J = 6.3 and 25.6 Hz, 2 H); 2.04 (m, 2 H); 2.12 to 2.23 (m, 3 H); 2.24 (s, 3 H); 2.38 (m, 1 H); 2.53 (m, 1 H); 2.63 (m, 1 H); 2.70 (t, J = 7.0 Hz, 2 H); 2.79 (dd, J = 6.4 and 10.4 Hz, 1 H); 4.47 (td, J = 6.3 and 47.7 Hz, 2 H); 4.72 (m, 1 H); 6.56 (s, 2 H); 6.59 (d, J = 8.8 Hz, 2 H); 6.70 (s, 1 H); 6.72 (d, J = 8.8 Hz, 2 H); 6.82 (d, J = 8.1 Hz, 1 H); 6.88 (d, J = 11.6 Hz, 1 H); 7.00 (t, J = 8.1 Hz, 1 H); 9.42 (s, 1 H) | 492 |
| 37 | 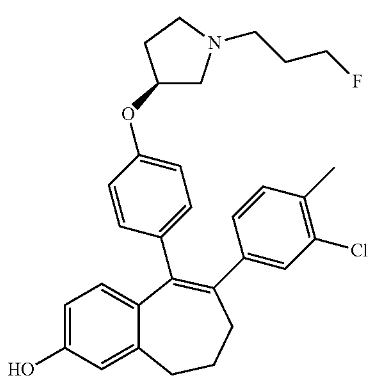 [SMILES: Cc1ccc(C2=C(c3ccc(O[C@H]4CCN(CCCF)C4)cc3)c3ccc(O)cc3CCC2)cc1Cl] | 6-(3-chloro-4-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.03 (m, 2 H); 2.15 to 2.28 (m, 3 H); 2.21 (s, 3 H); 2.39 (m, 1 H); 2.47 (t, J = 7.2 Hz, 2 H); 2.55 (dd, J = 3.2 and 10.5 Hz, 1 H); 2.65 (m, 3 H); 2.79 (dd, J = 6.3 and 10.4 Hz, 1 H); 4.47 (td, J = 6.1 and 47.5 Hz, 2 H); 4.76 (m, 1 H); 6.56 (s, 2 H); 6.64 (d, J = 9.0 Hz, 2 H); 6.70 (s, 1 H); 6.74 (d, J = 9.0 Hz, 2 H); 6.98 (dd, J = 1.9 and 8.0 Hz, 1 H); 7.10 (d, J = 1.9 Hz, 1 H); 7.12 (d, J = 8.0 Hz, 1 H); 9.41 (s, 1 H) | 506 |

TABLE 1-continued

| Examples | Structure | Name | Method | NMR | MASS: LC/MS (m/z, MH+): |
|---|---|---|---|---|---|
| 38 | 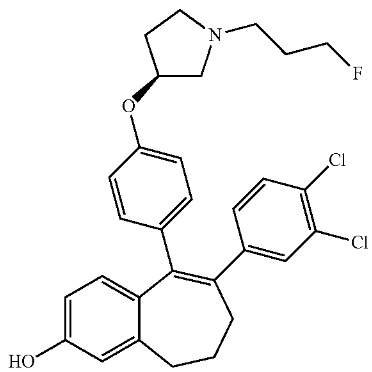 [SMILES: Oc1ccc2c(c1)CCCC(c1ccc(Cl)c(Cl)c1)=C2c1ccc(O[C@H]2CCN(CCCF)C2)cc1] | 6-(3,4-dichlorophenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.4 Hz, 2 H); 2.05 (m, 2 H); 2.20 (m, 1 H); 2.26 (t, J = 7.2 Hz, 2 H); 2.39 (m, 1 H); 2.47 (t, J = 7.2 Hz, 2 H); 2.54 (dd, J = 3.0 and 10.5 Hz, 1 H); 2.67 (m, 3 H); 2.80 (dd, J = 6.4 and 10.5 Hz, 1 H); 4.47 (td, J = 6.1 and 47.5 Hz, 2 H); 4.78 (m, 1 H); 6.57 (s, 2 H); 6.68 (d, J = 8.8 Hz, 2 H); 6.70 s, 1 H); 6.76 (d, J = 8.8 Hz, 2 H); 7.09 (dd, J = 2.2 and 8.5 Hz, 1 H); 7.32 (d, J = 2.2 Hz, 1 H); 7.40 (d, J = 8.5 Hz, 1 H); 9.47 (s, 1 H) | 526 |
| 39 | 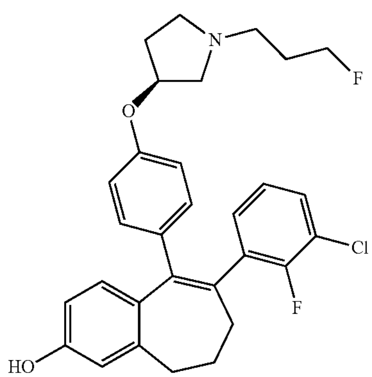 [SMILES: Oc1ccc2c(c1)CCCC(c1cccc(Cl)c1F)=C2c1ccc(O[C@H]2CCN(CCCF)C2)cc1] | 6-(3-chloro-2-fluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.07 (m, 2 H); 2.19 (m, 3 H); 2.38 to 2.58 (m, 4 H); 2.60 to 2.81 (m, 4 H); 4.47 (td, J = 6.1 and 47.5 Hz, 2 H); 4.75 (m, 1 H); 6.56 (s, 2 H); 6.61 (d, J = 8.8 Hz, 2 H); 6.71 (m, 3 H); 7.05 (t, J = 8.2 Hz, 1 H); 7.13 (m, 1 H); 7.36 (m, 1 H); 9.48 (s, 1 H) | 510 |
| 40 | 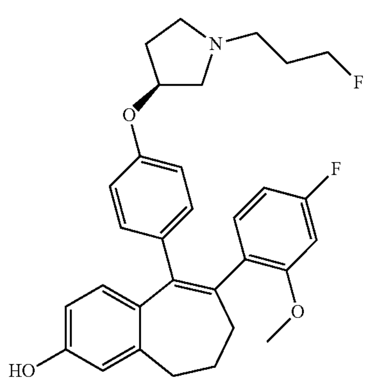 [SMILES: COc1cc(F)ccc1C1=C(c2ccc(O[C@H]3CCN(CCCF)C3)cc2)c2ccc(O)cc2CCC1] | 6-(4-fluoro-2-methoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.67 (m, 1 H); 1.79 (dm, J = 25.3 Hz, 2 H); 1.95 to 2.23 (m, 5 H); 2.31 to 2.55 (m, 4 H); 2.60 to 2.72 (m, 3 H); 2.79 (dd, J = 6.4 and 10.4 Hz, 1 H); 3.72 (s, 3 H); 4.45 (td, J = 6.1 and 47.5 Hz, 2 H); 4.72 (m, 1 H); 6.48 to 6.61 (m, 5 H); 6.71 (m, 3 H); 6.83 (m, 2 H); 9.37 (s, 1 H) | 506 |

TABLE 1-continued

| Examples | Structure | Name | Method | NMR | MASS: LC/MS (m/z, MH+): |
|---|---|---|---|---|---|
| 41 | 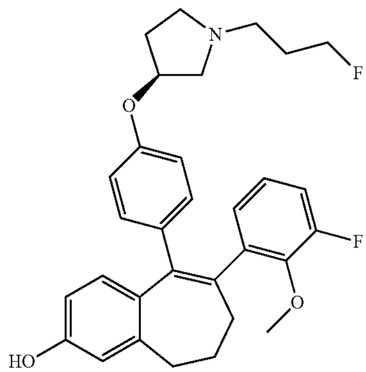 [SMILES: COc1c(F)cccc1C1=C(c2ccc(O[C@H]3CCN(CCCF)C3)cc2)c2ccc(O)cc2CCC1] | 6-(3-fluoro-2-methoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.67 (m, 1 H); 1.79 (dm, J = 25.3 Hz, 2 H); 2.04 (m, 2 H); 2.13 to 2.24 (m, 3 H); 2.37 (m, 1 H); 2.44 (t, J = 7.2 Hz, 2 H); 2.52 (m, 1 H); 2.62 (m, 1 H); 2.71 (t, J = 7.0 Hz, 2 H); 2.78 (dd, J = 6.4 and 10.4 Hz, 1 H); 3.74 (s, 3 H); 4.47 (td, J = 6.1 and 47.5 Hz, 2 H); 4.72 (m, 1 H); 6.57 (m, 2 H); 6.59 (d, J = 8.8 Hz, 2 H); 6.70 (s, 1 H); 6.73 (d, J = 8.8 Hz, 2 H); 6.78 (dd, J = 2.0 and 8.2 Hz, 1 H); 6.85 (td, J = 5.0 and 8.2 Hz, 1 H); 7.03 (ddd, J = 2.0 and 8.2 and 12.2 Hz, 1 H); 9.40 (s, 1 H) | 506 |
| 42 | 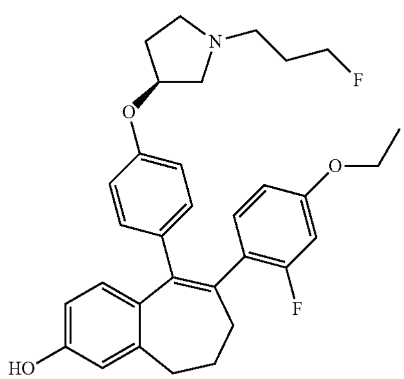 [SMILES: CCOc1ccc(C2=C(c3ccc(O[C@H]4CCN(CCCF)C4)cc3)c3ccc(O)cc3CCC2)c(F)c1] | 6-(4-ethoxy-2-fluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.38 (t, J = 7.1 Hz, 3 H); 1.68 (m, 1 H); 1.79 (dm, J = 25.3 Hz, 2 H); 2.04 (m, 2 H); 2.10 to 2.24 (m, 3 H); 2.38 (m, 1 H); 2.42 to 2.58 (m, 3 H); 2.59 to 2.71 (m, 3 H); 2.79 (m, 1 H); 6.98 (q, J = 7.1 Hz, 2 H); 4.46 (td, J = 6.1 and 47.5 Hz, 2 H); 4.72 (m, 1 H); 6.62 to 6.76 (m, 9 H); 7.00 (t, J = 8.8 Hz, 1 H); 9.40 (s, 1 H) | 520 |
| 43 | 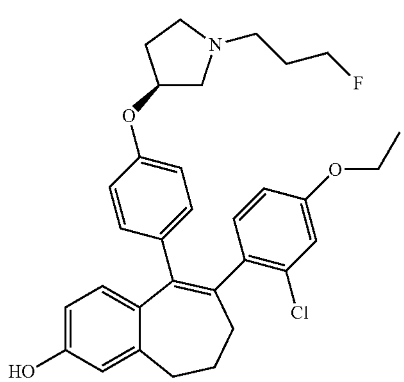 [SMILES: CCOc1ccc(C2=C(c3ccc(O[C@H]4CCN(CCCF)C4)cc3)c3ccc(O)cc3CCC2)c(Cl)c1] | 6-(2-chloro-4-ethoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.26 (t, J = 7.3 Hz, 3 H); 1.66 (m, 1 H); 1.79 (dm, J = 25.3 Hz, 2 H); 2.02 to 2.25 (m, 5 H); 2.35 (m, 1 H); 2.46 (t, J = 7.2 Hz, 2 H); 2.52 (m, 1 H); 2.59 to 2.82 (m, 4 H); 3.98 (q, J = 7.3 Hz, 2 H); 4.46 (td, J = 6.1 and 47.5 Hz, 2 H); 4.72 (m, 1 H); 6.54 (s, 2 H); 6.68 (d, J = 8.8 Hz, 2 H); 6.70 (m, 4 H); 6.93 (d, J = 2.4 Hz, 1 H); 6.99 (d, J = 8.9 Hz, 1 H); 9.41 (s, 1 H) | 536 |

TABLE 1-continued

| Examples | Structure | Name | Method | NMR | MASS: LC/MS (m/z, MH+): |
|---|---|---|---|---|---|
| 44 | 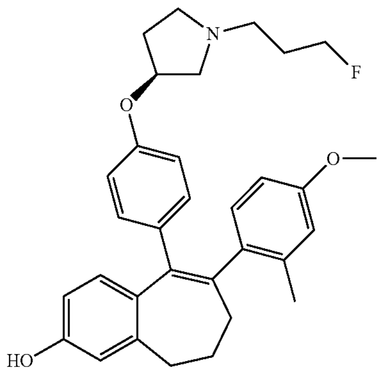 [SMILES: COc1ccc(C2=C(c3ccc(O[C@H]4CCN(CCCF)C4)cc3)c3ccc(O)cc3CCC2)c(C)c1] | 5-[4-[(3S)-1-(3-fluoropropyl)-pyrrolidin-3-yl]oxy-phenyl]-6-(4-methoxy-2-methyl-phenyl)-8,9-dihydro-7H-benzo[7]-annulen-2-ol | A | 1H NMR (400 MHz, DMSO-d6, δ ppm): 1.67 (m, 1 H); 1.79 (dm, J = 25.3 Hz, 2 H); 1.98 to 2.22 (m, 5 H); 2.08 (s, 3 H); 2.36 (m, 1 H); 2.43 (m, 2 H); 2.53 (m, 1 H); 2.59 to 2.82 (m, 4 H); 3.68 (s, 3 H); 4.46 (td, J = 6.1 and 47.5 Hz, 2 H); 4.71 (m, 1 H); 6.50 to 6.71 (m, 9 H); 6.91 (d, J = 8.3 Hz, 1 H); 9.36 (s, 1 H) | 502 |
| 45 | 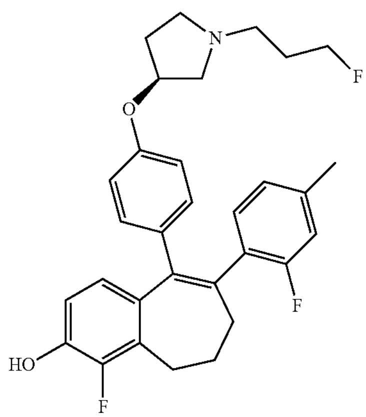 [SMILES: Cc1ccc(C2=C(c3ccc(O[C@H]4CCN(CCCF)C4)cc3)c3ccc(O)c(F)c3CCC2)c(F)c1] | 1-fluoro-6-(2-fluoro-4-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.03 (m, 2 H); 2.19 (m, 3 H); 2.22 (s, 3 H); 2.38 (m, 1 H); 2.47 (t, J = 7.2 Hz, 2 H); 2.53 (m, 1 H); 2.63 (m, 1 H); 2.79 (m, 3 H); 4.47 (td, J = 6.2 and 47.6 Hz, 2 H); 4.72 (m, 1 H); 6.40 (d, J = 8.5 Hz, 1 H); 6.60 (d, J = 8.8 Hz, 2 H); 6.73 d, J = 8.8 Hz, 2 H); 6.74 (t, J = 8.5 Hz, 1 H); 6.83 (d, J = 8.0 Hz, 1 H); 6.89 (d, J = 11.2 Hz, 1 H); 7.01 (t, J = 8.0 Hz, 1 H); 9.83 (s, 1 H) | 508 |
| 46 | 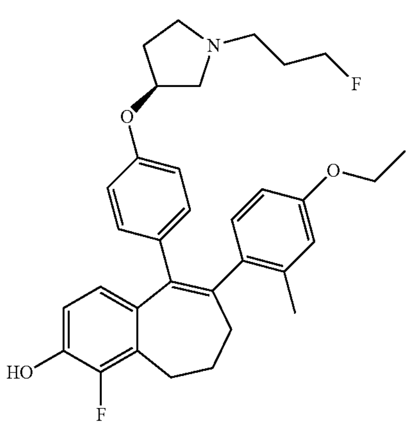 [SMILES: CCOc1ccc(C2=C(c3ccc(O[C@H]4CCN(CCCF)C4)cc3)c3ccc(O)c(F)c3CCC2)c(C)c1] | 6-(4-ethoxy-2-methyl-phenyl)-1-fluoro-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.28 (t, J = 7.1 Hz, 3 H); 1.67 (m, 1 H); 1.79 (dm, J = 25.3 Hz, 2 H); 2.00 to 2.23 (m, 5 H); 2.10 (s, 3 H); 2.37 (m, 1 H); 2.46 (t, J = 7.2 Hz, 2 H); 2.52 (m, 1 H); 2.62 (m, 1 H); 2.74 to 2.85 (m, 3 H); 3.93 (q, J = 7.1 Hz, 2 H); 4.47 (td, J = 6.1 and 47.5 Hz, 2 H); 4.71 (m, 1 H); 6.49 (d, J = 9.0 Hz, 1 H); 6.56 (d, J = 8.9 Hz, 2 H); 6.59 (dd, J = 2.6 and 8.6 Hz, 1 H); 6.65 (d, J = 2.6 Hz, 1 H); 6.68 (d, J = 8.6 Hz, 2 H); 6.71 (t, J = 9.0 Hz, 1 H); 6.90 (d, J = 8.6 Hz, 1 H); 9.80 (s, 1 H) | 534 |

TABLE 1-continued

| Examples | Structure | Name | Method | NMR | MASS: LC/MS (m/z, MH+): |
|---|---|---|---|---|---|
| 47 | 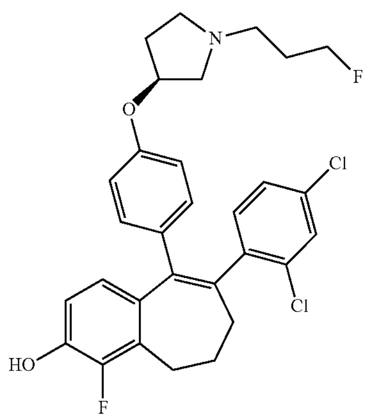 [SMILES: Oc1ccc2c(c1F)CCCC(c1ccc(Cl)cc1Cl)=C2c1ccc(O[C@H]2CCN(CCCF)C2)cc1] | 6-(2,4-dichlorophenyl)-1-fluoro-5-[4-[(3S)-1-(3-fluoropropyl)-pyrrolidin-3-yl]oxyphenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.06 (m, 2 H); 2.19 (m, 3 H); 2.38 (m, 1 H); 2.48 (t, J = 7.2 Hz, 2 H); 2.53 (m, 1 H); 2.64 (m, 1 H); 2.70 to 2.83 (m, 2 H); 2.98 (m, 1 H); 4.48 (td, J = 6.1 and 47.5 Hz, 2 H); 4.72 (m, 1 H); 6.40 (d, J = 8.6 Hz, 1 H); 6.62 (d, J = 8.8 Hz, 2 H); 6.73 (m, 3 H); 7.17 (d, J = 8.6 Hz, 1 H); 7.25 (dd, J = 1.5 and 8.6 Hz, 1 H); 7.58 (d, J = 1.5 Hz, 1 H); 9.89 (s, 1 H) | 544 |
| 48 | 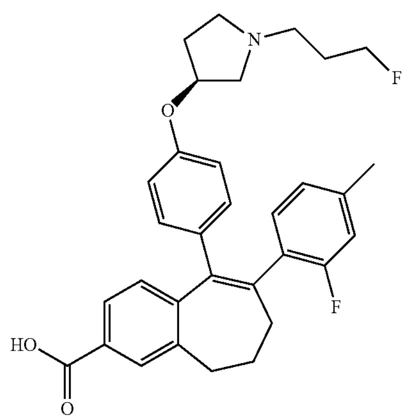 [SMILES: Cc1ccc(C2=C(c3ccc(O[C@H]4CCN(CCCF)C4)cc3)c3ccc(C(=O)O)cc3CCC2)c(F)c1] | 6-(2-fluoro-4-methylphenyl)-5-[4-[(3S)-1-(3-fluoropropyl)-pyrrolidin-3-yl]oxyphenyl]-8,9-dihydro-7H-benzo[7]-annulene-2-carboxylic acid | C | 1H NMR (400 MHz, DMSO-d6, δ ppm): 1.69 (m, 1 H); 1.79 (dm, J = 25.3 Hz, 2 H); 2.07 to 2.22 (m, 5 H); 2.25 (s, 3 H); 2.37 (m, 1 H); 2.47 (t, J = 7.2 Hz, 2 H); 2.52 (m, 1 H); 2.64 (m, 1 H); 2.89 (dd, J = 6.3 and 10.5 Hz, 1 H); 2.83 (t, J = 6.8 Hz, 2 H); 4.46 (td, J = 6.1 and 47.5 Hz, 2 H); 4.73 (m, 1 H) 6.62 (d, J = 8.9 Hz, 2 H); 6.72 (d, J = 8.9 Hz, 2 H); 6.80 to 6.89 (m, 2 H); 6.91 (dd, J = 1.7 and 11.4 Hz, 1 H); 7.05 (t, J = 7.8 Hz, 1 H); 7.72 (dd, J = 1.9 and 8.4 Hz, 1 H); 7.89 (d, J = 1.9 Hz, 1 H); 12.90 (m, 1 H) | 518 |
| 49 | 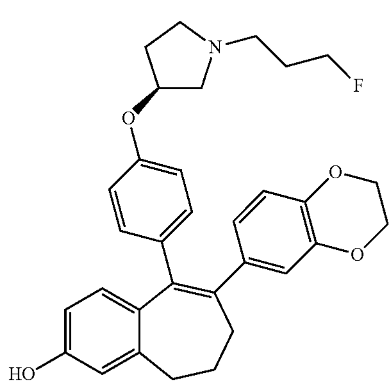 [SMILES: Oc1ccc2c(c1)CCCC(c1ccc3c(c1)OCCO3)=C2c1ccc(O[C@H]2CCN(CCCF)C2)cc1] | 6-(2,3-dihydro-1,4-benzodioxin-6-yl)-5-[4-[(3S)-1-(3-fluoropropyl)-pyrrolidin-3-yl]oxyphenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.02 (m, 2 H); 2.20 (m, 3 H); 2.39 (m, 1 H); 2.47 (t, J = 7.2 Hz, 2 H); 2.55 (dd, J = 3.0 and 10.4 Hz, 1 H); 2.64 (m, 3 H); 2.80 (dd, J = 6.3 and 10.4 Hz, 1 H); 4.15 (s, 4 H); 4.48 (td, J = 6.1 and 47.5 Hz, 2 H); 4.75 (m, 1 H); 6.50 to 6.65 (m, 7 H); 6.67 (s, 1 H); 6.74 (d, J = 8.8 Hz, 2 H); 9.37 (s, 1 H) | 516 |

TABLE 1-continued

| Examples | Structure | Name | Method | NMR | MASS: LC/MS (m/z, MH+): |
|---|---|---|---|---|---|
| 50 | 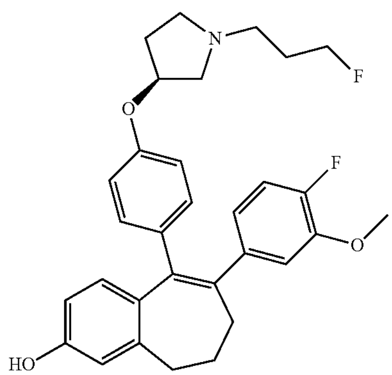 [SMILES: COc1cc(C2=C(c3ccc(O[C@H]4CCN(CCCF)C4)cc3)c3ccc(O)cc3CCC2)ccc1F] | 6-(4-fluoro-3-methoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.05 (m, 2 H); 2.20 (m, 1 H); 2.28 (t, J = 7.0 Hz, 2 H); 2.39 (m, 1 H); 2.45 (t, J = 7.2 Hz, 2 H); 2.54 (dd, J = 3.0 and 10.4 Hz, 1 H); 2.61 to 2.70 (m, 3 H); 2.80 (dd, J = 6.3 and 10.4 Hz, 1 H); 3.59 (s, 3 H); 4.48 (td, J = 6.1 and 47.5 Hz, 2 H); 4.75 (m, 1 H); 6.57 (m, 2 H); 6.64 (d, J = 8.8 Hz, 2 H); 6.68 (m, 1 H); 6.70 (d, J = 2.4 Hz, 1 H); 6.75 (d, J = 8.8 Hz, 2 H); 6.83 (dd, J = 2.4 and 8.7 Hz, 1 H); 6.98 (dd, J = 8.7 and 11.8 Hz, 1 H); 9.39 (s, 1 H) | 506 |
| 51 | 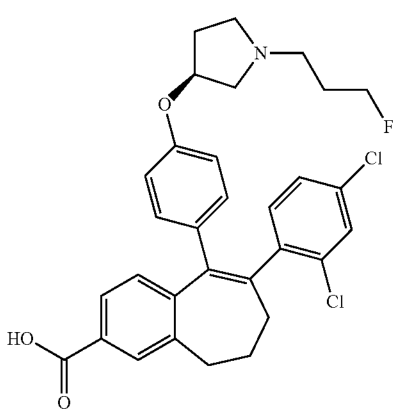 [SMILES: O=C(O)c1ccc2c(c1)CCCC(c1ccc(Cl)cc1Cl)=C2c1ccc(O[C@H]2CCN(CCCF)C2)cc1] | 6-(2,4-dichloro-phenyl)-5-[4-[(3S)-1-(3-fluoropropyl)-pyrrolidin-3-yl]oxy-phenyl]-8,9-dihydro-7H-benzo[7]-annulene-2-carboxylic acid | B | 1H NMR (400 MHz, DMSO-d6, δ ppm): 1.68 (m, 1 H); 1.79 (dm, J = 25.3 Hz, 2 H); 2.07 to 2.23 (m, 5 H); 2.38 (m, 1 H); 2.46 (t, J = 7.2 Hz, 2 H); 2.52 (m, 1 H); 2.62 (m, 1 H); 2.55 to 2.89 (m, 3 H); 4.47 (td, J = 6.2 and 47.6 Hz, 2 H); 4.72 (m, 1 H); 6.63 (d, J = 8.9 Hz, 2 H); 6.71 (m, 3 H); 7.18 (d, J = 8.4 Hz, 1 H); 8.26 (dd, J = 2.0 and 8.4 Hz, 1 H); 7.58 (d, J = 2.0 Hz, 1 H); 7.63 (d, J = 8.4 Hz, 1 H); 7.79 (s, 1 H); 12.3 (m, 1 H) | 554 |
| 52 | 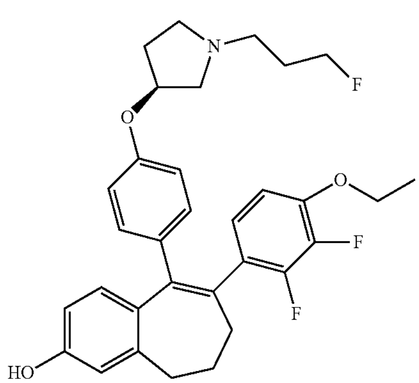 [SMILES: CCOc1ccc(C2=C(c3ccc(O[C@H]4CCN(CCCF)C4)cc3)c3ccc(O)cc3CCC2)c(F)c1F] | 6-(4-ethoxy-2,3-difluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.31 (t, J = 7.1 Hz, 3 H); 1.69 (m, 1 H); 1.79 (dm, J = 25.3 Hz, 2 H); 2.05 (m, 2 H); 2.18 (t, J = 7.0 Hz, 2 H); 2.20 (m, 1 H); 2.39 (m, 1 H); 2.48 (t, J = 7.2 Hz, 2 H); 2.53 (dd, J = 3.0 and 10.4 Hz, 1 H); 2.60 to 2.71 (m, 3 H); 2.79 (dd, J = 6.3 and 10.4 Hz, 1 H); 4.09 (q, J = 7.1 Hz, 2 H); 4.48 (td, J = 6.1 and 47.5 Hz, 2 H); 4.73 (m, 1 H); 6.57 (s, 2 H); 6.62 (d, J = 8.8 Hz, 2 H); 6.70 (s, 1 H); 6.72 (d, J = 8.8 Hz, 2 H); 6.80 to 6.91 (m, 2 H); 9.41 (s, 1 H) | 538 |

TABLE 1-continued

| Examples | Structure | Name | Method | NMR | MASS: LC/MS (m/z, MH+): |
|---|---|---|---|---|---|
| 53 | 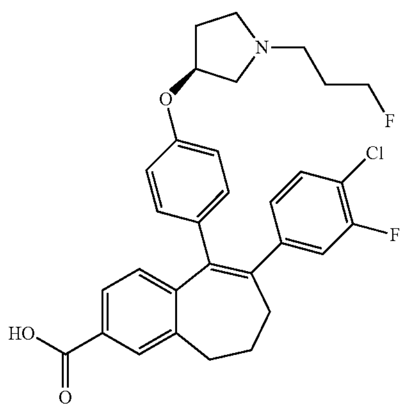 [SMILES: O=C(O)c1ccc2c(c1)CCCC(c1ccc(Cl)c(F)c1)=C2c1ccc(O[C@H]2CCN(CCCF)C2)cc1] | 6-(4-chloro-3-fluoro-phenyl)-5-[4-[(3S)-1-(3-fluoropropyl)-pyrrolidin-3-yl]oxy-phenyl]-8,9-dihydro-7H-benzo[7]-annulene-2-carboxylic acid | B | 1H NMR (400 MHz, DMSO-d6, δ ppm): 1.70 (m, 1 H); 1.80 (dm, J = 25.3 Hz, 2 H); 2.10 (m, 2 H); 2.17 to 2.28 (m, 3 H); 2.39 (m, 1 H); 2.47 (t, J = 7.2 Hz, 2 H); 2.55 (dd, J = 3.2 and 10.5 Hz, 1 H); 2.66 (m, 1 H); 2.80 (m, 3 H); 4.47 (td, J = 6.1 and 47.5 Hz, 2 H); 4.78 (m, 1 H); 6.68 (d, J = 8.9 Hz, 2 H); 6.73 (m, 1 H); 6.76 (d, J = 8.9 Hz, 2 H); 6.99 (dd, J = 2.3 and 8.4 Hz, 1 H); 7.20 (dd, J = 2.3 and 10.8 Hz, 1 H); 7.39 (t, J = 8.4 Hz, 1 H); 7.66 (d, J = 8.5 Hz, 1 H); 7.80 (s, 1 H); 12.90 (m, 1 H) | 538 |
| 54 | 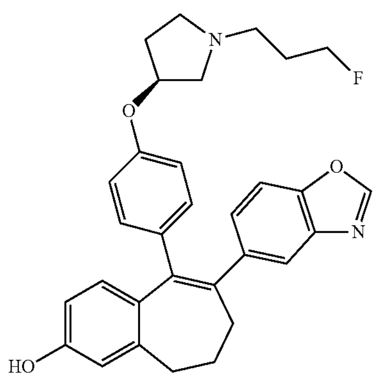 [SMILES: Oc1ccc2c(c1)CCCC(c1ccc3ocnc3c1)=C2c1ccc(O[C@H]2CCN(CCCF)C2)cc1] | 6-(1,3-benzoxazol-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.67 (m, 1 H); 1.78 (dm, J = 25.3 Hz, 2 H); 2.05 (m, 2 H); 2.17 (m, 1 H); 2.30 to 2.39 (m, 3 H); 2.44 (t, J = 7.2 Hz, 2 H); 2.52 (m, 1 H); 2.62 (m, 1 H); 2.70 (t, J = 7.0 Hz, 2 H); 2.77 (dd, J = 6.2 and 10.5 Hz, 1 H); 4.47 (td, J = 6.1 and 47.5 Hz, 2 H); 4.71 (m, 1 H); 6.55 (m, 4 H); 6.69 (s, 1 H); 6.72 (d, J = 8.8 Hz, 2 H); 7.19 (dd, J = 1.6 and 8.8 Hz, 1 H); 7.54 (m, 2 H); 8.65 (s, 1 H); 9.39 (s, 1 H) | 499 |
| 55 | 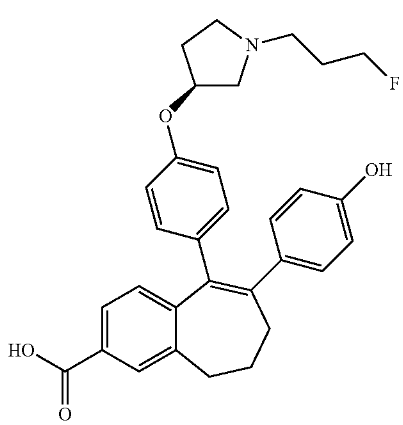 [SMILES: O=C(O)c1ccc2c(c1)CCCC(c1ccc(O)cc1)=C2c1ccc(O[C@H]2CCN(CCCF)C2)cc1] | 5-[4-[(3S)-1-(3-fluoropropyl)-pyrrolidin-3-yl]oxy-phenyl]-6-(4-hydroxy-phenyl)-8,9-dihydro-7H-benzo[7]-annulene-2-carboxylic acid | B | 1H NMR (400 MHz, DMSO-d6, δ ppm): 1.70 (m, 1 H); 1.80 (dm, J = 25.3 Hz, 2 H); 2.08 (m, 2 H); 2.20 (m, 3 H); 2.38 (m, 1 H); 2.47 (m, 2 H); 2.54 (dd, J = 3.0 and 10.4 Hz, 1 H); 2.64 (m, 1 H); 2.73 to 2.83 (m, 3 H); 4.48 (td, J = 6.1 and 47.5 Hz, 2 H); 4.75 (m, 1 H); 6.56 (d, J = 8.8 Hz, 2 H); 6.62 (d, J = 8.8 Hz, 2 H); 6.73 (d, J = 8.8 Hz, 2 H); 6.77 (d, J = 8.3 Hz, 1 H); 6.95 (d, J = 8.8 Hz, 2 H); 7.68 (dd, J = 2.0 and 8.3 Hz, 1 H); 7.82 (d, J = 2.0 Hz, 1 H); 9.36 (s, 1 H); 12.80 (m, 1 H) | 502 |

TABLE 1-continued

| Examples | Structure | Name | Method | NMR | MASS: LC/MS (m/z, MH+): |
|---|---|---|---|---|---|
| 56 | 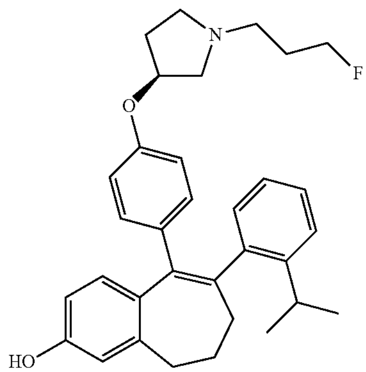 [SMILES: CC(C)c1ccccc1C1=C(c2ccc(O[C@H]3CCN(CCCF)C3)cc2)c2ccc(O)cc2CCC1] | 5-[4-[(3S)-1-(3-fluoropropyl)-pyrrolidin-3-yl]oxy-phenyl]-6-(2-isopropyl-phenyl)-8,9-dihydro-7H-benzo[7]-annulen-2-ol | A | 1H NMR (400 MHz, DMSO-d6, δ ppm): 0.70 (d, J = 6.8 Hz, 3 H); 1.09 (d, J = 6.8 Hz, 3 H); 1.63 (m, 1 H); 1.77 (dm, J = 25.3 Hz, 2 H); 2.05 (m, 2 H); 2.17 (m, 3 H); 2.35 (m, 1 H); 2.43 (t, J = 7.2 Hz, 2 H); 2.50 (m, 1 H); 2.61 (m, 1 H); 2.69 to 2.78 (m, 3 H); 3.11 (m, 1 H); 4.47 (td, J = 6.1 and 47.5 Hz, 2 H); 4.71 (m, 1 H); 6.52 to 6.60 (m, 4 H); 6.68 (d, J = 8.8 Hz, 2 H); 6.70 (d, J = 2.0 Hz, 1 H); 7.02 to 7.20 (m, 4 H); 9.36 (s, 1 H) | 500 |
| 57 | 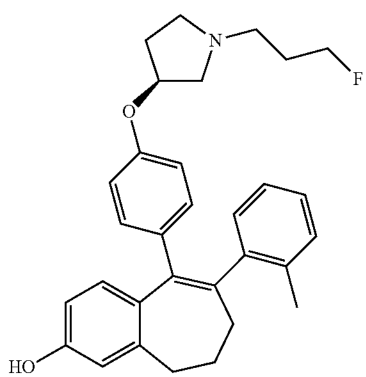 [SMILES: Cc1ccccc1C1=C(c2ccc(O[C@H]3CCN(CCCF)C3)cc2)c2ccc(O)cc2CCC1] | 5-[4-[(3S)-1-(3-fluoropropyl)-pyrrolidin-3-yl]oxy-phenyl]-6-(o-tolyl)-8,9-dihydro-7H-benzo[7]-annulen-2-ol | A | 1H NMR (400 MHz, DMSO-d6, δ ppm): 1.66 (m, 1 H); 1.79 (dm, J = 25.3 Hz, 2 H); 2.01 to 2.22 (m, 5 H); 2.12 (s, 3 H); 2.35 (m, 1 H); 2.44 (m, 2 H); 2.53 (m, 1 H); 2.59 to 2.82 (m, 4 H); 4.46 (td, J = 6.1 and 47.5 Hz, 2 H); 4.70 (m, 1 H); 6.54 (d, J = 8.8 Hz, 2 H); 6.57 (s, 2 H); 6.66 (d, J = 8.8 Hz, 2 H); 6.70 (s, 1 H); 6.99 to 7.11 (m, 4 H); 9.37 (s, 1 H) | 472 |
| 58 | 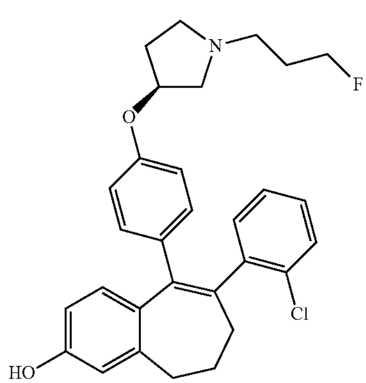 [SMILES: Oc1ccc2c(c1)CCCC(c1ccccc1Cl)=C2c1ccc(O[C@H]2CCN(CCCF)C2)cc1] | 6-(2-chlorophenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.66 (m, 1 H); 1.79 (dm, J = 25.3 Hz, 2 H); 2.06 (m, 2 H); 2.18 (m, 3 H); 2.37 (m, 1 H); 2.44 (t, J = 7.2 Hz, 2 H); 2.52 (m, 1 H); 2.61 (m, 1 H); 2.69 to 2.85 (m, 3 H); 4.46 (td, J = 6.1 and 47.5 Hz, 2 H); 4.71 (m, 1 H); 6.57 (m, 4 H); 6.71 (m, 3 H); 7.08 to 7.20 (m, 3 H); 7.39 (d, J = 8.2 Hz, 1 H); 9.40 (s, 1 H) | 492 |

TABLE 1-continued

| Examples | Structure | Name | Method | NMR | MASS: LC/MS (m/z, MH+): |
|---|---|---|---|---|---|
| 59 | 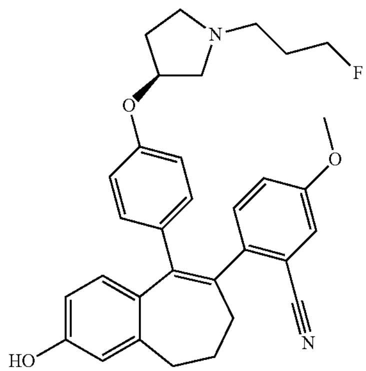 [SMILES: COc1ccc(C2=C(c3ccc(O[C@H]4CCN(CCCF)C4)cc3)c3ccc(O)cc3CCC2)c(C#N)c1] | 2-[5-[4-[(3S)-1-(3-fluoropropyl)-pyrrolidin-3-yl]oxy-phenyl]-2-hydroxy-8,9-dihydro-7H-benzo[7]-annulen-6-yl]-5-methoxy-benzonitrile | A | 1H NMR (400 MHz, DMSO-d6, δ ppm): 1.68 (m, 1 H); 1.80 (dm, J = 25.3 Hz, 2 H); 2.09 (m, 2 H); 2.14 to 2.26 (m, 3 H); 2.38 (m, 1 H); 2.46 (t, J = 7.2 Hz, 2 H); 2.54 (dd, J = 3.0 and 10.4 Hz, 1 H); 2.64 (m, 1 H); 2.80 (m, 3 H); 3.76 (s, 3 H); 4.47 (td, J = 6.1 and 47.5 Hz, 2 H); 4.73 (m, 1 H); 6.57 (m, 2 H); 6.61 (d, J = 8.8 Hz, 2 H); 6.70 (d, J = 8.8 Hz, 2 H); 6.72 (s, 1 H); 7.17 (dd, J = 2.8 and 8.6 Hz, 1 H); 7.21 (d, J = 2.8 Hz, 1 H); 7.33 (d, J = 8.6 Hz, 1 H); 9.44 (s, 1 H) | 513 |
| 60 | 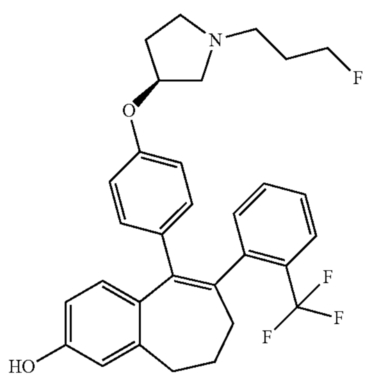 [SMILES: Oc1ccc2c(c1)CCCC(c1ccccc1C(F)(F)F)=C2c1ccc(O[C@H]2CCN(CCCF)C2)cc1] | 5-[4-[(3S)-1-(3-fluoropropyl)-pyrrolidin-3-yl]oxy-phenyl]-6-[2-(trifluoro-methyl)phenyl]-8,9-dihydro-7H-benzo[7]-annulen-2-ol | A | 1H NMR (400 MHz, DMSO-d6, δ ppm): 1.65 (m, 1 H); 1.78 (dm, J = 25.3 Hz, 2 H); 2.02 to 2.27 (m, 5 H); 2.36 (m, 1 H); 2.43 (t, J = 7.2 Hz, 2 H); 2.52 (m, 1 H); 2.58 to 2.69 (m, 2 H); 2.77 (m, 1 H); 2.85 (m, 1 H); 4.47 (td, J = 6.1 and 47.5 Hz, 2 H); 4.70 (m, 1 H); 6.57 (m, 4 H); 6.70 (m, 3 H); 7.14 (d, J = 8.2 Hz, 1 H); 7.32 to 7.45 (m, 2 H); 7.69 (d, J = 8.2 Hz, 1 H); 9.40 (s, 1 H) | 526 |
| 61 | 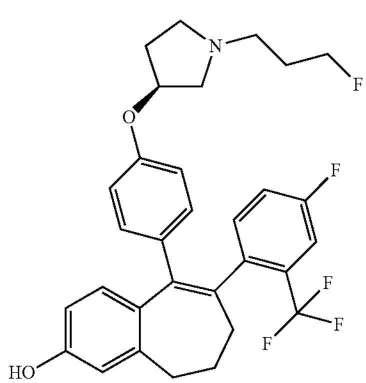 [SMILES: Oc1ccc2c(c1)CCCC(c1ccc(F)cc1C(F)(F)F)=C2c1ccc(O[C@H]2CCN(CCCF)C2)cc1] | 5-[4-[(3S)-1-(3-fluoropropyl)-pyrrolidin-3-yl]oxy-phenyl]-6-[4-fluoro-2-(trifluoro-methyl)phenyl]-8,9-dihydro-7H-benzo[7]-annulen-2-ol | A | 1H NMR (400 MHz, DMSO-d6, δ ppm): 1.65 (m, 1 H); 1.79 (dm, J = 25.3 Hz, 2 H); 2.03 to 2.24 (m, 5 H); 2.37 (m, 1 H); 2.46 (t, J = 7.2 Hz, 2 H); 2.54 (m, 1 H); 2.63 (m, 2 H); 2.73 to 2.80 (m, 2 H); 4.47 (td, J = 6.1 and 47.5 Hz, 2 H); 4.71 (m, 1 H); 6.55 (m, 2 H); 6.60 (d, J = 8.8 Hz, 2 H); 6.69 (d, J = 8.8 Hz, 2 H); 6.71 (s, 1 H); 7.20 (dd, J = 6.0 and 8.8 Hz, 1 H); 7.32 (dt, J = 2.8 and 8.8 Hz, 1 H); 7.60 (dd, J = 2.8 and 9.6 Hz, 1 H); 9.41 (s, 1 H) | 544 |

TABLE 1-continued

| Examples | Structure | Name | Method | NMR | MASS: LC/MS (m/z, MH+): |
|---|---|---|---|---|---|
| 62 | 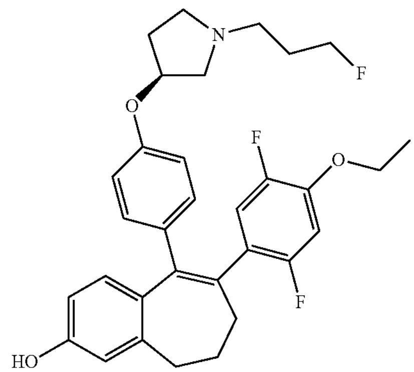 | 6-(4-ethoxy-2,5-difluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.30 (t, J = 7.0 Hz, 3 H); 1.69 (m, 1 H); 1.79 (dm, J = 25.3 Hz, 2 H); 2.05 (m, 2 H); 2.11 to 2.23 (m, 3 H); 2.39 (m, 1 H); 2.47 (t, J = 7.2 Hz, 2 H); 2.52 (m, 1 H); 2.60 to 2.71 (m, 3 H); 2.80 (dd, J = 6.4 and 10.5 Hz, 1 H); 4.04 (q, J = 7.0 Hz, 2 H); 4.48 (td, J = 6.2 and 47.6 Hz, 2 H); 4.74 (m, 1 H); 6.57 (s, 2 H); 6.62 (d, J = 8.9 Hz, 2 H); 6.70 (s, 1 H); 6.73 (d, J = 8.9 Hz, 2 H); 6.92 (dd, J = 7.4 and 11.2 Hz, 1 H); 7.00 (dd, J = 7.0 and 11.8 Hz, 1 H); 9.41 (s, 1 H) | 538 |
| 63 | 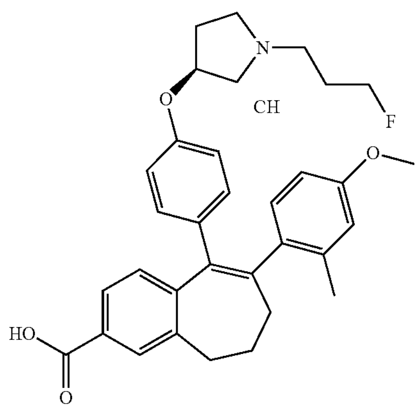 | 5-[4-[(3S)-1-(3-fluoropropyl)-pyrrolidin-3-yl]oxy-phenyl]-6-(4-methoxy-2-methyl-phenyl)-8,9-dihydro-7H-benzo[7]-annulene-2-carboxylic acid hydrochloride | B | 1H NMR (500 MHz, DMSO-d6, δ ppm): 1.92 to 2.30 (m, 8 H); 2.12 (s, 3 H); 2.89 (m, 2 H); 3.09 to 3.40 (m, 4 H); 3.67 (m, 2 H); 3.70 (s, 3 H); 4.52 (td, J = 5.7 and 47.0 Hz, 2 H); 4.95 to 5.08 (m, 1 H); 6.63 (dd, J = 2.6 and 8.5 Hz, 1 H); 6.68 (d, J = 9.0 Hz, 2 H); 6.70 (d, J = 2.6 Hz, 1 H); 6.73 (d, J = 9.0 Hz, 2 H); 6.84 (d, J = 8.0 Hz, 1 H); 6.97 (d, J = 8.5 Hz, 1 H); 7.84 (dd, J = 1.9 and 8.0 Hz, 1 H); 7.90 (d, J = 1.9 Hz, 1 H); 10.30 (s, 0.5 H); 10.64 (s, 0.5 H); 12.86 (s, 1 H) | 530 |
| 64 | 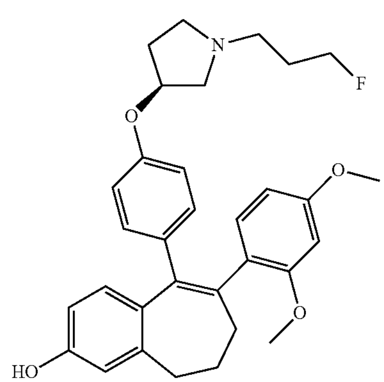 [SMILES: COc1ccc(C2=C(c3ccc(O[C@H]4CCN(CCCF)C4)cc3)c3ccc(O)cc3CCC2)c(OC)c1] | 6-(2,4-dimethoxy phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 1.99 (m, 2 H); 2.09 (m, 2 H); 2.19 (m, 1 H); 2.38 (m, 1 H); 2.46 (t, J = 7.2 Hz, 2 H); 2.52 (m, 1 H); 2.59 to 2.71 (m, 3 H); 2.78 (dd, J = 6.4 and 10.4 Hz, 1 H); 3.70 (s, 6 H); 4.46 (td, J = 6.1 and 47.5 Hz, 2 H); 4.71 (m, 1 H); 6.29 (dd, J = 2.5 and 8.5 Hz, 1 H); 6.49 (d, J = 2.5 Hz, 1 H); 6.54 (d, J = 1.5 Hz, 2 H); 6.56 (d, J = 8.8 Hz, 2 H); 6.68 (t, J = 1.5 Hz, 1 H); 6.70 (d, J = 8.8 Hz, 2 H); 6.75 (d, J = 8.5 Hz, 1 H); 9.30 (s, 1 H) | 518 |

TABLE 1-continued

| Examples | Structure | Name | Method | NMR | MASS: LC/MS (m/z, MH+): |
|---|---|---|---|---|---|
| 65 | 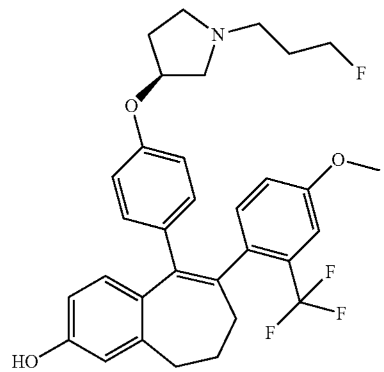 [SMILES: COc1ccc(C2=C(c3ccc(O[C@H]4CCN(CCCF)C4)cc3)c3ccc(O)cc3CCC2)c(C(F)(F)F)c1] | 5-[4-[(3S)-1-(3-fluoropropyl)-pyrrolidin-3-yl]oxy-phenyl]-6-[4-methoxy-2-(trifluoro-methyl)phenyl]-8,9-dihydro-7H-benzo[7]-annulen-2-ol | A | 1H NMR (400 MHz, DMSO-d6, δ ppm): 1.65 (m, 1 H); 1.79 (dm, J = 25.3 Hz, 2 H); 2.00 to 2.25 (m, 5 H); 2.37 (m, 1 H); 2.45 (t, J = 7.2 Hz, 2 H); 2.52 (m, 2 H); 2.62 (m, 1 H); 2.72 to 2.81 (m, 2 H); 3.78 (s, 3 H); 4.45 (td, J = 6.1 and 47.5 Hz, 2 H); 4.70 (m, 1 H); 6.55 (s, 2 H); 6.59 (d, J = 8.8 Hz, 2 H); 6.70 (s, 1 H); 6.72 (d, J = 8.8 Hz, 2 H); 7.00 (dd, J = 2.8 and 8.7 Hz, 1 H); 7.17 (d, J = 8.7 Hz, 1 H); 7.27 (d, J = 2.8 Hz, 1 H); 9.39 (s, 1 H) | 556 |
| 66 | 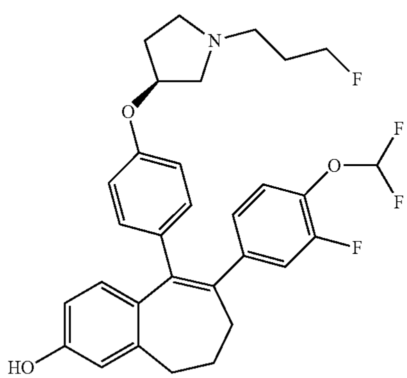 [SMILES: Oc1ccc2c(c1)CCCC(c1ccc(OC(F)F)c(F)c1)=C2c1ccc(O[C@H]2CCN(CCCF)C2)cc1] | 6-[4-(difluoro-methoxy)-3-fluoro-phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.05 (m, 2 H); 2.15 to 2.28 (m, 3 H); 2.39 (m, 1 H); 2.48 (m, 2 H); 2.54 (m, 1 H); 2.68 (m, 3 H); 2.79 (dd, J = 6.3 and 10.4 Hz, 1 H); 4.46 (td, J = 6.1 and 47.5 Hz, 2 H); 4.77 (m, 1 H); 6.56 (s, 2 H); 6.64 (d, J = 8.8 Hz, 2 H); 6.70 (s, 1 H); 6.74 (d, J = 8.8 Hz, 2 H); 6.96 (d, J = 8.6 Hz, 1 H); 7.07 to 7.18 (m, 2 H); 7.19 (t, J = 73.8 Hz, 1 H); 9.41 (s, 1 H) | 542 |
| 67 | 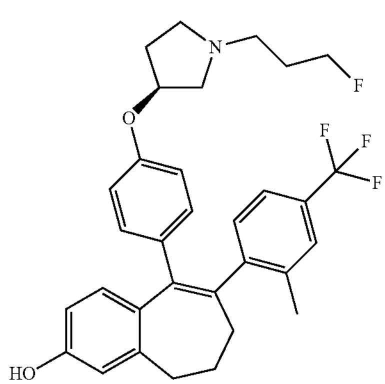 [SMILES: Cc1cc(C(F)(F)F)ccc1C1=C(c2ccc(O[C@H]3CCN(CCCF)C3)cc2)c2ccc(O)cc2CCC1] | 5-[4-[(3S)-1-(3-fluoropropyl)-pyrrolidin-3-yl]oxy-phenyl]-6-[2-methyl-4-(trifluoro-methyl)phenyl]-8,9-dihydro-7H-benzo[7]-annulen-2-ol | A | 1H NMR (400 MHz, DMSO-d6, δ ppm): 1.65 (m, 1 H); 1.78 (dm, J = 25.3 Hz, 2 H); 2.01 to 2.25 (m, 5 H); 2.21 (s, 3 H); 2.36 (m, 1 H); 2.45 (t, J = 7.2 Hz, 2 H); 2.52 (m, 1 H); 2.59 to 2.81 (m, 4 H); 4.46 (td, J = 6.1 and 47.5 Hz, 2 H); 4.70 (m, 1 H); 6.58 (m, 4 H); 6.66 (d, J = 8.8 Hz, 2 H); 6.72 (s, 1 H); 7.22 (dd, J = 3.0 and 8.6 Hz, 1 H); 7.38 (d, J = 8.6 Hz, 1 H); 7.47 (s, 1 H); 9.40 (s, 1 H) | 540 |

TABLE 1-continued

| Examples | Structure | Name | Method | NMR | MASS: LC/MS (m/z, MH+): |
|---|---|---|---|---|---|
| 68 | 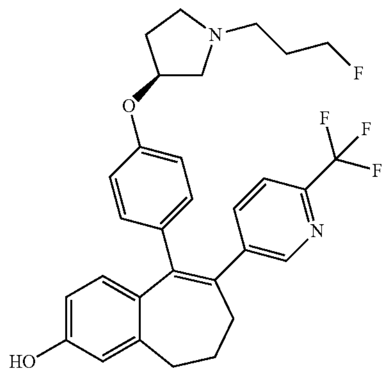 [SMILES: Oc1ccc2c(c1)CCCC(c1ccc(C(F)(F)F)nc1)=C2c1ccc(O[C@H]2CCN(CCCF)C2)cc1] | 5-[4-[(3S)-1-(3-fluoropropyl)-pyrrolidin-3-yl]oxy-phenyl]-6-[6-(trifluoro-methyl)-3-pyridyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.08 (m, 2 H); 2.20 (m, 1 H); 2.31 (t, J = 7.0 Hz, 2 H); 2.38 (m, 1 H); 2.48 (t, J = 7.2 Hz, 2 H); 2.54 (dd, J = 3.0 and 10.4 Hz, 1 H); 2.65 (m, 1 H); 2.70 (t, J = 7.2 Hz, 2 H); 2.79 (dd, J = 6.3 and 10.4 Hz, 1 H); 4.46 (td, J = 6.1 and 47.5 Hz, 2 H); 4.75 (m, 1 H); 6.59 (s, 2 H); 6.66 (d, J = 8.8 Hz, 2 H); 6.72 (s, 1 H); 6.76 (d, J = 8.8 Hz, 2 H); 7.72 (d, J = 8.2 Hz, 1 H); 7.83 (dd, J = 2.5 and 8.2 Hz, 1 H); 8.40 (d, J = 2.5 Hz, 1 H); 9.50 (s, 1 H) | 527 |
| 69 | 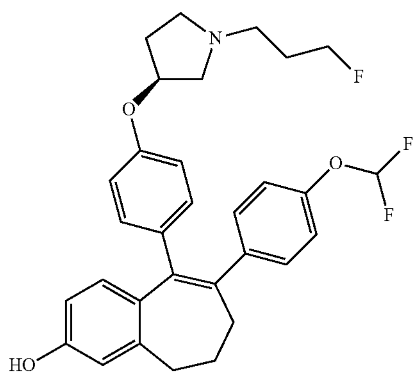 [SMILES: Oc1ccc2c(c1)CCCC(c1ccc(OC(F)F)cc1)=C2c1ccc(O[C@H]2CCN(CCCF)C2)cc1] | 6-[4-(difluoro-methoxy)phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.80 (dm, J = 25.3 Hz, 2 H); 2.04 (m, 2 H); 2.05 to 2.29 (m, 3 H); 2.39 (m, 1 H); 2.48 (m, 2 H); 2.53 (m, 1 H); 2.65 (m, 3 H); 2.79 (m, 1 H); 4.47 (td, J = 6.1 and 47.5 Hz, 2 H); 4.73 (m, 1 H); 6.55 (d, J = 1.5 Hz, 2 H); 6.61 (d, J = 8.8 Hz, 2 H); 6.70 (d, J = 8.8 Hz, 2 H); 6.73 (s, 1 H); 6.97 (d, J = 8.5 Hz, 2 H); 7.25 (d, J = 8.5 Hz, 2 H); 7.29 (t, J = 74.5 Hz, 1 H); 9.38 (s, 1 H) | 524 |
| 70 | 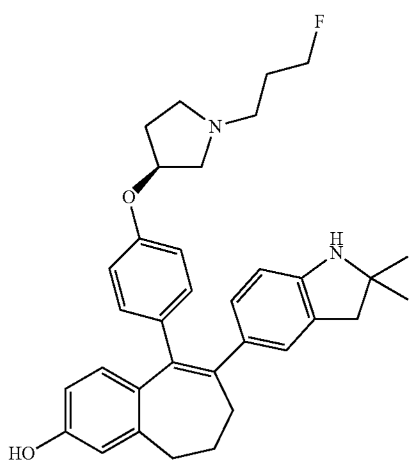 [SMILES: CC1(C)Cc2cc(C3=C(c4ccc(O[C@H]5CCN(CCCF)C5)cc4)c4ccc(O)cc4CCC3)ccc2N1] | 6-(2,2-dimethyl-indolin-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.13 (m, 2 H); 1.18 (s, 6 H); 1.65 to 1.88 (m, 3 H); 2.01 (m, 2 H); 2.20 (m, 3 H); 2.33 to 2.70 (m, 7 H); 2.79 (m, 1 H); 4.46 (td, J = 6.1 and 47.5 Hz, 2 H); 4.73 (m, 1 H); 5.34 (s, 1 H); 6.19 (d, J = 8.0 Hz, 1 H); 6.48 to 6.75 (m, 9 H); 9.28 (s, 1 H) | 527 |

TABLE 1-continued

| Examples | Structure | Name | Method | NMR | MASS: LC/MS (m/z, MH+): |
|---|---|---|---|---|---|
| 71 | 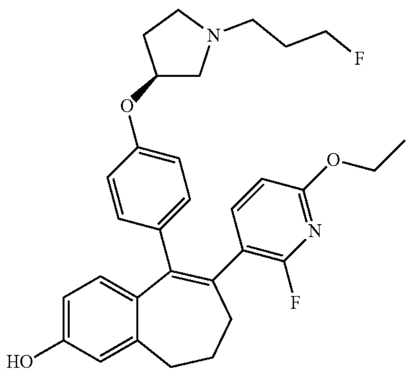 [SMILES: CCOc1ccc(C2=C(c3ccc(O[C@H]4CCN(CCCF)C4)cc3)c3ccc(O)cc3CCC2)c(F)n1] | 6-(6-ethoxy-2-fluoro-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 0.77 (t, J = 7.1 Hz, 3 H); 1.71 (m, 1 H); 1.81 (dm, J = 25.3 Hz, 2 H); 2.05 (m, 2 H); 2.17 (t, J = 7.0 Hz, 2 H); 2.22 (m, 1 H); 2.35 to 2.93 (m, 6 H); 2.68 (t, J = 7.0 Hz, 2 H); 4.18 (q, J = 7.1 Hz, 2 H); 4.48 (td, J = 6.1 and 47.5 Hz, 2 H); 4.78 (m, 1 H); 6.55 (s, 2 H); 6.59 (d, J = 8.3 Hz, 1 H); 6.64 (d, J = 8.8 Hz, 2 H); 6.70 (s, 1 H); 6.74 (d, J = 8.8 Hz, 2 H); 7.58 (dd, J = 8.3 and 10.2 Hz, 1 H); 9.42 (s, 1 H) | 521 |
| 72 | 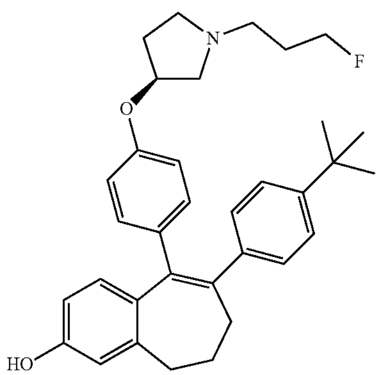 [SMILES: CC(C)(C)c1ccc(C2=C(c3ccc(O[C@H]4CCN(CCCF)C4)cc3)c3ccc(O)cc3CCC2)cc1] | 6-(4-tert-butyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.21 (s, 9 H); 1.70 (m, 1 H); 1.79 (dm, J = 25.3 Hz, 2 H); 2.03 (m, 2 H); 2.20 (m, 1 H); 2.25 (t, J = 7.0 Hz, 2 H); 2.38 (m, 1 H); 2.47 (t, J = 7.2 Hz, 2 H); 2.54 (dd, J = 3.2 and 10.4 Hz, 1 H); 2.65 (m, 3 H); 2.78 (dd, J = 6.4 and 10.4 Hz, 1 H); 4.47 (td, J = 6.1 and 47.5 Hz, 2 H); 4.74 (m, 1 H); 6.55 (m, 2 H); 6.59 (d, J = 8.8 Hz, 2 H); 6.69 (s, 1 H); 6.72 (d, J = 8.8 Hz, 2 H); 7.03 (d, J = 8.6 Hz, 2 H); 7.18 (d, J = 8.6 Hz, 2 H); 9.35 (s, 1 H) | 514 |
| 73 | 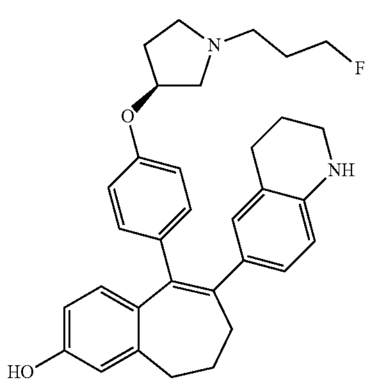 [SMILES: Oc1ccc2c(c1)CCCC(c1ccc3c(c1)CCCN3)=C2c1ccc(O[C@H]2CCN(CCCF)C2)cc1] | 5-[4-[(3S)-1-(3-fluoropropyl)-pyrrolidin-3-yl]oxy-phenyl]-6-(1,2,3,4-tetrahydroquinolin-6-yl)-8,9-dihydro-7H-benzo[7]-annulen-2-ol | A | 1H NMR (400 MHz, DMSO-d6, δ ppm): 1.65 to 1.88 (m, 5 H); 2.00 (m, 2 H); 2.19 (m, 3 H); 2.39 (m, 1 H); 2.43 to 2.52 (m, 4 H); 2.55 (dd, J = 3.0 and 10.4 Hz, 1 H); 2.59 to 2.69 (m, 3 H); 2.80 (dd, J = 6.4 and 10.4 Hz, 1 H); 3.10 (m, 2 H); 4.47 (td, J = 6.1 and 47.5 Hz, 2 H); 4.75 (m, 1 H); 5.52 (s, 1 H); 6.17 (d, J = 8.3 Hz, 1 H); 6.52 (m, 2 H); 6.59 to 6.66 (m, 5 H); 6.74 (d, J = 8.8 Hz, 2 H); 9.28 (s, 1 H) | 513 |

TABLE 1-continued

| Examples | Structure | Name | Method | NMR | MASS: LC/MS (m/z, MH+): |
|---|---|---|---|---|---|
| 74 | 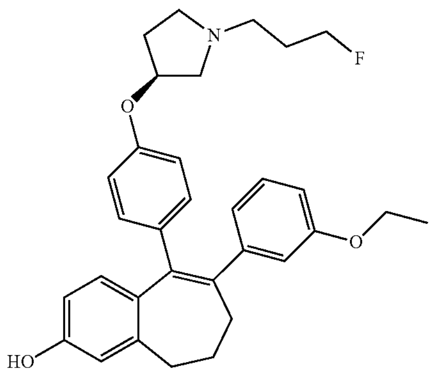 [SMILES: CCOc1cccc(C2=C(c3ccc(O[C@H]4CCN(CCCF)C4)cc3)c3ccc(O)cc3CCC2)c1] | 6-(3-ethoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.20 (t, J = 7.1 Hz, 3 H); 1.69 (m, 1 H); 1.80 (dm, J = 25.3 Hz, 2 H); 2.04 (m, 2 H); 2.19 (m, 1 H); 2.25 (t, J = 7.0 Hz, 2 H); 2.39 (m, 1 H); 2.48 (t, J = 7.2 Hz, 2 H); 2.54 (m, 1 H); 2.66 (m, 3 H); 2.80 (dd, J = 6.4 and 10.4 Hz, 1 H); 3.82 (q, J = 7.1 Hz, 2 H); 4.47 (td, J = 6.1 and 47.5 Hz, 2 H); 4.75 (m, 1 H); 6.55 (m, 2 H); 6.59 to 6.71 (m, 6 H); 6.73 (d, J = 8.8 Hz, 2 H); 7.07 (t, J = 8.0 Hz, 1 H); 9.37 (s, 1 H) | 502 |
| 75 | 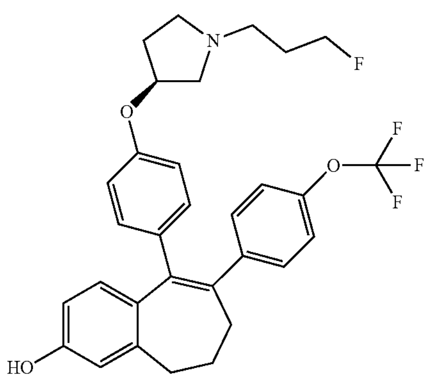 [SMILES: Oc1ccc2c(c1)CCCC(c1ccc(OC(F)(F)F)cc1)=C2c1ccc(O[C@H]2CCN(CCCF)C2)cc1] | 5-[4-[(3S)-1-(3-fluoropropyl)-pyrrolidin-3-yl]oxy-phenyl]-6-[4-(trifluoro-methoxy)-phenyl]-8,9-dihydro-7H-benzo[7]-annulen-2-ol | A | 1H NMR (400 MHz, DMSO-d6, δ ppm): 1.28 (t, J = 7.0 Hz, 6 H); 1.70 (m, 1 H); 1.80 (dm, J = 25.3 Hz, 2 H); 2.10 (m, 2 H); 2.20 (m, 1 H); 2.27 (t, J = 7.0 Hz, 2 H); 2.41 (m, 1 H); 2.48 (m, 2 H); 2.57 (m, 1 H); 2.68 (m, 1 H); 2.78 (t, J = 7.0 Hz, 2 H); 2.82 (m, 1 H); 4.17 (m, 4 H); 4.47 (td, J = 6.1 and 47.5 Hz, 2 H); 4.76 (m, 1 H); 6.64 (d, J = 8.8 Hz, 2 H); 6.73 (d, J = 8.8 Hz, 2 H); 6.79 (d, J = 8.6 Hz, 1 H); 7.03 (ddd, J = 1.3 and 2.8 and 8.6 Hz, 1 H); 7.16 (d, J = 2.8 Hz, 1 H); 7.18 (d, J = 8.9 Hz, 2 H); 7.28 (d, J = 8.9 Hz, 2 H) | 542 |
| 76 | 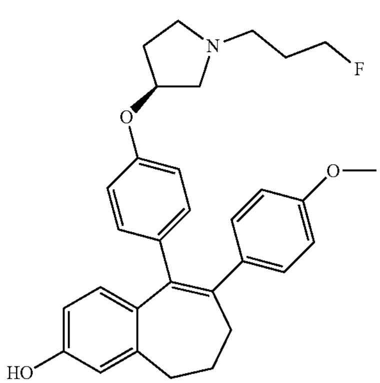 [SMILES: COc1ccc(C2=C(c3ccc(O[C@H]4CCN(CCCF)C4)cc3)c3ccc(O)cc3CCC2)cc1] | 5-[4-[(3S)-1-(3-fluoropropyl)-pyrrolidin-3-yl]oxy-phenyl]-6-(4-methoxy-phenyl)-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.03 (m, 2 H); 2.17 (m, 1 H); 2.23 (t, J = 7.0 Hz, 2 H); 2.39 (m, 1 H); 2.46 (t, J = 7.2 Hz, 2 H); 2.54 (m, 1 H); 2.65 (m, 3 H); 2.80 (dd, J = 6.4 and 10.4 Hz, 1 H); 3.69 (s, 3 H); 4.46 (td, J = 6.1 and 47.5 Hz, 2 H); 4.73 (m, 1 H); 6.54 (s, 2 H); 6.60 (d, J = 8.7 Hz, 2 H); 6.68 (s, 1 H); 6.72 (m, 4 H); 7.04 (d, J = 8.7 Hz, 2 H); 9.31 (s, 1 H) | 488 |

TABLE 1-continued

| Examples | Structure | Name | Method | NMR | MASS: LC/MS (m/z, MH+): |
|---|---|---|---|---|---|
| 77 | 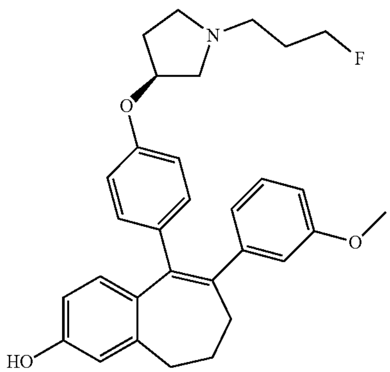 [SMILES: COc1cccc(C2=C(c3ccc(O[C@H]4CCN(CCCF)C4)cc3)c3ccc(O)cc3CCC2)c1] | 5-[4-[(3S)-1-(3-fluoropropyl)-pyrrolidin-3-yl]oxy-phenyl]-6-(3-methoxy-phenyl)-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.04 (m, 2 H); 2.19 (m, 1 H); 2.26 (t, J = 7.0 Hz, 2 H); 2.39 (m, 1 H); 2.47 (t, J = 7.2 Hz, 2 H); 2.54 (dd, J = 3.0 and 10.4 Hz, 1 H); 2.60 to 2.71 (m, 3 H); 2.79 (dd, J = 6.4 and 10.4 Hz, 1 H); 3.49 (s, 3 H); 4.47 (td, J = 6.1 and 47.5 Hz, 2 H); 4.74 (m, 1 H); 6.55 (s, 2 H); 6.61 (d, J = 8.8 Hz, 2 H); 6.62 to 6.70 (m, 4 H); 6.73 (d, J = 8.8 Hz, 2 H); 7.08 (m, 1 H); 9.38 (s, 1 H) | 488 |
| 78 | 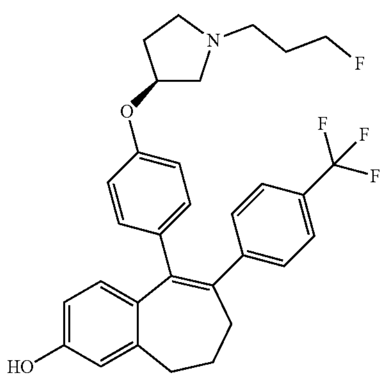 [SMILES: Oc1ccc2c(c1)CCCC(c1ccc(C(F)(F)F)cc1)=C2c1ccc(O[C@H]2CCN(CCCF)C2)cc1] | 5-[4-[(3S)-1-(3-fluoropropyl)-pyrrolidin-3-yl]oxy-phenyl]-6-[4-(trifluoro-methyl)-phenyl)-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.03 (m, 2 H); 2.19 (m, 1 H); 2.29 (m, 2 H); 2.39 (m, 1 H); 2.48 to 2.55 (m, 3 H); 2.60 to 2.71 (m, 3 H); 2.79 (m, 1 H); 4.47 (td, J = 6.1 and 47.5 Hz, 2 H); 4.73 (m, 1 H); 6.57 (m, 2 H); 6.61 (d, J = 8.8 Hz, 2 H); 6.72 (m, 3 H); 7.32 (d, J = 8.3 Hz, 2 H); 7.52 (d, J = 8.3 Hz, 2 H); 9.43 (s, 1 H) | 526 |
| 79 | 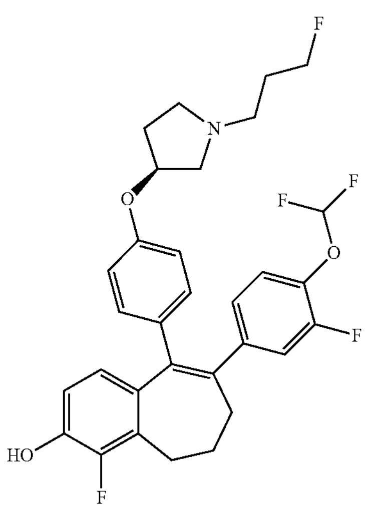 [SMILES: Oc1ccc2c(c1F)CCCC(c1ccc(OC(F)F)c(F)c1)=C2c1ccc(O[C@H]2CCN(CCCF)C2)cc1] | 6-[4-(difluoro-methoxy)-3-fluoro-phenyl]-1-fluoro-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.05 (m, 2 H); 2.20 (m, 1 H); 2.28 (t, J = 7.0 Hz, 2 H); 2.39 (m, 1 H); 2.47 (t, J = 7.2 Hz, 2 H); 2.54 (dd, J = 3.0 and 10.4 Hz, 1 H); 2.65 (m, 1 H); 2.79 (m, 3 H); 4.47 (td, J = 6.1 and 47.5 Hz, 2 H); 4.77 (m, 1 H); 6.40 (d, J = 8.6 Hz, 1 H); 6.65 (d, J = 8.8 Hz, 2 H); 6.73 (t, J = 8.6 Hz, 1 H); 6.77 (d, J = 8.8 Hz, 2 H); 6.98 (dd, J = 2.5 and 8.5 Hz, 1 H); 7.10 to 7.18 (m, 2 H); 7.19 (t, J = 73.5 Hz, 1 H); 9.87 (m, 1 H) | 560 |

TABLE 1-continued

| Examples | Structure | Name | Method | NMR | MASS: LC/MS (m/z, MH+): |
|---|---|---|---|---|---|
| 80 | 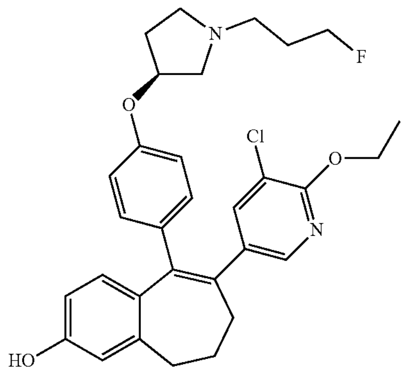 [SMILES: CCOc1ncc(C2=C(c3ccc(O[C@H]4CCN(CCCF)C4)cc3)c3ccc(O)cc3CCC2)cc1Cl] | 6-(5-chloro-6-ethoxy-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.29 (t, J = 7.1 Hz, 3 H); 1.70 (m, 1 H); 1.79 (dm, J = 25.3 Hz, 2 H); 2.06 (m, 2 H); 2.15 to 2.18 (m, 3 H); 2.39 (m, 1 H); 2.48 (t, J = 7.2 Hz, 2 H); 2.57 (dd, J = 3.2 and 10.4 Hz, 1 H); 2.67 (m, 3 H); 2.79 (dd, J = 6.3 and 10.4 Hz, 1 H); 4.30 (q, J = 7.1 Hz, 2 H); 4.46 (td, J = 6.1 and 47.5 Hz, 2 H); 4.78 (m, 1 H); 6.57 (s, 2 H); 6.68 (d, J = 8.8 Hz, 2 H); 6.70 (s, 1 H); 6.78 (d, J = 8.8 Hz, 2 H); 7.60 (d, J = 2.4 Hz, 1 H); 7.80 (d, J = 2.4 Hz, 1 H); 9.42 (s, 1 H) | 537 |
| 81 | 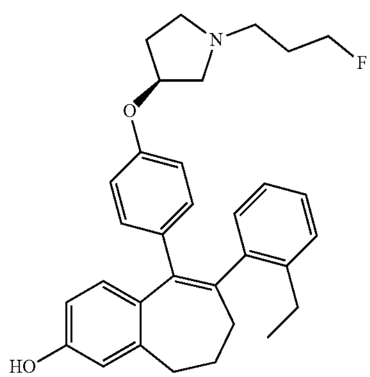 [SMILES: CCc1ccccc1C1=C(c2ccc(O[C@H]3CCN(CCCF)C3)cc2)c2ccc(O)cc2CCC1] | 6-(2-ethylphenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.08 (t, J = 7.6 Hz, 3 H); 1.65 (m, 1 H); 1.78 (dm, J = 25.3 Hz, 2 H); 2.01 to 2.22 (m, 5 H); 2.35 (m, 1 H); 2.45 (t, J = 7.2 Hz, 2 H); 2.52 (m, 1 H); 2.58 to 2.82 (m, 6 H); 4.46 (td, J = 6.1 and 47.5 Hz, 2 H); 4.70 (m, 1 H); 6.54 (d, J = 8.8 Hz, 2 H); 6.57 (s, 2 H); 6.65 (d, J = 8.8 Hz, 2 H); 6.70 (s, 1 H); 6.98 to 7.05 (m, 2 H); 7.11 (m, 1 H); 7.18 (d, J = 8.2 Hz, 1 H); 9.35 (s, 1 H) | 486 |
| 82 | 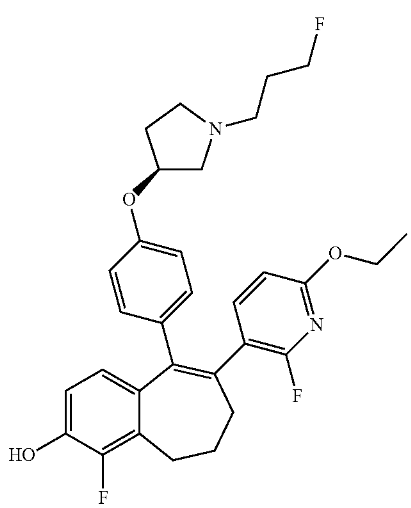 [SMILES: CCOc1ccc(C2=C(c3ccc(O[C@H]4CCN(CCCF)C4)cc3)c3ccc(O)c(F)c3CCC2)c(F)n1] | 6-(6-ethoxy-2-fluoro-3-pyridyl)-1-fluoro-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.28 (t, J = 7.1 Hz, 3 H); 1.69 (m, 1 H); 1.79 (dm, J = 25.3 Hz, 2 H); 2.05 (m, 2 H); 2.13 to 2.25 (m, 3 H); 2.39 (m, 1 H); 2.47 (t, J = 7.2 Hz, 2 H); 2.54 (dd, J = 3.0 and 10.4 Hz, 1 H); 2.63 (m, 1 H); 2.79 (m, 3 H); 4.19 (q, J = 7.1 Hz, 2 H); 4.46 (td, J = 6.1 and 47.5 Hz, 2 H); 4.75 (m, 1 H); 6.40 (d, J = 8.3 Hz, 1 H); 6.60 (dd, J = 1.4 and 8.3 Hz, 1 H); 6.64 (d, J = 8.8 Hz, 2 H); 6.74 (m, 3 H); 7.59 (dd, J = 8.3 and 10.2 Hz, 1 H); 9.89 (m, 1 H) | 539 |

TABLE 1-continued

| Examples | Structure | Name | Method | NMR | MASS: LC/MS (m/z, MH+): |
|---|---|---|---|---|---|
| 83 | 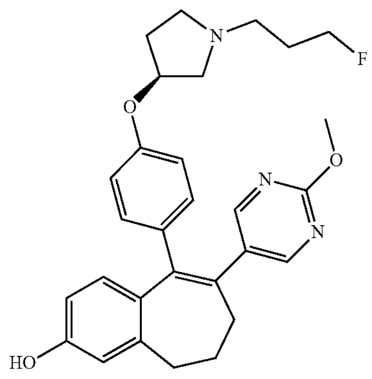 [SMILES: COc1ncc(C2=C(c3ccc(O[C@H]4CCN(CCCF)C4)cc3)c3ccc(O)cc3CCC2)cn1] | 5-[4-[(3S)-1-(3-fluoropropyl)-pyrrolidin-3-yl]oxy-phenyl]-6-(2-methoxy-pyrimidin-5-yl)-8,9-dihydro-7H-benzo[7]-annulen-2-ol | A | 1H NMR (400 MHz, DMSO-d6, δ ppm): 1.71 (m, 1 H); 1.80 (dm, J = 25.3 Hz, 2 H); 2.08 (m, 2 H); 2.16 to 2.30 (m, 3 H); 2.39 (m, 1 H); 2.48 (m, 2 H); 2.56 (dd, J = 3.0 and 10.4 Hz, 1 H); 2.68 (m, 3 H); 2.80 (dd, J = 6.4 and 10.4 Hz, 1 H); 3.86 (s, 3 H); 4.46 (td, J = 6.1 and 47.5 Hz, 2 H); 4.78 (m, 1 H); 6.57 (s, 2 H); 6.69 (d, J = 8.8 Hz, 2 H); 6.71 (s, 1 H); 6.80 (d, J = 8.8 Hz, 2 H); 8.31 (s, 2 H); 9.46 (s, 1 H) | 490 |
| 84 | 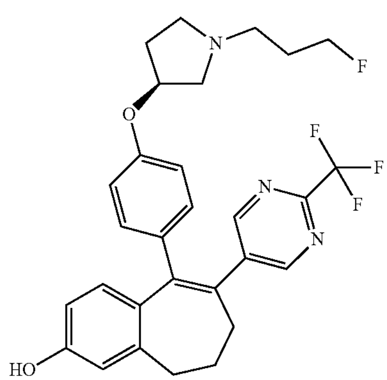 [SMILES: Oc1ccc2c(c1)CCCC(c1cnc(C(F)(F)F)nc1)=C2c1ccc(O[C@H]2CCN(CCCF)C2)cc1] | 5-[4-[(3S)-1-(3-fluoropropyl)-pyrrolidin-3-yl]oxy-phenyl]-6-[2-(trifluoro-methyl)-pyrimidin-5-yl]-8,9-dihydro-7H-benzo[7]-annulen-2-ol | A | 1H NMR (400 MHz, DMSO-d6, δ ppm): 1.67 to 1.86 (m, 3 H); 2.10 (m, 2 H); 2.21 (m, 1 H); 2.30 to 2.58 (m, 6 H); 2.61 to 2.82 (m, 4 H); 4.46 (td, J = 6.1 and 47.5 Hz, 2 H); 4.79 (m, 1 H); 6.59 (s, 2 H); 6.69 (d, J = 8.8 Hz, 2 H); 6.72 (s, 1 H); 6.80 (d, J = 8.8 Hz, 2 H); 8.74 (s, 2 H); 9.56 (s, 1 H) | 528 |
| 85 | 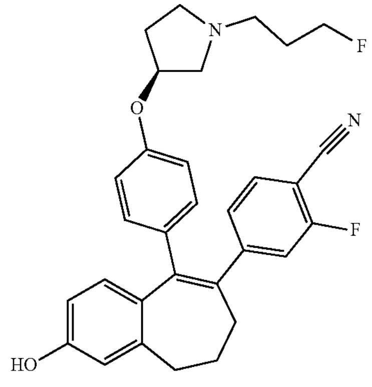 [SMILES: N#Cc1ccc(C2=C(c3ccc(O[C@H]4CCN(CCCF)C4)cc3)c3ccc(O)cc3CCC2)cc1F] | 2-fluoro-4-5-[4-[(3S)-1-(3-fluoropropyl)-pyrrolidin-3-yl]oxy-phenyl]-2-hydroxy-8,9-dihydro-7H-benzo[7]-annulen-6-yl]benzo-nitrile | A | 1H NMR (400 MHz, DMSO-d6, δ ppm): 1.70 (m, 1 H); 1.80 (dm, J = 25.3 Hz, 2 H); 2.05 (m, 2 H); 2.20 (m, 1 H); 2.29 (t, J = 7.0 Hz, 2 H); 2.39 (m, 1 H); 2.48 (m, 2 H); 2.55 (m, 1 H); 2.79 (m, 3 H); 2.80 (m, 1 H); 4.47 (td, J = 6.1 and 47.5 Hz, 2 H); 4.78 (m, 1 H); 6.58 (s, 2 H); 6.68 (d, J = 8.8 Hz, 2 H); 6.70 (s, 1 H); 6.73 (d, J = 8.8 Hz, 2 H); 7.10 (d, J = 8.1 Hz, 1 H); 7.28 (d, J = 11.5 Hz, 1 H); 7.68 (t, J = 8.1 Hz, 1 H); 9.50 (s, 1 H) | 501 |

TABLE 1-continued

| Examples | Structure | Name | Method | NMR | MASS: LC/MS (m/z, MH+): |
|---|---|---|---|---|---|
| 86 | 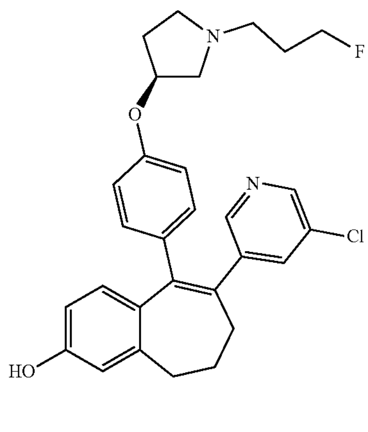 [SMILES: Oc1ccc2c(c1)CCCC(c1cncc(Cl)c1)=C2c1ccc(O[C@H]2CCN(CCCF)C2)cc1] | 6-(5-chloro-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.08 (m, 2 H); 2.20 (m, 1 H); 2.29 (t, J = 7.0 Hz, 2 H); 2.39 (m, 1 H); 2.48 (t, J = 7.2 Hz, 2 H); 2.55 (dd, J = 3.0 and 10.4 Hz, 1 H); 2.61 to 2.72 (m, 3 H); 2.80 (dd, J = 6.3 and 10.4 Hz, 1 H); 4.48 (td, J = 6.1 and 47.5 Hz, 2 H); 4.78 (m, 1 H); 6.59 (s, 2 H); 6.68 (d, J = 8.8 Hz, 2 H); 6.71 (s, 1 H); 6.77 (d, J = 8.8 Hz, 2 H); 7.70 (d, J = 2.5 Hz, 1 H); 8.18 (d, J = 2.5 Hz, 1 H); 8.31 (d, J = 2.5 Hz, 1 H); 9.49 (s, 1 H) | 493 |
| 87 | 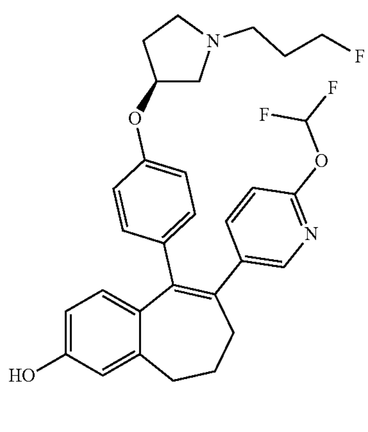 [SMILES: Oc1ccc2c(c1)CCCC(c1ccc(OC(F)F)nc1)=C2c1ccc(O[C@H]2CCN(CCCF)C2)cc1] | 6-[6-(difluoro-methoxy)-3-pyridyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.07 (m, 2 H); 2.20 (m, 1 H); 2.28 (t, J = 7.0 Hz, 2 H); 2.39 (m, 1 H); 2.48 (t, J = 7.2 Hz, 2 H); 2.56 (dd, J = 3.2 and 10.4 Hz, 1 H); 2.68 (m, 3 H); 2.80 (dd, J = 6.3 and 10.4 Hz, 1 H); 4.47 (td, J = 6.1 and 47.5 Hz, 2 H); 4.76 (m, 1 H); 6.56 (s, 2 H); 6.67 (d, J = 8.8 Hz, 2 H); 6.71 (s, 1 H); 6.78 (d, J = 8.8 Hz, 2 H); 6.91 (d, J = 8.6 Hz, 1 H); 7.62 (t, J = 73.1 Hz, 1 H); 7.68 (dd, J = 2.0 and 8.6 Hz, 1 H); 7.96 (d, J = 2.0 Hz, 1 H); 9.46 (s, 1 H) | 525 |
| 88 | 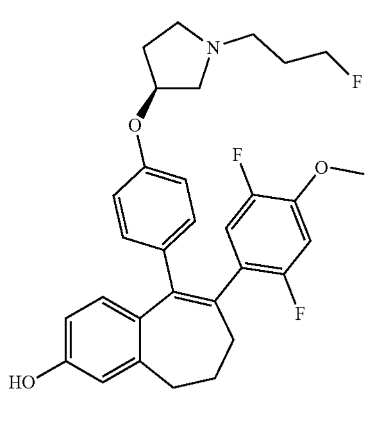 [SMILES: COc1cc(F)c(C2=C(c3ccc(O[C@H]4CCN(CCCF)C4)cc3)c3ccc(O)cc3CCC2)cc1F] | 6-(2,5-difluoro-4-methoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.04 (m, 2 H); 2.15 (t, J = 7.0 Hz, 2 H); 2.20 (m, 1 H); 2.39 (m, 1 H); 2.47 (t, J = 7.2 Hz, 2 H); 2.54 (dd, J = 3.0 and 10.4 Hz, 1 H); 2.60 to 2.72 (m, 3 H); 2.80 (dd, J = 6.4 and 10.4 Hz, 1 H); 3.79 (s, 3 H); 4.48 (td, J = 6.1 and 47.5 Hz, 2 H); 4.75 (m, 1 H); 6.55 (s, 2 H); 6.62 (d, J = 8.8 Hz, 2 H); 6.70 (s, 1 H); 6.74 (d, J = 8.8 Hz, 2 H); 6.93 (dd, J = 7.3 and 11.2 Hz, 1 H); 6.99 (dd, J = 7.1 and 12.1 Hz, 1 H); 9.40 (s, 1 H) | 524 |

TABLE 1-continued

| Examples | Structure | Name | Method | NMR | MASS: LC/MS (m/z, MH+): |
|---|---|---|---|---|---|
| 89 | 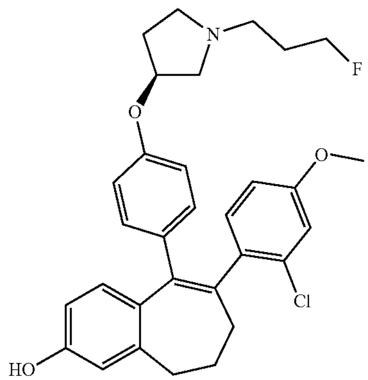 | 6-(2-chloro-4-methoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.05 (m, 2 H); 2.12 to 2.23 (m, 3 H); 2.38 (m, 1 H); 2.45 (t, J = 7.2 Hz, 2 H); 2.52 (dd, J = 3.0 and 10.4 Hz, 1 H); 2.62 (m, 1 H); 2.70 to 2.82 (m, 3 H); 3.71 (s, 3 H); 4.46 (td, J = 6.1 and 47.5 Hz, 2 H); 4.72 (m, 1 H); 6.55 (s, 2 H); 6.59 (d, J = 8.8 Hz, 2 H); 6.70 (s, 1 H); 6.72 (dd, J = 2.6 and 8.8 Hz, 1 H); 6.73 (d, J = 8.8 Hz, 2 H); 6.97 (d, J = 2.6 Hz, 1 H); 7.00 (d, J = 8.8 Hz, 1 H); 9.38 (s, 1 H) | 522 |
| 90 | 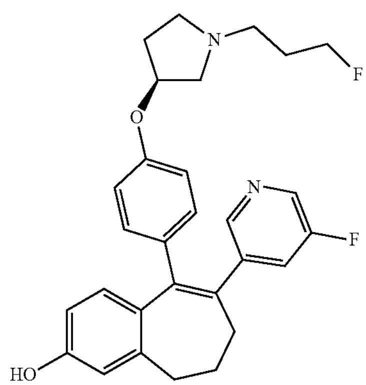 [SMILES: Oc1ccc2c(c1)CCCC(c1cncc(F)c1)=C2c1ccc(O[C@H]2CCN(CCCF)C2)cc1] | 5-[4-[(3S)-1-(3-fluoropropyl)-pyrrolidin-3-yl]oxy-phenyl]-6-(5-fluoro-3-pyridyl)-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.09 (m, 2 H); 2.20 (m, 1 H); 2.29 (t, J = 7.0 Hz, 2 H); 2.39 (m, 1 H); 2.47 (t, J = 7.2 Hz, 2 H); 2.55 (dd, J = 3.1 and 10.4 Hz, 1 H); 2.61 to 2.72 (m, 3 H); 2.80 (dd, J = 6.4 and 10.4 Hz, 1 H); 4.47 (td, J = 6.1 and 47.5 Hz, 2 H); 4.76 (m, 1 H); 6.58 (m, 2 H); 6.66 (d, J = 8.8 Hz, 2 H); 6.71 (s, 1 H); 6.77 (d, J = 8.8 Hz, 2 H); 7.52 (td, J = 2.9 and 10.4 Hz, 1 H); 8.09 (t, J = 2.9 Hz, 1 H); 8.27 (d, J = 2.9 Hz, 1 H); 9.48 (s, 1 H) | 477 |
| 91 | 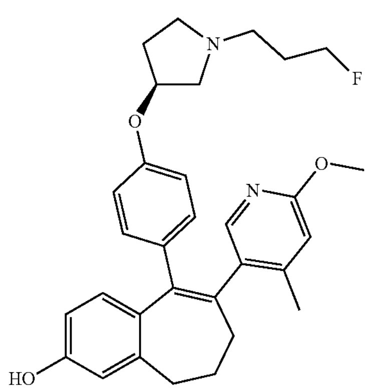 [SMILES: COc1cc(C)c(C2=C(c3ccc(O[C@H]4CCN(CCCF)C4)cc3)c3ccc(O)cc3CCC2)cn1] | 5-[4-[(3S)-1-(3-fluoropropyl)-pyrrolidin-3-yl]oxy-phenyl]-6-(6-methoxy-4-methyl-3-pyridyl)-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.03 to 2.23 (m, 5 H); 2.12 (s, 3 H); 2.38 (m, 1 H); 2.45 (t, J = 7.2 Hz, 2 H); 2.52 (dd, J = 3.0 and 10.4 Hz, 1 H); 2.64 (m, 2 H); 2.79 (m, 2 H); 3.75 (s, 3 H); 4.46 (td, J = 6.1 and 47.5 Hz, 2 H); 4.72 (m, 1 H); 6.55 (s, 2 H); 6.57 (s, 1 H); 6.60 (d, J = 8.8 Hz, 2 H); 6.69 (d, J = 8.8 Hz, 2 H); 6.71 (s, 1 H); 7.71 (s, 1 H); 9.39 (s, 1 H) | 503 |

TABLE 1-continued

| Examples | Structure | Name | Method | NMR | MASS: LC/MS (m/z, MH+): |
|---|---|---|---|---|---|
| 92 | 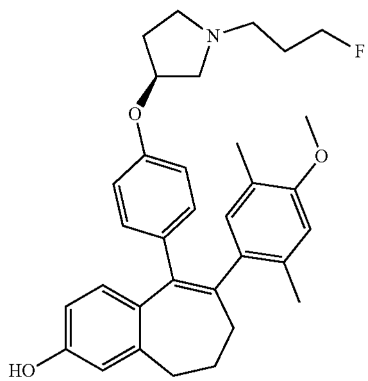 [SMILES: COc1cc(C)c(C2=C(c3ccc(O[C@H]4CCN(CCCF)C4)cc3)c3ccc(O)cc3CCC2)cc1C] | 5-[4-[(3S)-1-(3-fluoropropyl)-pyrrolidin-3-yl]oxy-phenyl]-6-(4-methoxy-2,5-dimthyl-phenyl)-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 1.98 to 2.22 (m, 5 H); 2.01 (s, 3 H); 2.04 (s, 3 H); 2.37 (m, 1 H); 2.45 (t, J = 7.2 Hz, 2 H); 2.52 (m, 1 H); 2.62 (m, 1 H); 2.71 (t, J = 7.0 Hz, 2 H, 1 H); 2.78 (dd, J = 6.4 and 10.4 Hz, 1 H); 3.71 (s, 3 H); 4.46 (td, J = 6.1 and 47.5 Hz, 2 H); 4.71 (m, 1 H); 6.54 (s, 2 H); 6.55 (d, J = 8.8 Hz, 2 H); 6.61 (s, 1 H); 6.68 (d, J = 8.8 Hz, 2 H); 6.81 (s, 1 H); 9.34 (s, 1 H) | 516 |
| 93 | 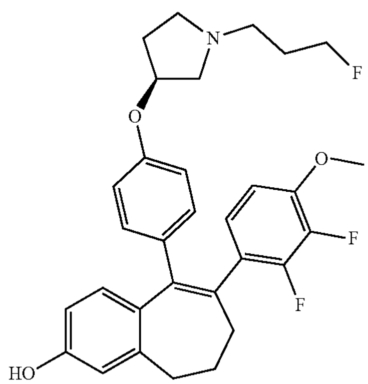 [SMILES: COc1ccc(C2=C(c3ccc(O[C@H]4CCN(CCCF)C4)cc3)c3ccc(O)cc3CCC2)c(F)c1F] | 6-(2,3-difluoro-4-methoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.05 (m, 2 H); 2.14 to 2.25 (m, 3 H); 2.39 (m, 1 H); 2.48 (t, J = 7.2 Hz, 2 H); 2.54 (dd, J = 3.0 and 10.4 Hz, 1 H); 2.61 to 2.71 (m, 3 H); 2.79 (dd, J = 6.4 and 10.4 Hz, 1 H); 3.82 (s, 3 H); 4.47 (td, J = 6.1 and 47.5 Hz, 2 H); 4.74 (m, 1 H); 6.57 (m, 2 H); 6.62 (d, J = 8.8 Hz, 2 H); 6.70 (s, 1 H); 6.72 (d, J = 8.8 Hz, 2 H); 6.80 to 6.94 (m, 2 H); 9.43 (s, 1 H) | 524 |
| 94 | 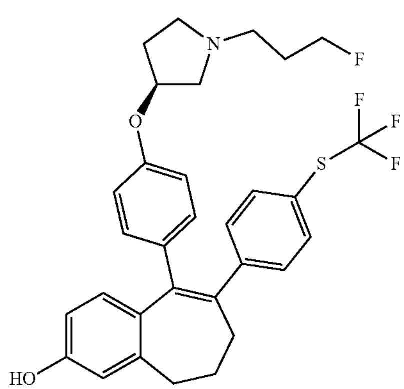 [SMILES: Oc1ccc2c(c1)CCCC(c1ccc(SC(F)(F)F)cc1)=C2c1ccc(O[C@H]2CCN(CCCF)C2)cc1] | 5-[4-[(3S)-1-(3-fluoropropyl)-pyrrolidin-3-yl]oxy-phenyl]-6-[4-(trifluoro-methyl-sulfanyl)-phenyl]-8,9-dihydro-7H-benzo[7]-annulen-2-ol | A | 1H NMR (400 MHz, DMSO-d6, δ ppm): 1.69 (m, 1 H); 1.80 (dm, J = 25.3 Hz, 2 H); 2.05 (m, 2 H); 2.19 (m, 1 H); 2.29 (t, J = 7.0 Hz, 2 H); 2.38 (m, 1 H); 2.45 (t, J = 7.2 Hz, 2 H); 2.54 (dd, J = 3.2 and 10.4 Hz, 1 H); 2.60 to 2.71 (m, 3 H); 2.78 (dd, J = 6.4 and 10.4 Hz, 1 H); 4.47 (td, J = 6.1 and 47.5 Hz, 2 H); 4.72 (m, 1 H); 6.57 (s, 2 H); 6.60 (d, J = 8.8 Hz, 2 H); 6.70 (s, 1 H); 6.71 (d, J = 8.8 Hz, 2 H); 7.25 (d, J = 8.4 Hz, 2 H); 7.50 (d, J = 8.4 Hz, 2 H); 9.46 (s, 1 H) | 558 |

TABLE 1-continued

| Examples | Structure | Name | Method | NMR | MASS: LC/MS (m/z, MH+): |
|---|---|---|---|---|---|
| 95 | 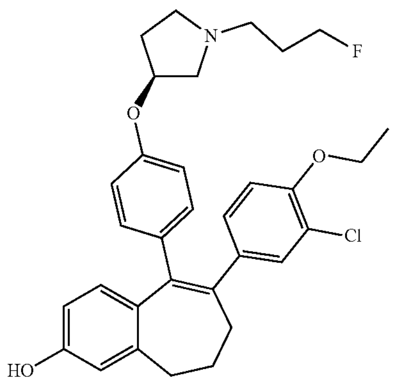 [SMILES: CCOc1ccc(C2=C(c3ccc(O[C@H]4CCN(CCCF)C4)cc3)c3ccc(O)cc3CCC2)cc1Cl] | 6-(3-chloro-4-ethoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.31 (t, J = 7.1 Hz, 3 H); 1.70 (m, 1 H); 1.79 (dm, J = 25.3 Hz, 2 H); 2.03 (m, 2 H); 2.15 to 2.27 (m, 3 H); 2.39 (m, 1 H); 2.48 (t, J = 7.2 Hz, 2 H); 2.55 (dd, J = 3.1 and 10.4 Hz, 1 H); 2.66 (m, 3 H); 2.80 (dd, J = 6.4 and 10.4 Hz, 1 H); 4.03 (q, J = 7.1 Hz, 2 H); 4.47 (td, J = 6.1 and 47.5 Hz, 2 H); 4.75 (m, 1 H); 6.54 (s, 2 H); 6.65 (d, J = 8.8 Hz, 2 H); 6.69 (s, 1 H); 6.75 (d, J = 8.8 Hz, 2 H); 6.92 (d, J = 8.6 Hz, 1 H); 7.03 (dd, J = 2.6 and 8.6 Hz, 1 H); 7.11 (d, J = 2.6 Hz, 1 H); 9.38 (s, 1 H) | 536 |
| 96 | 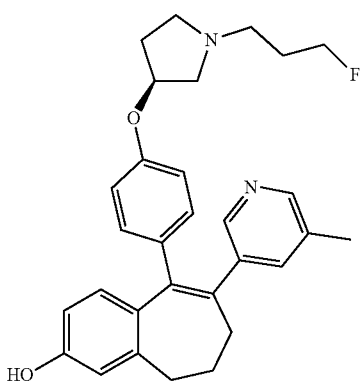 [SMILES: Cc1cncc(C2=C(c3ccc(O[C@H]4CCN(CCCF)C4)cc3)c3ccc(O)cc3CCC2)c1] | 5-[4-[(3S)-1-(3-fluoropropyl)-pyrrolidin-3-yl]oxy-phenyl]-6-(5-methyl-3-pyridyl)-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.05 (m, 2 H); 2.19 (m, 1 H); 2.20 (s, 3 H); 2.26 (t, J = 7.0 Hz, 2 H); 2.39 (m, 1 H); 2.47 (t, J = 7.2 Hz, 2 H); 2.54 (dd, J = 3.0 and 10.4 Hz, 1 H); 2.61 to 2.71 (m, 3 H); 2.80 (dd, J = 6.4 and 10.4 Hz, 1 H); 4.47 (td, J = 6.1 and 47.5 Hz, 2 H); 4.75 (m, 1 H); 6.57 (m, 2 H); 6.63 (d, J = 8.8 Hz, 2 H); 6.70 (s, 1 H); 6.74 (d, J = 8.8 Hz, 2 H); 7.42 (t, J = 2.3 Hz, 1 H); 8.01 (d, J = 2.3 Hz, 1 H); 8.10 (d, J = 2.3 Hz, 1 H); 9.43 (s, 1 H) | 473 |
| 97 | 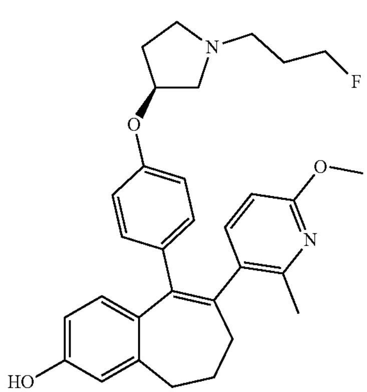 [SMILES: COc1ccc(C2=C(c3ccc(O[C@H]4CCN(CCCF)C4)cc3)c3ccc(O)cc3CCC2)c(C)n1] | 5-[4-[(3S)-1-(3-fluoropropyl)-pyrrolidin-3-yl]oxy-phenyl]-6-(6-methoxy-2-methyl-3-pyridyl)-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.03 to 2.24 (m, 5 H); 2.20 (s, 3 H); 2.38 (m, 1 H); 2.47 (t, J = 7.2 Hz, 2 H); 2.52 (m, 1 H); 2.62 (m, 1 H); 2.71 (t, J = 7.2 Hz, 2 H); 2.79 (dd, J = 6.3 and 10.4 Hz, 1 H); 3.77 (s, 3 H); 4.47 (td, J = 6.1 and 47.5 Hz, 2 H); 4.72 (m, 1 H); 6.51 (d, J = 8.4 Hz, 1 H); 6.55 (s, 2 H); 6.60 (d, J = 9.0 Hz, 2 H); 6.69 (d, J = 9.0 Hz, 2 H); 6.71 (s, 1 H); 7.33 (d, J = 8.4 Hz, 1 H); 9.41 (s, 1 H) | 503 |

TABLE 1-continued

| Examples | Structure | Name | Method | NMR | MASS: LC/MS (m/z, MH+): |
|---|---|---|---|---|---|
| 98 | 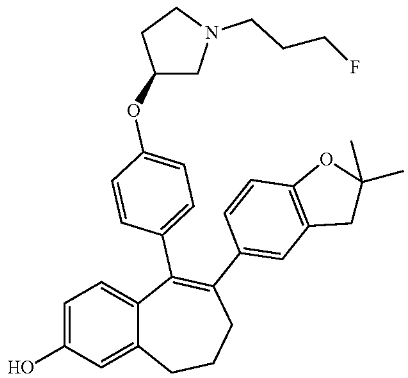 [SMILES: CC1(C)Cc2cc(C3=C(c4ccc(O[C@H]5CCN(CCCF)C5)cc4)c4ccc(O)cc4CCC3)ccc2O1] | 6-(2,2-dimethyl-3H-benzo-furan-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.35 (s, 6 H); 1.70 (m, 1 H); 1.80 (dm, J = 25.3 Hz, 2 H); 2.03 (m, 2 H); 2.13 to 2.25 (m, 3 H); 2.39 (m, 1 H); 2.47 (t, J = 7.2 Hz, 2 H); 2.54 (dd, J = 3.0 and 10.4 Hz, 1 H); 2.60 to 2.71 (m, 3 H); 2.79 (dd, J = 6.4 and 10.4 Hz, 1 H); 2.84 (s, 2 H); 4.47 (td, J = 6.1 and 47.5 Hz, 2 H); 4.76 (m, 1 H); 6.47 (d, J = 8.3 Hz, 1 H); 6.54 (m, 2 H); 6.61 (d, J = 8.8 Hz, 2 H); 6.68 (s, 1 H); 6.72 (d, J = 8.8 Hz, 2 H); 6.81 (dd, J = 2.5 and 8.3 Hz, 1 H); 6.91 (d, J = 2.5 Hz, 1 H); 9.33 (s, 1 H) | 528 |
| 99 | 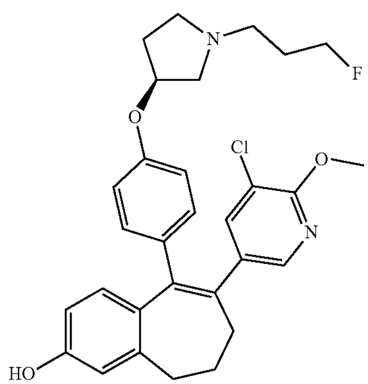 [SMILES: COc1ncc(C2=C(c3ccc(O[C@H]4CCN(CCCF)C4)cc3)c3ccc(O)cc3CCC2)cc1Cl] | 6-(5-chloro-6-methoxy-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.07 (m, 2 H); 2.20 (m, 1 H); 2.33 (t, J = 7.2 Hz, 2 H); 2.39 (m, 1 H); 2.48 (t, J = 7.3 Hz, 2 H); 2.55 (dd, J = 3.2 and 10.5 Hz, 1 H); 2.61 to 2.70 (m, 3 H); 2.80 (dd, J = 6.1 and 10.5 Hz, 1 H); 3.86 (s, 3 H); 4.48 (td, J = 6.1 and 47.5 Hz, 2 H); 4.79 (m, 1 H); 6.56 (s, 2 H); 6.69 (d, J = 8.9 Hz, 2 H); 6.70 (s, 1 H); 6.79 (d, J = 8.9 Hz, 2 H); 7.61 (dd, J = 2.3 Hz, 1 H); 7.82 (d, J = 2.3 Hz, 1 H); 9.43 (s, 1 H) | 523 |
| 100 | 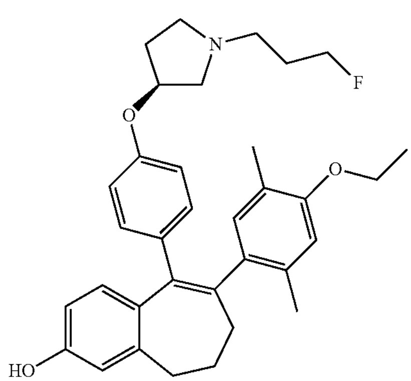 [SMILES: CCOc1cc(C)c(C2=C(c3ccc(O[C@H]4CCN(CCCF)C4)cc3)c3ccc(O)cc3CCC2)cc1C] | 6-(4-ethoxy-2,5-dimethyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.31 (t, J = 7.1 Hz, 3 H); 1.68 (m, 1 H); 1.79 (dm, J = 25.3 Hz, 2 H); 2.01 (s, 6 H); 2.03 (m, 2 H); 2.10 (m, 2 H); 2.19 (m, 1 H); 2.37 (m, 1 H); 2.45 (t, J = 7.2 Hz, 2 H); 2.52 (dd, J = 3.0 and 10.4 Hz, 1 H); 2.61 (m, 1 H); 2.70 (m, 2 H); 2.79 (dd, J = 6.3 and 10.4 Hz, 1 H); 3.95 (m, 2 H); 4.46 (td, J = 6.1 and 47.5 Hz, 2 H); 4.71 (m, 1 H); 6.53 (s, 2 H); 6.55 (d, J = 8.8 Hz, 2 H); 6.60 (s, 1 H); 6.67 (d, J = 8.8 Hz, 2 H); 6.69 (t, J = 1.0 Hz, 1 H); 6.80 (s, 1 H); 9.33 (s, 1 H) | 530 |

TABLE 1-continued

| Examples | Structure | Name | Method | NMR | MASS: LC/MS (m/z, MH+): |
|---|---|---|---|---|---|
| 101 | 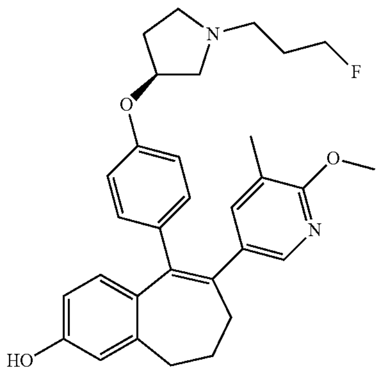 [SMILES: COc1ncc(C2=C(c3ccc(O[C@H]4CCN(CCCF)C4)cc3)c3ccc(O)cc3CCC2)cc1C] | 5-[4-[(3S)-1-(3-fluoropropyl)-pyrrolidin-3-yl]oxy-phenyl]-6-(6-methoxy-5-methyl-3-pyridyl)-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.03 (s, 3 H); 2.05 (m, 2 H); 2.15 to 2.25 (m, 3 H); 2.38 (m, 1 H); 2.47 (t, J = 7.2 Hz, 2 H); 2.54 (dd, J = 3.0 and 10.4 Hz, 1 H); 2.64 (m, 3 H); 2.79 (dd, J = 6.4 and 10.4 Hz, 1 H); 3.79 (s, 3 H); 4.46 (td, J = 6.1 and 47.5 Hz, 2 H); 4.76 (m, 1 H); 6.54 (s, 2 H); 6.65 (d, J = 8.8 Hz, 2 H); 6.70 (s, 1 H); 6.76 (d, J = 8.8 Hz, 2 H); 7.32 (d, J = 3.0 Hz, 1 H); 7.67 (d, J = 3.0 Hz, 1 H); 9.39 (s, 1 H) | 503 |
| 102 | 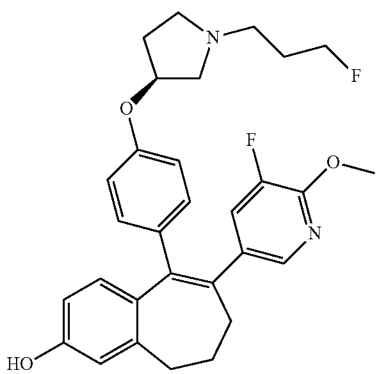 [SMILES: COc1ncc(C2=C(c3ccc(O[C@H]4CCN(CCCF)C4)cc3)c3ccc(O)cc3CCC2)cc1F] | 6-(5-fluoro-6-methoxy-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.06 (m, 2 H); 2.13 to 2.28 (m, 3 H); 2.38 (m, 1 H); 2.47 (t, J = 7.2 Hz, 2 H); 2.55 (dd, J = 3.0 and 10.4 Hz, 1 H); 2.68 (m, 3 H); 2.80 (dd, J = 6.4 and 10.4 Hz, 1 H); 3.86 (s, 3 H); 4.47 (td, J = 6.1 and 47.5 Hz, 2 H); 4.78 (m, 1 H); 6.56 (s, 2 H); 6.68 (d, J = 8.8 Hz, 2 H); 6.70 (s, 1 H); 6.79 (d, J = 8.8 Hz, 2 H); 7.42 (dd, J = 2.0 and 11.9 Hz, 1 H); 7.68 (d, J = 2.0 Hz, 1 H); 9.42 (s, 1 H) | 507 |
| 103 | 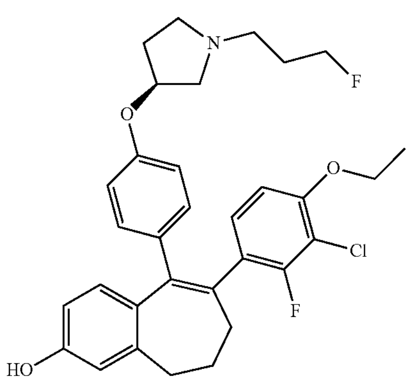 [SMILES: CCOc1ccc(C2=C(c3ccc(O[C@H]4CCN(CCCF)C4)cc3)c3ccc(O)cc3CCC2)c(F)c1Cl] | 6-(3-chloro-4-ethoxy-2-fluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.33 (t, J = 7.2 Hz, 3 H); 1.68 (m, 1 H); 1.81 (dm, J = 25.3 Hz, 2 H); 2.05 (m, 2 H); 2.16 to 2.23 (m, 3 H); 2.40 (m, 1 H); 2.46 (t, J = 7.2 Hz, 2 H); 2.54 (dd, J = 3.0 and 10.4 Hz, 1 H); 2.63 (m, 1 H); 2.68 (t, J = 7.0 Hz, 2 H); 2.79 (dd, J = 6.4 and 10.4 Hz, 1 H); 4.10 (q, J = 7.2 Hz, 2 H); 4.47 (td, J = 6.1 and 47.5 Hz, 2 H); 4.74 (m, 1 H); 6.56 (m, 2 H); 6.63 (d, J = 8.8 Hz, 2 H); 6.71 (s, 1 H); 6.73 (d, J = 8.8 Hz, 2 H); 6.83 (d, J = 9.0 Hz, 1 H); 7.03 (t, J = 9.0 Hz, 1 H); 9.40 (s, 1 H) | 554 |

TABLE 1-continued

| Examples | Structure | Name | Method | NMR | MASS: LC/MS (m/z, MH+): |
|---|---|---|---|---|---|
| 104 | 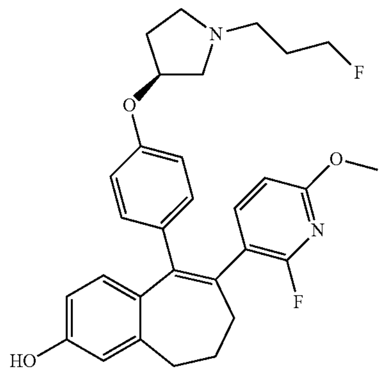 [SMILES: COc1ccc(C2=C(c3ccc(O[C@H]4CCN(CCCF)C4)cc3)c3ccc(O)cc3CCC2)c(F)n1] | 6-(2-fluoro-6-methoxy-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.05 (m, 2 H); 2.13 to 2.25 (m, 3 H); 2.39 (m, 1 H); 2.47 (t, J = 7.2 Hz, 2 H); 2.54 (dd, J = 3.1 and 10.4 Hz, 1 H); 2.60 to 2.71 (m, 3 H); 2.80 (dd, J = 6.4 and 10.4 Hz, 1 H); 3.78 (s, 3 H); 4.48 (td, J = 6.1 and 47.5 Hz, 2 H); 4.75 (m, 1 H); 6.56 (s, 2 H); 6.61 (d, J = 8.2 Hz, 1 H); 6.64 (d, J = 8.8 Hz, 2 H); 6.70 (s, 1 H); 6.74 (d, J = 8.8 Hz, 2 H); 7.59 (dd, J = 8.2 and 10.1 Hz, 1 H); 9.44 (s, 1 H) | 507 |
| 105 | 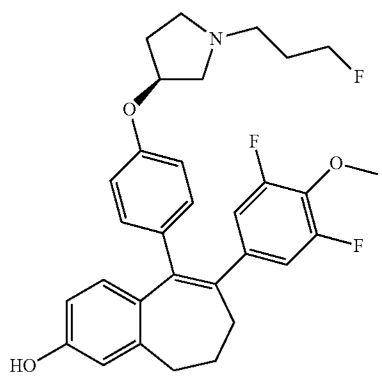 [SMILES: COc1c(F)cc(C2=C(c3ccc(O[C@H]4CCN(CCCF)C4)cc3)c3ccc(O)cc3CCC2)cc1F] | 6-(3,5-difluoro-4-methoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.05 (m, 2 H); 2.21 (m, 3 H); 2.39 (m, 1 H); 2.47 (t, J = 7.2 Hz, 2 H); 2.53 (dd, J = 3.2 and 10.5 Hz, 1 H); 2.66 (m, 3 H); 2.80 (dd, J = 6.2 and 10.5 Hz, 1 H); 3.85 (s, 3 H); 4.47 (td, J = 6.1 and 47.5 Hz, 2 H); 4.79 (m, 1 H); 6.55 (s, 2 H); 6.68 (d, J = 8.8 Hz, 2 H); 6.70 (s, 1 H); 6.76 (d, J = 8.8 Hz, 2 H); 6.83 (d, J = 10.0 Hz, 2 H); 9.44 (s, 1 H) | 524 |
| 106 | 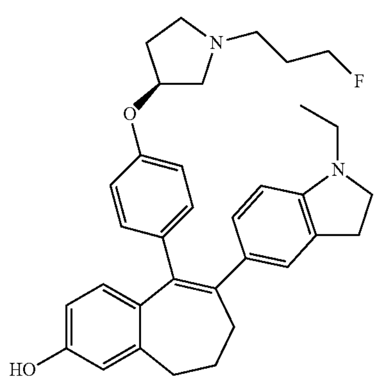 [SMILES: CCN1CCc2cc(C3=C(c4ccc(O[C@H]5CCN(CCCF)C5)cc4)c4ccc(O)cc4CCC3)ccc21] | 6-(1-ethylindolin-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.07 (t, J = 7.4 Hz, 3 H); 1.70 (m, 1 H); 1.80 (dm, J = 25.3 Hz, 2 H); 2.00 (m, 2 H); 2.20 (m, 3 H); 2.38 (m, 1 H); 2.47 (m, 2 H); 2.54 (m, 1 H); 2.65 (m, 3 H); 2.74 (t, J = 7.2 Hz, 2 H); 2.80 (dd, J = 6.4 and 10.4 Hz, 1 H); 3.02 (q, J = 7.4 Hz, 2 H); 3.22 (t, J = 7.2 Hz, 2 H); 4.47 (td, J = 6.1 and 47.5 Hz, 2 H); 4.75 (m, 1 H); 6.25 (d, J = 8.2 Hz, 1 H); 6.52 (s, 2 H); 6.60 (d, J = 8.8 Hz, 2 H); 6.65 (s, 1 H); 6.73 (m, 3 H); 6.81 (s, 1 H); 9.29 (s, 1 H) | 527 |

TABLE 1-continued

| Examples | Structure | Name | Method | NMR | MASS: LC/MS (m/z, MH+): |
|---|---|---|---|---|---|
| 107 | 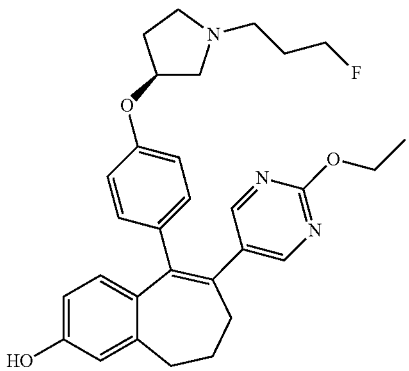 [SMILES: CCOc1ncc(C2=C(c3ccc(O[C@H]4CCN(CCCF)C4)cc3)c3ccc(O)cc3CCC2)cn1] | 6-(2-ethoxy-pyrimidin-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.28 (t, J = 7.1 Hz, 3 H); 1.65 to 1.88 (m, 3 H); 2.08 (m, 2 H); 2.16 to 2.29 (m, 3 H); 2.35 to 2.58 (m, 4 H); 3.68 (m, 3 H); 2.80 (m, 1 H); 4.27 (q, J = 7.1 Hz, 2 H); 4.47 (td, J = 6.1 and 47.5 Hz, 2 H); 4.78 (m, 1 H); 6.57 (s, 2 H); 6.69 (d, J = 8.8 Hz, 2 H); 6.71 (s, 1 H); 6.80 (d, J = 8.8 Hz, 2 H); 8.29 (s, 2 H); 9.46 (s, 1 H) | 504 |
| 108 | 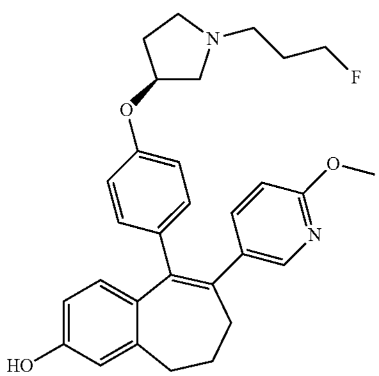 [SMILES: COc1ccc(C2=C(c3ccc(O[C@H]4CCN(CCCF)C4)cc3)c3ccc(O)cc3CCC2)cn1] | 5-[4-[(3S)-1-(3-fluoropropyl)-pyrrolidin-3-yl]oxy-phenyl]-6-(6-methoxy-3-pyridyl)-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.05 (m, 2 H); 2.15 to 2.27 (m, 3 H); 2.38 (m, 1 H); 2.46 (t, J = 7.2 Hz, 2 H); 2.54 (dd, J = 3.2 and 10.4 Hz, 1 H); 2.65 (m, 3 H); 2.80 (dd, J = 6.4 and 10.3 Hz, 1 H); 3.78 (s, 3 H); 4.48 (td, J = 6.1 and 47.5 Hz, 2 H); 4.75 (m, 1 H); 6.56 (s, 2 H); 6.63 (m, 3 H); 6.70 (s, 1 H); 6.75 (d, J = 8.8 Hz, 2 H); 7.45 (dd, J = 2.5 and 8.7 Hz, 1 H); 7.89 (d, J = 2.5 Hz. 1 H); 9.40 (s, 1 H) | 489 |
| 109 | 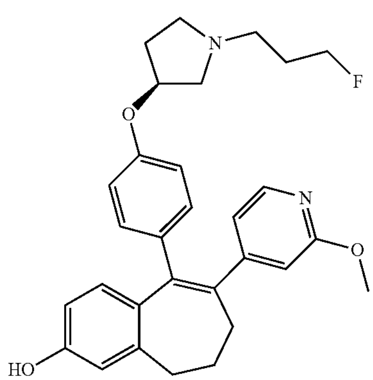 [SMILES: COc1cc(C2=C(c3ccc(O[C@H]4CCN(CCCF)C4)cc3)c3ccc(O)cc3CCC2)ccn1] | 5-[4-[(3S)-1-(3-fluoropropyl)-pyrrolidin-3-yl]oxy-phenyl]-6-(2-methoxy-4-pyridyl)-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.02 (m, 2 H); 2.15 to 2.27 (m, 3 H); 2.39 (m, 1 H); 2.47 (t, J = 7.2 Hz, 2 H); 2.55 (dd, J = 3.0 and 10.5 Hz, 1 H); 2.64 (m, 3 H); 2.80 (dd, J = 6.4 and 10.4 Hz, 1 H); 3.76 (s, 3 H); 4.48 (td, J = 6.1 and 47.5 Hz, 2 H); 4.78 (m, 1 H); 6.51 (s, 1 H); 6.57 (m, 2 H); 6.67 (m, 3 H); 6.70 (s, 1 H); 6.76 (d, J = 8.8 Hz, 2 H); 7.92 (d, J = 5.4 Hz, 1 H); 9.47 (s, 1 H) | 489 |

TABLE 1-continued

| Examples | Structure | Name | Method | NMR | MASS: LC/MS (m/z, MH+): |
|---|---|---|---|---|---|
| 110 | 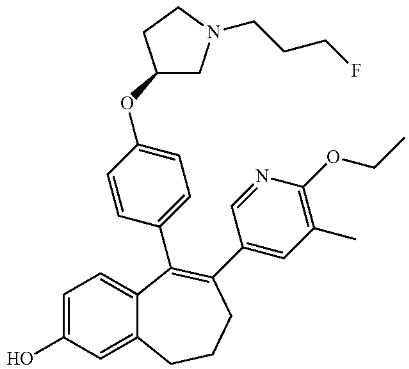 [SMILES: CCOc1ncc(C2=C(c3ccc(O[C@H]4CCN(CCCF)C4)cc3)c3ccc(O)cc3CCC2)cc1C] | 6-(6-ethoxy-5-methyl-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.36 (t, J = 7.3 Hz, 3 H); 1.70 (m, 1 H); 1.79 (dm, J = 25.3 Hz, 2 H); 2.02 (s, 3 H); 2.04 (m, 2 H); 2.15 to 2.25 (m, 3 H); 2.38 (m, 1 H); 2.47 (t, J = 7.2 Hz, 2 H); 2.54 (dd, J = 3.1 and 10.4 Hz, 1 H); 2.66 (m, 3 H); 2.79 (dd, J = 6.4 and 10.4 Hz, 1 H); 4.22 (q, J = 7.3 Hz, 2 H); 4.47 (td, J = 6.1 and 47.5 Hz, 2 H); 4.76 (m, 1 H); 6.55 (s, 2 H); 6.64 (d, J = 8.8 Hz, 2 H); 6.79 (s, 1 H); 6.75 (d, J = 8.8 Hz, 2 H); 7.32 (d, J = 2.6 Hz, 1 H); 7.62 (d, J = 2.6 Hz, 1 H); 9.39 (s, 1 H) | 517 |
| 111 | 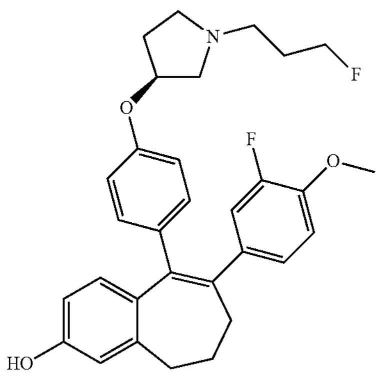 [SMILES: COc1ccc(C2=C(c3ccc(O[C@H]4CCN(CCCF)C4)cc3)c3ccc(O)cc3CCC2)cc1F] | 6-(3-fluoro-4-methoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.04 (m, 2 H); 2.15 to 2.27 (m, 3 H); 2.39 (m, 1 H); 2.47 (t, J = 7.2 Hz, 2 H); 2.54 (m, dd, J = 3.0 and 10.4 Hz, 1 H); 2.65 (m, 3 H); 2.80 (dd, J = 6.4 and 10.4 Hz, 1 H); 3.77 (s, 3 H); 4.47 (td, J = 6.1 and 47.5 Hz, 2 H); 4.76 (m, 1 H); 6.54 (s, 2 H); 6.63 (d, J = 8.8 Hz, 2 H); 6.69 (s, 1 H); 6.74 (d, J = 8.8 Hz, 2 H); 6.86, 85 to 6.92 (m, 2 H); 6.95 (t, J = 8.7 Hz, 1 H); 9.38 (s, 1 H) | 506 |
| 112 | 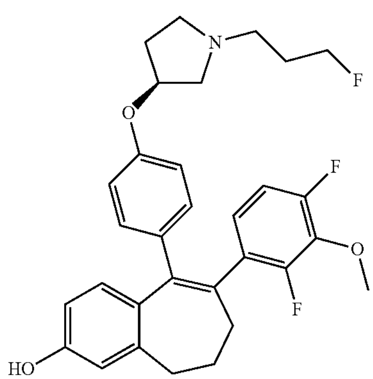 [SMILES: COc1c(F)ccc(C2=C(c3ccc(O[C@H]4CCN(CCCF)C4)cc3)c3ccc(O)cc3CCC2)c1F] | 6-(2,4-difluoro-3-methoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.07 (m, 2 H); 2.18 (m, 3 H); 2.39 (m, 1 H); 2.45 (t, J = 7.2 Hz, 2 H); 2.52 (m, 1 H); 2.62 (m, 1 H); 2.69 (t, J = 7.0 Hz, 2 H); 2.79 (dd, J = 6.4 and 10.4 Hz, 1 H); 3.74 (s, 3 H); 4.48 (td, J = 6.1 and 47.5 Hz, 2 H); 4.72 (m, 1 H); 6.58 (s, 2 H); 6.61 (d, J = 8.8 Hz, 2 H); 6.71 (m, 3 H); 6.90 (ddd, J = 6.2 and 8.5 and 9.0 Hz, 1 H); 6.98 (ddd, J = 2.2 and 9.0 and 11.0 Hz, 1 H); 9.43 (s, 1 H) | 524 |

TABLE 1-continued

| Examples | Structure | Name | Method | NMR | MASS: LC/MS (m/z, MH+): |
|---|---|---|---|---|---|
| 113 | 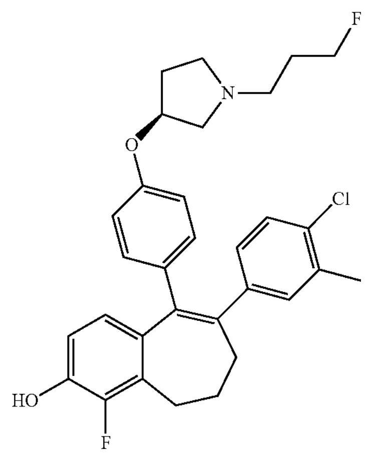 [SMILES: Cc1cc(C2=C(c3ccc(O[C@H]4CCN(CCCF)C4)cc3)c3ccc(O)c(F)c3CCC2)ccc1Cl] | 6-(4-chloro-3-methyl-phenyl)-1-fluoro-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.03 (m, 2 H); 2.18 (m, 1 H); 2.20 (s, 3 H); 2.26 (t, J = 7.0 Hz, 2 H); 2.39 (m, 1 H); 2.47 (t, J = 7.2 Hz, 2 H); 2.55 (dd, J = 3.0 and 10.4 Hz, 1 H); 2.65 (m, 1 H); 2.73 to 2.82 (m, 3 H); 4.46 (td, J = 6.1 and 47.5 Hz, 2 H); 4.77 (m, 1 H); 6.40 (d, J = 8.7 Hz, 1 H); 6.62 (d, J = 8.8 Hz, 2 H); 6.72 (t, J = 8.7 Hz, 1 H); 6.75 (d, J = 8.8 Hz, 2 H); 6.91 (dd, J = 2.5 and 8.5 Hz, 1 H); 7.13 (d, J = 2.5 Hz, 1 H); 7.18 (d, J = 8.5 Hz, 1 H); 9.80 (m, 1 H) | 524 |
| 114 | 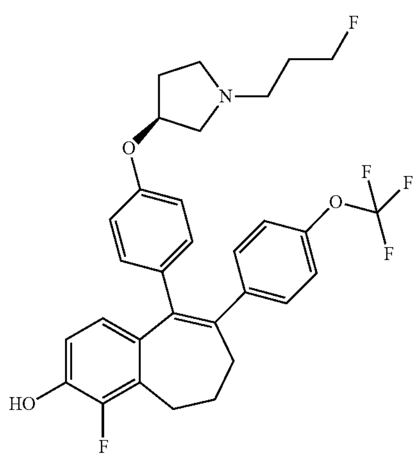 [SMILES: Oc1ccc2c(c1F)CCCC(c1ccc(OC(F)(F)F)cc1)=C2c1ccc(O[C@H]2CCN(CCCF)C2)cc1] | 1-fluoro-5-[4-[(3S)-1-(3-fluoropropyl)-pyrrolidin-3-yl]oxy-phenyl]-6-[4-(trifluoro-methoxy)-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.05 (m, 2 H); 2.19 (m, 1 H); 2.29 (t, J = 7.0 Hz, 2 H); 2.39 (m, 1 H); 2.45 (t, J = 7.2 Hz, 2 H); 2.54 (dd, J = 3.2 and 10.4 Hz, 1 H); 2.63 (m, 1 H); 2.79 (m, 3 H); 4.46 (td, J = 6.1 and 47.5 Hz, 2 H); 4.73 (m, 1 H); 6.40 (d, J = 8.3 Hz, 1 H); 6.61 (d, J = 8.8 Hz, 2 H); 6.72 (m, 3 H); 7.15 (d, J = 8.9 Hz, 2 H); 7.23 (d, J = 8.9 Hz, 2 H); 9.79 (s, 1 H) | 560 |
| 115 | 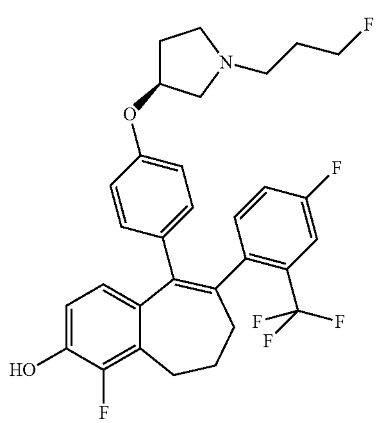 [SMILES: Oc1ccc2c(c1F)CCCC(c1ccc(F)cc1C(F)(F)F)=C2c1ccc(O[C@H]2CCN(CCCF)C2)cc1] | 1-fluoro-5-[4-[(3S)-1-(3-fluoropropyl)-pyrrolidin-3-yl]oxy-phenyl]-6-[4-fluoro-2-(trifluoromethyl)phenyl]-8,9-dihydro-7H-benzo[7]-annulen-2-ol | A | 1H NMR (400 MHz, DMSO-d6, δ ppm): 1.65 (m, 1 H); 1.79 (dm, J = 25.3 Hz, 2 H); 2.08 (m, 2 H); 2.18 (m, 3 H); 2.37 (m, 1 H); 2.45 (t, J = 7.2 Hz, 2 H); 2.52 (m, 1 H); 2.59 to 2.81 (m, 3 H); 2.99 (s, 1 H); 4.46 (td, J = 6.1 and 47.5 Hz, 2 H); 4.71 (m, 1 H); 6.40 (d, J = 8.6 Hz, 1 H); 6.60 (d, J = 8.8 Hz, 2 H); 6.70 (d, J = 8.8 Hz, 2 H); 6.74 (t, J = 8.6 Hz, 1 H); 7.21 (dd, J = 6.0 and 8.9 Hz, 1 H); 7.32 (dt, J = 3.0 and 8.9 Hz, 1 H); 7.60 (dd, J = 3.0 and 9.5 Hz, 1 H); 9.80 (s, 1 H) | 562 |

TABLE 1-continued

| Examples | Structure | Name | Method | NMR | MASS: LC/MS (m/z, MH+): |
|---|---|---|---|---|---|
| 116 | 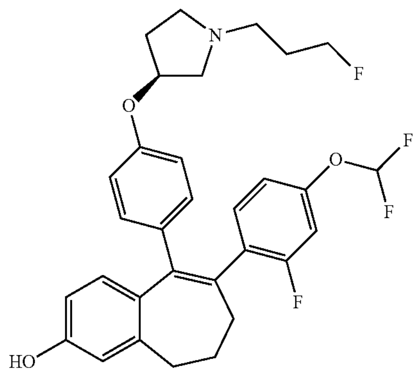 [SMILES: Oc1ccc2c(c1)CCCC(c1ccc(OC(F)F)cc1F)=C2c1ccc(O[C@H]2CCN(CCCF)C2)cc1] | 6-[4-(difluoromethoxy)-2-fluorophenyl]-5-[4-[(3S)-1-(3-fluoropropyl)pyrrolidin-3-yl]oxyphenyl]-8,9-dihydro-7H-benzo[7]annulen-2-ol | A | 1H NMR (400 MHz, DMSO-d6, δ ppm): 1.68 (m, 1 H); 1.79 (dm, J = 25.3 Hz, 2 H); 2.05 (m, 2 H); 2.12 to 2.25 (m, 3 H); 2.38 (m, 1 H); 2.45 (t, J = 7.2 Hz, 2 H); 2.53 (dd, J = 3.0 and 10.4 Hz, 1 H); 2.59 to 2.72 (m, 3 H); 2.79 (dd, J = 6.4 and 10.4 Hz, 1 H); 4.47 (td, J = 6.1 and 47.5 Hz, 2 H); 4.72 (m, 1 H); 6.56 (m, 2 H); 6.61 (d, J = 8.8 Hz, 2 H); 6.70 (s, 1 H); 6.72 (d, J = 8.8 Hz, 2 H); 6.87 (dd, J = 2.7 and 8.7 Hz, 1 H); 6.97 (dd, J = 2.7 and 10.7 Hz, 1 H); 7.20 (t, J = 8.7 Hz, 1 H); 7.23 (t, J = 73.8 Hz, 1 H); 9.43 (s, 1 H) | 542 |
| 117 | 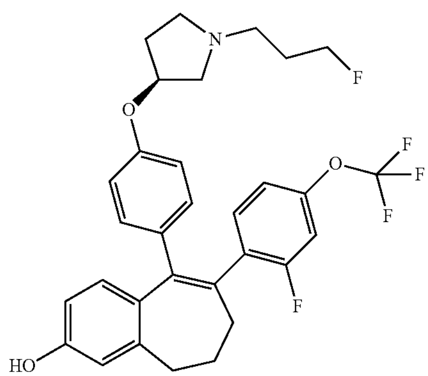 [SMILES: Oc1ccc2c(c1)CCCC(c1ccc(OC(F)(F)F)cc1F)=C2c1ccc(O[C@H]2CCN(CCCF)C2)cc1] | 5-[4-[(3S)-1-(3-fluoropropyl)pyrrolidin-3-yl]oxyphenyl]-6-[2-fluoro-4-(trifluoromethoxy)phenyl]-8,9-dihydro-7H-benzo[7]annulen-2-ol | A | 1H NMR (400 MHz, DMSO-d6, δ ppm): 1.68 (m, 1 H); 1.79 (dm, J = 25.3 Hz, 2 H); 2.07 (m, 2 H); 2.19 (m, 3 H); 2.38 (m, 1 H); 2.46 (t, J = 7.2 Hz, 2 H); 2.53 (m, 1 H); 2.63 (m, 1 H); 2.71 (t, J = 7.0 Hz, 2 H); 2.78 (dd, J = 6.4 and 10.4 Hz, 1 H); 4.47 (td, J = 6.1 and 47.5 Hz, 2 H); 4.72 (m, 1 H); 6.58 (s, 2 H); 6.61 (d, J = 8.8 Hz, 2 H); 6.70 (d, J = 8.8 Hz, 2 H); 6.72 (s, 1 H); 7.08 (d, J = 8.6 Hz, 1 H); 7.22 (d, J = 10.2 Hz, 1 H); 7.29 (t, J = 8.6 Hz, 1 H); 9.44 (s, 1 H) | 560 |
| 118 | 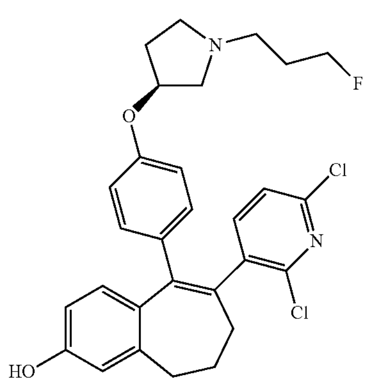 [SMILES: Oc1ccc2c(c1)CCCC(c1ccc(Cl)nc1Cl)=C2c1ccc(O[C@H]2CCN(CCCF)C2)cc1] | 6-(2,6-dichloro-3-pyridyl)-5-[4-[(3S)-1-(3-fluoropropyl)pyrrolidin-3-yl]oxyphenyl]-8,9-dihydro-7H-benzo[7]annulen-2-ol | A | 1H NMR (400 MHz, DMSO-d6, d ppm): 1.68 (m, 1 H); 1.79 (dm, J = 25.3 Hz, 2 H); 2.03 to 2.17 (m, 5 H); 2.38 (m, 1 H); 2.47 (t, J = 7.2 Hz, 2 H); 2.53 (m, 1 H); 2.63 (m, 1 H); 2.78 (m, 3 H); 4.47 (td, J = 6.1 and 47.5 Hz, 2 H); 4.74 (m, 1 H); 6.57 (s, 2 H); 6.65 (d, J = 8.8 Hz, 2 H); 6.71 (s, 1 H); 6.73 (d, J = 8.8 Hz, 2 H); 7.41 (d, J = 8.7 Hz, 1 H); 7.68 (d, J = 8.7 Hz, 1 H); 9.99 (s, 1 H) | 527 |

TABLE 1-continued

| Examples | Structure | Name | Method | NMR | MASS: LC/MS (m/z, MH+): |
|---|---|---|---|---|---|
| 119 | 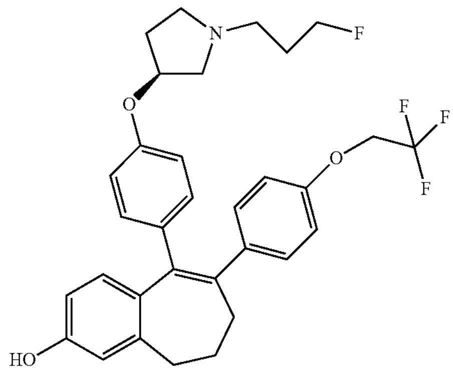 [SMILES: Oc1ccc2c(c1)CCCC(c1ccc(OCC(F)(F)F)cc1)=C2c1ccc(O[C@H]2CCN(CCCF)C2)cc1] | 5-[4-[(3S)-1-(3-fluoropropyl)-pyrrolidin-3-yl]oxy-phenyl]-6-[4-(2,2,2-trifluoro-ethoxy)phenyl]-8,9-dihydro-7H-benzo[7]-annulen-2-ol | A | 1H NMR (400 MHz, DMSO-d6, δ ppm): 1.71 (m, 1 H); 1.80 (dm, J = 25.3 Hz, 2 H); 2.02 (m, 2 H); 2.13 to 2.27 (m, 3 H); 2.40 (m, 1 H); 2.48 (m, 2 H); 2.55 (m, 1 H); 2.65 (m, 3 H); 2.80 (m, 1 H); 4.47 (td, J = 6.1 and 47.5 Hz, 2 H); 4.68 (q, J = 8.9 Hz, 2 H); 4.74 (m, 1 H); 6.54 (s, 2 H); 6.60 (d, J = 8.8 Hz, 2 H); 6.69 (s, 1 H); 6.72 (d, J = 8.8 Hz, 2 H); 6.85 (d, J = 9.0 Hz, 2 H); 7.08 (d, J = 9.0 Hz, 2 H); 9.34 (s, 1 H) | 556 |
| 120 | 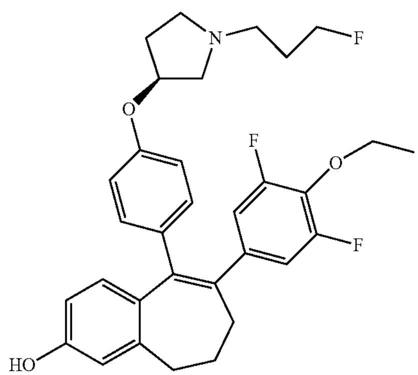 [SMILES: CCOc1c(F)cc(C2=C(c3ccc(O[C@H]4CCN(CCCF)C4)cc3)c3ccc(O)cc3CCC2)cc1F] | 6-(4-ethoxy-3,5-difluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.34 (t, J = 7.2 Hz, 3 H); 1.70 (m, 1 H); 1.80 (dm, J = 25.3 Hz, 2 H); 2.05 (m, 2 H); 2.27 to 2.37 (m, 3 H); 2.39 (m, 1 H); 2.48 (t, J = 7.2 Hz, 2 H); 2.56 (dd, J = 3.0 and 10.4 Hz, 1 H); 2.67 (m, 3 H); 2.80 (dd, J = 6.4 and 10.4 Hz, 1 H); 4.09 (q, J = 7.2 Hz, 2 H); 4.48 (td, J = 6.1 and 47.5 Hz, 2 H); 4.72 (m, 1 H); 6.55 (s, 2 H); 6.67 (d, J = 8.8 Hz, 2 H); 6.69 (s, 1 H); 6.74 (d, J = 8.8 Hz, 2 H); 6.82 (d, J = 9.9 Hz, 2 H); 9.41 (s, 1 H) | 538 |
| 121 | 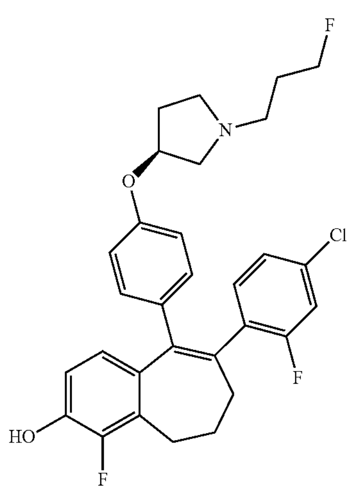 [SMILES: Oc1ccc2c(c1F)CCCC(c1ccc(Cl)cc1F)=C2c1ccc(O[C@H]2CCN(CCCF)C2)cc1] | 6-(4-chloro-2-fluoro-phenyl)-1-fluoro-5-[4-(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.03 (m, 2 H); 2.19 (m, 3 H); 2.38 (m, 1 H); 2.47 (t, J = 7.2 Hz, 2 H); 2.53 (dd, J = 3.2 and 10.4 Hz, 1 H); 2.63 (m, 1 H); 2.79 (m, 3 H); 4.47 (td, J = 6.1 and 47.5 Hz, 2 H); 4.74 (m, 1 H); 6.42 (d, J = 8.0 Hz, 1 H); 6.62 (d, J = 8.8 Hz, 2 H); 6.72 (m, 3 H); 7.12 (dd, J = 2.5 and 8.3 Hz, 1 H); 7.20 (t, J = 8.3 Hz, 1 H); 7.29 (dd, J = 2.2 and 9.8 Hz, 1 H); 9.87 (s, 1 H) | 528 |

TABLE 1-continued

| Examples | Structure | Name | Method | NMR | MASS: LC/MS (m/z, MH+): |
|---|---|---|---|---|---|
| 122 | 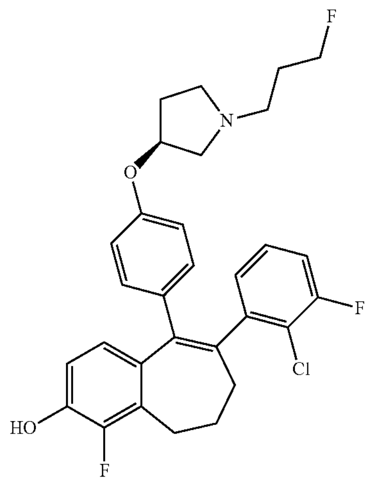 [SMILES: Oc1ccc2c(c1F)CCCC(c1cccc(F)c1Cl)=C2c1ccc(O[C@H]2CCN(CCCF)C2)cc1] | 6-(2-chloro-3-fluoro-phenyl)-1-fluoro-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.65 (m, 1 H); 1.79 (dm, J = 25.3 Hz, 2 H); 2.07 (m, 2 H); 2.19 (m, 3 H); 2.36 (m, 1 H); 2.44 (t, J = 7.2 Hz, 2 H); 2.53 (m, 1 H); 2.62 (m, 1 H); 2.77 (m, 2 H); 2.99 (m, 1 H); 4.47 (td, J = 6.1 and 47.5 Hz, 2 H); 4.71 (m, 1 H); 6.41 (d, J = 8.6 Hz, 1 H); 6.61 (d, J = 8.8 Hz, 2 H); 6.73 (d, J = 8.8 Hz, 2 H); 6.75 (t, J = 8.6 Hz, 1 H); 7.00 (m, 1 H); 7.20 (m, 2 H); 9.87 (s, 1 H) | 528 |
| 123 | 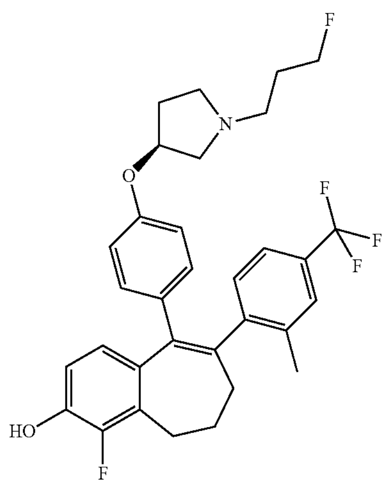 [SMILES: Cc1cc(C(F)(F)F)ccc1C1=C(c2ccc(O[C@H]3CCN(CCCF)C3)cc2)c2ccc(O)c(F)c2CCC1] | 1-fluoro-5-[4-[(3S)-1-(3-fluoropropyl)-pyrrolidin-3-yl]oxy-phenyl]-6-[2-methyl-4-(trifluoromethyl)phenyl]-8,9-dihydro-7H-benzo[7]-annulen-2-ol | A | 1H NMR (400 MHz, DMSO-d6, δ ppm): 1.66 (m, 1 H); 1.78 (dm, J = 25.3 Hz, 2 H); 2.07 (m, 2 H); 2.18 (m, 3 H); 2.22 (s, 3 H); 2.35 (m, 1 H); 2.43 (t, J = 7.2 Hz, 2 H); 2.51 (m, 1 H); 2.62 (m, 1 H); 2.77 (m, 1 H); 2.87 (m, 2 H); 4.46 (td, J = 6.1 and 47.5 Hz, 2 H); 4.71 (m, 1 H); 6.41 (d, J = 8.8 Hz, 1 H); 6.58 (d, J = 8.8 Hz, 2 H); 6.67 (d, J = 8.8 Hz, 2 H); 6.75 (t, J = 8.8 Hz, 1 H); 7.22 (dd, J = 3.1 and 7.9 Hz, 1 H); 7.38 (d, J = 7.9 Hz, 1 H); 7.48 (s, 1 H); 9.82 (s, 1 H) | 558 |
| 124 | 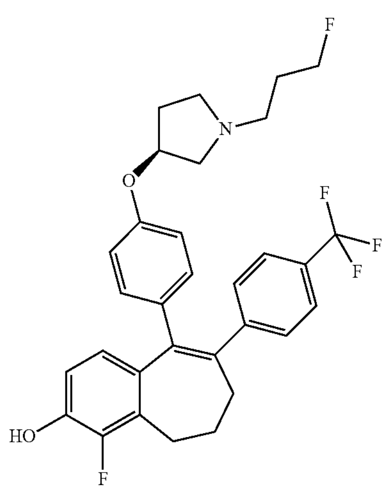 [SMILES: Oc1ccc2c(c1F)CCCC(c1ccc(C(F)(F)F)cc1)=C2c1ccc(O[C@H]2CCN(CCCF)C2)cc1] | 1-fluoro-5-[4-[(3S)-1-(3-fluoropropyl)-pyrrolidin-3-yl]oxy-phenyl]-6-[4-(trifluoromethyl)phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.04 (m, 2 H); 2.19 (m, 1 H); 2.30 (t, J = 7.0 Hz, 2 H); 2.38 (m, 1 H); 2.46 (t, J = 7.2 Hz, 2 H); 2.53 (dd, J = 3.0 and 10.4 Hz, 1 H); 2.63 (m, 1 H); 2.79 (m, 3 H); 4.48 (td, J = 6.1 and 47.5 Hz, 2 H); 4.74 (m, 1 H); 6.41 (d, J = 8.7 Hz, 1 H); 6.63 (d, J = 8.8 Hz, 2 H); 6.74 (t, J = 8.7 Hz, 1 H); 6.75 (d, J = 8.8 Hz, 2 H); 7.35 (d, J = 8.7 Hz, 2 H); 7.53 (d, J = 8.7 Hz, 2 H); 9.88 (s, 1 H) | 544 |

TABLE 1-continued

| Examples | Structure | Name | Method | NMR | MASS: LC/MS (m/z, MH+): |
|---|---|---|---|---|---|
| 125 | 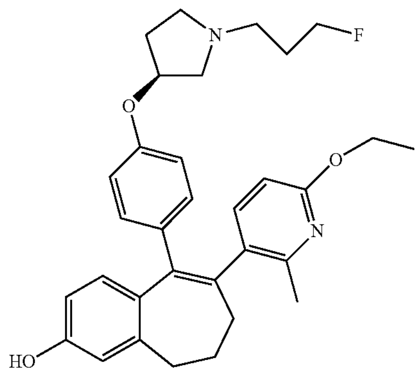 [SMILES: CCOc1ccc(C2=C(c3ccc(O[C@H]4CCN(CCCF)C4)cc3)c3ccc(O)cc3CCC2)c(C)n1] | 6-(6-ethoxy-2-methyl-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.25 (t, J = 7.1 Hz, 3 H); 1.69 (m, 1 H); 1.79 (dm, J = 25.3 Hz, 2 H); 2.03 to 2.23 (m, 5 H); 2.15 (s, 3 H); 2.33 to 2.58 (m, 4 H); 2.60 to 2.73 (m, 4 H); 4.20 (q, J = 7.1 Hz, 2 H); 4.47 (td, J = 6.1 and 47.5 Hz, 2 H); 4.72 (m, 1 H); 6.48 (d, J = 8.7 Hz, 1 H); 6.55 (s, 2 H); 6.60 (d, J = 8.8 Hz, 2 H); 6.69 (d, J = 8.8 Hz, 2 H); 6.71 (s, 1 H); 7.32 (d, J = 8.7 Hz, 1 H); 9.38 (s, 1 H) | 517 |
| 126 | 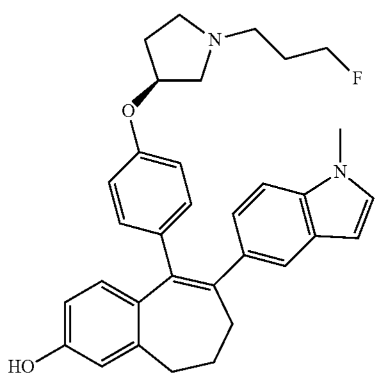 [SMILES: Cn1ccc2cc(C3=C(c4ccc(O[C@H]5CCN(CCCF)C5)cc4)c4ccc(O)cc4CCC3)ccc21] | 5-[4-[(3S)-1-(3-fluoropropyl)-pyrrolidin-3-yl]oxy-phenyl]-6-(1-methyl-indol-5-yl)-8,9-dihydro-7H-benzo[7]-annulen-2-ol | A | 1H NMR (400 MHz, DMSO-d6, δ ppm): 1.66 (m, 1 H); 1.78 (dm, J = 25.3 Hz, 2 H); 2.02 (m, 2 H); 2.17 (m, 1 H); 2.31 (t, J = 7.0 Hz, 2 H); 2.37 (m, 1 H); 2.44 (t, J = 7.2 Hz, 2 H); 2.52 (m, 1 H); 2.61 (m, 1 H); 2.69 (t, J = 7.0 Hz, 2 H); 2.76 (dd, J = 6.4 and 10.4 Hz, 1 H); 3.71 (s, 3 H); 4.45 (td, J = 6.1 and 47.5 Hz, 2 H); 4.69 (m, 1 H); 6.27 (d, J = 3.2 Hz, 1 H); 6.63 (d, J = 8.8 Hz, 2 H); 6.65 (s, 2 H); 6.69 (s, 1 H); 6.73 (d, J = 8.8 Hz, 2 H); 6.93 (dd, J = 1.8 and 8.6 Hz, 1 H); 7.19 (d, J = 8.6 Hz, 1 H); 7.22 (d, J = 3.2 Hz, 1 H); 7.32 (d, J = 1.8 Hz, 1 H); 9.32 (s, 1 H) | 511 |
| 127 | 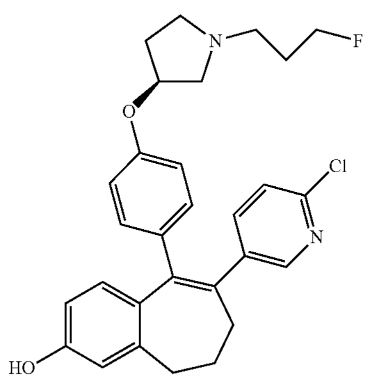 [SMILES: Oc1ccc2c(c1)CCCC(c1ccc(Cl)nc1)=C2c1ccc(O[C@H]2CCN(CCCF)C2)cc1] | 6-(6-chloro-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.05 (m, 2 H); 2.21 (m, 1 H); 2.27 (t, J = 7.0 Hz, 2 H); 2.35 to 2.59 (m, 4 H); 2.69 (m, 3 H); 2.81 (m, 1 H); 4.48 (td, J = 6.1 and 47.5 Hz, 2 H); 4.77 (m, 1 H); 6.57 (s, 2 H); 6.68 (d, J = 8.8 Hz, 2 H); 6.70 (s, 1 H); 6.77 (d, J = 8.8 Hz, 2 H); 7.34 (d, J = 8.3 Hz, 1 H); 7.62 (dd, J = 2.6 and 8.3 Hz, 1 H); 8.08 (d, J = 2.6 Hz, 1 H); 9.46 (s, 1 H) | 493 |

TABLE 1-continued

| Examples | Structure | Name | Method | NMR | MASS: LC/MS (m/z, MH+): |
|---|---|---|---|---|---|
| 128 | 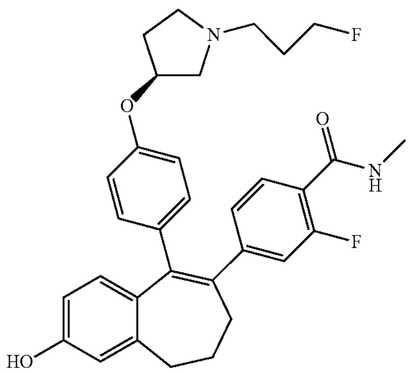 [SMILES: CNC(=O)c1ccc(C2=C(c3ccc(O[C@H]4CCN(CCCF)C4)cc3)c3ccc(O)cc3CCC2)cc1F] | 2-fluoro-4-5-[4-[(3S)-1-(3-fluoropropyl)-pyrrolidin-3-yl]oxy-phenyl]-2-hydroxy-8,9-dihydro-7H-benzo[7]-annulen-6-yl]-N-methyl-benzamide | A | 1H NMR (400 MHz, DMSO-d6, δ ppm): 1.70 (m, 1 H); 1.79 (dm, J = 25.3 Hz, 2 H); 2.05 (m, 2 H); 2.15 to 2.30 (m, 3 H); 2.39 (m, 1 H); 2.48 (t, J = 7.2 Hz, 2 H); 2.55 (dd, J = 3.0 and 10.4 Hz, 1 H); 2.67 (m, 3 H); 2.74 (d, J = 4.8 Hz, 3 H); 2.80 (dd, = 6.4 and 10.4 Hz, 1 H); 4.47 (td, J = 6.1 and 47.5 Hz 2 H); 4.77 (m, 1 H); 6.56 (s, 2 H); 6.65 (d, J = 8.8 Hz, 2 H); 6.71 (s, 1 H); 6.76 (d, J = 8.8 Hz, 2 H); 6.98 (dd, J = 1.6 and 4.8 Hz, 1 H); 7.01 (s, 1 H); 7.42 (t, J = 8.1 Hz, 1 H); 8.09 (m, 1 H); 9.43 (s, 1 H) | :533 |
| 129 | 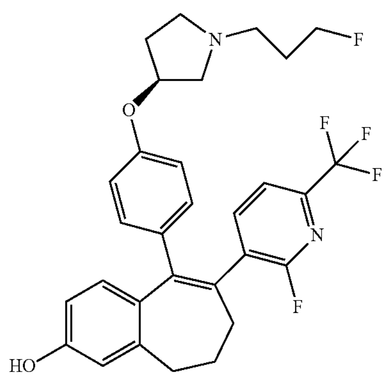 [SMILES: Oc1ccc2c(c1)CCCC(c1ccc(C(F)(F)F)nc1F)=C2c1ccc(O[C@H]2CCN(CCCF)C2)cc1] | 5-[4-[(3S)-1-(3-fluoropropyl)-pyrrolidin-3-yl]oxy-phenyl]-6-[2-fluoro-6-(trifluoro-methyl)-3-pyridyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.10 (m, 2 H); 2.20 (m, 1 H); 2.26 (t, J = 7.0 Hz, 2 H); 2.40 (m, 1 H); 2.48 (t, J = 7.0 Hz, 2 H); 2.54 (m, 1 H); 2.66 (m, 1 H); 2.71 (t, J = 7.0 Hz, 2 H); 2.79 (m, 1 H); 4.47 (td, J = 6.1 and 47.5 Hz, 2 H); 4.75 (m, 1 H); 6.59 (s, 2 H); 6.66 (d, J = 8.8 Hz, 2 H); 6.72 (d, J = 8.8 Hz, 2 H); 6.74 (s, 1 H); 7.74 (dd, J = 17 and 8.2 Hz, 1 H); 8.02 (t, J = 8.2 Hz, 1 H); 9.50 (s, 1 H) | 545 |
| 130 | 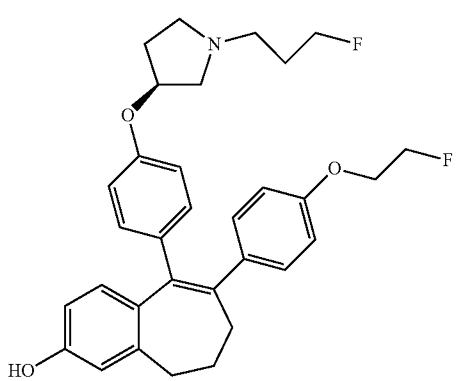 [SMILES: Oc1ccc2c(c1)CCCC(c1ccc(OCCF)cc1)=C2c1ccc(O[C@H]2CCN(CCCF)C2)cc1] | 6-[4-(2-fluoro-ethoxy)phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.03 (m, 2 H); 2.15 to 2.27 (m, 3 H); 2.39 (m, 1 H); 2.47 (t, J = 7.2 Hz, 2 H); 2.55 (dd, J = 3.0 and 10.4 Hz, 1 H); 2.64 (m, 3 H); 2.79 (dd, J = 6.4 and 10.4 Hz, 1 H); 4.16 (dm, J = 30.3 Hz, 2 H); 4.47 (td, J = 6.1 and 47.5 Hz, 2 H); 4.69 (dm, J = 48.6 Hz, 2 H); 4.74 (m, 1 H); 6.54 (s, 2 H); 6.61 (d, J = 8.8 Hz, 2 H); 6.68 (s, 1 H); 6.72 (d, J = 8.8 Hz, 2 H); 6.76 (d, J = 8.9 Hz, 2 H); 7.04 (d, J = 8.9 Hz, 2 H); 9.31 (s, 1 H) | 520 |

TABLE 1-continued

| Examples | Structure | Name | Method | NMR | MASS: LC/MS (m/z, MH+): |
|---|---|---|---|---|---|
| 131 | 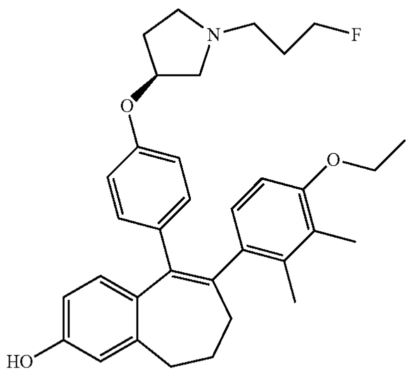 [SMILES: CCOc1ccc(C2=C(c3ccc(O[C@H]4CCN(CCCF)C4)cc3)c3ccc(O)cc3CCC2)c(C)c1C] | 6-(4-ethoxy-2,3-dimethyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 0.80 (t, J = 7.1 Hz, 3 H); 1.68 (m, 1 H); 1.79 (dm, J = 25.3 Hz, 2 H); 2.02 (m, 2 H); 2.03 (s, 3 H); 2.10 (s, 3 H); 2.12 to 2.22 (m, 3 H); 2.25 to 2.58 (m, 4 H); 2.63 (m, 2 H); 2.79 (m, 2 H); 3.92 (m, 2 H); 4.47 (td, J = 6.1 and 47.5 Hz, 2 H); 4.72 (m, 1 H); 6.54 (d, J = 8.8 Hz, 2 H); 6.56 (s, 2 H); 6.59 (d, J = 8.6 Hz, 1 H); 6.65 (d, J = 8.8 Hz, 2 H); 6.69 (s, 1 H); 6.72 (d, J = 8.6 Hz, 1 H); 9.30 (s, 1 H) | 530 |
| 132 | 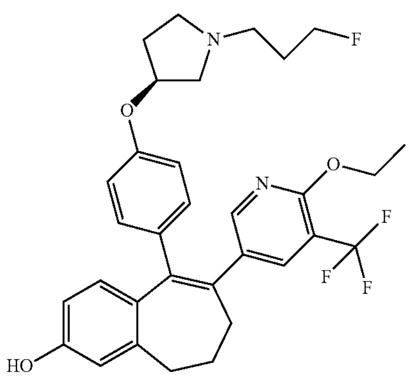 [SMILES: CCOc1ncc(C2=C(c3ccc(O[C@H]4CCN(CCCF)C4)cc3)c3ccc(O)cc3CCC2)cc1C(F)(F)F] | 6-[6-ethoxy-5-(trifluoro-methyl)-3-pyridyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.28 (t, J = 7.1 Hz, 3 H); 1.70 (m, 1 H); 1.79 (dm, J = 25.3 Hz, 2 H); 2.08 (m, 2 H); 2.20 (m, 1 H); 2.30 (t, J = 7.0 Hz, 2 H); 2.39 (m, 1 H); 2.47 (t, J = 7.2 Hz, 2 H); 2.53 (dd, J = 3.0 and 10.4 Hz, 1 H); 2.60 to 2.71 (m, 3 H); 2.79 (dd, J = 6.4 and 10.4 Hz, 1 H); 4.37 (q, J = 7.1 Hz, 2 H); 4.47 (td, J = 6.1 and 47.5 Hz, 2 H); 4.79 (m, 1 H); 6.58 (m, 2 H); 6.69 (d, J = 8.8 Hz, 2 H); 6.71 (m, 1 H); 6.78 (d, J = 8.8 Hz, 2 H); 7.68 (d, J = 2.7 Hz, 1 H); 8.15 (d, J = 2.7 Hz, 1 H); 9.43 (s, 1 H) | 571 |
| 133 | 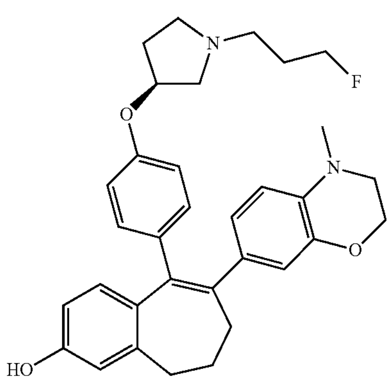 [SMILES: CN1CCOc2cc(C3=C(c4ccc(O[C@H]5CCN(CCCF)C5)cc4)c4ccc(O)cc4CCC3)ccc21] | 5-[4-[(3S)-1-(3-fluoropropyl)-pyrrolidin-3-yl]oxy-phenyl]-6-(4-methyl-2,3-dihydro-1,4-benzoxazin-7-yl)-8,9-dihydro-7H-benzo[7]-annulen-2-ol | A | 1H NMR (400 MHz, DMSO-d6, δ ppm): 1.71 (m, 1 H); 1.81 (dm, J = 25.3 Hz, 2 H); 2.00 (m, 2 H); 2.15 to 2.25 (m, 3 H); 2.40 (m, 1 H); 2.47 (t, J = 7.2 Hz, 2 H); 2.56 (dd, J = 3.2 and 10.4 Hz, 1 H); 2.60 to 2.71 (m, 3 H); 2.76 (s, 3 H); 2.81 (dd, J = 6.4 and 10.4 Hz, 1 H); 3.17 (m, 2 H); 4.12 (m, 2 H); 4.47 (td, J = 6.1 and 47.5 Hz, 2 H); 4.75 (m, 1 H); 6.42 (d, J = 2.2 Hz, 1 H); 6.47 (d, J = 8.5 Hz, 1 H); 6.52 (s, 2 H); 6.53 (dd, J = 2.2 and 8.5 Hz, 1 H); 6.62 (d, J = 8.8 Hz, 2 H); 6.65 (s, 1 H); 6.74 (d, J = 8.8 Hz, 2 H); 9.28 (s, 1 H) | 529 |

TABLE 1-continued

| Examples | Structure | Name | Method | NMR | MASS: LC/MS (m/z, MH+): |
|---|---|---|---|---|---|
| 134 | 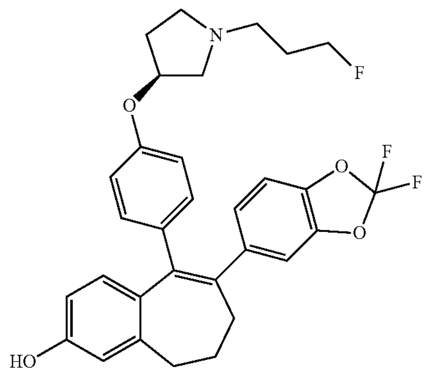 [SMILES: Oc1ccc2c(c1)CCCC(c1ccc3c(c1)OC(F)(F)O3)=C2c1ccc(O[C@H]2CCN(CCCF)C2)cc1] | 6-(2,2-difluoro-1,3-benzodioxol-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.05 (m, 2 H); 2.19 (m, 1 H); 2.25 (t, J = 7.0 Hz, 2 H); 2.39 (m, 1 H); 2.47 (t, J = 7.2 Hz, 2 H); 2.54 (dd, J = 3.0 and 10.4 Hz, 1 H); 2.61 to 2.71 (m, 3 H); 2.79 (dd, J = 6.4 and 10.4 Hz, 1 H); 4.47 (td, J = 6.1 and 47.5 Hz, 2 H); 4.75 (m, 1 H); 6.56 (s, 2 H); 6.64 (d, J = 8.8 Hz, 2 H); 6.70 (s, 1 H); 6.75 (d, J = 8.8 Hz, 2 H); 6.92 (dd, J = 2.0 and 8.5 Hz, 1 H); 7.25 (d, J = 2.0 Hz, 1 H); 7.28 (d, J = 8.5 Hz, 1 H); 9.39 (s, 1 H) | 538 |
| 135 | 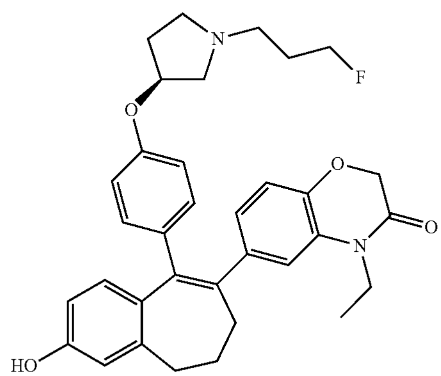 [SMILES: CCN1C(=O)COc2ccc(C3=C(c4ccc(O[C@H]5CCN(CCCF)C5)cc4)c4ccc(O)cc4CCC3)cc21] | 4-ethyl-6-5-[4-[(3S)-1-(3-fluoropropyl)-pyrrolidin-3-yl]oxy-phenyl]-2-hydroxy-8,9-dihydro-7H-benzo[7]-annulen-6-yl]-1,4-benzoxazin-3-one | A | 1H NMR (400 MHz, DMSO-d6, δ ppm): 0.80 (t, J = 7.1 Hz, 3 H); 1.68 (m, 1 H); 1.79 (dm, J = 25.3 Hz, 2 H); 2.05 (m, 2 H); 2.19 (m, 1 H); 2.28 (t, J = 7.0 Hz, 2 H); 2.39 (m, 1 H); 2.46 (t, J = 7.2 Hz, 2 H); 2.53 (m, 1 H); 2.60 to 2.72 (m, 3 H); 2.79 (dd, J = 6.4 and 10.4 Hz, 1 H); 3.67 (q, J = 7.1 Hz, 2 H); 4.47 (td, J = 6.1 and 47.5 Hz, 2 H); 4.55 (s, 2 H); 4.73 (m, 1 H); 6.55 (s, 2 H); 6.65 (d, J = 8.8 Hz, 2 H); 6.69 (s, 1 H); 6.78 (d, J = 8.8 Hz, 2 H); 6.82 (s, 1 H); 6.85 (s, 2 H); 9.38 (s, 1 H) | 557 |
| 136 | 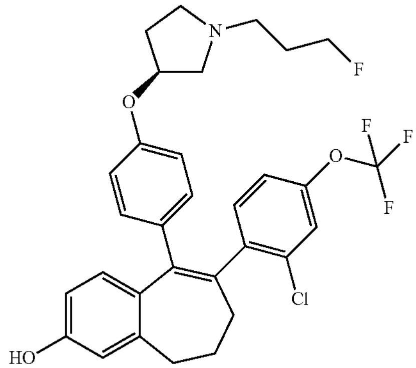 [SMILES: Oc1ccc2c(c1)CCCC(c1ccc(OC(F)(F)F)cc1Cl)=C2c1ccc(O[C@H]2CCN(CCCF)C2)cc1] | 6-[2-chloro-4-(trifluoromethoxy)-phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.67 (m, 1 H); 1.79 (dm, J = 25.3 Hz, 2 H); 2.08 (m, 2 H); 2.19 (m, 3 H); 2.36 (m, 1 H); 2.45 (t, J = 7.2 Hz, 2 H); 2.52 (m, 1 H); 2.62 (m, 1 H); 2.78 (m, 3 H); 4.47 (td, J = 6.1 and 47.5 Hz, 2 H); 4.72 (m, 1 H); 6.57 (s, 2 H); 6.59 (d, J = 8.8 Hz, 2 H); 6.70 (d, J = 8.8 Hz, 2 H); 6.71 (s, 1 H); 7.19 (d, J = 8.3 Hz, 1 H); 7.25 (d, J = 8.3 Hz, 1 H); 7.50 (s, 1 H); 9.45 (s, 1 H) | 576 |

TABLE 1-continued

| Examples | Structure | Name | Method | NMR | MASS: LC/MS (m/z, MH+): |
|---|---|---|---|---|---|
| 137 | 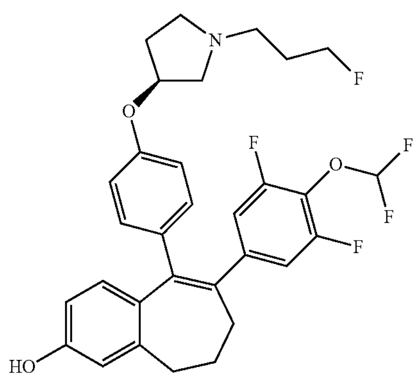 [SMILES: Oc1ccc2c(c1)CCCC(c1cc(F)c(OC(F)F)c(F)c1)=C2c1ccc(O[C@H]2CCN(CCCF)C2)cc1] | 6-[4-(difluoro-methoxy)-3,5-difluoro-phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.05 (m, 2 H); 2.16 to 2.28 (m, 3 H); 2.39 (m, 1 H); 2.48 (t, J = 7.2 Hz, 2 H); 2.55 (dd, J = 3.0 and 10.4 Hz, 1 H); 2.67 (m, 3 H); 2.80 (dd, J = 6.4 and 10.4 Hz, 1 H); 4.48 (td, J = 6.1 and 47.5 Hz, 2 H); 4.78 (m, 1 H); 6.57 (s, 2 H); 6.68 (d, J = 8.8 Hz, 2 H); 6.69 (s, 1 H); 6.78 (d, J = 8.8 Hz, 2 H); 6.99 (d, J = 8.4 Hz, 2 H); 7.19 (t, J = 72.5 Hz, 1 H); 9.38 (s, 1 H) | 560 |
| 138 | 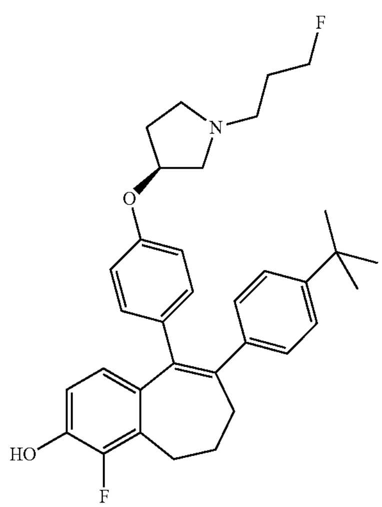 [SMILES: CC(C)(C)c1ccc(C2=C(c3ccc(O[C@H]4CCN(CCCF)C4)cc3)c3ccc(O)c(F)c3CCC2)cc1] | 6-(4-tert-butylphenyl)-1-fluoro-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.22 (s, 9 H); 1.70 (m, 1 H); 1.79 (dm, J = 25.3 Hz, 2 H); 2.03 (m, 2 H); 2.19 (m, 1 H); 2.25 (t, J = 7.0 Hz, 2 H); 2.38 (m, 1 H); 2.46 (t, J = 7.2 Hz, 2 H); 2.53 (m, 1 H); 2.65 (m, 1 H); 2.77 (m, 3 H); 4.47 (td, J = 6.1 and 47.5 Hz, 2 H); 4.74 (m, 1 H); 6.39 (d, J = 8.5 Hz, 1 H); 6.59 (d, J = 8.8 Hz, 2 H); 6.72 (m, 3 H); 7.04 (d, J = 8.5 Hz, 2 H); 7.19 (d, J = 8.5 Hz, 2 H); 9.74 (s, 1 H) | 532 |
| 139 | 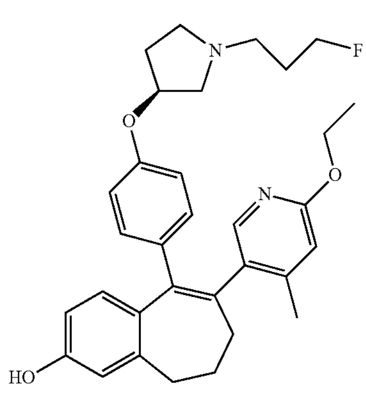 [SMILES: CCOc1cc(C)c(C2=C(c3ccc(O[C@H]4CCN(CCCF)C4)cc3)c3ccc(O)cc3CCC2)cn1] | 6-(6-ethoxy-4-methyl-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.25 (t, J = 7.2 Hz, 3 H); 1.69 (m, 1 H); 1.80 (dm, J = 25.3 Hz, 2 H); 2.01 to 2.25 (m, 5 H); 2.12 (s, 3 H); 2.35 to 2.88 (m, 8 H); 4.19 (m, 2 H); 4.46 (td, J = 6.1 and 47.5 Hz, 2 H); 4.74 (m, 1 H); 6.54 (s, 2 H); 6.56 (s, 2 H); 6.60 (d, J = 8.8 Hz, 2 H); 6.69 (d, J = 8.8 Hz, 2 H); 6.71 (s, 1 H); 7.70 (s, 1 H); 9.38 (s, 1 H) | 517 |

| Examples | Structure | Name | Method | NMR | MASS: LC/MS (m/z, MH+): |
|---|---|---|---|---|---|
| 140 | 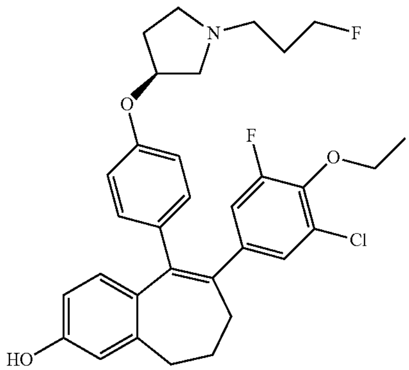 [SMILES: CCOc1c(F)cc(C2=C(c3ccc(O[C@H]4CCN(CCCF)C4)cc3)c3ccc(O)cc3CCC2)cc1Cl] | 6-(3-chloro-4-ethoxy-5-fluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.25 (t, J = 7.2 Hz, 3 H); 1.70 (m, 1 H); 1.81 (dm, J = 25.3 Hz, 2 H); 2.05 (m, 2 H); 2.15 to 2.17 (m, 3 H); 2.39 (m, 1 H); 2.46 (t, J = 7.2 Hz, 2 H); 2.55 (dd, J = 3.0 and 10.4 Hz, 1 H); 2.65 (m, 3 H); 2.79 (dd, J = 6.4 and 10.4 Hz, 1 H); 4.05 (q, J = 7.2 Hz, 2 H); 4.47 (td, J = 6.1 and 47.5 Hz, 2 H); 4.78 (m, 1 H); 6.56 (m, 2 H); 6.67 (d, J = 8.8 Hz, 2 H); 6.68 (s, 1 H); 6.75 (d, J = 8.8 Hz, 2 H); 6.97 (dd, J = 2.5 and 12.5 Hz, 1 H); 6.99 (t, J = 2.5 Hz, 1 H); 9.42 (s, 1 H) | 554 |
| 141 | 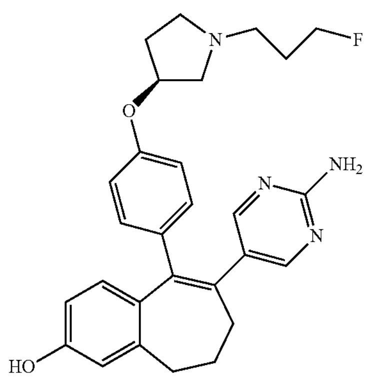 [SMILES: Nc1ncc(C2=C(c3ccc(O[C@H]4CCN(CCCF)C4)cc3)c3ccc(O)cc3CCC2)cn1] | 6-(2-amino-pyrimidin-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.71 (m, 1 H); 1.80 (dm, J = 25.3 Hz, 2 H); 2.08 (m, 2 H); 2.17 to 2.26 (m, 3 H); 2.40 (m, 1 H); 2.48 (t, J = 7.2 Hz, 2 H); 2.57 (dd, J = 3.0 and 10.4 Hz, 1 H); 2.65 (m, 3 H); 2.82 (dd, J = 6.4 and 10.4 Hz, 1 H); 4.48 (td, J = 6.1 and 47.5 Hz, 2 H); 4.78 (m, 1 H); 6.43 (s, 2 H); 6.55 (s, 2 H); 6.68 (s, 1 H); 6.69 (d, J = 8.8 Hz, 2 H); 6.81 (d, J = 8.8 Hz, 2 H); 7.95 (s, 2 H); 9.34 (s, 1 H) | 475 |
| 142 | 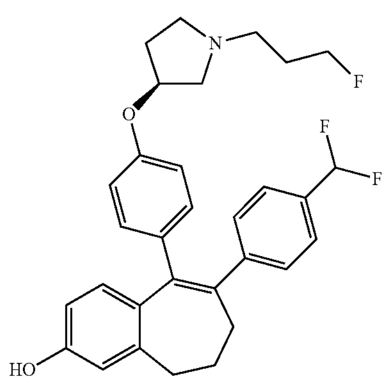 [SMILES: Oc1ccc2c(c1)CCCC(c1ccc(C(F)F)cc1)=C2c1ccc(O[C@H]2CCN(CCCF)C2)cc1] | 6-[4-(difluoro-methyl)-phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.04 (m, 2 H); 2.19 (m, 1 H); 2.29 (t, J = 7.0 Hz, 2 H); 2.39 (m, 1 H); 2.48 (m, 2 H); 2.55 (m, 1 H); 2.68 (m, 3 H); 2.80 (m, 1 H); 4.47 (td, J = 6.1 and 47.5 Hz, 2 H); 4.74 (m, 1 H); 6.56 (s, 2 H); 6.61 (d, J = 8.8 Hz, 2 H); 6.70 (s, 1 H); 6.72 (d, J = 8.8 Hz, 2 H); 6.92 (t, J = 56.1 Hz, 1 H); 7.24 (d, J = 8.3 Hz, 2 H); 7.36 (d, J = 8.3 Hz, 2 H); 9.40 (s, 1 H) | 508 |

| Examples | Structure | Name | Method | NMR | MASS: LC/MS (m/z, MH+): |
|---|---|---|---|---|---|
| 143 | 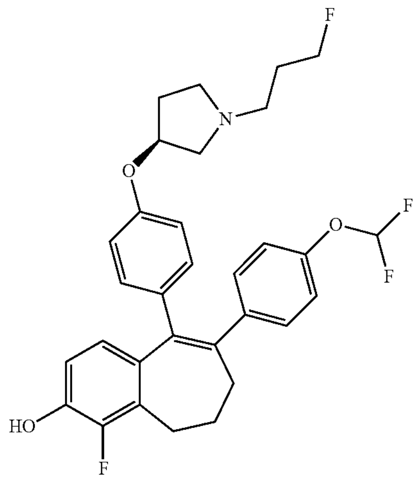 [SMILES: Oc1ccc2c(c1F)CCCC(c1ccc(OC(F)F)cc1)=C2c1ccc(O[C@H]2CCN(CCCF)C2)cc1] | 6-[4-(difluoro-methoxy)-phenyl]-1-fluoro-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.03 (m, 2 H); 2.20 (m, 1 H); 2.26 (t, J = 7.0 Hz, 2 H); 2.39 (m, 1 H); 2.48 (t, J = 7.2 Hz, 2 H); 2.54 (dd, J = 3.0 and 10.4 Hz, 1 H); 2.65 (m, 1 H); 2.78 (m, 3 H); 4.47 (td, J = 6.1 and 47.5 Hz, 2 H); 4.73 (m, 1 H); 6.40 (d, J = 8.6 Hz, 1 H); 6.61 (d, J = 8.8 Hz, 2 H); 6.73 (d, J = 8.8 Hz, 3 H); 6.98 (d, J = 8.8 Hz, 2 H); 7.18 (d, J = 8.8 Hz, 2 H); 7.19 (t, J = 74.3 Hz, 1 H); 9.80 (s, 1 H) | 542 |
| 144 | 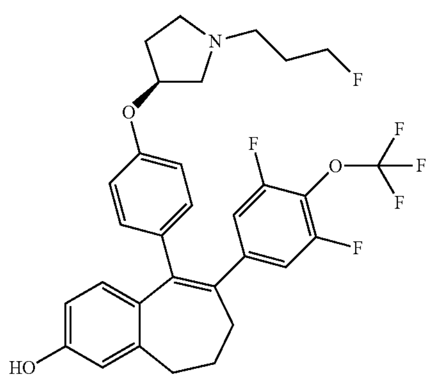 [SMILES: Oc1ccc2c(c1)CCCC(c1cc(F)c(OC(F)(F)F)c(F)c1)=C2c1ccc(O[C@H]2CCN(CCCF)C2)cc1] | 6-[3,5-difluoro-4-(trifluoro-methoxy)-phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.06 (m, 2 H); 2.20 (m, 1 H); 2.25 (t, J = 7.0 Hz, 2 H); 2.39 (m, 1 H); 2.46 (t, J = 7.2 Hz, 2 H); 2.53 (dd, J = 3.0 and 10.4 Hz, 1 H); 2.67 (m, 3 H); 2.79 (dd, J = 6.4 and 10.4 Hz, 1 H); 4.47 (td, J = 6.1 and 47.5 Hz, 2 H); 4.79 (m, 1 H); 6.57 (s, 2 H); 6.69 (d, J = 8.8 Hz, 2 H); 6.71 (s, 1 H); 6.76 (d, J = 8.8 Hz, 2 H); 7.10 (d, J = 9.8 Hz, 2 H); 9.48 (s, 1 H) | 578 |
| 145 | 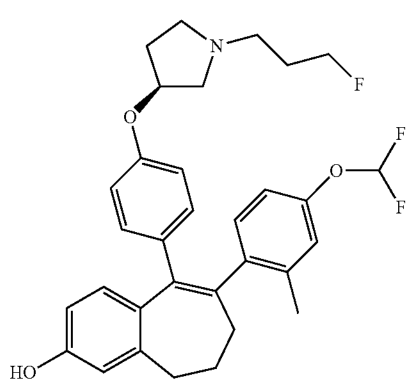 [SMILES: Cc1cc(OC(F)F)ccc1C1=C(c2ccc(O[C@H]3CCN(CCCF)C3)cc2)c2ccc(O)cc2CCC1] | 6-[4-(difluoro-methoxy)-2-methyl-phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.02 to 2.23 (m, 5 H); 2.12 (s, 3 H); 2.37 (m, 1 H); 2.46 (t, J = 7.2 Hz, 2 H); 2.53 (m, 1 H); 2.59 to 2.81 (m, 4 H); 4.47 (td, J = 6.1 and 47.5 Hz, 2 H); 4.71 (m, 1 H); 6.56 (s, 2 H); 6.58 (d, J = 8.8 Hz, 2 H); 6.65 (d, J = 8.8 Hz, 2 H); 6.69 (s, 1 H); 6.83 (dd, J = 2.5 and 8.7 Hz, 1 H); 6.91 (d, J = 2.5 Hz, 1 H); 7.05 (d, J = 8.7 Hz, 1 H); 7.15 (t, J = 74.5 Hz, 1 H); 9.38 (s, 1 H) | 538 |

TABLE 1-continued

| Examples | Structure | Name | Method | NMR | MASS: LC/MS (m/z, MH+): |
|---|---|---|---|---|---|
| 146 | 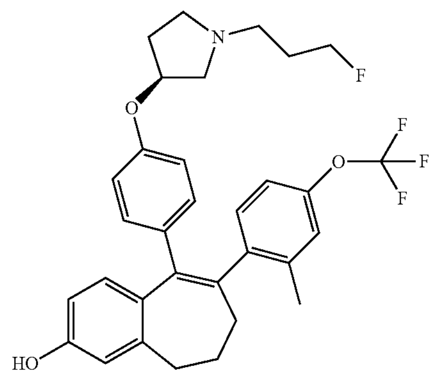 [SMILES: Cc1cc(OC(F)(F)F)ccc1C1=C(c2ccc(O[C@H]3CCN(CCCF)C3)cc2)c2ccc(O)cc2CCC1] | 5-[4-[(3S)-1-(3-fluoropropyl)-pyrrolidin-3-yl]oxy-phenyl]-6-[2-methyl-4-(trifluoro-methoxy)-phenyl]-8,9-dihydro-7H-benzo[7]-annulen-2-ol | A | 1H NMR (400 MHz, DMSO-d6, δ ppm): 1.65 (m, 1 H); 1.78 (dm, J = 25.3 Hz, 2 H); 2.02 to 2.13 (m, 5 H); 2.16 (s, 3 H); 2.37 (m, 1 H); 2.44 (t, J = 7.2 Hz, 2 H); 2.54 (m, 1 H); 2.59 to 2.81 (m, 4 H); 4.46 (td, J = 6.1 and 47.5 Hz, 2 H); 4.71 (m, 1 H); 6.55 (d, J = 8.8 Hz, 2 H); 6.58 (s, 2 H); 6.65 (d, J = 8.8 Hz, 2 H); 6.71 (s, 1 H); 7.01 (d, J = 9.1 Hz, 1 H); 7.10 (d, J = 2.8 Hz, 1 H); 7.12 (dd, J = 2.9 and 9.1 Hz, 1 H); 9.40 (s, 1 H) | 556 |
| 147 | 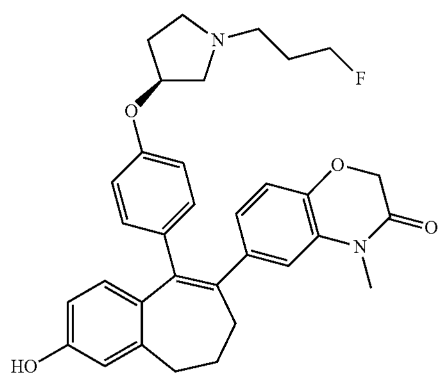 [SMILES: CN1C(=O)COc2ccc(C3=C(c4ccc(O[C@H]5CCN(CCCF)C5)cc4)c4ccc(O)cc4CCC3)cc21] | 6-[5-[4-[(3S)-1-(3-fluoropropyl)-pyrrolidin-3-yl]oxy-phenyl]-2-hydroxy-8,9-dihydro-7H-benzo[7]-annulen-6-yl]-4-methyl-1,4-benzoxazin-3-one | A | 1H NMR (400 MHz, DMSO-d6, δ ppm): 1.69 (m, 1 H); 1.80 (dm, J = 25.3 Hz, 2 H); 2.04 (m, 2 H); 2.20 (m, 1 H); 2.29 (t, J = 7.0 Hz, 2 H); 2.39 (m, 1 H); 2.47 (t, J = 7.2 Hz, 2 H); 2.54 (m, 1 H); 2.68 (m, 3 H); 2.79 (dd, J = 6.4 and 10.4 Hz, 1 H); 3.00 (s, 3 H); 4.47 (td, J = 6.1 and 47.5 Hz, 2 H); 4.59 (s, 2 H); 4.75 (m, 1 H); 6.58 (m, 2 H); 6.64 (d, J = 8.8 Hz, 2 H); 6.69 (m, 1 H); 6.77 (d, J = 8.8 Hz, 2 H); 6.79 (m, 2 H); 6.82 (s, 1 H); 9.39 (s, 1 H) | 543 |
| 148 | 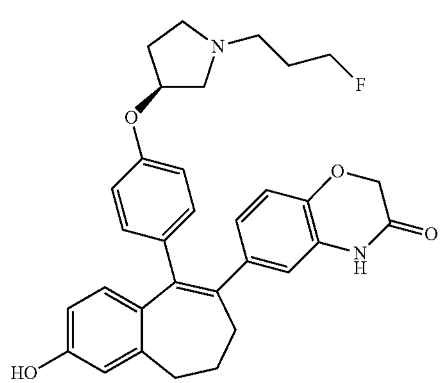 [SMILES: O=C1COc2ccc(C3=C(c4ccc(O[C@H]5CCN(CCCF)C5)cc4)c4ccc(O)cc4CCC3)cc2N1] | 6-[5-[4-[(3S)-1-(3-fluoropropyl)-pyrrolidin-3-yl]oxy-phenyl]-2-hydroxy-8,9-dihydro-7H-benzo[7]-annulen-6-yl]-4H-1,4-benzoxazin-3-one | A | 1H NMR (400 MHz, DMSO-d6, δ ppm): 1.70 (m, 1 H); 1.79 (dm, J = 25.3 Hz, 2 H); 2.03 (m, 2 H); 2.20 (m, 3 H); 2.39 (m, 1 H); 2.48 (t, J = 7.2 Hz, 2 H); 2.54 (dd, J = 3.0 and 10.4 Hz, 1 H); 2.65 (m, 3 H); 2.80 (d, J = 6.4 and 10.4 Hz, 1 H); 4.47 (td, J = 6.1 and 47.5 Hz, 2 H); 4.51 (s, 2 H); 4.75 (m, 1 H); 6.55 (s, 2 H); 6.62 (d, J = 8.8 Hz, 2 H); 6.64 (s, 1 H); 6.68 to 6.76 (m, 5 H); 9.38 (s, 1 H); 10.51 (s, 1 H) | 529 |

TABLE 1-continued

| Examples | Structure | Name | Method | NMR | MASS: LC/MS (m/z, MH+): |
|---|---|---|---|---|---|
| 149 | 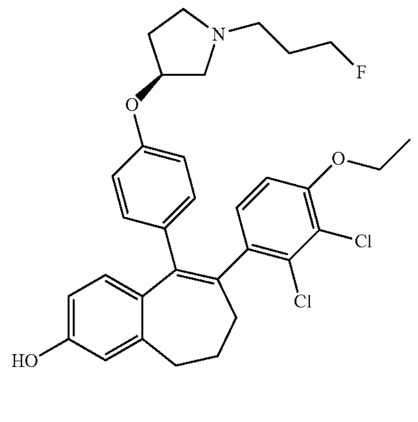 | 6-(2,3-dichloro-4-ethoxy-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.31 (t, J = 7.1 Hz, 3 H); 1.68 (m, 1 H); 1.79 (dm, J = 25.3 Hz, 2 H); 2.07 (m, 2 H); 2.12 to 2.25 (m, 3 H); 2.38 (m, 1 H); 2.42 to 2.56 (m, 3 H); 2.60 to 2.85 (m, 4 H); 4.08 (m, 2 H); 4.47 (td, J = 6.1 and 47.5 Hz, 2 H); 4.72 (m, 1 H); 6.56 (s, 2 H); 6.61 (d, J = 8.8 Hz, 2 H); 6.70 (s, 1 H); 6.72 (d, J = 8.8 Hz, 2 H); 6.92 (d, J = 8.9 Hz, 1 H); 7.02 (d, J = 8.9 Hz, 1 H); 9.40 (s, 1 H) | 570 |
| 150 | 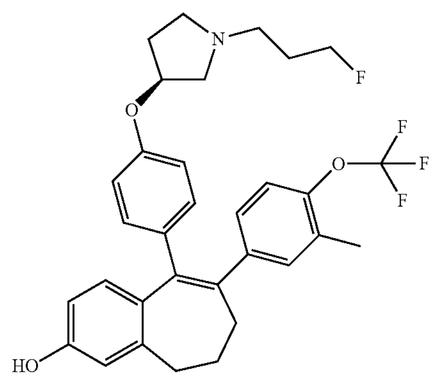 [SMILES: Cc1cc(C2=C(c3ccc(O[C@H]4CCN(CCCF)C4)cc3)c3ccc(O)cc3CCC2)ccc1OC(F)(F)F] | 5-[4-[(3S)-1-(3-fluoropropyl)-pyrrolidin-3-yl]oxy-phenyl]-6-[3-methyl-4-(trifluoro-methoxy)-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.05 (m, 2 H); 2.13 (s, 3 H); 2.19 (m, 1 H); 2.26 (m, 2 H); 2.38 (m, 1 H); 2.46 (t, J = 7.2 Hz, 2 H); 2.53 (dd, J = 3.0 and 10.4 Hz, 1 H); 2.65 (m, 3 H); 2.78 (dd, J = 6.4 and 10.4 Hz, 1 H); 4.47 (td, J = 6.1 and 47.5 Hz, 2 H); 4.75 (m, 1 H); 6.57 (s, 2 H); 6.61 (d, J = 8.8 Hz, 2 H); 6.70 (s, 1 H); 6.72 (d, J = 8.8 Hz, 2 H); 7.00 (dd, J = 2.3 and 8.5 Hz, 1 H); 7.17 (d, J = 8.5 Hz, 1 H); 7.25 (d, J = 2.3 Hz, 1 H); 9.40 (s, 1 H) | 556 |
| 151 | 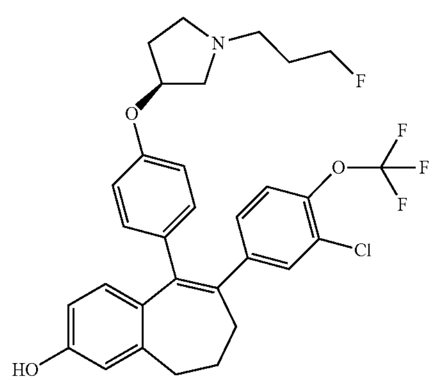 [SMILES: Oc1ccc2c(c1)CCCC(c1ccc(OC(F)(F)F)c(Cl)c1)=C2c1ccc(O[C@H]2CCN(CCCF)C2)cc1] | 6-[3-chloro-4-(trifluoro-methoxy)-phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.08 (m, 2 H); 2.19 (m, 1 H); 2.28 (t, J = 7.0 Hz, 2 H); 2.38 (m, 1 H); 2.47 (t, J = 7.2 Hz, 2 H); 2.54 (m, 1 H); 2.67 (m, 3 H); 2.78 (dd, J = 6.4 and 10.4 Hz, 1 H); 4.47 (td, J = 6.1 and 47.5 Hz, 2 H); 4.77 (m, 1 H); 6.58 (s, 2 H); 6.65 (d, J = 8.8 Hz, 2 H); 6.70 (s, 1 H); 6.74 (d, J = 8.8 Hz, 2 H); 7.19 (dd, J = 2.2 and 8.6 Hz, 1 H); 7.34 (qd, J = 1.6 and 8.6 Hz, 1 H); 7.36 (d, J = 2.2 Hz, 1 H); 9.44 (s, 1 H) | 576 |

TABLE 1-continued

| Examples | Structure | Name | Method | NMR | MASS: LC/MS (m/z, MH+): |
|---|---|---|---|---|---|
| 152 | 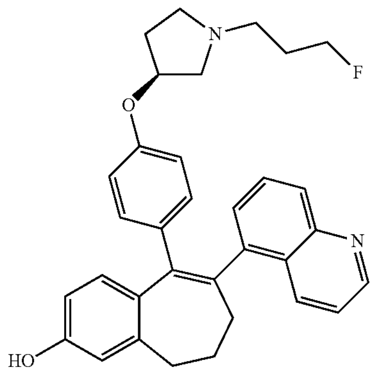 [SMILES: Oc1ccc2c(c1)CCCC(c1cccc3ncccc13)=C2c1ccc(O[C@H]2CCN(CCCF)C2)cc1] | 5-[4-[(3S)-1-(3-fluoropropyl)-pyrrolidin-3-yl]oxy-phenyl]-6-(5-quinolyl)-8,9-dihydro-7H-benzo[7]-annulen-2-ol | A | 1H NMR (400 MHz, DMSO-d6, δ ppm): 1.57 (m, 1 H); 1.75 (dm, J = 25.3 Hz, 2 H); 2.08 (m, 3 H); 2.21 (m, 1 H); 2.31 (m, 1 H); 2.36 to 2.52 (m, 4 H); 2.58 (m, 1 H); 2.69 (m, 1 H); 2.79 (m, 1 H); 2.90 (m, 1 H); 4.43 (td, J = 6.1 and 47.5 Hz, 2 H); 4.61 (m, 1 H); 6.43 (d, J = 8.8 Hz, 2 H); 6.61 (m, 4 H); 6.75 (d, J = 2.5 Hz, 1 H); 7.31 (d, J = 7.8 Hz, 1 H); 7.48 (dd, J = 4.5 and 8.5 Hz, 1 H); 7.59 (m, 1 H); 7.82 (d, J = 8.5 Hz, 1 H); 8.30 (d, J = 8.9 Hz, 1 H); 8.84 (dd, J = 2.0 and 4.5 Hz, 1 H); 9.42 (s, 1 H) | 509 |
| 153 | 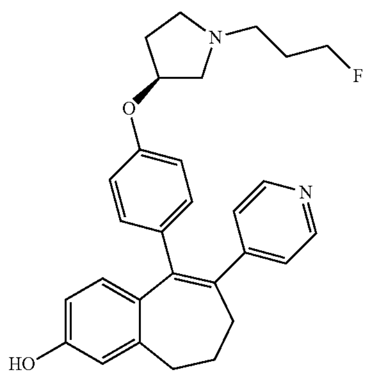 [SMILES: Oc1ccc2c(c1)CCCC(c1ccncc1)=C2c1ccc(O[C@H]2CCN(CCCF)C2)cc1] | 5-[4-[(3S)-1-(3-fluoropropyl)-pyrrolidin-3-yl]oxy-phenyl]-6-(4-pyridyl)-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.03 (m, 2 H); 2.20 (m, 1 H); 2.28 (t, J = 7.0 Hz, 2 H); 2.38 (m, 1 H); 2.47 (t, J = 7.2 Hz, 2 H); 2.55 (dd, J = 3.0 and 10.4 Hz, 1 H); 2.63 (m, 3 H); 2.80 (dd, J = 6.3 and 10.4 Hz, 1 H); 4.47 (td, J = 6.1 and 47.5 Hz, 2 H); 4.76 (m, 1 H); 6.55 (s, 2 H); 6.62 (d, J = 8.8 Hz, 2 H); 6.70 (s, 1 H); 6.73 (d, J = 8.8 Hz, 2 H); 7.08 (d, J = 6.3 Hz, 2 H); 8032 (d, J = 6.3 Hz, 2 H); 9.48 (s, 1 H) | 459 |
| 154 | 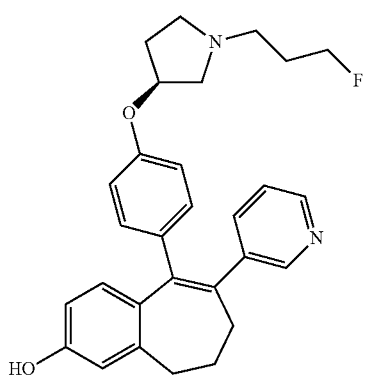 [SMILES: Oc1ccc2c(c1)CCCC(c1cccnc1)=C2c1ccc(O[C@H]2CCN(CCCF)C2)cc1] | 5-[4-[(3S)-1-(3-fluoropropyl)-pyrrolidin-3-yl]oxy-phenyl]-6-(3-pyridyl)-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.05 (m, 2 H); 2.20 (m, 1 H); 2.29 (t, J = 7.0 Hz, 2 H); 2.38 (m, 1 H); 2.47 (t, J = 7.2 Hz, 2 H); 2.54 (dd, J = 3.0 and 10.4 Hz, 1 H); 2.60 to 2.72 (m, 3 H); 2.80 (dd, J = 6.4 and 10.4 Hz, 1 H); 4.47 (td, J = 6.1 and 47.5 Hz, 2 H); 4.74 (m, 1 H); 6.57 (s, 2 H); 6.62 (d, J = 8.8 Hz, 2 H); 6.71 (s, 1 H); 6.74 (d, J = 8.8 Hz, 2 H); 7.22 (dd, J = 5.0 and 8.3 Hz, 1 H); 7.57 (td, J = 2.3 and 8.3 Hz, 1 H); 8.23 (d, J = 2.3 Hz, 1 H); 8.27 (dd, J = 2.3 and 5.0 Hz, 1 H); 9.44 (s, 1 H) | 459 |

TABLE 1-continued

| Examples | Structure | Name | Method | NMR | MASS: LC/MS (m/z, MH+): |
|---|---|---|---|---|---|
| 155 | 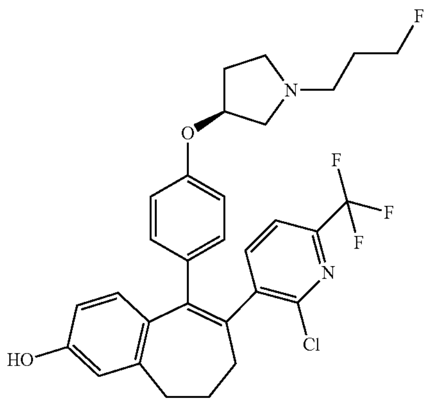 [SMILES: Oc1ccc2c(c1)CCCC(c1ccc(C(F)(F)F)nc1Cl)=C2c1ccc(O[C@H]2CCN(CCCF)C2)cc1] | 6-[2-chloro-6-(trifluoromethyl)-3-pyridyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.78 (dm, J = 25.3 Hz, 2 H); 2.06 to 2.31 (m, 5 H); 2.38 (m, 1 H); 2.46 (t, J = 7.2 Hz, 2 H); 2.54 (m, 1 H); 2.64 (m, 1 H); 2.79 (m, 3 H); 4.46 (td, J = 6.1 and 47.5 Hz, 2 H); 4.73 (m, 1 H); 6.59 (s, 2 H); 6.65 (d, J = 8.8 Hz, 2 H); 6.73 (m, 3 H); 7.78 (d, J = 9.0 Hz, 1 H); 7.89 (d, J = 9.0 Hz, 1 H); 9.49 (s, 1 H) | 561 |
| 156 | 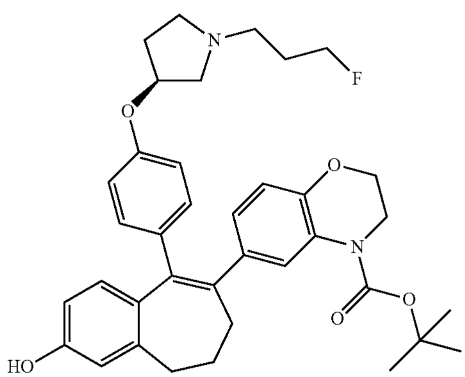 [SMILES: CC(C)(C)OC(=O)N1CCOc2ccc(C3=C(c4ccc(O[C@H]5CCN(CCCF)C5)cc4)c4ccc(O)cc4CCC3)cc21] | tert-butyl 6-[5-[4-[(3S)-1-(3-fluoropropyl)-pyrrolidin-3-yl]oxy-phenyl]-2-hydroxy-8,9-dihydro-7H-benzo[7]-annulen-6-yl]-2,3-dihydro-1,4-benzoxazine-4-carboxylate | A | 1H NMR (400 MHz, DMSO-d6, δ ppm): 1.34 (s, 9 H); 1.70 (m, 1 H); 1.80 (dm, J = 25.3 Hz, 2 H); 2.03 (m, 2 H); 2.13 to 2.27 (m, 3 H); 2.39 (m, 1 H); 2.47 (t, J = 7.2 Hz, 2 H); 2.54 (m, 1 H); 2.65 (m, 3 H); 2.80 (dd, J = 6.4 and 10.4 Hz, 1 H); 3.71 (t, J = 4.5 Hz, 2 H); 4.15 (t, J = 4.5 Hz, 2 H); 4.47 (td, J = 6.1 and 47.5 Hz, 2 H); 4.75 (m, 1 H); 6.54 (m, 2 H); 6.58 to 6.65 (m, 4 H); 6.68 (s, 1 H); 6.74 (d, J = 8.8 Hz, 2 H); 7.58 (s, 1 H); 9.32 (s, 1 H) | 615 |
| 157 | 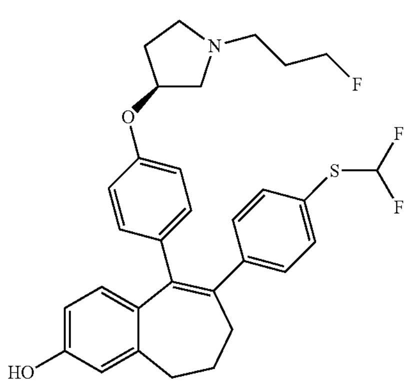 [SMILES: Oc1ccc2c(c1)CCCC(c1ccc(SC(F)F)cc1)=C2c1ccc(O[C@H]2CCN(CCCF)C2)cc1] | 6-[4-(difluoromethylsulfanyl)-phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.04 (m, 2 H); 2.19 (m, 1 H); 2.27 (t, J = 7.0 Hz, 2 H); 2.38 (m, 1 H); 2.47 (t, J = 7.2 Hz, 2 H); 2.54 (m, 1 H); 2.66 (m, 3 H); 2.79 (dd, J = 6.4 and 10.4 Hz, 1 H); 4.47 (td, J = 6.1 and 47.5 Hz, 2 H); 4.74 (m, 1 H); 6.57 (s, 2 H); 6.60 (d, J = 8.8 Hz, 2 H); 6.70 (s, 1 H); 6.72 (d, J = 8.8 Hz, 2 H); 7.20 (d, J = 8.6 Hz, 2 H); 7.36 (d, J = 8.6 Hz, 2 H); 7.42 (t, J = 56.1 Hz, 1 H); 9.41 (s, 1 H) | 540 |

TABLE 1-continued

| Examples | Structure | Name | Method | NMR | MASS: LC/MS (m/z, MH+): |
|---|---|---|---|---|---|
| 158 | 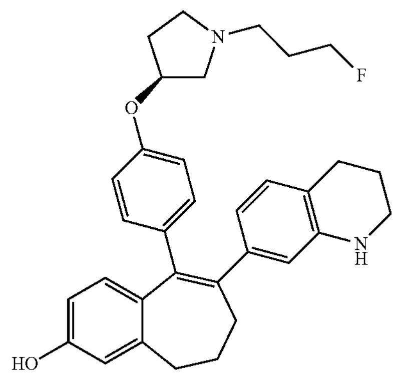 [SMILES: Oc1ccc2c(c1)CCCC(c1ccc3c(c1)NCCC3)=C2c1ccc(O[C@H]2CCN(CCCF)C2)cc1] | 5-[4-[(3S)-1-(3-fluoropropyl)-pyrrolidin-3-yl]oxy-phenyl]-6-(1,2,3,4-tetrahydroquinolin-7-yl)-8,9-dihydro-7H-benzo[7]-annulen-2-ol | A | 1H NMR (400 MHz, DMSO-d6, δ ppm): 1.66 to 1.88 (m, 5 H); 2.01 (m, 2 H); 2.15 (t, J = 7.0 Hz, 2 H); 2.21 (m, 1 H); 2.39 (m, 1 H); 2.43 to 2.79 (m, 8 H); 2.80 (m, 1 H); 3.10 (m, 2 H); 4.47 (td, J = 6.1 and 47.5 Hz, 2 H); 4.74 (m, 1 H); 5.40 (s, 1 H); 6.15 (d, J = 8.3 Hz, 1 H); 6.25 (s, 1 H); 6.53 (s, 2 H); 6.55 to 6.62 (m, 3 H); 6.67 (s, 1 H); 6.78 (d, J = 8.8 Hz, 2 H); 9.31 (s, 1 H) | 513 |
| 159 | 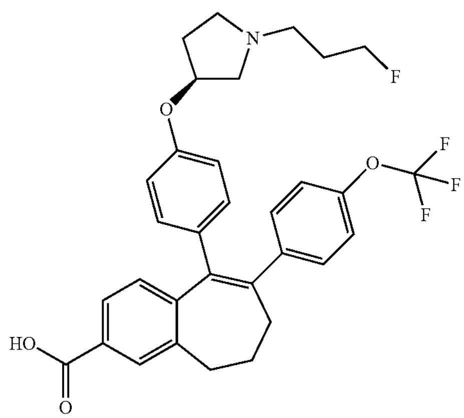 [SMILES: O=C(O)c1ccc2c(c1)CCCC(c1ccc(OC(F)(F)F)cc1)=C2c1ccc(O[C@H]2CCN(CCCF)C2)cc1] | 5-[4-[(3S)-1-(3-fluoropropyl)-pyrrolidin-3-yl]oxy-phenyl]-6-[4-(trifluoro-methoxy)-phenyl]-8,9-dihydro-7H-benzo[7]-annulen-2-carboxylic acid | B | 1H NMR (400 MHz, DMSO-d6, δ ppm): 1.69 (m, 1 H); 1.79 (dm, J = 25.3 Hz, 2 H); 2.12 (t, J = 7.0 Hz, 2 H); 2.20 (m, 1 H); 2.27 (t, J = 7.0 Hz, 2 H); 2.39 (m, 1 H); 2.48 (t, J = 7.2 Hz, 2 H); 2.55 (dd, J = 3.0 and 10.5 Hz, 1 H); 2.65 (m, 1 H); 2.79 (dd, J = 6.4 and 10.4 Hz, 1 H); 2.84 (t, J = 7.0 Hz, 2 H); 4.47 (td, J = 6.1 and 47.5 Hz, 2 H); 4.75 (m, 1 H); 6.65 (d, J = 8.8 Hz, 2 H); 6.73 (d, J = 8.8 Hz, 2 H); 6.87 (d, J = 8.4 Hz, 1 H); 7.19 (d, J = 8.5 Hz, 2 H); 7.28 (d, J = 8.5 Hz, 2 H); 7.74 (dd. J = 1.9 and 8.4 Hz, 1 H); 7.90 (d, J = 1.9 Hz, 1 H); 12.84 (m, 1 H) | 570 |
| 160 | 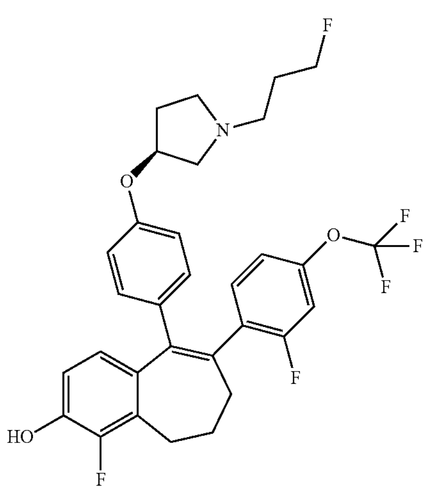 [SMILES: Oc1ccc2c(c1F)CCCC(c1ccc(OC(F)(F)F)cc1F)=C2c1ccc(O[C@H]2CCN(CCCF)C2)cc1] | 1-fluoro-5-[4-[(3S)-1-(3-fluoropropyl)-pyrrolidin-3-yl]oxy-phenyl]-6-[2-fluoro-4-(trifluoro-methoxy)-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.08 (m, 2 H); 2.03 to 2.24 (m, 3 H); 2.38 (m, 1 H); 2.46 (t, J = 7.2 Hz, 2 H); 2.53 (dd, J = 3.1 and 10.4 Hz, 1 H); 2.63 (m, 1 H); 2.79 (m, 3 H); 4.46 (td, J = 6.1 and 47.5 Hz, 2 H); 4.72 (m, 1 H); 6.41 (d, J = 8.7 Hz, 1 H); 6.62 (d, J = 8.8 Hz, 2 H); 6.72 (d, J = 8.8 Hz, 2 H); 6.75 (t, J = 8.7 Hz, 1 H); 7.09 (dd, J = 3.0 and 8.6 Hz, 1 H); 7.23 (dd, J = 3.0 and 10.3 Hz, 1 H); 7.30 (t, J = 8.6 Hz, 1 H); 9.89 (m, 1 H) | 578 |

TABLE 1-continued

| Examples | Structure | Name | Method | NMR | MASS: LC/MS (m/z, MH+): |
|---|---|---|---|---|---|
| 161 | 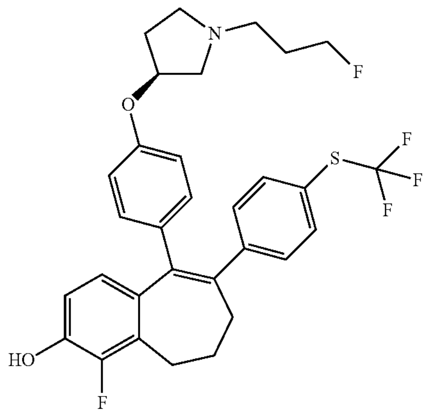 [SMILES: Oc1ccc2c(c1F)CCCC(c1ccc(SC(F)(F)F)cc1)=C2c1ccc(O[C@H]2CCN(CCCF)C2)cc1] | 1-fluoro-5-[4-[(3S)-1-(3-fluoropropyl)-pyrrolidin-3-yl]oxy-phenyl]-6-[4-(trifluoro-methyl-sulfanyl)-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.05 (m, 2 H); 2.19 (m, 1 H); 2.30 (t, J = 7.0 Hz, 2 H); 2.38 (m, 1 H); 2.47 (t, J = 7.2 Hz, 2 H); 2.53 (dd, J = 3.0 and 10.5 Hz, 1 H); 2.64 (m, 1 H); 2.79 (m, 3 H); 4.47 (td, J = 6.1 and 47.5 Hz, 2 H); 4.72 (m, 1 H); 6.41 (d, J = 8.7 Hz, 1 H); 6.60 (d, J = 8.8 Hz, 2 H); 6.72 (d, J = 8.8 Hz, 2 H); 6.73 (t, J = 8.7 Hz, 1 H); 7.28 (d, J = 8.4 Hz, 2 H); 7.50 (d, J = 8.4 Hz, 2 H); 9.82 (m, 1 H) | 576 |
| 162 | 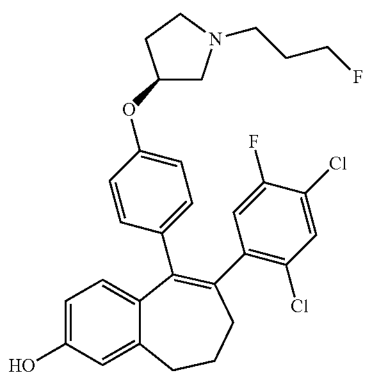 [SMILES: Oc1ccc2c(c1)CCCC(c1cc(F)c(Cl)cc1Cl)=C2c1ccc(O[C@H]2CCN(CCCF)C2)cc1] | 6-(2,4-dichloro-5-fluoro-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.08 (m, 2 H); 2.12 to 2.14 (m, 3 H); 2.38 (m, 1 H); 2.47 (t, J = 7.2 Hz, 2 H); 2.53 (dd, J = 3.0 and 10.4 Hz, 1 H); 2.60 to 2.86 (m, 4 H); 4.48 (td, J = 6.1 and 47.5 Hz, 2 H); 4.75 (m, 1 H); 6.57 (s, 2 H); 6.65 (d, J = 8.8 Hz, 2 H); 6.71 (s, 1 H); 6.75 (d, J = 8.8 Hz, 2 H); 7.29 (d, J = 9.9 Hz, 1 H); 7.73 (d, J = 7.1 Hz, 1 H); 9.47 (s, 1 H) | 544 |
| 163 | 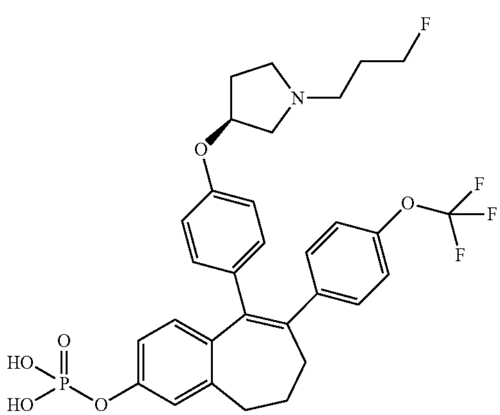 [SMILES: O=P(O)(O)Oc1ccc2c(c1)CCCC(c1ccc(OC(F)(F)F)cc1)=C2c1ccc(O[C@H]2CCN(CCCF)C2)cc1] | 5-[4-[(3S)-1-(3-fluoropropyl)-pyrrolidin-3-yl]oxy-phenyl]-6-[4-(trifluoro-methoxy)-phenyl]-8,9-dihydro-7H-benzo[7]-annulen-2-yl] dihydrogen phosphate | | 1H NMR (400 MHz, DMSO-d6, δ ppm): 1.82 to 2.11 (m, 5 H); 2.27 (m, 3 H); 2.70 (t, J = 7.0 Hz, 2 H); 2.80 to 3.30 (m, 6 H); 4.50 (td, J = 6.1 and 47.5 Hz, 2 H); 4.83 (m, 1 H); 6.57 (d, J = 8.8 Hz, 1 H); 6.61 (d, J = 8.8 Hz, 2 H); 6.70 (d, J = 8.8 Hz, 2 H); 6.90 (dd, J = 3.3 and 8.8 Hz, 1 H); 7.10 (d, J = 3.3 Hz, 1 H); 7.15 (d, J = 8.8 Hz, 2 H); 7.23 (d, J = 8.8 Hz, 2 H) | 622 |

TABLE 1-continued

| Examples | Structure | Name | Method | NMR | MASS: LC/MS (m/z, MH+): |
|---|---|---|---|---|---|
| 164 | 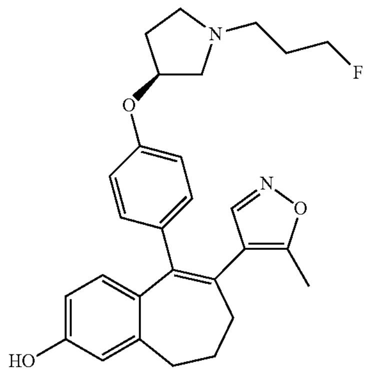 [SMILES: Cc1oncc1C1=C(c2ccc(O[C@H]3CCN(CCCF)C3)cc2)c2ccc(O)cc2CCC1] | 5-[4-[(3S)-1-(3-fluoropropyl)-pyrrolidin-3-yl]oxy-phenyl]-6-(5-methyl-isoxazol-4-yl)-8,9-dihydro-7H-benzo[7]-annulen-2-ol | A | 1H NMR (400 MHz, DMSO-d6, δ ppm): 1.67 to 1.90 (m, 3 H); 1.81 (s, 3 H); 2.04 (m, 2 H); 2.12 (m, 2 H); 2.22 (m, 1 H); 2.39 (m, 1 H); 2.48 (t, J = 7.2 Hz, 2 H); 2.58 (dd, J = 3.2 and 10.4 Hz, 1 H); 2.59 to 2.71 (m, 3 H); 2.81 (dd, J = 6.4 and 10.4 Hz, 1 H); 4.48 (td, J = 6.1 and 47.5 Hz, 2 H); 4.80 (m, 1 H); 6.57 (s, 2 H); 6.70 (s, 1 H); 6.71 (d, J = 8.8 Hz, 2 H); 6.80 (d, J = 8.8 Hz, 2 H); 8.39 (s, 1 H); 9.42 (s, 1 H) | 463 |
| 165 | 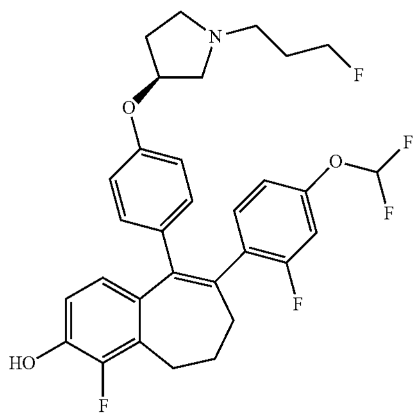 [SMILES: Oc1ccc2c(c1F)CCCC(c1ccc(OC(F)F)cc1F)=C2c1ccc(O[C@H]2CCN(CCCF)C2)cc1] | 6-[4-(difluoro-methoxy)-2-fluoro-phenyl]-1-fluoro-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.05 (m, 2 H); 2.19 (m, 3 H); 2.38 (m, 1 H); 2.46 (t, J = 7.2 Hz, 2 H); 2.53 (dd, J = 3.0 and 10.4 Hz, 1 H); 2.63 (m, 1 H); 2.79 (m, 3 H); 4.47 (td, J = 6.1 and 47.5 Hz, 2 H); 4.73 (m, 1 H); 6.40 (d, J = 8.5 Hz, 1 H); 6.62 (d, J = 8.8 Hz, 2 H); 6.72 (d, J = 8.8 Hz, 2 H); 6.74 (t, J = 8.5 Hz, 1 H); 6.89 (dd, J = 2.5 and 8.7 Hz, 1 H); 6.99 (dd, J = 2.5 and 10.8 Hz, 1 H); 7.22 (t, J = 8.7 Hz, 1 H); 7.25 (t, J = 73.8 Hz, 1 H); 9.83 (s, 1 H) | 560 |
| 166 | 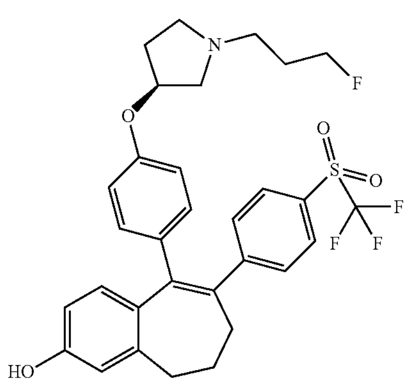 [SMILES: O=S(=O)(c1ccc(C2=C(c3ccc(O[C@H]4CCN(CCCF)C4)cc3)c3ccc(O)cc3CCC2)cc1)C(F)(F)F] | 5-[4-[(3S)-1-(3-fluoropropyl)-pyrrolidin-3-yl]oxy-phenyl]-6-[4-(trifluoro-methyl-sulfonyl)-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.07 (m, 2 H); 2.17 (m, 1 H); 2.30 to 2.40 (m, 3 H); 2.46 (t, J = 7.2 Hz, 2 H); 2.54 (dd, J = 3.0 and 10.4 Hz, 1 H); 2.60 to 2.72 (m, 3 H); 2.78 (dd, J = 6.4 and 10.4 Hz, 1 H); 4.47 (td, J = 6.1 and 47.5 Hz, 2 H); 4.74 (m, 1 H); 6.59 (s, 2 H); 6.62 (d, J = 8.8 Hz, 2 H); 6.71 (d, J = 8.8 Hz, 2 H); 6.73 (s, 1 H); 7.54 (d, J = 8.8 Hz, 2 H); 7.90 (d, J = 8.8 Hz, 2 H); 9.55 (s, 1 H) | 590 |

TABLE 1-continued

| Examples | Structure | Name | Method | NMR | MASS: LC/MS (m/z, MH+): |
|---|---|---|---|---|---|
| 167 | 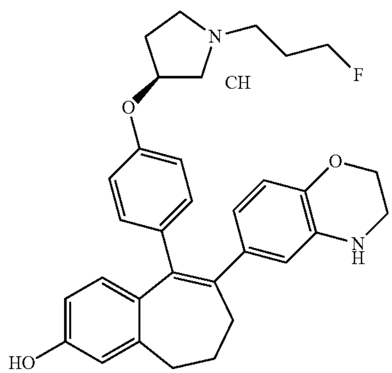 | 6-(3,4-dihydro-2H-1,4-benzoxazin-6-yl)-5-[4-[(3S)-1-(3-fluoropropyl)-pyrrolidin-3-yl]oxy-phenyl]-8,9-dihydro-7H-benzo[7]-annulen-2-ol hydrochloride | A | 1H NMR (400 MHz, DMSO-d6, δ ppm): 1.92 to 2.60 (m, 8 H); 2.62 (t, J = 7.0 Hz, 2 H); 3.11 to 4.00 (m, 8 H); 4.11 (m, 2 H); 4.53 (td, J = 6.1 and 47.5 Hz, 2 H); 5.03 (m, 0.5 H); 5.09 (m, 0.5 H); 6.31 (d, J = 8.5 Hz, 1 H); 6.47 (d, J = 8.5 Hz, 1 H); 6.50 to 6.58 m, 3 H); 6.69 (s, 1 H); 6.72 (d, J = 8.8 Hz, 2 H); 6.80 (d, J = 8.8 Hz, 2 H); 9.38 (m, 1 H); 10.50 (m, 0.5 H); 11.03 (m, 0.5 H) | 515 |
| 168 | 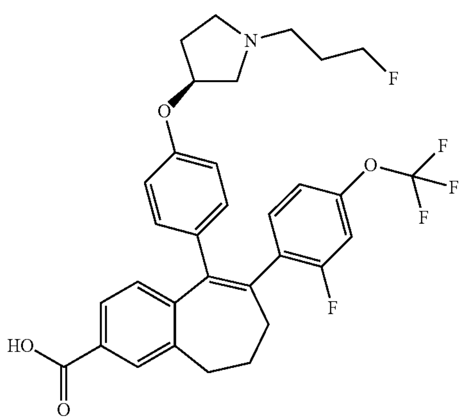 [SMILES: O=C(O)c1ccc2c(c1)CCCC(c1ccc(OC(F)(F)F)cc1F)=C2c1ccc(O[C@H]2CCN(CCCF)C2)cc1] | 5-[4-[(3S)-1-(3-fluoropropyl)-pyrrolidin-3-yl]oxy-phenyl]-6-[2-fluoro-4-(trifluoromethoxy)-phenyl]-8,9-dihydro-7H-benzo[7]-annulen-2-carboxylic acid | B | 1H NMR (400 MHz, DMSO-d6, δ ppm): 1.69 (m, 1 H); 1.80 (dm, J = 25.3 Hz, 2 H); 2.10 to 2.23 (m, 5 H); 2.38 (m, 1 H); 2.42 to 2.55 (m, 3 H); 2.62 (m, 1 H); 2.79 (dd, J = 6.3 and 10.4 Hz, 1 H); 2.85 (m, 2 H); 4.48 (td, J = 6.1 and 47.5 Hz, 2 H); 4.75 (m, 1 H); 6.64 (d, J = 8.8 Hz, 2 H); 6.72 (d, J = 8.8 Hz, 2 H); 6.86 (d, J = 8.2 Hz, 1 H); 7.11 (d, J = 8.6 Hz, 1 H); 7.29 (d, J = 10.2 Hz, 1 H); 7.35 (t, J = 8.6 Hz, 1 H); 7.73 (dd, J = 2.0 and 8.2 Hz, 1 H); 7.89 (d, J = 2.0 Hz, 1 H); 12.96 (m, 1 H) | 588 |
| 169 | 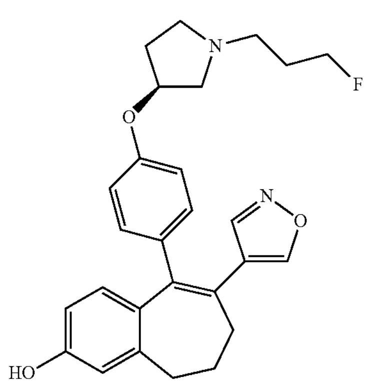 [SMILES: Oc1ccc2c(c1)CCCC(c1cnoc1)=C2c1ccc(O[C@H]2CCN(CCCF)C2)cc1] | 5-[4-[(3S)-1-(3-fluoropropyl)-pyrrolidin-3-yl]oxy-phenyl]-6-isoxazol-4-yl-8,9-dihydro-7H-benzo[7]-annulen-2-ol | A | 1H NMR (400 MHz, DMSO-d6, δ ppm): 1.75 to 1.90 (m, 3 H); 2.11 (m, 2 H); 2.27 (m, 3 H); 2.38 to 2.55 (m, 4 H); 2.60 (t, J = 7.0 Hz, 2 H); 2.62 to 2.75 (m, 2 H); 2.85 (m, 1 H); 4.49 (td, J = 6.1 and 47.5 Hz, 2 H); 4.85 (m, 1 H); 6.55 (m, 2 H); 6.69 (d, J = 1.5 Hz, 1 H); 6.82 (d, J = 8.8 Hz, 2 H); 6.92 (d, J = 8.8 Hz, 2 H); 7.55 (s, 1 H); 8.74 (s, 1 H); 9.43 (s, 1 H) | 449 |

TABLE 1-continued

| Examples | Structure | Name | Method | NMR | MASS: LC/MS (m/z, MH+): |
|---|---|---|---|---|---|
| 170 | 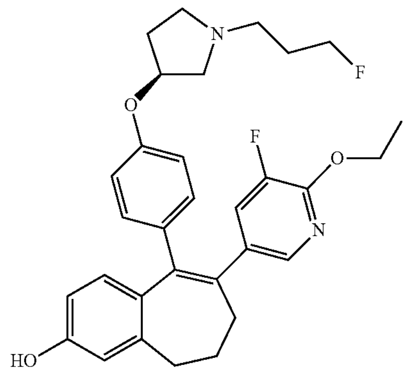 [SMILES: CCOc1ncc(C2=C(c3ccc(O[C@H]4CCN(CCCF)C4)cc3)c3ccc(O)cc3CCC2)cc1F] | 6-(6-ethoxy-5-fluoro-3-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.30 t, J = 7.1 Hz, 3 H); 1.70 (m, 1 H); 1.80 (dm, J = 25.3 Hz, 2 H); 2.05 (m, 2 H); 2.15 to 2.18 (m, 3 H); 2.39 (m, 1 H); 2.48 (m, 2 H); 2.56 (dd, J = 3.0 and 10.4 Hz, 1 H); 2.60 to 2.72 (m, 3 H); 2.80 (dd, J = 6.4 and 10.4 Hz, 1 H); 4.30 (q, J = 7.1 Hz, 2 H); 4.48 (td, J = 6.1 and 47.5 Hz, 2 H); 4.78 (m, 1 H); 6.55 (s, 2 H); 6.68 (d, J = 8.8 Hz, 2 H); 6.70 (s, 1 H); 6.78 (d, J = 8.6 Hz, 2 H); 7.43 (dd, J = 2.1 and 11.9 Hz, 1 H); 7.65 (d, J = 2.1 Hz, 1 H); 9.44 (s, 1 H) | 521 |
| 171 | 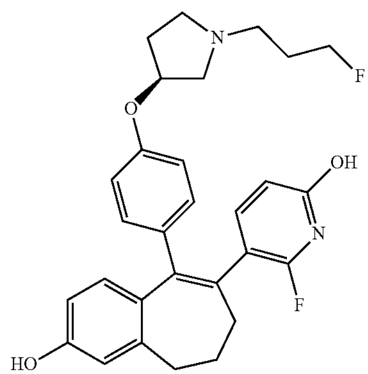 [SMILES: Oc1ccc2c(c1)CCCC(c1ccc(O)nc1F)=C2c1ccc(O[C@H]2CCN(CCCF)C2)cc1] | 6-fluoro-5-[5-[4-[(3S)-1-(3-fluoropropyl)-pyrrolidin-3-yl]oxy-phenyl]-2-hydroxy-8,9-dihydro-7H-benzo[7]-annulen-6-yl]pyridin-2-ol | A | 1H NMR (400 MHz, DMSO-d6, δ ppm): 1.69 (m, 1 H); 1.79 (dm, J = 25.3 Hz, 2 H); 2.05 (m, 2 H); 2.15 (t, J = 7.0 Hz, 2 H); 2.20 (m, 1 H); 2.39 (m, 1 H); 2.48 (t, J = 7.2 Hz, 2 H); 2.54 (m, 1 H); 2.67 (m, 3 H); 2.80 (m, 1 H); 4.47 (td, J = 6.1 and 47.5 Hz, 2 H); 4.74 (m, 1 H); 6.40 (dd, J = 1.5 and 8.2 Hz, 1 H); 6.56 (m, 2 H); 6.65 (d, J = 8.8 Hz, 2 H); 6.70 (s, 1 H); 7.72 (d, J = 8.8 Hz, 2 H); 7.48 (dd, J = 8.2 and 10.4 Hz, 1 H); 9.42 (s, 1 H); 11.11 (m, 1 H) | 493 |
| 172 | 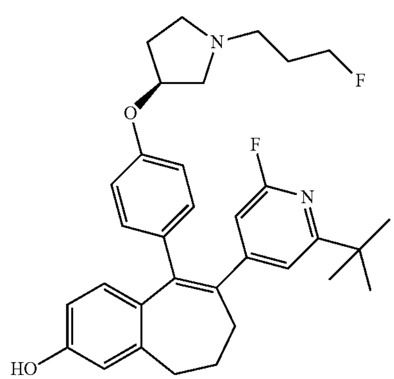 [SMILES: CC(C)(C)c1cc(C2=C(c3ccc(O[C@H]4CCN(CCCF)C4)cc3)c3ccc(O)cc3CCC2)cc(F)n1] | 6-(6-tert-butyl-2-fluoro-4-pyridyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.01 (s, 9 H); 1.67 (m, 1 H); 1.77 (dm, J = 25.3 Hz, 2 H); 2.05 (m, 2 H); 2.19 (m, 1 H); 2.30 (t, J = 7.0 Hz, 2 H); 2.37 (m, 1 H); 2.44 (t, J = 7.2 Hz, 2 H); 2.51 (m, 1 H); 2.60 to 2.70 (m, 3 H); 2.79 (dd, J = 6.4 and 10.4 Hz, 1 H); 4.45 (td, J = 6.1 and 47.5 Hz, 2 H); 4.75 (m, 1 H); 6.57 (m, 2 H); 6.67 (d, J = 8.8 Hz, 2 H); 6.71 (s, 1 H); 6.73 (d, J = 8.8 Hz, 2 H); 6.78 (s, 1 H); 6.81 (s, 1 H); 9.51 (s, 1 H) | 533 |

TABLE 1-continued

| Examples | Structure | Name | Method | NMR | MASS: LC/MS (m/z, MH+): |
|---|---|---|---|---|---|
| 173 | 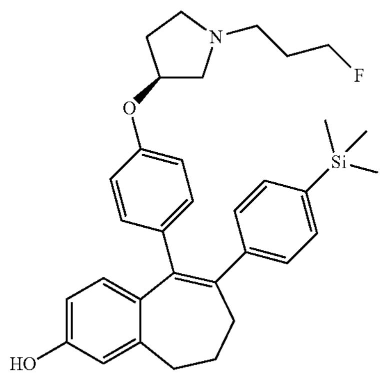 [SMILES: C[Si](C)(C)c1ccc(C2=C(c3ccc(O[C@H]4CCN(CCCF)C4)cc3)c3ccc(O)cc3CCC2)cc1] | 5-[4-[(3S)-1-(3-fluoropropyl)-pyrrolidin-3-yl]oxy-phenyl]-6-(4-(trimethylsilyl-phenyl)-8,9-dihydro-7H-benzo[7]-annulen-2-ol | A | 1H NMR (400 MHz, DMSO-d6, δ ppm): 0.20 (s, 9 H); 1.69 (m, 1 H); 1.79 (dm, J = 25.3 Hz, 2 H); 2.02 (m, 2 H); 2.19 (m, 1 H); 2.26 (t, J = 7.0 Hz, 2 H); 2.27 (m, 1 H); 2.46 (t, J = 7.2 Hz, 2 H); 2.54 (m, 1 H); 2.62 to 2.70 (m, 3 H); 2.78 (dd, J = 6.4 and 10.4 Hz, 1 H); 4.47 (td, J = 6.1 and 47.5 Hz, 2 H); 4.73 (m, 1 H); 6.54 (s, 2 H); 6.60 (d, J = 8.8 Hz, 2 H); 6.69 (s, 1 H); 6.74 (d, J = 8.8 Hz, 2 H); 7.11 (d, J = 8.0 Hz, 2 H); 7.30 (d, J = 8.0 Hz, 2 H); 9.41 (s, 1 H) | 530 |
| 174 | 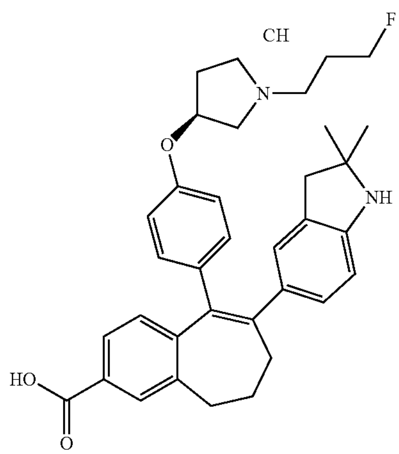 | 6-(2,2-dimethyl-indolin-5-yl)-5-[4-[(3S)-1-(3-fluoropropyl)-pyrrolidin-3-yl]oxy-phenyl]-8,9-dihydro-7H-benzo[7]-annulen-2-carboxylic acid hydrochloride | B | 1H NMR (400 MHz, DMSO-d6, δ ppm): 1.18 (s, 6 H); 1.70 to 3.00 (m, 12 H); 2.22 (t, J = 7.0 Hz, 2 H); 2.58 (s, 2 H); 2.79 (t, J = 7.0 Hz, 2 H); 4.50 (td, J = 6.1 and 47.5 Hz, 2 H); 4.89 (m, 1 H); 5.51 (s, 1 H); 6.20 (d, J = 8.2 Hz, 1 H); 6.65 to 3.73 (m, 3 H); 6.79 (m, 3 H); 6.82 (d, J = 8.2 Hz, 1 H); 7.70 (dd, J = 2.5 and 8.2 Hz, 1 H); 7.85 (d, J = 2.5 Hz, 1 H); 12.79 (s, 1 H) | 555 |
| 175 | 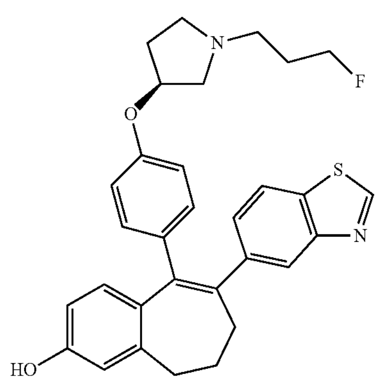 | 6-(1,3-benzo-thiazol-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (500 MHz, DMSO-d6, δ ppm): 1.65 (m, 1 H); 1.78 (dm, J = 25.3 Hz, 2 H); 2.07 (m, 2 H); 2.17 (m, 1 H); 2.34 (m, 3 H); 2.44 (t, J = 7.2 Hz, 2 H); 2.52 (m, 1 H); 2.62 (m, 1 H); 2.71 (t, J = 7.0 Hz, 2 H); 2.76 (dd, J = 6.4 and 10.4 Hz, 1 H); 4.46 (td, J = 6.1 and 47.5 Hz, 2 H); 4.71 (m, 1 H); 6.58 (m, 4 H); 6.71 (s, 1 H); 6.78 (d, J = 8.8 Hz, 2 H); 7.23 (dd, J = 1.8 and 8.4 Hz, 1 H); 7.83 (d, J = 1.8 Hz, 1 H); 7.92 (d, J = 8.4 Hz, 1 H); 9.31 (s, 1 H); 9.41 (s, 1 H) | 515 |

TABLE 1-continued

| Examples | Structure | Name | Method | NMR | MASS: LC/MS (m/z, MH+): |
|---|---|---|---|---|---|
| 176 | 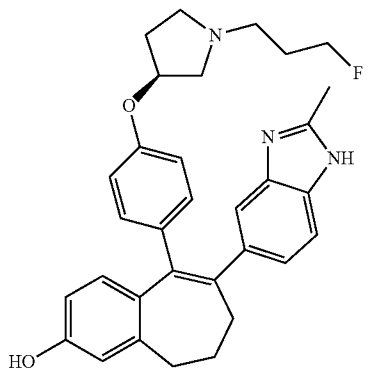 [SMILES: Cc1nc2cc(C3=C(c4ccc(O[C@H]5CCN(CCCF)C5)cc4)c4ccc(O)cc4CCC3)ccc2[nH]1] | 5-[4-[(3S)-1-(3-fluoropropyl)-pyrrolidin-3-yl]oxy-phenyl]-6-(2-methyl-1H-benzimi-dazol-5-yl)-8,9-dihydro-7H-benzo[7]-annulen-2-ol | A | 1H NMR (400 MHz, DMSO-d6, δ ppm): 1.67 (m, 1 H); 1.78 (dm, J = 25.3 Hz, 2 H); 2.03 (m, 2 H); 2.17 (m, 1 H); 2.30 (t, J = 7.0 Hz, 2 H); 2.38 (m, 1 H); 2.41 (s, 3 H); 2.47 (t, J = 7.2 Hz, 2 H); 2.53 (m, 1 H); 2.62 (m, 1 H); 2.69 (t, J = 7.0 Hz, 2 H); 2.78 (dd, J = 6.5 and 10.4 Hz, 1 H); 4.46 (td, J = 6.1 and 47.5 Hz, 2 H); 4.70 (m, 1 H); 6.54 (d, J = 8.8 Hz, 2 H); 6.56 (s, 2 H); 6.69 (s, 1 H); 6.72 (d, J = 8.8 Hz, 2 H); 6.89 (dd, J = 1.7 and 8.4 Hz, 1 H); 7.10 to 7.28 (m, 2 H); 9.38 (s, 1 H); 12.00 (m, 1 H) | 512 |
| 177 | 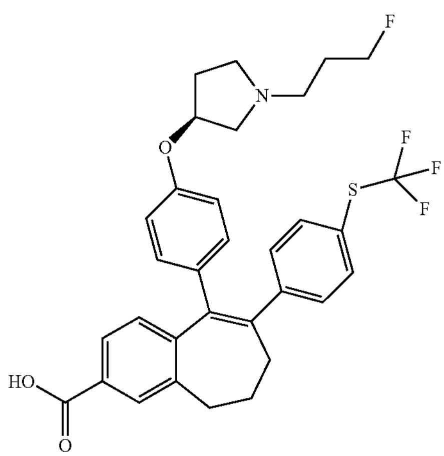 [SMILES: O=C(O)c1ccc2c(c1)CCCC(c1ccc(SC(F)(F)F)cc1)=C2c1ccc(O[C@H]2CCN(CCCF)C2)cc1] | 5-[4-[(3S)-1-(3-fluoropropyl)-pyrrolidin-3-yl]oxy-phenyl]-6-[4-(trifluoro-methyl-sulfanyl)-phenyl]-8,9-dihydro-7H-benzo[7]-annulene-2-carboxylic acid | B | 1H NMR (400 MHz, DMSO-d6, δ ppm): 1.70 (m, 1 H); 1.80 (dm, J = 25.3 Hz, 2 H); 2.11 (m, 2 H); 2.20 (m, 1 H); 2.29 (t, J = 7.0 Hz, 2 H); 2.38 (m, 1 H); 2.46 (t, J = 7.2 Hz, 2 H); 2.54 (m, 1 H); 2.65 (m, 1 H); 2.79 (dd, J = 6.3 and 10.4 Hz, 1 H); 2.83 (t, J = 7.0 Hz, 2 H); 4.48 (td, J = 6.1 and 47.5 Hz, 2 H); 4.74 (m, 1 H); 6.62 (d, J = 8.8 Hz, 2 H); 6.72 (d, J = 8.8 Hz, 2 H); 6.83 (d, J = 8.1 Hz, 1 H); 7.31 (d, J = 8.3 Hz, 2 H); 7.53 (d, J = 8.3 Hz, 2 H); 7.72 (dd, J = 1.9 and 8.3 Hz, 1 H); 7.88 (d, J = 1.9 Hz, 1 H); 12.90 (m, 1 H) | 586 |
| 178 | 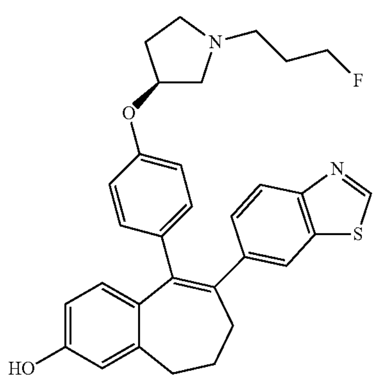 | 6-(1,3-benzo-thiazol-6-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.67 (m, 1 H); 1.78 (dm, J = 25.3 Hz, 2 H); 2.07 (m, 2 H); 2.16 (m, 1 H); 2.35 (m, 3 H); 2.43 (t, J = 7.2 Hz, 2 H); 2.52 (m, 1 H); 2.61 (m, 1 H); 2.71 (t, J = 7.2 Hz, 2 H); 2.76 (dd, J = 6.3 and 10.5 Hz, 1 H); 4.45 (td, J = 6.1 and 47.5 Hz, 2 H); 4.71 (m, 1 H); 6.55 to 6.62 (m, 4 H); 6.71 (d, J = 2.5 Hz, 1 H); 6.73 (d, J = 8.9 Hz, 2 H); 7.25 (dd, J = 1.8 and 8.5 Hz, 1 H); 7.82 (d, J = 8.5 Hz, 1 H); 7.94 (d, J = 1.8 Hz, 1 H); 9.29 (s, 1 H); 9.31 (s, 1 H) | 515 |

TABLE 1-continued

| Examples | Structure | Name | Method | NMR | MASS: LC/MS (m/z, MH+): |
|---|---|---|---|---|---|
| 179 | 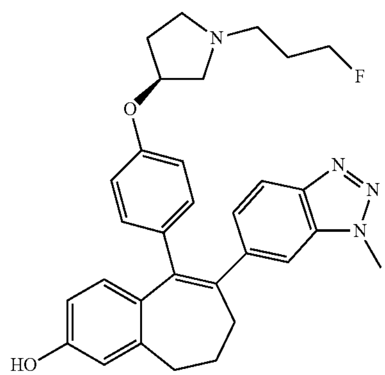 [SMILES: Cn1nnc2ccc(C3=C(c4ccc(O[C@H]5CCN(CCCF)C5)cc4)c4ccc(O)cc4CCC3)cc21] | 5-[4-[(3S)-1-(3-fluoropropyl)-pyrrolidin-3-yl]oxy-phenyl]-6-(3-methyl-benzotriazol-5-yl)-8,9-dihydro-7H-benzo[7]-annulen-2-ol | A | 1H NMR (400 MHz, DMSO-d6, δ ppm): 1.66 (m, 1 H); 1.78 (dm, J = 25.3 Hz, 2 H); 2.08 (m, 2 H); 2.17 (m, 1 H); 2.31 to 2.53 (m, 6 H); 2.62 (m, 1 H); 2.72 (t, J = 7.2 Hz, 2 H); 2.77 (dd, J = 6.1 and 10.4 Hz, 1 H); 4.20 (s, 3 H); 4.46 (td, J = 6.1 and 47.5 Hz, 2 H); 4.72 (m, 1 H); 6.57 (d, J = 8.9 Hz, 2 H); 6.59 (s, 2 H); 6.71 (s, 1 H); 6.72 (d, J = 8.9 Hz, 2 H); 7.05 (dd, J = 1.5 and 8.7 Hz, 1 H); 7.68 (s, 1 H); 7.70 (d, J = 8.7 Hz, 1 H); 9.42 (s, 1 H) | 513 |
| 180 | 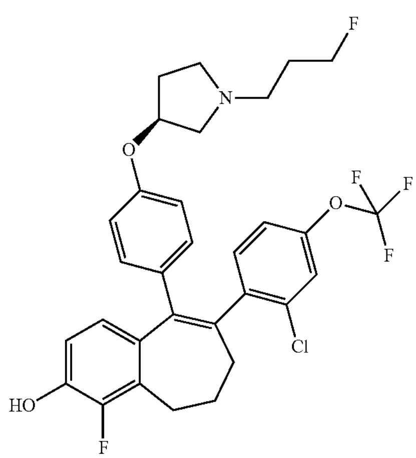 [SMILES: Oc1ccc2c(c1F)CCCC(c1ccc(OC(F)(F)F)cc1Cl)=C2c1ccc(O[C@H]2CCN(CCCF)C2)cc1] | 6-[2-chloro-4-(trifluoromethoxy)-phenyl]-1-fluoro-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.66 (m, 1 H); 1.78 (dm, J = 25.3 Hz, 2 H); 2.03 to 2.28 (m, 5 H); 2.38 (m, 1 H); 2.45 (t, J = 7.2 Hz, 2 H); 2.52 (m, 1 H); 2.62 (m, 1 H); 2.70 to 2.81 (m, 2 H); 2.99 (m, 1 H); 4.45 (td, J = 6.1 and 47.5 Hz, 2 H); 4.72 (m, 1 H); 6.42 (d, J = 8.6 Hz, 1 H); 6.60 (d, J = 8.8 Hz, 2 H); 6.72 (d, J = 8.8 Hz, 2 H); 6.75 (t, J = 8.6 Hz, 1 H); 7.20 (d, J = 8.5 Hz, 1 H); 7.27 (dd, J = 2.1 and 8.5 Hz, 1 H); 7.51 (d, J = 2.1 Hz, 1 H); 9.85 (s, 1 H) | 594 |
| 181 | 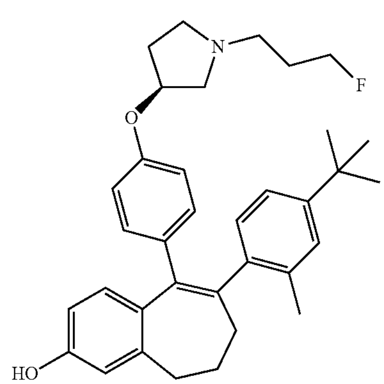 [SMILES: Cc1cc(C(C)(C)C)ccc1C1=C(c2ccc(O[C@H]3CCN(CCCF)C3)cc2)c2ccc(O)cc2CCC1] | 6-(4-tert-butyl-2-methyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.21 (s, 9 H); 1.68 (m, 1 H); 1.78 (dm, J = 25.3 Hz, 2 H); 2.00 to 2.24 (m, 5 H); 2.11 (s, 3 H); 2.37 (m, 1 H); 2.44 (t, J = 7.2 Hz, 2 H); 2.52 (m, 1 H); 2.62 (m, 1 H); 2.69 to 2.80 (m, 3 H); 4.47 (td, J = 6.1 and 47.5 Hz, 2 H); 4.70 (m, 1 H); 6.53 (d, J = 8.8 Hz, 2 H); 6.56 (s, 2 H); 6.66 (d, J = 8.8 Hz, 2 H); 6.70 (s, 1 H); 6.92 (dd, J = 3.3 and 8.1 Hz, 1 H); 7.04 (d, J = 8.1 Hz, 1 H); 7.09 (s, 1 H); 9.33 (s, 1 H) | 528 |

| Examples | Structure | Name | Method | NMR | MASS: LC/MS (m/z, MH+): |
|---|---|---|---|---|---|
| 182 | 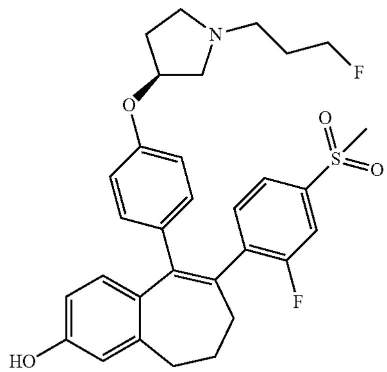 [SMILES: CS(=O)(=O)c1ccc(C2=C(c3ccc(O[C@H]4CCN(CCCF)C4)cc3)c3ccc(O)cc3CCC2)c(F)c1] | 6-(2-fluoro-4-methyl-sulfonyl-phenyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.07 (m, 2 H); 2.12 to 2.26 (m, 3 H); 2.38 (m, 1 H); 2.45 (t, J = 7.2 Hz, 2 H); 2.53 (dd, J = 3.0 and 10.4 Hz, 1 H); 2.62 (m, 1 H); 2.71 (t, J = 7.3 Hz, 2 H); 2.79 (dd, J = 6.1 and 10.4 Hz, 1 H); 3.22 (s, 3 H); 4.47 (td, J = 6.2 and 47.6 Hz, 2 H); 4.72 (m, 1 H); 6.59 (s, 2 H); 6.62 (d, J = 8.8 Hz, 2 H); 6.72 (m, 3 H); 7.47 (t, J = 8.0 Hz, 1 H); 7.59 (dd, J = 1.8 and 8.0 Hz, 1 H); 7.62 (dd, J = 1.8 and 9.1 Hz, 1 H); 9.49 (s, 1 H) | 554 |
| 183 | 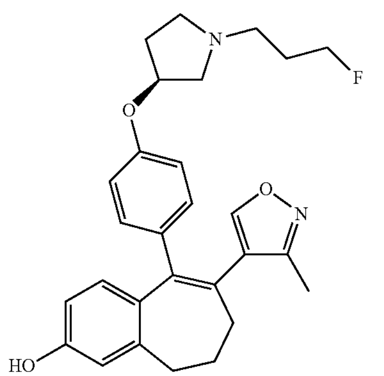 [SMILES: Cc1nocc1C1=C(c2ccc(O[C@H]3CCN(CCCF)C3)cc2)c2ccc(O)cc2CCC1] | 5-[4-[(3S)-1-(3-fluoropropyl)-pyrrolidin-3-yl]oxy-phenyl]-6-(3-methyl-isoxazol-4-yl)-8,9-dihydro-7H-benzo[7]-annulen-2-ol | A | 1H NMR (400 MHz, DMSO-d6, δ ppm): 1.64 (s, 3 H); 1.71 (m, 1 H); 1.80 (dm, J = 25.3 Hz, 2 H); 2.05 (m, 2 H); 2.15 (m, 2 H); 2.21 (m, 1 H); 2.40 (m, 1 H); 2.49 (m, 2 H); 2.53 to 2.71 (m, 4 H); 2.82 (m, 1 H); 4.47 (td, J = 6.0 and 47.5 Hz, 2 H); 4.80 (m, 1 H); 6.58 (m, 2 H); 6.70 (s, 1 H); 6.72 (d, J = 8.9 Hz, 2 H); 6.81 (d, J = 8.9 Hz, 2 H); 8.72 (s, 1 H); 9.42 (s, 1 H) | 463 |
| 184 | 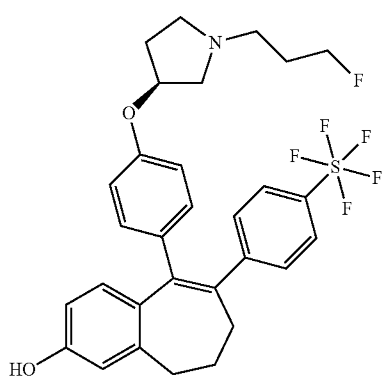 [SMILES: Oc1ccc2c(c1)CCCC(c1ccc(S(F)(F)(F)(F)F)cc1)=C2c1ccc(O[C@H]2CCN(CCCF)C2)cc1] | 5-[4-[(3S)-1-(3-fluoropropyl)-pyrrolidin-3-yl]oxy-phenyl]-6-[4-(pentafluoro-sulfanyl)-phenyl]-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 2.05 (m, 2 H); 2.20 (m, 1 H); 2.29 (t, J = 7.0 Hz, 2 H); 2.39 (m, 1 H); 2.47 (t, J = 7.2 Hz, 2 H); 2.55 (m, 1 H); 2.60 to 2.71 (m, 3 H); 2.79 (dd, J = 6.3 and 10.4 Hz, 1 H); 4.47 (td, J = 6.1 and 47.5 Hz, 2 H); 4.76 (m, 1 H); 6.56 (s, 2 H); 6.64 (d, J = 8.8 Hz, 2 H); 6.70 (s, 1 H); 6.73 (d, J = 8.8 Hz, 2 H); 7.31 (d, J = 9.0 Hz, 2 H); 7.68 (d, J = 9.0 Hz, 2 H); 9.46 (s, 1 H) | 584 |

| Examples | Structure | Name | Method | NMR | MASS: LC/MS (m/z, MH+): |
|---|---|---|---|---|---|
| 185 | 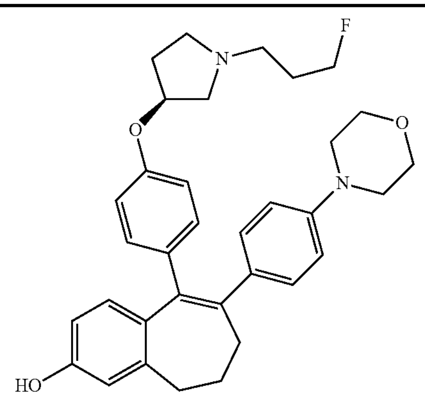 | 5-[4-[(3S)-1-(3-fluoropropyl)-pyrrolidin-3-yl]oxy-phenyl]-6-(4-morpholino phenyl)-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.01 (m, 2 H); 2.15 to 2.26 (m, 3 H); 2.39 (m, 1 H); 2.47 (t, J = 7.2 Hz, 2 H); 2.54 (dd, J = 3.0 and 10.4 Hz, 1 H); 2.64 (m, 3 H); 2.80 (dd, J = 6.4 and 10.4 Hz, 1 H); 3.05 (m, 4 H); 3.70 (m, 4 H); 4.47 (td, J = 6.1 and 47.5 Hz, 2 H); 4.73 (m, 1 H); 6.54 (s, 2 H); 6.60 (d, J = 8.8 Hz, 2 H); 6.67 (s, 1 H); 6.71 (d, J = 8.8 Hz, 2 H); 6.74 (d, J = 9.0 Hz, 2 H); 6.98 (d, J = 9.0 Hz, 2 H); 9.31 (s, 1 H) | 543 |
| 186 | 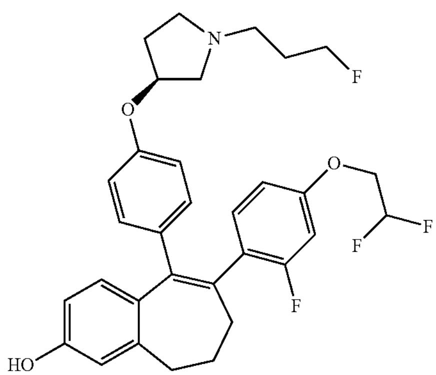 [SMILES: Oc1ccc2c(c1)CCCC(c1ccc(OCC(F)F)cc1F)=C2c1ccc(O[C@H]2CCN(CCCF)C2)cc1] | 6-[4-(2,2-difluoro-ethoxy)-2-fluoro-phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.80 (dm, J = 25.3 Hz, 2 H); 2.04 (m, 2 H); 2.13 to 2.23 (m, 3 H); 2.38 (m, 1 H); 2.47 (t, J = 7.2 Hz, 2 H); 2.53 (dd, J = 3.0 and 10.4 Hz, 1 H); 2.62 (m, 1 H); 2.69 (t, J = 7.0 Hz, 2 H); 2.80 (dd, J = 6.4 and 10.4 Hz, 1 H); 4.29 (dt, J = 3.7 and 14.8 Hz, 2 H); 4.47 (td, J = 6.1 and 47.5 Hz, 2 H); 4.72 (m, 1 H); 6.35 (tt, J = 3.7 and 54.5 Hz, 1 H); 6.55 (s, 2 H); 6.60 (d, J = 8.8 Hz, 2 H); 6.69 (dd, J = 2.7 and 8.7 Hz, 1 H); 6.70 (s, 1 H); 6.72 (d, J = 8.8 Hz, 2 H); 6.79 (dd, J = 2.7 and 11.9 Hz, 1 H); 7.07 (t, J = 8.7 Hz, 1 H); 9.39 (s, 1 H) | 556 |
| 187 | 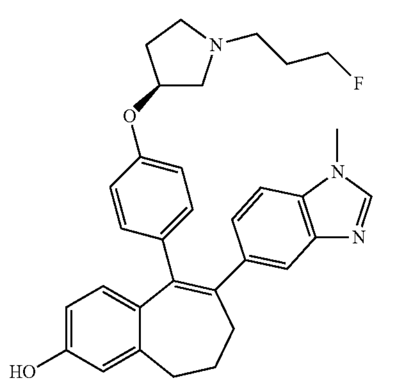 | 5-[4-[(3S)-1-(3-fluoropropyl)-pyrrolidin-3-yl]oxy-phenyl]-6-(1-methyl-benzimi-dazol-5-yl)-8,9-dihydro-7H-benzo[7]-annulen-2-ol | A | 1H NMR (400 MHz, DMSO-d6, δ ppm): 1.67 (m, 1 H); 1.78 (dm, J = 25.3 Hz, 2 H); 2.04 (m, 2 H); 2.17 (m, 1 H); 2.32 (t, J = 7.2 Hz, 2 H); 2.48 (m, 1 H); 2.44 (t, J = 7.0 Hz, 2 H); 2.52 (m, 1 H); 2.61 (m, 1 H); 2.70 (t, J = 7.0 Hz, 2 H); 2.78 (dd, J = 6.4 and 10.4 Hz, 1 H); 3.78 (s, 3 H); 4.45 (td, J = 6.1 and 47.5 Hz, 2 H); 4.70 (m, 1 H); 6.54 (d, J = 8.8 Hz, 2 H); 6.57 (s, 2 H); 6.70 (s, 1 H); 6.74 (d, J = 8.8 Hz, 2 H); 7.03 (d, J = 8.4 Hz, 1 H); 7.32 (d, J = 8.4 Hz, 1 H); 7.40 (s, 1 H); 8.07 (s, 1 H); 9.31 (s, 1 H) | 512 |

TABLE 1-continued

| Examples | Structure | Name | Method | NMR | MASS: LC/MS (m/z, MH+): |
|---|---|---|---|---|---|
| 188 | 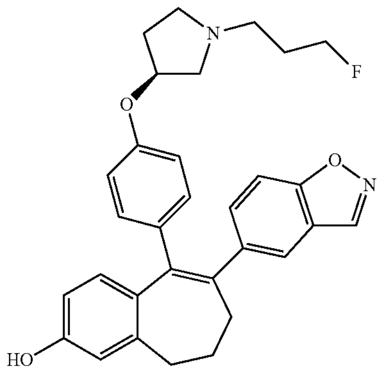 | 6-(1,2-benzoxazol-5-yl)-5-[4-[(3S)-1-(3-fluoropropyl)-pyrrolidin-3-yl]oxyphenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.04 (m, 2 H); 2.21 (m, 3 H); 2.40 (m, 1 H); 2.48 (t, J = 7.3 Hz, 2 H); 2.56 (dd, J = 3.0 and 10.4 Hz, 1 H); 2.65 (m, 3 H); 2.80 (dd, J = 6.3 and 10.4 Hz, 1 H); 4.48 (td, J = 6.1 and 47.5 Hz, 2 H); 4.78 (m, 1 H); 6.54 (s, 2 H); 6.65 (d, J = 8.8 Hz, 2 H); 6.69 (s, 1 H); 6.72 (d, J = 8.8 Hz, 2 H); 6.79 (d, J = 9.0 Hz, 1 H); 7.20 (dd, J = 2.0 and 9.0 Hz, 1 H); 7.27 (d, J = 2.0 Hz, 1 H); 9.35 (s, 1 H); 11.00 (m, 1 H) | 499 |
| 189 | 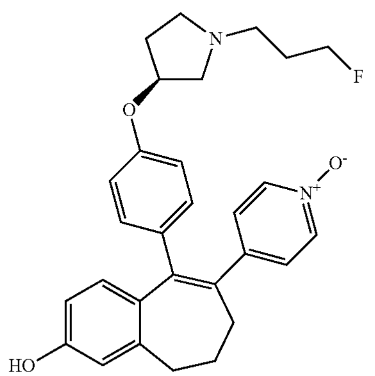 [SMILES: [O-][n+]1ccc(C2=C(c3ccc(O[C@H]4CCN(CCCF)C4)cc3)c3ccc(O)cc3CCC2)cc1] | 5-[4-[(3S)-1-(3-fluoropropyl)-pyrrolidin-3-yl]oxyphenyl]-6-(1-oxidopyridin-1-ium-4-yl)-8,9-dihydro-7H-benzo[7]-annulen-2-ol | A | 1H NMR (400 MHz, DMSO-d6, δ ppm): 1.71 (m, 1 H); 1.80 (dm, J = 25.3 Hz, 2 H); 2.07 (m, 2 H); 2.20 (m, 1 H); 2.25 (t, J = 7.0 Hz, 2 H); 2.40 (m, 1 H); 2.48 (m, 2 H); 2.58 (dd, J = 3.0 and 10.4 Hz, 1 H); 2.66 (t, J = 7.0 Hz, 2 H); 2.82 (dd, J = 6.3 and 10.4 Hz, 1 H); 4.48 (td, J = 6.1 and 47.5 Hz, 2 H); 4.79 (m, 1 H); 6.57 (s, 2 H); 6.70 (m, 3 H); 6.80 (t, J = 8.8 Hz, 2 H); 7.08 (d, J = 7.3 Hz, 2 H); 7.97 (d, J = 7.3 Hz, 2 H); 9.45 (s, 1 H) | 475 |
| 190 | 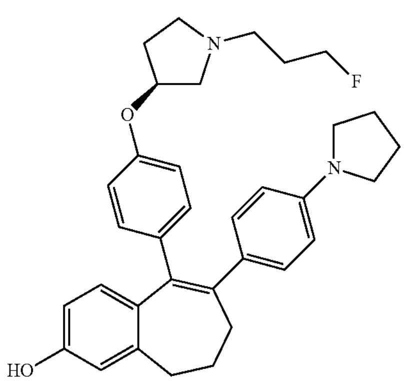 [SMILES: Oc1ccc2c(c1)CCCC(c1ccc(N3CCCC3)cc1)=C2c1ccc(O[C@H]2CCN(CCCF)C2)cc1] | 5-[4-[(3S)-1-(3-fluoropropyl)-pyrrolidin-3-yl]oxyphenyl]-6-(4-pyrrolidin-1-ylphenyl)-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 1.90 (m, 4 H); 2.00 (m, 2 H); 2.14 to 2.25 (m, 3 H); 2.39 (m, 1 H); 2.47 (t, J = 7.2 Hz, 2 H); 2.54 (dd, J = 3.0 and 10.4 Hz, 1 H); 2.62 (m, 3 H); 2.79 (dd, J = 6.4 and 10.4 Hz, 1 H); 3.14 (m, 4 H); 4.47 (td, J = 6.1 and 47.5 Hz, 2 H); 4.73 (m, 1 H); 6.32 (d, J = 8.8 Hz, 2 H); 6.52 (d, J = 1.5 Hz, 2 H); 6.60 (d, J = 8.8 Hz, 2 H); 6.66 (t, J = 1.5 Hz, 1 H); 6.74 (d, J = 8.8 Hz, 2 H); 6.92 (d, J = 8.8 Hz, 2 H); 9.39 (s, 1 H) | 527 |

TABLE 1-continued

| Examples | Structure | Name | Method | NMR | MASS: LC/MS (m/z, MH+): |
|---|---|---|---|---|---|
| 191 | 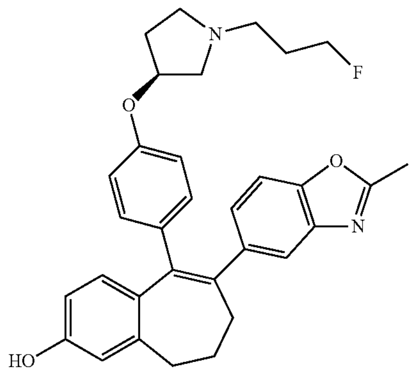 [SMILES: Cc1nc2cc(C3=C(c4ccc(O[C@H]5CCN(CCCF)C5)cc4)c4ccc(O)cc4CCC3)ccc2o1] | 5-[4-[(3S)-1-(3-fluoropropyl)-pyrrolidin-3-yl]oxy-phenyl]-6-(2-methyl-1,3-benzo-xazol-5-yl)-8,9-dihydro-7H-benzo[7]-annulen-2-ol | A | 1H NMR (400 MHz, DMSO-d6, δ ppm): 1.68 (m, 1 H); 1.79 (dm, J = 25.3 Hz, 2 H); 2.05 (t, J = 7.0 Hz, 2 H); 2.15 (m, 1 H); 2.30 (t, J = 7.0 Hz, 2 H); 2.36 (m, 1 H); 2.45 (t, J = 7.2 Hz, 2 H); 2.52 (m, 1 H); 2.53 (s, 3 H); 2.62 (m, 1 H); 2.71 (t, J = 7.0 Hz, 2 H); 2.78 (dd, J = 6.4 and 10.4 Hz, 1 H); 4.45 (td, J = 6.1 and 47.5 Hz, 2 H); 4.71 (m, 1 H); 6.55 (s, 2 H); 6.58 (d, J = 8.8 Hz, 2 H); 6.70 (s, 1 H); 6.72 (d, J = 8.8 Hz, 2 H); 7.10 (dd, J = 1.8 and 8.5 Hz, 1 H); 7.38 (d, J = 1.8 Hz, 1 H); 7.41 (d J = 8.5 Hz, 1 H); 9.38 (s, 1 H) | 513 |
| 192 | 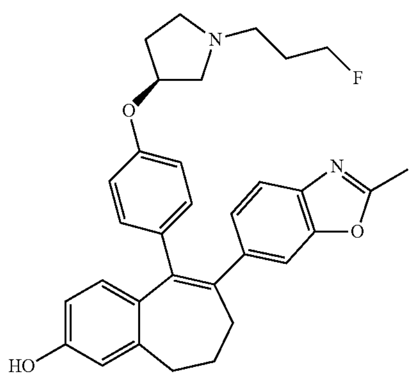 [SMILES: Cc1nc2ccc(C3=C(c4ccc(O[C@H]5CCN(CCCF)C5)cc4)c4ccc(O)cc4CCC3)cc2o1] | 5-[4-[(3S)-1-(3-fluoropropyl)-pyrrolidin-3-yl]oxy-phenyl]-6-(2-methyl-1,3-benzo-xazol-6-yl)-8,9-dihydro-7H-benzo[7]-annulen-2-ol | A | 1H NMR (400 MHz, DMSO-d6, δ ppm): 1.67 (m, 1 H); 1.79 (dm, J = 25.3 Hz, 2 H); 2.04 (m, 2 H); 2.18 (m, 1 H); 2.30 (t, J = 7.0 Hz, 2 H); 2.37 (m, 1 H); 2.44 (t, J = 7.2 Hz, 2 H); 2.52 (m, 1 H); 2.54 (s, 3 H); 2.60 to 2.73 (m, 3 H); 2.78 (dd, J = 6.4 and 10.4 Hz, 1 H); 4.46 (td, J = 6.1 and 47.5 Hz, 2 H); 4.71 (m, 1 H); 6.55 (s, 2 H); 6.58 (d, J = 8.8 Hz, 2 H); 6.70 (s, 1 H); 6.72 (d, J = 8.8 Hz, 2 H); 7.08 (dd, J = 1.6 and 8.3 Hz, 1 H); 7.40 (m, 2 H); 9.39 (s, 1 H) | 513 |
| 193 | 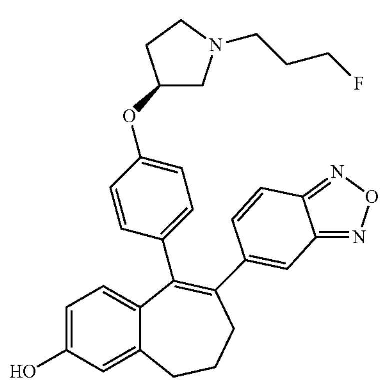 | 6-(2,1,3-benzo-xadiazol-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.09 (m, 2 H); 2.19 (m, 1 H); 2.31 to 2.40 (m, 3 H); 2.45 (t, J = 7.2 Hz, 2 H); 2.54 (m, 1 H); 2.60 to 2.72 (m, 3 H); 2.78 (dd, J = 6.4 and 10.4 Hz, 1 H); 4.48 (td, J = 6.1 and 47.5 Hz, 2 H); 4.75 (m, 1 H); 6.60 (s, 2 H); 6.66 (d, J = 8.8 Hz, 2 H); 6.73 (s, 1 H); 6.81 (d, J = 8.8 Hz, 2 H); 7.20 (dd, J = 1.3 and 9.4 Hz, 1 H); 7.72 (dd, J = 1.3 and 9.4 Hz, 1 H); 7.83 (t, J = 1.3 Hz, 1 H); 9.52 (s, 1 H) | 500 |

TABLE 1-continued

| Examples | Structure | Name | Method | NMR | MASS: LC/MS (m/z, MH+): |
|---|---|---|---|---|---|
| 194 | 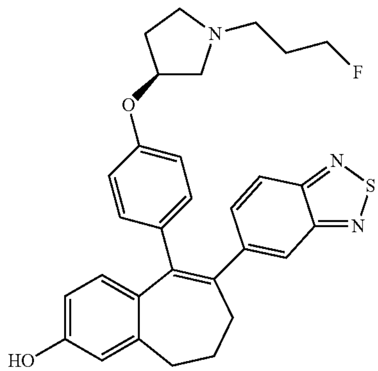 [SMILES: Oc1ccc2c(c1)CCCC(c1ccc3nonc3c1)=C2c1ccc(O[C@H]2CCN(CCCF)C2)cc1] | 6-(2,1,3-benzothia-diazol-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.67 (m, 1 H); 1.79 (dm, J = 25.3 Hz, 2 H); 2.09 (m, 2 H); 2.18 (m, 1 H); 2.30 to 2.52 (m, 6 H); 2.62 (m, 1 H); 2.70 to 2.80 (m, 3 H); 4.47 (td, J = 6.1 and 47.5 Hz, 2 H); 4.72 (m, 1 H); 6.59 (s, 2 H); 6.61 (d, J = 8.8 Hz, 2 H); 6.72 (s, 1 H); 6.80 (d, J = 8.8 Hz, 2 H); 7.40 (dd, J = 2.0 and 9.2 Hz, 1 H); 7.80 (d, J = 9.2 Hz, 1 H); 7.89 (d, J = 2.0 Hz, 1 H); 9.48 (s, 1 H) | 516 |
| 195 | 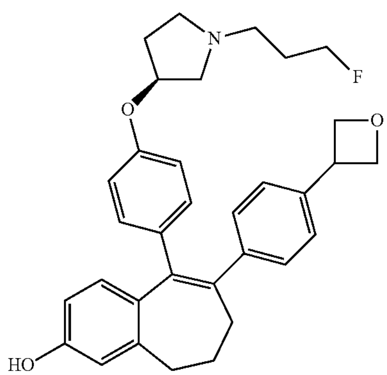 [SMILES: Oc1ccc2c(c1)CCCC(c1ccc(C3COC3)cc1)=C2c1ccc(O[C@H]2CCN(CCCF)C2)cc1] | 5-[4-[(3S)-1-(3-fluoropropyl)-pyrrolidin-3-yl]oxy-phenyl]-6-[4-(oxetan-3-yl)phenyl]-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.02 (m, 2 H); 2.19 (m, 1 H); 2.24 (t, J = 7.0 Hz, 2 H); 2.38 (m, 1 H); 2.47 (t, J = 7.2 Hz, 2 H); 2.54 (dd, J = 3.2 and 10.4 Hz, 1 H); 2.65 (m, 3 H); 2.79 (dd, J = 6.4 and 10.3 Hz, 1 H); 4.17 (m, 1 H); 4.47 (td, J = 6.1 and 47.5 Hz, 2 H); 4.56 (dd, J = 5.9 and 6.9 Hz, 2 H); 4.72 (m, 1 H); 4.89 (dd, J = 5.9 and 8.5 Hz, 2 H); 6.55 (s, 2 H); 6.59 (d, J = 8.8 Hz, 2 H); 6.69 (s, 1 H); 6.72 (d, J = 8.8 Hz, 2 H); 7.12 (d, J = 8.3 Hz, 2 H); 7.19 (d, J = 8.3 Hz, 2 H); 9.38 (s, 1 H) | 514 |
| 196 | 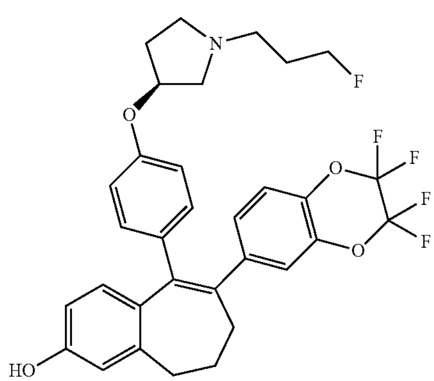 [SMILES: Oc1ccc2c(c1)CCCC(c1ccc3c(c1)OC(F)(F)C(F)(F)O3)=C2c1ccc(O[C@H]2CCN(CCCF)C2)cc1] | 5-[4-[(3S)-1-(3-fluoropropyl)-pyrrolidin-3-yl]oxy-phenyl]-6-(2,2,3,3-tetra-fluoro-1,4-benzo-dioxon-6-yl)-8,9-dihydro-7H-benzo[7]-annulen-2-ol | A | 1H NMR (400 MHz, DMSO-d6, δ ppm): 1.69 (m, 1 H); 1.79 (dm, J = 25.3 Hz, 2 H); 2.05 (m, 2 H); 2.20 (m, 1 H); 2.27 (t, J = 7.0 Hz, 2 H); 2.38 (m, 1 H); 2.47 (t, J = 7.2 Hz, 2 H); 2.54 (dd, J = 3.0 and 10.4 Hz, 1 H); 2.66 (m, 3 H); 2.79 (dd, J = 6.4 and 10.4 Hz, 1 H); 4.47 (td, J = 6.1 and 47.5 Hz, 2 H); 4.77 (m, 1 H); 6.57 (s, 2 H); 6.66 (d, J = 8.8 Hz, 2 H); 6.70 (s, 1 H); 6.74 (d, J = 8.8 Hz, 2 H); 7.07 (dd, J = 2.0 and 8.6 Hz, 1 H); 7.15 (d, J = 2.0 Hz, 1 H); 7.24 (d, J = 8.6 Hz, 1 H); 9.44 (s, 1 H) | 588 |

TABLE 1-continued

| Examples | Structure | Name | Method | NMR | MASS: LC/MS (m/z, MH+): |
|---|---|---|---|---|---|
| 197 | 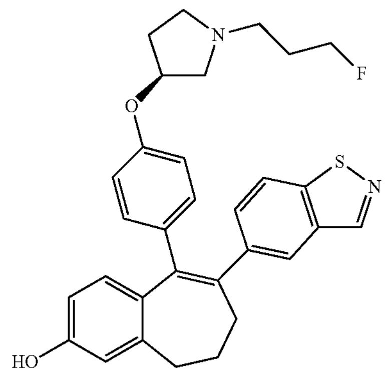 [SMILES: Oc1ccc2c(c1)CCCC(c1ccc3sncc3c1)=C2c1ccc(O[C@H]2CCN(CCCF)C2)cc1] | 6-(1,2-benzo-thiazol-5-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.65 (m, 1 H); 1.78 (dm, J = 25.3 Hz, 2 H); 2.08 (m, 2 H); 2.17 (m, 1 H); 2.34 (m, 3 H); 2.44 (t, J = 7.2 Hz, 2 H); 2.52 (m, 1 H); 2.61 (m, 1 H); 2.73 (m, 3 H); 4.46 (td, J = 6.1 and 47.5 Hz, 2 H); 4.70 (m, 1 H); 6.58 (m, 4 H); 6.71 (s, 1 H); 6.75 (d, J = 8.8 Hz, 2 H); 7.32 (dd, J = 1.8 and 8.6 Hz, 1 H); 7.97 (d, J = 8.6 Hz, 1 H); 7.99 (d, J = 1.8 Hz, 1 H); 8.97 (s, 1 H); 9.40 (s, 1 H) | 515 |
| 198 | 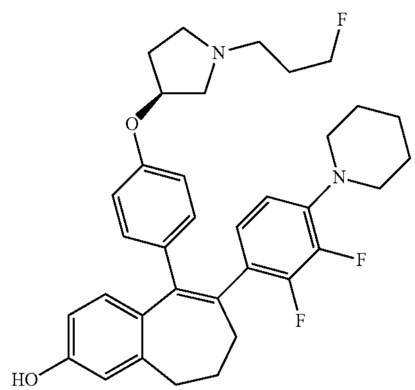 [SMILES: Oc1ccc2c(c1)CCCC(c1ccc(N3CCCCC3)c(F)c1F)=C2c1ccc(O[C@H]2CCN(CCCF)C2)cc1] | 6-[2,3-difluoro-4-(1-piperidyl)-phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.50 (m, 2 H); 1.60 (m, 4 H); 1.69 (m, 1 H); 1.79 (dm, J = 25.3 Hz, 2 H); 2.04 (m, 2 H); 2.12 to 2.25 (m, 3 H); 2.38 (m, 1 H); 2.46 (t, J = 7.2 Hz, 2 H); 2.53 (dd, J = 3.0 and 10.4 Hz, 1 H); 2.60 to 2.70 (m, 3 H); 2.79 (dd, J = 6.4 and 10.4 Hz, 1 H); 2.94 (m, 4 H); 4.47 (td, J = 6.1 and 47.5 Hz, 2 H); 4.74 (m, 1 H); 6.56 (s, 2 H); 6.61 (d, J = 8.8 Hz, 2 H); 6.66 (s, 1 H); 6.70 (s, 1 H); 6.72 (d, J = 8.8 Hz, 2 H); 6.83 (dt, J = 2.0 and 8.6 Hz, 1 H); 9.41 (s, 1 H) | 577 |
| 199 | 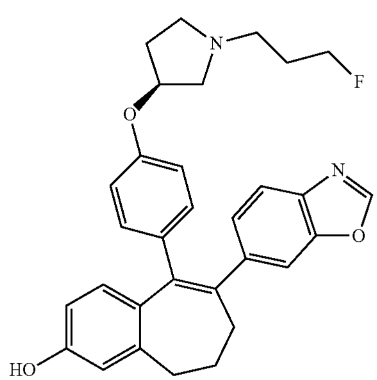 [SMILES: Oc1ccc2c(c1)CCCC(c1ccc3ncoc3c1)=C2c1ccc(O[C@H]2CCN(CCCF)C2)cc1] | 6-(1,3-benzo-xazol-6-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.67 (m, 1 H); 1.78 (dm, J = 25.4 Hz, 2 H); 2.06 (m, 2 H); 2.18 (m, 1 H); 2.30 to 2.40 (m, 3 H); 2.44 (t, J = 7.2 Hz, 2 H); 2.52 (m, 1 H); 2.61 (m, 1 H); 2.70 (t, J = 7.2 Hz, 2 H); 2.78 (dd, J = 6.3 and 10.4 Hz, 1 H); 4.46 (td, J = 6.1 and 47.5 Hz, 2 H); 4.71 (m, 1 H); 6.57 (d, J = 1.5 Hz, 2 H); 6.59 (d, J = 8.8 Hz, 2 H); 6.70 (t, J = 1.5 Hz, 1 H); 6.72 (d, J = 8.8 Hz, 2 H); 7.14 (dd, J = 1.7 and 8.3 Hz, 1 H); 7.51 (d, J = 1.7 Hz, 1 H); 7.55 (d, J = 8.3 Hz, 1 H); 8.62 (s, 1 H); 9.40 (s, 1 H) | 499 |

TABLE 1-continued

| Examples | Structure | Name | Method | NMR | MASS: LC/MS (m/z, MH+): |
|---|---|---|---|---|---|
| 200 | 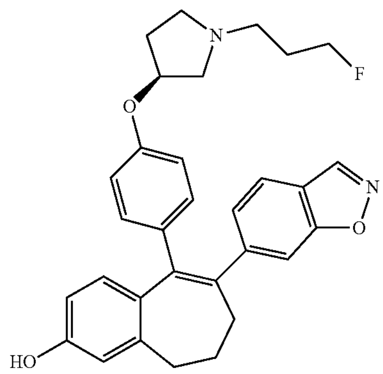 [SMILES: Oc1ccc2c(c1)CCCC(c1ccc3cnoc3c1)=C2c1ccc(O[C@H]2CCN(CCCF)C2)cc1] | 6-(1,2-benzo-xazol-6-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.80 (dm, J = 25.3 Hz, 2 H); 2.03 (m, 2 H); 2.20 (m, 3 H); 2.39 (m, 1 H); 2.47 (t, J = 7.2 Hz, 2 H); 2.54 (dd, J = 3.0 and 10.4 Hz, 1 H); 2.64 (m, 3 H); 2.80 (dd, J = 6.4 and 10.4 Hz, 1 H); 4.47 (td, J = 6.1 and 47.5 Hz, 2 H); 4.77 (m, 1 H); 6.57 (s, 2 H); 6.65 (d, J = 8.8 Hz, 2 H); 6.67 (s, 1 H); 6.70 to 6.78 (m, 4 H); 7.37 (d, J = 8.3 Hz, 1 H); 9.43 (s, 1 H); 10.82 (m, 1 H) | 499 |
| 201 | 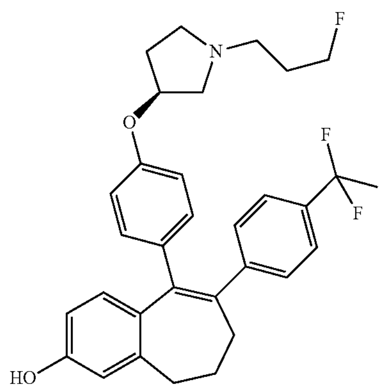 [SMILES: CC(F)(F)c1ccc(C2=C(c3ccc(O[C@H]4CCN(CCCF)C4)cc3)c3ccc(O)cc3CCC2)cc1] | 6-[4-(1,1-difluoro-ethyl)phenyl]-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 (m, 1 H); 1.79 (dm, J = 25.3 Hz, 2 H); 1.91 (t, J = 18.8 Hz, 3 H); 2.04 (m, 2 H); 2.20 (m, 1 H); 2.28 (t, J = 7.0 Hz, 2 H); 2.38 (m, 1 H); 2.46 (t, J = 7.2 Hz, 2 H); 2.54 (dd, J = 3.2 and 10.4 Hz, 1 H); 2.60 to 2.71 (m, 3 H); 2.79 (dd, J = 6.3 and 10.4 Hz, 1 H); 4.47 (td, J = 6.1 and 47.5 Hz, 2 H); 4.73 (m, 1 H); 6.55 (s, 2 H); 6.60 (d, J = 8.8 Hz, 2 H); 6.69 (s, 1 H); 6.72 (d, J = 8.8 Hz, 2 H); 7.21 (d, J = 8.5 Hz, 2 H); 7.35 (d, J = 8.5 Hz, 2 H); 9.40 (s, 1 H) | 522 |
| 202 | 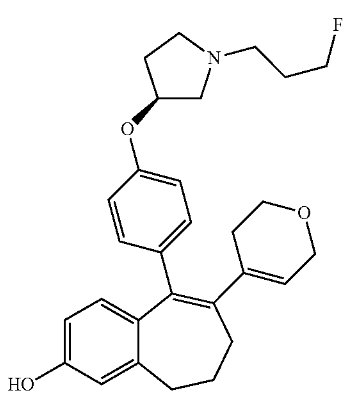 [SMILES: Oc1ccc2c(c1)CCCC(C1=CCOCC1)=C2c1ccc(O[C@H]2CCN(CCCF)C2)cc1] | 6-(3,6-dihydro-2H-pyran-4-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 to 1.89 (m, 3 H); 1.92 (m, 2 H); 1.98 to 2.09 (m, 4 H); 2.25 (m, 1 H); 2.41 (m, 1 H); 2.48 (t, J = 7.2 Hz, 2 H); 2.55 (t, J = 7.0 Hz, 2 H); 2.60 (dd, J = 3.0 and 10.4 Hz, 1 H); 2.68 (m, 1 H); 2.83 (dd, J = 6.4 and 10.4 Hz, 1 H); 3.53 (t, J = 5.4 Hz, 2 H); 3.98 (m, 2 H); 4.48 (td, J = 6.1 and 47.5 Hz, 2 H); 4.81 (m, 1 H); 5.51 (m, 1 H); 6.52 (m, 2 H); 6.64 (s, 1 H); 6.76 (d, J = 8.8 Hz, 2 H); 6.92 (d, J = 8.8 Hz, 2 H); 9.31 (s, 1 H) | 464 |

TABLE 1-continued

| Examples | Structure | Name | Method | NMR | MASS: LC/MS (m/z, MH+): |
|---|---|---|---|---|---|
| 203 | 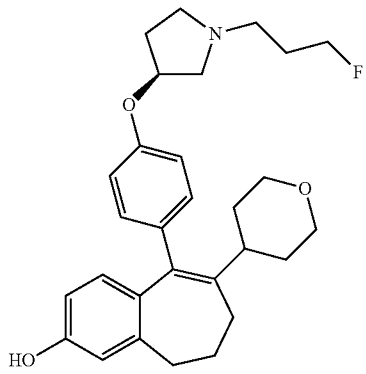 [SMILES: Oc1ccc2c(c1)CCCC(C1CCOCC1)=C2c1ccc(O[C@H]2CCN(CCCF)C2)cc1] | 5-[4-[(3S)-1-(3-fluoropropyl)-pyrrolidin-3-yl]oxy-phenyl]-6-tetra-hydro-pyran-4-yl-8,9-dihydro-7H-benzo[7]-annulen-2-ol | A | 1H NMR (400 MHz, DMSO-d6, δ ppm): 1.40 (m, 2 H); 1.65 (m, 2 H); 1.73 to 1.89 (m, 5 H); 2.05 (m, 2 H); 2.25 (m, 1 H); 2.40 to 2.72 (m, 8 H); 2.86 (dd, J = 6.4 and 10.4 Hz, 1 H); 3.14 (m, 2 H); 3.84 (m, 2 H); 4.48 (td, J = 6.1 and 47.5 Hz, 2 H); 4.82 (m, 1 H); 6.42 (d, J = 8.5 Hz, 1 H); 6.48 (dd, J = 2.6 and 8.5 Hz, 1 H); 6.62 (d, J = 2.6 Hz, 1 H); 6.81 (d, J = 8.8 Hz, 2 H); 6.92 (d, J = 8.8 Hz, 2 H); 9.22 (s, 1 H) | 466 |
| 204 | 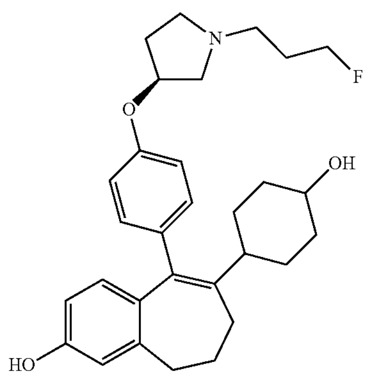 [SMILES: Oc1ccc2c(c1)CCCC(C1CCC(O)CC1)=C2c1ccc(O[C@H]2CCN(CCCF)C2)cc1] | 5-[4-[(3S)-1-(3-fluoropropyl)-pyrrolidin-3-yl]oxy-phenyl]-6-(4-hydroxy-cyclohexyl)-8,9-dihydro-7H-benzo[7]-annulen-2-ol | A | 1H NMR (400 MHz, DMSO-d6, δ ppm): trans diaxialisomer: 0.97 (m, 2 H); 1.38 to 1.58 (m, 4 H); 1.72 to 1.89 (m, 5 H); 2.02 (m, 2 H); 2.28 (m, 2 H); 2.32 (m, 1 H); 2.48 to 2.55 (m, 6 H); 2.61 (dd, J = 3.0 and 10.4 Hz, 1 H); 2.69 (m, 1 H); 2.87 (dd, J = 6.4 and 10.4 Hz, 1 H); 3.32 (m, 1 H); 4.40 (d, J = 4.9 Hz, 1 H); 4.49 (td, J = 6.1 and 47.5 Hz, 2 H); 4.83 (m, 1 H); 6.41 (d, J = 8.6 Hz, 1 H); 6.48 (dd, J = 2.7 and 8.6 Hz, 1 H); 6.61 (d, J = 2.7 Hz, 1 H); 6.81 (d, J = 8.9 Hz, 2 H); 6.89 (d, J = 8.9 Hz, 2 H); 9.20 (s, 1 H) | 480 |
| 205 | 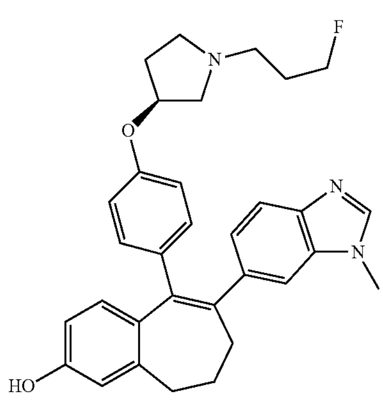 [SMILES: Cn1cnc2ccc(C3=C(c4ccc(O[C@H]5CCN(CCCF)C5)cc4)c4ccc(O)cc4CCC3)cc21] | 5-[4-[(3S)-1-(3-fluoropropyl)-pyrrolidin-3-yl]oxy-phenyl]-6-(3-methyl-benzimi-dazol-5-yl)-8,9-dihydro-7H-benzo[7]-annulen-2-ol | A | 1H NMR (400 MHz, DMSO-d6, δ ppm): 1.68 (m, 1 H); 1.78 (dm, J = 25.3 Hz, 2 H); 2.06 (m, 2 H); 2.17 (m, 1 H); 2.37 (m, 3 H); 2.45 (t, J = 7.2 Hz, 2 H); 2.52 (m, 1 H); 2.61 (m, 1 H); 2.71 (t, J = 7.0 Hz, 2 H); 2.77 (dd, J = 6.4 and 10.3 Hz, 1 H); 3.71 (s, 3 H); 4.47 (td, J = 6.1 and 47.5 Hz, 2 H); 4.71 (m, 1 H); 6.67 (m, 4 H); 6.70 (d, J = 1.5 Hz, 1 H); 6.72 (d, J = 8.8 Hz, 2 H); 6.91 (dd, J = 1.6 and 8.6 Hz, 1 H); 7.35 (m, 2 H); 8.08 (s, 1 H); 9.36 (s, 1 H) | 510 |

TABLE 1-continued

| Examples | Structure | Name | Method | NMR | MASS: LC/MS (m/z, MH+): |
|---|---|---|---|---|---|
| 206 | 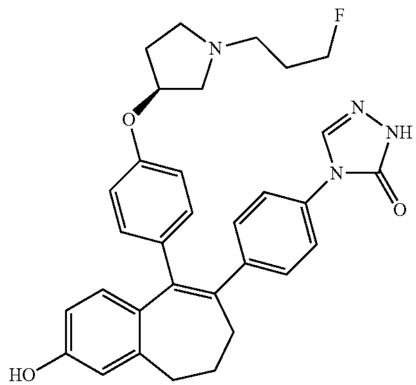 [SMILES: O=c1[nH]ncn1-c1ccc(C2=C(c3ccc(O[C@H]4CCN(CCCF)C4)cc3)c3ccc(O)cc3CCC2)cc1] | 4-[4-[5-[4-[(3S)-1-(3-fluoropropyl)-pyrrolidin-3-yl]oxy-phenyl]-2-hydroxy-8,9-dihydro-7H-benzo[7]-annulen-6-yl]phenyl]-1H-1,2,4-triazol-5-one | A | 1H NMR (400 MHz, DMSO-d6, δ ppm): 1.70 (m, 1 H); 1.79 (dm, J = 25.3 Hz, 2 H); 2.05 (m, 2 H); 2.20 (m, 1 H); 2.28 (t, J = 7.0 Hz, 2 H); 2.38 (m, 1 H); 2.47 (t, J = 7.2 Hz, 2 H); 2.54 (dd, J = 3.0 and 10.4 Hz, 1 H); 2.60 to 2.71 (m, 3 H); 2.80 (dd, J = 6.4 and 10.4 Hz, 1 H); 4.47 (td, J = 6.1 and 47.5 Hz, 2 H); 4.73 (m, 1 H); 6.56 (s, 2 H); 6.62 (d, J = 8.8 Hz, 2 H); 6.69 (s, 1 H); 6.77 (d, J = 8.8 Hz, 2 H); 7.22 (d, J = 8.8 Hz, 2 H); 7.49 (t, J = 8.8 Hz, 2 H); 8.31 (s, 1 H); 9.40 (s, 1 H); 11.92 (s, 1 H) | 541 |
| 207 | 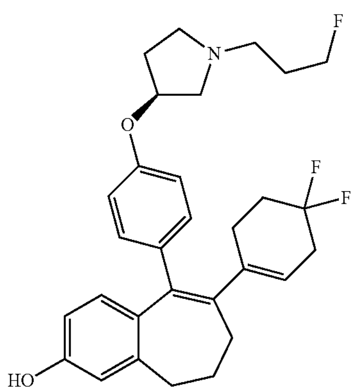 [SMILES: Oc1ccc2c(c1)CCCC(C1=CCC(F)(F)CC1)=C2c1ccc(O[C@H]2CCN(CCCF)C2)cc1] | 6-(4,4-difluoro-cyclohexen-1-yl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.70 to 1.95 (m, 5 H); 1.98 to 2.09 (m, 4 H); 2.15 (m, 2 H); 2.23 (m, 1 H); 2.37 to 2.58 (m, 7 H); 2.60 (dd, J = 3.0 and 10.4 Hz, 1 H); 2.69 (m, 1 H); 2.82 (dd, J = 6.4 and 10.4 Hz, 1 H); 4.48 (td, J = 6.1 and 47.5 Hz, 2 H); 4.81 (m, 1 H); 5.35 (m, 1 H); 6.53 (s, 2 H); 6.63 (s, 1 H); 6.73 (d, J = 8.9 Hz, 2 H); 6.92 (d, J = 8.9 Hz, 2 H); 9.31 (s, 1 H) | 498 |
| 208 | 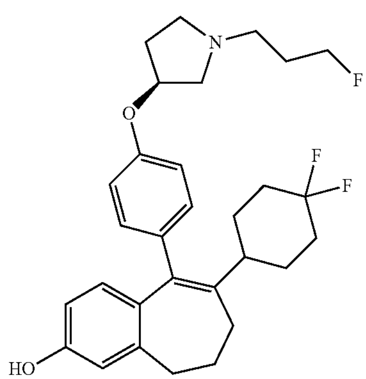 [SMILES: Oc1ccc2c(c1)CCCC(C1CCC(F)(F)CC1)=C2c1ccc(O[C@H]2CCN(CCCF)C2)cc1] | 6-(4,4-difluoro-cyclohexyl)-5-[4-[(3S)-1-(3-fluoropropyl)-pyrrolidin-3-yl]oxy-phenyl]-8,9-dihydro-7H-benzo[7]-annulen-2-ol | A | 1H NMR (400 MHz, DMSO-d6, δ ppm): 1.55 to 1.90 (m, 11 H); 1.95 to 2.10 (m, 4 H); 2.25 (m, 1 H); 2.42 (m, 1 H); 2.46 to 2.52 (m, 3 H); 2.56 (t, J = 7.2 Hz, 2 H); 2.62 (dd, J = 3.0 and 10.3 Hz, 1 H); 2.69 (m, 1 H); 2.86 (dd, J = 6.3 and 10.6 Hz, 1 H); 4.49 (td, J = 6.1 and 47.5 Hz, 2 H); 4.83 (m, 1 H); 6.42 (d, J = 8.4 Hz, 1 H); 6.49 (dd, J = 2.6 and 8.4 Hz, 1 H); 6.62 (d, J = 2.6 Hz, 1 H); 6.83 (d, J = 8.8 Hz, 2 H); 6.93 (d, J = 8.8 Hz, 2 H); 9.23 (s, 1 H) | 500 |

TABLE 1-continued

| Examples | Structure | Name | Method | NMR | MASS: LC/MS (m/z, MH+): |
|---|---|---|---|---|---|
| 209 | 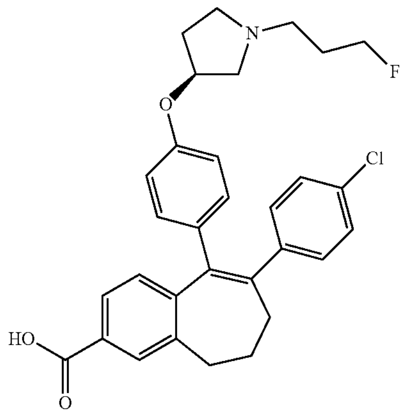 [SMILES: O=C(O)c1ccc2c(c1)CCCC(c1ccc(Cl)cc1)=C2c1ccc(O[C@H]2CCN(CCCF)C2)cc1] | 6-(4-chlorophenyl)-5-[4-[(3S)-1-(3-fluoropropyl)-pyrrolidin-3-yl]oxy-phenyl]-8,9-dihydro-7H-benzo[7]-annulene-2-carboxylic acid | B | 1H NMR (400 MHz, DMSO-d6, δ ppm): 1.70 (m, 1 H); 1.80 (dm, J = 25.3 Hz, 2 H); 2.10 (m, 2 H); 2.15 to 2.28 (m, 3 H); 2.38 (m, 1 H); 2.48 (t, J = 7.2 Hz, 2 H); 2.55 (dd, J = 3.2 and 10.4 Hz, 1 H); 2.65 (m, 1 H); 2.81 (m, 3 H); 4.48 (td, J = 6.1 and 47.5 Hz, 2 H); 4.77 (m, 1 H); 6.65 (d, J = 8.8 Hz, 2 H); 6.73 (d, J = 8.8 Hz, 2 H); 6.81 (d, J = 8.1 Hz, 1 H); 7.18 (d, J = 8.8 Hz, 2 H); 7.25 (d, J = 8.8 Hz, 2 H); 7.71 (dd, J = 1.9 and 8.1 Hz, 1 H); 7.87 (d, J = 1.9 Hz, 1 H); 12.05 (m, 1 H) | 520 |
| 210 | 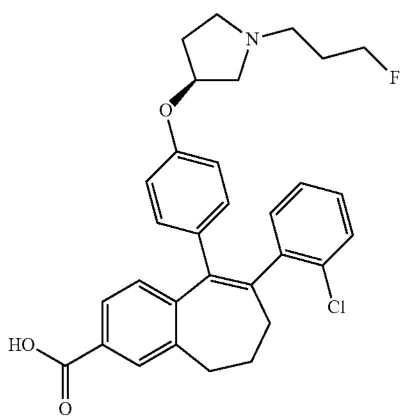 [SMILES: O=C(O)c1ccc2c(c1)CCCC(c1ccccc1Cl)=C2c1ccc(O[C@H]2CCN(CCCF)C2)cc1] | 6-(2-chlorophenyl)-5-[4-[(3S)-1-(3-fluoropropyl)-pyrrolidin-3-yl]oxy-phenyl]-8,9-dihydro-7H-benzo[7]-annulene-2-carboxylic acid | B | 1H NMR (400 MHz, DMSO-d6, δ ppm): 1.66 (m, 1 H); 1.79 (dm, J = 25.3 Hz, 2 H); 2.08 to 2.24 (m, 5 H); 2.38 (m, 1 H); 2.45 (t, J = 7.2 Hz, 2 H); 2.52 (dd, J = 3.0 and 10.4 Hz, 1 H); 2.62 (m, 1 H); 2.79 (m, 1 H); 2.93 (m, 2 H); 4.47 (td, J = 6.1 and 47.5 Hz, 2 H); 4.71 (m, 1 H); 6.60 (d, J = 8.8 Hz, 2 H); 6.72 (d, J = 8.8 Hz, 2 H); 6.88 (d, J = 8.5 Hz, 1 H); 7.13 to 7.25 (m, 3 H); 7.41 (d, J = 8.3 Hz, 1 H); 7.75 (dd, J = 2.0 and 8.5 Hz, 1 H); 7.90 (d, J = 2.0 Hz, 1 H); 12.67 (m, 1 H) | 520 |
| 211 | 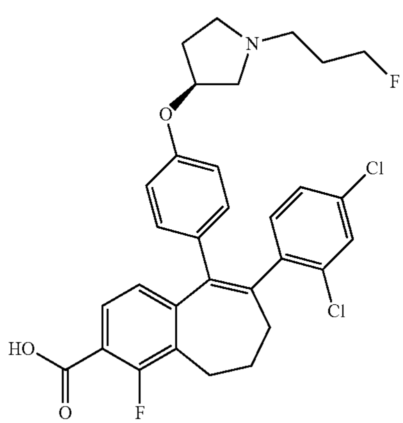 [SMILES: O=C(O)c1ccc2c(c1F)CCCC(c1ccc(Cl)cc1Cl)=C2c1ccc(O[C@H]2CCN(CCCF)C2)cc1] | 6-(2,4-dichlorophenyl)-1-fluoro-5-[4-[(3S)-1-(3-fluoropropyl)-pyrrolidin-3-yl]oxy-phenyl]-8,9-dihydro-7H-benzo[7]-annulene-2-carboxylic acid | B | 1H NMR (400 MHz, DMSO-d6, δ ppm): 1.69 (m, 1 H); 1.80 (dm, J = 25.3 Hz, 2 H); 2.09 to 2.27 (m, 5 H); 2.40 (m, 1 H); 2.48 (t, J = 7.2 Hz, 2 H); 2.55 (dd, J = 3.2 and 10.6 Hz, 1 H); 2.65 (m, 1 H); 2.81 (m, 2 H); 3.04 (m, 1 H); 4.47 (td, J = 6.1 and 47.5 Hz, 2 H); 4.76 (m, 1 H); 6.67 (d, J = 8.8 Hz, H); 6.69 (d, J = 7.8 Hz, 1 H); 6.76 (d, J = 8.8 Hz, 2 H); 7.21 (d, J = 8.3 Hz, 1 H); 7.30 (dd, J = 2.2 and 8.3 Hz, 1 H); 7.60 (d, J = 2.2 Hz, 1 H); 7.65 (t, J = 7.8 Hz, 1 H) | 572 |

TABLE 1-continued

| Examples | Structure | Name | Method | NMR | MASS: LC/MS (m/z, MH+): |
|---|---|---|---|---|---|
| 212 | 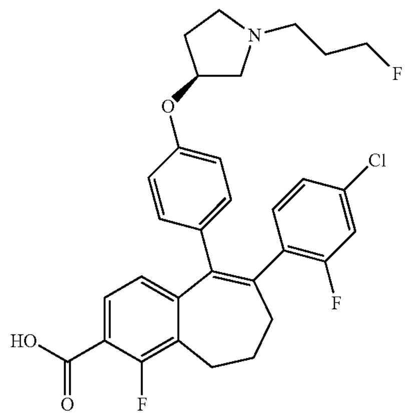 [SMILES: O=C(O)c1ccc2c(c1F)CCCC(c1ccc(Cl)cc1F)=C2c1ccc(O[C@H]2CCN(CCCF)C2)cc1] | 6-(4-chloro-2-fluoro-phenyl)-1-fluoro-5-[4-[(3S)-1-(3-fluoropropyl)-pyrrolidin-3-yl]oxy-phenyl]-8,9-dihydro-7H-benzo[7]-annulene-2-carboxylic acid | B | 1H NMR (400 MHz, DMSO-d6, δ ppm): 1.69 (m, 1 H); 1.80 (dm, J = 25.3 Hz, 2 H); 2.08 to 2.26 (m, 5 H); 2.39 (m, 1 H); 2.48 (t, J = 7.2 Hz, 2 H); 2.54 (dd, J = 2.8 and 10.4 Hz, 1 H); 2.64 (m, 1 H); 2.80 (dd, J = 6.4 and 10.4 Hz, 1 H); 2.87 (t, J = 7.2 Hz, 2 H); 4.48 (td, J = 6.2 and 47.6 Hz, 2 H); 4.76 (m, 1 H); 6.67 (d, J = 8.8 Hz, 3 H); 6.77 (d, J = 8.8 Hz, 2 H); 7.18 (dd, J = 2.1 and 8.3 Hz, 1 H); 7.24 (t, J = 8.3 Hz, 1 H); 7.32 (dd, J = 2.1 and 9.8 Hz, 1 H); 7.60 (t, J = 8.0 Hz, 1 H); 12.40 (m, 1 H) | 556 |
| 213 | 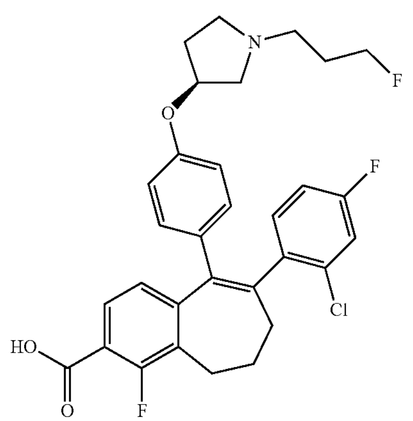 [SMILES: O=C(O)c1ccc2c(c1F)CCCC(c1ccc(F)cc1Cl)=C2c1ccc(O[C@H]2CCN(CCCF)C2)cc1] | 6-(2-chloro-4-fluoro-phenyl)-1-fluoro-5-[4-[(3S)-1-(3-fluoropropyl)-pyrrolidin-3-yl]oxy-phenyl]-8,9-dihydro-7H-benzo[7]-annulene-2-carboxylic acid | B | 1H NMR (400 MHz, DMSO-d6, δ ppm): 1.68 (m, 1 H); 1.79 (dm, J = 25.4 Hz, 2 H); 2.04 to 2.25 (m, 5 H); 2.38 (m, 1 H); 2.46 (t, J = 7.2 Hz, 2 H); 2.52 (m, 1 H); 2.63 (m, 1 H); 2.79 (m, 2 H); 3.00 (m, 1 H); 4.47 (td, J = 6.1 and 47.5 Hz, 2 H); 4.73 (m, 1 H); 6.51 (d, J = 8.2 Hz, 1 H); 6.62 (d, J = 8.9 Hz, 2 H); 6.73 (d, J = 8.9 Hz, 2 H); 7.08 (dt, J = 2.7 and 8.7 Hz, 1 H); 7.21 (dt, J = 6.4 and 8.7 Hz, 1 H); 7.32 (t, J = 8.2 Hz, 1 H); 7.40 (dd, J = 2.7 and 8.7 Hz, 1 H); 12.00 (m, 1 H) | 556 |
| 214 | 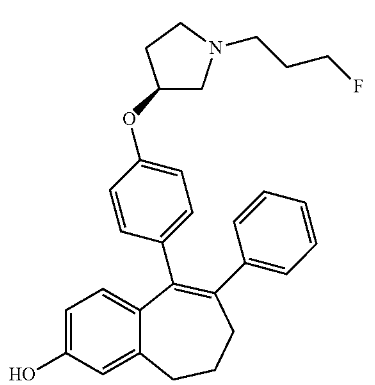 [SMILES: Oc1ccc2c(c1)CCCC(c1ccccc1)=C2c1ccc(O[C@H]2CCN(CCCF)C2)cc1] | 9-(4-{[(3S)-1-(3-fluoropropyl)-pyrrolidin-3-yl]oxy}-phenyl]-8-phenyl-6,7-dihydro-5H-benzo[7]-annulen-3-ol | A | 1H NMR (400 MHz, DMSO-d6, δ ppm): 1.70 (m, 1 H); 1.80 (dm, J = 25.3 Hz, 2 H); 2.04 (m, 2 H); 2.19 (m, 1 H); 2.27 (t, J = 7.0 Hz, 2 H); 2.40 (m, 1 H); 2.48 (m, 2 H); 2.55 (m, 1 H); 2.60 to 2.71 (m, 3 H); 2.80 (m, 1 H); 4.48 (td, J = 6.1 and 47.5 Hz, 2 H); 4.73 (m, 1 H); 6.56 (m, 2 H); 6.59 (d, J = 8.8 Hz, 2 H); 6.69 (s, 1 H); 6.71 (d, J = 8.8 Hz, 2 H); 7.05 to 7.19 (m, 5 H); 9.37 (s, 1 H) | 457 |

TABLE 1-continued

| Examples | Structure | Name | Method | NMR | MASS: LC/MS (m/z, MH+): |
|---|---|---|---|---|---|
| 215 | 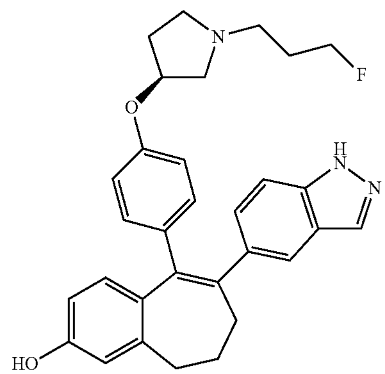 | 5-[4-[(3S)-1-(3-fluoropropyl)-pyrrolidin-3-yl]oxy-phenyl]-6-(1H-indazol-5-yl)-8,9-dihydro-7H-benzo[7]-annulen-2-ol | A | 1H NMR (400 MHz, DMSO-d6, δ ppm): 1.66 (m, 1 H); 1.78 (dm, J = 25.3 Hz, 2 H); 2.06 (m, 2 H); 2.17 (m, 1 H); 2.29 to 2.40 (m, 3 H); 2.43 (t, J = 7.2 Hz, 2 H); 2.53 (m, 1 H); 2.61 (m, 1 H); 2.70 (t, J = 7.0 Hz, 2 H); 2.77 (dd, J = 6.4 and 10.4 Hz, 1 H); 4.47 (td, J = 6.1 and 47.5 Hz, 2 H); 4.70 (m, 1 H); 6.54 (d, J = 8.8 Hz, 2 H); 6.56 (s, 2 H); 6.70 (s, 1 H); 6.72 (d, J = 8.8 Hz, 2 H); 7.09 (d, J = 8.7 Hz, 1 H); 7.30 (d, J = 8.7 Hz, 1 H); 7.52 (s, 1 H); 7.91 (s, 1 H); 9.35 (s, 1 H); 12.90 (s, 1 H) | 498 |
| 216 | 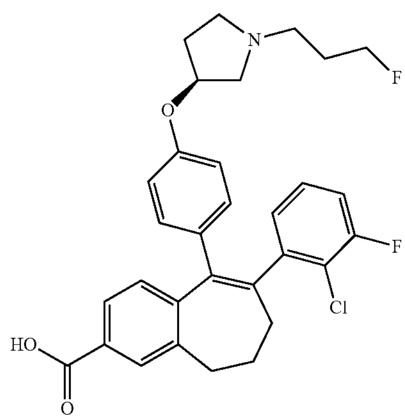 [SMILES: O=C(O)c1ccc2c(c1)CCCC(c1cccc(F)c1Cl)=C2c1ccc(O[C@H]2CCN(CCCF)C2)cc1] | 6-(2-Chloro-3-fluoro-phenyl)-5-{4-[(S)-1-(3-fluoro-propyl)-pyrrolidin-3-yloxy]-phenyl}-8,9-dihydro-7H-benzocyclo-heptene-2-carboxylic acid | B | 1H NMR (400 MHz, DMSO-d6, δ ppm): 1.68 (m, 1 H); 1.79 (dm, J = 25.3 Hz, 2 H); 2.10 to 2.25 (m, 5 H); 2.18 (m, 1 H); 2.46 (t, J = 7.2 Hz, 2 H); 2.53 (dd, J = 3.0 and 10.4 Hz, 1 H); 2.63 (m, 1 H); 2.79 (m, 1 H); 2.93 (t, J = 7.0 Hz, 2 H); 4.46 (td, J = 6.1 and 47.5 Hz, 2 H); 4.73 (m, 1 H); 6.63 (d, J = 8.8 Hz, 2 H); 6.73 (d, J = 8.8 Hz, 2 H); 6.89 (d, J = 8.1 Hz, 1 H); 7.05 (m, 1 H); 7.24 (m, 2 H); 7.77 (dd, J = 2.0 and 8.1 Hz, 1 H); 7.91 (d, J = 2.0 Hz, 1 H); 12.60 (m, 1 H) | 538 |
| 217 | 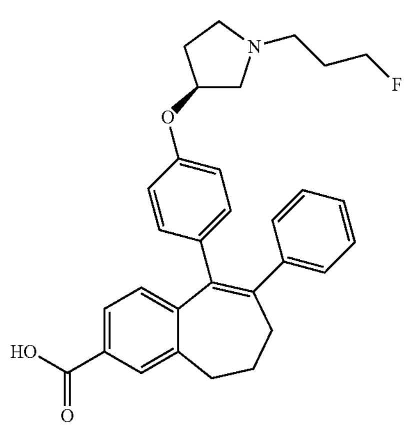 [SMILES: O=C(O)c1ccc2c(c1)CCCC(c1ccccc1)=C2c1ccc(O[C@H]2CCN(CCCF)C2)cc1] | 5-{4-[(S)-1-(3-Fluoro-propyl)-pyrrolidin-3-yloxy]-phenyl}-6-phenyl-8,9-dihydro-7H-benzocyclo-heptene-2-carboxylic acid | B | 1H NMR (400 MHz, DMSO-d6, δ ppm): 1.70 (m, 1 H); 1.80 (dm, J = 25.3 Hz, 2 H); 2.11 (m, 2 H); 2.20 (m, 1 H); 2.27 (t, J = 7.0 Hz, 2 H); 2.41 (m, 1 H); 2.48 (m, 2 H); 2.58 (dd, J = 3.0 and 10.4 Hz, 1 H); 2.67 (m, 1 H); 2.83 (m, 3 H); 4.48 (td, J = 6.1 and 47.5 Hz, 2 H); 4.74 (m, 1 H); 6.62 (d, J = 8.8 Hz, 2 H); 6.72 (d, J = 8.8 Hz, 2 H); 6.89 (d, J = 8.1 Hz, 1 H); 7.10 to 7.25 (m, 5 H); 7.73 (dd, J = 2.0 and 8.1 Hz, 1 H); 7.89 (d, J = 2.0 Hz, 1 H); 12.84 (m, 1 H) | 486 |

TABLE 1-continued

| Examples | Structure | Name | Method | NMR | MASS: LC/MS (m/z, MH+): |
|---|---|---|---|---|---|
| 218 | 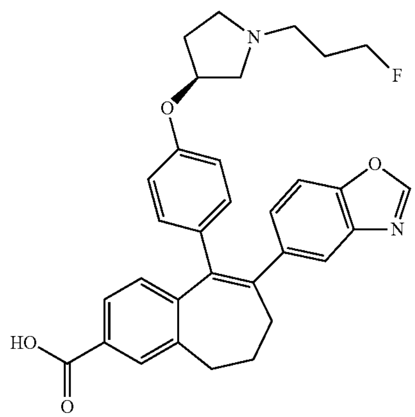 [SMILES: O=C(O)c1ccc2c(c1)CCCC(c1ccc3ocnc3c1)=C2c1ccc(O[C@H]2CCN(CCCF)C2)cc1] | 6-Benzo-oxazol-5-yl-5-{4-[(S)-1-(3-fluoro-propyl)-pyrrolidin-3-yloxy]-phenyl}-8,9-dihydro-7H-benzocyclo-heptene-2-carboxylic acid | B | 1H NMR (400 MHz, DMSO-d6, δ ppm): 1.90 to 2.08 (m, 4 H); 2.14 (m, 2 H); 2.32 (t, J = 7.0 Hz, 2 H); 2.90 (t, J = 7.0 Hz, 2 H); 3.00 to 3.40 (m, 6 H); 4.51 (td, J = 6.1 and 47.5 Hz, 2 H); 4.98 (m, 1 H); 6.70 (d, J = 8.8 Hz, 2 H); 6.81 (d, J = 8.8 Hz, 2 H); 6.88 (d, J = 8.1 Hz, 1 H); 7.25 (dd, J = 2.0 and 8.6 Hz, 1 H); 7.60 (m, 2 H); 7.77 (dd, J = 2.0 and 8.1 Hz, 1 H); 7.92 (d, J = 2.0 Hz, 1 H); 8.69 (s, 1 H); 9.92 (m, 1 H); 12.85 (m, 1 H) | 527 |
| 219 | 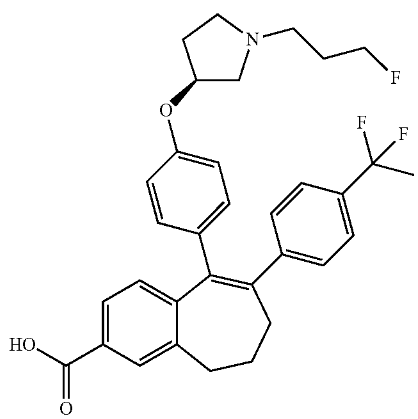 [SMILES: CC(F)(F)c1ccc(C2=C(c3ccc(O[C@H]4CCN(CCCF)C4)cc3)c3ccc(C(=O)O)cc3CCC2)cc1] | 6-[4-(1,1-Difluoro-ethyl)-phenyl]-5-{4-[(S)-1-(3-fluoro-propyl)-pyrrolidin-3-yloxy]-phenyl}-8,9-dihydro-7H-benzocyclo-heptene-2-carboxylic acid | B | 1H NMR (400 MHz, DMSO-d6, δ ppm): 1.70 (m, 1 H); 1.79 (dm, J = 25.3 Hz, 2 H); 1.92 (t, J = 19.0 Hz, 3 H); 2.11 (m, 2 H); 2.20 (m, 1 H); 2.28 (t, J = 7.0 Hz, 2 H); 2.39 (m, 1 H); 2.46 (t, J = 7.2 Hz, 2 H); 2.55 (dd, J = 3.0 and 10.4 Hz, 1 H); 2.65 (m, 1 H); 2.79 (dd, J = 6.4 and 10.4 Hz, 1 H); 2.84 (t, J = 7.0 Hz, 2 H); 4.47 (td, J = 6.1 and 47.5 Hz, 2 H); 4.74 (m, 1 H); 6.64 (d, J = 8.8 Hz, 2 H); 6.76 (d, J = 8.8 Hz, 2 H); 6.86 (d, J = 8.1 Hz, 1 H); 7.27 (d, J = 8.8 Hz, 2 H); 7.39 (d, J = 8.8 Hz, 2 H); 7.73 (dd, J = 2.0 and 8.1 Hz, 1 H); 7.90 (d, J = 2.0 Hz, 1 H); 12.48 (m, 1 H) | 550 |

The examples which follow describe the preparation of some compounds of formula (I). The numbers of the compounds exemplified below match those given in the Table 1 above. All reactions are performed under inert atmosphere, unless otherwise stated.

Intermediates

Compound (c). Tert-butyl (3S)-3-[4-(4,4,5,5-tetramethyl-1,3,2-dioxaborolan-2yl)phenoxy]pyrrolidine-1-carboxylate

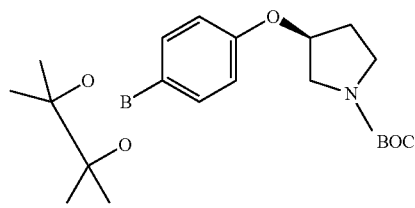

To a solution of 4-(4,4,5,5-tetramethyl-1,3,2-dioxaborolan-2-yl)phenol (a) (82.7 g, 364.51 mmol) in THF (2 L) was added under argon (R)-1-N-Boc-3-hydroxypyrrolidine (b) (84.43 g, 437.41 mmol) followed by N,N,N',N'-tetramethylazodicarboxamide (99.1 g, 546.77 mmol). The clear reaction mixture turned orange and triphenylphosphine (143.41 g, 546.77 mmol) was added. The reaction mixture was stirred at room temperature for 24 hours, meanwhile a precipitate of triphenylphosphine oxide formed (Ph$_3$P=O). The reaction mixture was poured in water (1.5 L) and extracted with ethyl acetate (AcOEt) (3×1.5 L). Gathered organic phases were dried over magnesium sulfate (MgSO$_4$), filtered and concentrated under reduced pressure. The residue was taken up into diisopropylether (1.5 L) and the solid formed (Ph$_3$P=O) was filtered. The solvent was concentrated under reduced pressure and the residue purified by column chromatography eluting with a mixture of heptane with AcOEt (90/10; v/v) to give 145 g (100%) of tert-butyl (3S)-3-[4-(4,4,5,5-tetramethyl-1,3,2-dioxaborolan-2-yl)phenoxy]pyrrolidine-1-carboxylate (c) as a colorless oil.

$^1$H NMR (400 MHz, DMSO-d6, δ ppm): 1.27 (s, 12H); 1.39 (s, 9H); 2.05 (m, 1H); 2.14 (m, 1H); 3.37 (3H); 3.55 (m, 1H); 5.05 (s, 1H); 6.94 (d, J=8.4 Hz, 2H); 7.61 (d, J=8.4 Hz, 2H)

Compound (d). (3S)-3-[4-(4,4,5,5-tetramethyl-1,3,2-dioxaborolan-2yl)phenoxy]pyrrolidine, hydrochloride

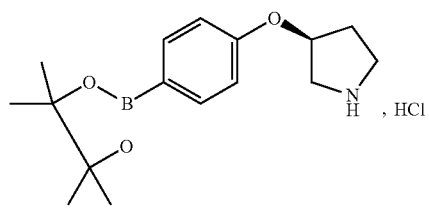

To a solution of (S)-tert-butyl 3-(4-(4,4,5,5-tetramethyl-1,3,2-dioxaborolan-2-yl)phenoxy)pyrrolidine-1-carboxylate (c) (80 g, 195.23 mmol) in MeOH (450 ml) was added slowly HCl 4N in dioxane (250 ml).

After 1.5 hours, the reaction mixture was concentrated under reduced pressure and the residue was taken up into Et$_2$O with stirring to give a solid which then was filtered and dried under vacuum to give compound (d) 61.8 g (95%) as a white powder.

$^1$H NMR (400 MHz, DMSO-d6, δ ppm): 1.28 (s, 12H); 2.10 (m, 1H); 2.21 (m, 1H); 3.31 (3H); 3.48 (m, 1H); 5.19 (m, 1H); 6.97 (d, J=8.4 Hz, 2H); 7.63 (d, J=8.4 Hz, 2H); 9.48 (s, 1H); 9.71 (s, 1H).

LC/MS (m/z, MH$^+$): 290

Reagent (1). (3S)-1-(3-fluoropropyl)-3-[4-(4,4,5,5-tetramethyl-1,3,2-dioxaborolan-2-yl)phenoxy]pyrrolidine

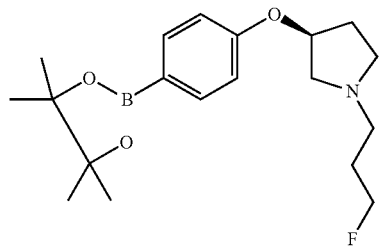

To a suspension of (S)-3-(4-(4,4,5,5-tetramethyl-1,3,2-dioxaborolan-2-yl)phenoxy)pyrrolidine hydrochloride (d) (20 g, 61.42 mmol) in acetonitrile (100 ml), was added K$_2$CO$_3$ (21.22 g, 153.54 mmol) and 1-iodo-3-fluoropropane (12.15 g, 61.42 mmol), under argon. The reaction mixture was stirred at 40° C. for 24 hours. After cooling to room temperature, the reaction mixture was filtered and washed with acetonitrile. The filtrate was concentrated under reduced pressure and the residue was taken up in DCM and the solid formed was filtered and washed with DCM. The filtrate was concentrated to give reagent (1) 21.5 g (100%) as a yellow foam.

$^1$H NMR (400 MHz, DMSO-d6, δ ppm): 1.27 (s, 12H); 1.77 (m, 2H); 1.84 (m, 1H); 2.27 (m, 1H); 2.41 (m, 1H); 2.49 (2H); 2.62 (dd, J=2.6 and 10.4 Hz, 1H); 2.69 (m, 1H); 2.83 (dd, J=6.2 and 10.4 Hz, 1H); 4.47 (td, J=6.2 and 47 Hz, 2H); 4.99 (m, 1H); 6.77 (d, J=8.4 Hz, 2H); 7.58 (d, J=8.4 Hz, 2H).

LC/MS (m/z, MH$^+$): 350

Intermediate (A1). 9-oxo-6,7,8,9-tetrahydro-5H-benzo[7]annulen-2-yl 2,2-dimethylpropanoate

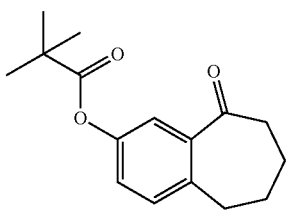 [SMILES: CC(C)(C)C(=O)Oc1ccc2c(c1)C(=O)CCCC2]

To a solution of 3-hydroxy-6,7,8,9-tetrahydro-5H-benzo[7]annulen-5-one (2.42 g, 13.73 mmol), in acetone (100 ml), was added K$_2$CO$_3$ (1.90 g, 13.73 mmol) and pivaloyl chloride (1.69 ml, 13.73 mmol). The reaction mixture was stirred at room temperature for 18 hours, then was filtered and concentrated under reduced pressure. The residue was purified by flash chromatography eluting with a gradient of heptane in AcOEt (100/0 to 85/15, v/v) to give 2.62 g (73%) of 9-oxo-6,7,8,9-tetrahydro-5H-benzo[7]annulen-2-yl 2,2-dimethylpropanoate (A1) which was used as such in the next step.

Intermediate (B1). 9-(trifluoromethanesulfonyloxy)-6,7-dihydro-5H-benzo[7]annulen-2-yl 2,2-dimethylpropanoate

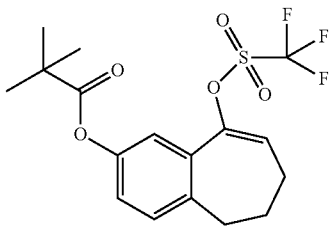 [SMILES: CC(C)(C)C(=O)Oc1ccc2c(c1)C(OS(=O)(=O)C(F)(F)F)=CCCC2]

To a solution of 9-oxo-6,7,8,9-tetrahydro-5H-benzo[7]annulen-2-yl 2,2-dimethylpropanoate (A1) (2.6 g, 10 mmol) in DCM (100 ml) was added under argon pyridine (1.26 ml, 14.98 mmol) and trifluoromethanesulfonic anhydride (3.39 ml, 19.97 mmol) dropwise. The reaction mixture was stirred at room temperature for 16 hours and ice (200 g) and DCM (200 ml) were added. The phases were separated, the aqueous phase was washed with DCM and the gathered organic phases were dried over MgSO$_4$, filtered and evaporated under reduced pressure. The residue was purified by flash chromatography eluting with a gradient of heptane in AcOEt (100/0 to 90/10, v/v) to give 3.65 g (93%) of 9-(trifluoromethanesulfonyloxy)-6,7-dihydro-5H-benzo[7]annulen-2-yl 2,2-dimethylpropanoate (B1) as an orange oil.

$^1$H NMR (400 MHz, DMSO-d6, δ ppm): 1.30 (s, 9H); 1.98 (m, 2H); 2.26 (m, 2H); 2.72 (m, 2H); 6.46 (t, J=6.2 Hz, 1H); 7.10 to 7.14 (m, 2H); 7.38 (m, 1H)

Intermediate (C1). 9-(4-{[(3S)-1-(3-fluoropropyl)pyrrolidin-3-yl]oxy}phenyl)-6,7-dihydro-5H-benzo[7]annulen-2-yl 2,2-dimethylpropanoate

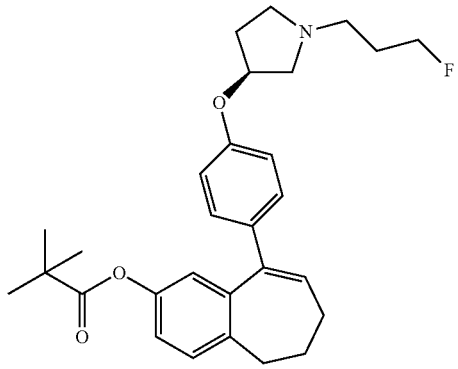 [SMILES: CC(C)(C)C(=O)Oc1ccc2c(c1)C(c1ccc(O[C@H]3CCN(CCCF)C3)cc1)=CCCC2]

To a solution of 9-(trifluoromethanesulfonyloxy)-6,7-dihydro-5H-benzo[7]annulen-2-yl 2,2-dimethylpropanoate (B1) (600 mg, 1.53 mmol) and (S)-1-(3-fluoropropyl)-3-(4-(4,4,5,5-tetramethyl-1,3,2-dioxaborolan-2-yl)phenoxy)pyrrolidine (1) (534 mg, 1.53 mmol) in dioxane (24 ml) and water (6 ml), Cs$_2$CO$_3$ (1.05 g, 3.21 mmol) was added under argon, followed by Pd(dppf)Cl$_2$ (124.87 mg, 0.15 mmol). The reaction mixture was stirred for 20 minutes at 60° C. After cooling to room temperature, water (40 ml) and DCM (200 ml) were added. After decantation, the organic phase was dried over MgSO$_4$, then was filtered and concentrated under reduced pressure. The obtained residue was purified by column chromatography eluting with a gradient of MeOH in DCM (0 to 4%; V/V) to give 0.7 g (98%) of 9-(4-{[(3S)-1-(3-fluoropropyl)pyrrolidin-3-yl]oxy}phenyl)-6,7-dihydro-5H-benzo[7]annulen-2-yl 2,2-dimethylpropanoate (C1).

$^1$H NMR (400 MHz, DMSO-d6, δ ppm): 1.24 (s, 9H); 1.70 to 1.92 (m, 5H); 2.11 (m, 2H); 2.26 (m, 1H); 2.42 (m, 1H); 2.48 (t, J=7.2 Hz, 2H); 2.52 to 2.74 (m, 4H); 2.85 (dd, J=6.2 and 10.4 Hz, 1H); 4.49 (td, J=6.1 and 47.5 Hz, 2H); 4.85 (m, 1H); 6.39 (t, J=7.4 Hz, 1H); 6.59 (d, J=2.6 Hz, 1H); 6.84 (d, J=8.8 Hz, 2H); 6.97 (dd, J=2.6 and 8.2 Hz, 1H); 7.11 (d, J=8.8 Hz, 2H); 7.35 (d, J=8.2 Hz, 1H)

Intermediate (D1). 8-bromo-9-(4-{[(3S)-1-(3-fluoropropyl)pyrrolidin-3-yl]oxy}phenyl)-6,7-dihydro-5H-benzo[7]annulen-2-yl-2,2-dimethylpropanoate

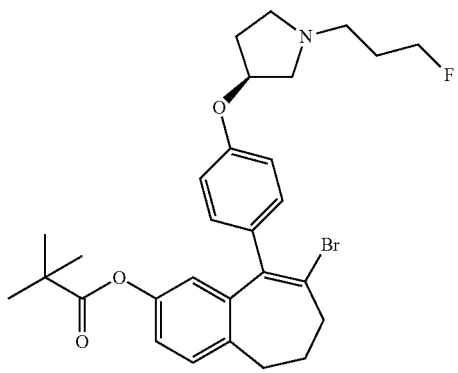 [SMILES: CC(C)(C)C(=O)Oc1ccc2c(c1)C(c1ccc(O[C@H]3CCN(CCCF)C3)cc1)=C(Br)CCC2]

To a solution of 9-(4-{[(3S)-1-(3-fluoropropyl)pyrrolidin-3-yl]oxy}phenyl)-6,7-dihydro-5H-benzo[7]annulen-2-yl 2,2-dimethylpropanoate (C1) (700 mg, 1.50 mmol) in THF (30 ml), was added pyridinium tribromide (481 mg, 1.50 mmol). The reaction mixture was stirred for 2.5 hours at room temperature. Water (20 ml) was added and pH was adjusted to 7 with concentrated solution of NaHCO$_3$. DCM (60 ml) was added. The aqueous phase was washed with DCM, 3 times and the gathered organic phases were dried over MgSO$_4$, filtered and concentrated under reduced pressure. The residue was purified by column chromatography eluting with a gradient of MeOH in DCM (0 to 5%; V/V) to give 0.667 g (82%) of 8-bromo-9-(4-{[(3S)-1-(3-fluoropropyl)pyrrolidin-3-yl]oxy}phenyl)-6,7-dihydro-5H-benzo[7]annulen-2-yl 2,2-dimethylpropanoate (D1).

$^1$H NMR (400 MHz, DMSO-d6, δ ppm): 1.21 (s, 9H); 1.71 to 1.91 (m, 3H); 2.18 to 2.33 (m, 3H); 2.42 (m, 1H); 2.48 (t, J=7.2 Hz, 2H); 2.50 (m, 2H); 2.62 (dd, J=3.0 and 10.4 Hz, 1H); 2.65 to 2.77 (m, 3H); 2.86 (dd, J=6.2 and 10.4 Hz, 1H); 4.49 (td, J=6.1 and 47.5 Hz, 2H); 4.87 (m, 1H); 6.44 (d, J=2.6 Hz, 1H); 6.88 (d, J=8.8 Hz, 2H); 6.97 (dd, J=2.6 and 8.2 Hz, 1H); 7.10 (d, J=8.8 Hz, 2H); 7.34 (d, J=8.2 Hz, 1H)

Intermediate (D2). 8-bromo-9-(4-{[(3S)-1-(3-fluoropropyl)pyrrolidin-3-yl]oxy}phenyl)-6,7-dihydro-5H-benzo[7]annulen-2-ol

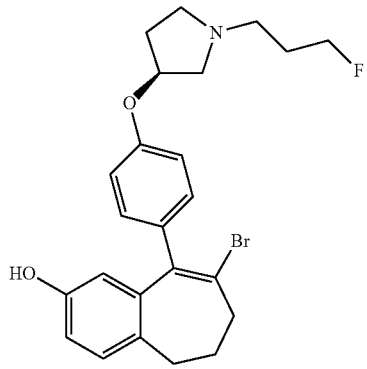 [SMILES: Oc1ccc2c(c1)C(c1ccc(O[C@H]3CCN(CCCF)C3)cc1)=C(Br)CCC2]

To a solution of 8-bromo-9-(4-{[(3S)-1-(3-fluoropropyl)pyrrolidin-3-yl]oxy}phenyl)-6,7-dihydro-5H-benzo[7]annulen-2-yl-2,2-dimethylpropanoate (D1) (665 mg, 1.22 mmol) in methanol (30 ml), was added NaOH (5N, 2 ml, 10.00 mmol). The reaction mixture was stirred 15 minutes at room temperature and 2 ml of HCl 5N was added. The solvent was removed under reduced pressure. The residue was taken up into AcOEt. The phases were separated and the aqueous phase was washed with AcOEt. The organic phases were combined and dried over MgSO$_4$, then were filtered and concentrated under reduced pressure and the residue was purified by column chromatography eluting with a gradient of MeOH in DCM (0 to 3%; V/V) to give 0.4 g (72%) of 8-bromo-9-(4-{[(3S)-1-(3-fluoropropyl)pyrrolidin-3-yl]oxy}phenyl)-6,7-dihydro-5H-benzo[7]annulen-2-ol (D2).

$^1$H NMR (400 MHz, DMSO-d6, δ ppm): 1.71 to 1.89 (m, 3H); 2.14 (m, 2H); 2.28 (m, 1H); 2.38 to 2.55 (m, 5H); 2.58 to 2.72 (m, 4H); 2.87 (dd, J=6.4 and 10.4 Hz, 1H); 4.49 (td, J=6.1 and 47.5 Hz, 2H); 4.85 (m, 1H); 6.20 (d, J=2.7 Hz, 1H); 6.60 (dd, J=2.7 and 8.2 Hz, 1H); 6.87 (d, J=8.8 Hz, 2H); 7.18 (d, J=8.8 Hz, 3H); 9.11 (s, 1H)

LC/MS (m/z, MH$^+$): 460

Intermediate (A2). 2-hydroxy-6,7,8,9-tetrahydro-5H-benzo[7]annulen-5-one

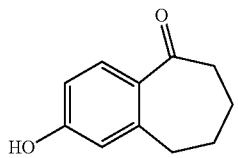

To a solution of 2-methoxy-6,7,8,9-tetrahydro-5H-benzo[7]annulen-5-one (15 g, 78.85 mmol) in toluene (400 ml) was added AlCl$_3$ (25 g, 187.49 mmol). The reaction mixture was stirred at 91° C. (bath temperature) for 45 minutes, cooled to room temperature and poured onto ice (900 g). The slurry was stirred for 20 minutes and the solid formed was filtered, washed with water (200 ml), and diisopropyl ether (200 ml), and then was dried to give 14.1 g (100%) of 2-hydroxy-6,7,8,9-tetrahydro-5H-benzo[7]annulen-5-one (A2) as a beige powder.

$^1$H NMR (400 MHz, DMSO-d6, δ ppm): 10.1 (s, 1H); 7.53 (d, 1H); 6.68 (dd, 1H); 6.62 (d, 1H); 2.84 (t, 2H); 2.52 (t, 2H); 1.65 (q, 2H); 1.55 (q, 2H).

LC/MS (m/z, MH$^+$): 177

Intermediate (A3). 5-oxo-6,7,8,9-tetrahydro-5H-benzo[7]annulen-2-yl 2,2-dimethylpropanoate

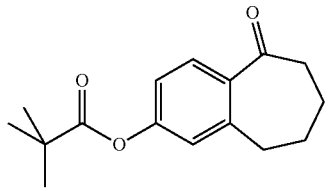 [SMILES: CC(C)(C)C(=O)Oc1ccc2c(c1)CCCCC2=O]

To a solution of 2-hydroxy-6,7,8,9-tetrahydro-5H-benzo[7]annulen-5-one (A2) (1.52 g, 8.63 mmol), in acetone (60 ml), was added K$_2$CO$_3$ (1.19 g, 8.63 mmol) and pivaloyl chloride (1.06 ml, 8.63 mmol). The reaction mixture was stirred at room temperature for 16 hours, filtered and concentrated under reduced pressure. The residue was purified by flash chromatography eluting with a gradient of heptane in AcOEt (100/0 to 85/15, v/v) to give 1.55 g (69%) of 5-oxo-6,7,8,9-tetrahydro-5H-benzo[7]annulen-2-yl 2,2-dimethylpropanoate (A3) as a colorless oil.

$^1$H NMR (400 MHz, DMSO-d6, δ ppm): 7.65 (d, 1H); 7.10-7.04 (m, 2H); 2.95 (t, 2H); 2.68 (t, 2H); 1.85-1.65 (m, 4H).

LC/MS (m/z, MH$^+$): 261

Intermediate (B2). 9-(trifluoromethanesulfonyloxy)-6,7-dihydro-5H-benzo[7]annulen-3-yl 2,2-dimethylpropanoate

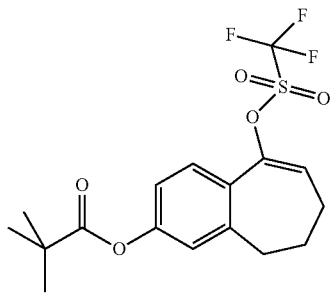 [SMILES: CC(C)(C)C(=O)Oc1ccc2c(c1)CCCC=C2OS(=O)(=O)C(F)(F)F]

To a solution of 5-oxo-6,7,8,9-tetrahydro-5H-benzo[7]annulen-2-yl 2,2-dimethylpropanoate (A3) (15 g, 57.62 mmol) in DCM (500 ml) was added dropwise under argon pyridine (7.28 ml, 86.43 mmol) and trifluoromethanesulfonic anhydride (19.58 ml, 115.24 mmol). The reaction mixture was stirred at room temperature for 2 hours and ice (200 g) was added. The phases were separated, the aqueous phase was washed with DCM and the gathered organic phases were dried over MgSO$_4$, filtered and evaporated under reduced pressure to give 22 g (97%) of 9-(trifluoromethanesulfonyloxy)-6,7-dihydro-5H-benzo[7]annulen-3-yl 2,2-dimethylpropanoate (B2) as a white solid.

LC/MS (m/z, MH$^-$): 391

Intermediate (C2). 9-(4-{[(3S)-1-(3-fluoropropyl)pyrrolidin-3-yl]oxy}phenyl)-6,7-dihydro-5H-benzo[7]annulen-3-yl-2,2-dimethylpropanoate

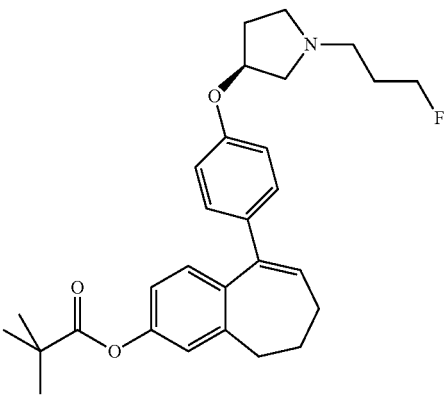 [SMILES: CC(C)(C)C(=O)Oc1ccc2c(c1)CCCC=C2c1ccc(O[C@H]2CCN(CCCF)C2)cc1]

To a solution of 9-(trifluoromethanesulfonyloxy)-6,7-dihydro-5H-benzo[7]annulen-3-yl-2,2-dimethylpropanoate (B2) (22 g, 56.07 mmol) and (3S)-1-(3-fluoropropyl)-3-[4-(tetramethyl-1,3,2-dioxaborolan-2-yl)phenoxy]pyrrolidine (1) (20.56 g, 58.87 mmol) in dioxane (420 ml) and water (120 ml) were added under argon Pd(dppf)Cl$_2$ (2.75 g, 3.36 mmol) and Cs$_2$CO$_3$ (36.57 g, 112.13 mmol). The reaction mixture was stirred for 1 hour at room temperature and was partitioned between water and DCM. The aqueous phase was washed with DCM and the gathered organic phases dried over MgSO$_4$, filtered and concentrated under reduced pressure. The residue was purified by column chromatography eluting with a gradient of MeOH in DCM (0 to 5%; V/V) to give 31 g (100%) of 9-(4-{[(3S)-1-(3-fluoropropyl)pyrrolidin-3-yl]oxy}phenyl)-6,7-dihydro-5H-benzo[7]annulen-3-yl-2,2-dimethylpropanoate (C2).

LC/MS (m/z, MH$^+$): 466

Intermediate (D3). 8-bromo-9-(4-{[(3S)-1-(3-fluoropropyl)pyrrolidin-3-yl]oxy}phenyl)-6,7-dihydro-5H-benzo[7]annulen-3-yl-2,2-dimethylpropanoate

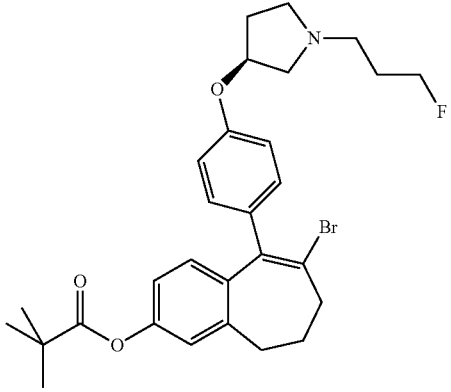 [SMILES: CC(C)(C)C(=O)Oc1ccc2c(c1)CCCC(Br)=C2c1ccc(O[C@H]2CCN(CCCF)C2)cc1]

To a solution of 9-(4-{[(3S)-1-(3-fluoropropyl)pyrrolidin-3-yl]oxy}phenyl)-6,7-dihydro-5H-benzo[7]annulen-3-yl-2,2-dimethylpropanoate (C2) (11 g, 22.44 mmol) in THF (250 ml), was added pyridinium tribromide (7.98 g, 22.44 mmol). The reaction mixture was stirred for 1 hour at room temperature and 100 ml of water was added followed by a saturated solution of sodium bicarbonate ($NaHCO_3$) until pH 7. The aqueous phase was washed with DCM, 3 times and the gathered organic phases were dried over $MgSO_4$, filtered and concentrated under reduced pressure. The residue was purified by column chromatography eluting with a gradient of MeOH in DCM (0 to 4%; V/V) to give 9.2 g (75%) of 8-bromo-9-(4-{[(3S)-1-(3-fluoropropyl)pyrrolidin-3-yl]oxy}phenyl)-6,7-dihydro-5H-benzo[7]annulen-3-yl-2,2-dimethylpropanoate (D3).

LC/MS (m/z, $MH^+$): 545

Intermediate (D4). 8-bromo-9-(4-{[(3S)-1-(3-fluoropropyl)pyrrolidin-3-yl]oxy}phenyl)-6,7-dihydro-5H-benzo[7]annulen-3-ol

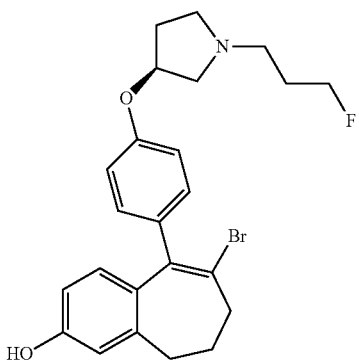 [SMILES: Oc1ccc2c(c1)CCCC(Br)=C2c1ccc(O[C@H]2CCN(CCCF)C2)cc1]

To a solution of 8-bromo-9-(4-{[(3S)-1-(3-fluoropropyl)pyrrolidin-3-yl]oxy}phenyl)-6,7-dihydro-5H-benzo[7]annulen-3-yl-2,2-dimethylpropanoate (D3) (9.2 g, 16.90 mmol) in MeOH (250 ml), was added NaOH (2N, 50 ml, 100 mmol). The reaction mixture was stirred 15 minutes at room temperature and 22 ml of aqueous HCl 5N was added. The solvent was removed under reduced pressure and the residue was taken up into DCM. The phases were separated and the aqueous phase was washed with DCM and AcOEt. The organic phase was dried over $MgSO_4$, filtered and concentrated under reduced pressure. The residue was purified by column chromatography eluting with a gradient of MeOH in DCM (0 to 05%; V/V) to give 6.03 g (78%) of 8-bromo-9-(4-{[(3S)-1-(3-fluoropropyl)pyrrolidin-3-yl]oxy}phenyl)-6,7-dihydro-5H-benzo[7]annulen-3-ol (D4).

$^1$H NMR (400 MHz, DMSO-d6, δ ppm): 1.71 to 1.89 (m, 3H); 2.19 (m, 2H); 2.28 (m, 1H); 2.39 to 2.52 (m, 5H); 2.59 to 2.72 (m, 4H); 2.87 (dd, J=6.4 and 10.4 Hz, 1H); 4.49 (td, J=6.1 and 47.5 Hz, 2H); 4.83 (m, 1H); 6.52 (s, 2H); 6.68 (s, 1H); 6.83 (d, J=8.8 Hz, 2H); 7.07 (d, J=8.8 Hz, 2H); 9.50 (s, 1H)

LC/MS (m/z, $MH^+$): 461

Intermediate (A4). 5-oxo-6,7,8,9-tetrahydro-5H-benzo[7]annulen-2-yltrifluoromethanesulfonate

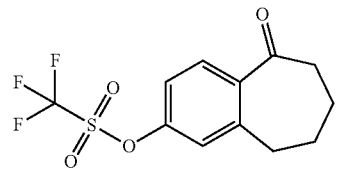 [SMILES: O=C1CCCCc2cc(OS(=O)(=O)C(F)(F)F)ccc21]

To a solution of 2-hydroxy-6,7,8,9-tetrahydro-5H-benzo[7]annulen-5-one (A2) (18.5 g, 105 mmol) in DCM (185 ml) and lutidine (13.35 ml, 113.505 mmol), cooled at 5° C. under argon, was added dropwise trifluoromethanesulfonic anhydride (20.22 ml, 123.29 mmol) while keeping temperature between 10 and 20° C. The reaction mixture was stirred for 1 hour at 5° C. then at room temperature for 1 hour.

Then, ice (200 g) was added and the slurry partitioned between water and DCM. The organic phase was washed with aqueous $NaHCO_3$ solution, dried over $MgSO_4$, filtered off and concentrated under reduced pressure. The residue was purified by flash chromatography eluting with a gradient of heptane/AcOEt from 100 to 90/10 to give 28.2 g (87%) of 5-oxo-6,7,8,9-tetrahydro-5H-benzo[7]annulen-2-yl trifluoromethanesulfonate (A4) as an orange oil.

LC/MS (m/z, $MH^+$): 309

Intermediate (A5). Methyl 5-oxo-6,7,8,9-tetrahydro-5H-benzo[7]annulene-2-carboxylate

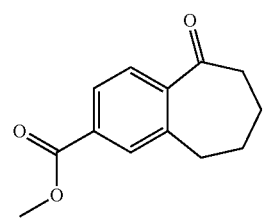 [SMILES: COC(=O)c1ccc2c(c1)CCCCC2=O]

To a solution of 5-oxo-6,7,8,9-tetrahydro-5H-benzo[7]annulen-2-yl trifluoromethanesulfonate (A4) (5.03 g, 16.32 mmol) in DMF (24 ml) and MeOH (12 ml), were added $Pd(dppf)Cl_2$ (754 mg, 0.98 mmol) and diisopropylethylamine (6 ml). The black suspension was carbonylated in an autoclave at 70° C. under 5 bars of CO for 2.5 hours. The reaction mixture was filtered, then the filtrate was partially concentrated under reduced pressure, and the residue, was partitioned between AcOEt and water. The organic phase was washed with water (2×75 ml) and aqueous HCl 0.5 N, dried over MgSO₄ and concentrated under reduced pressure. The residue was purified by flash chromatography eluting with a gradient of heptane/AcOEt from 100/0 to 90/10 to give 3.4 g (95%) of methyl 5-oxo-6,7,8,9-tetrahydro-5H-benzo[7]annulene-2-carboxylate (A5) as a colorless oil.

LC/MS (m/z, MH$^+$): 219

Intermediate (B3). methyl 9-(trifluoromethanesulfonyloxy)-6,7-dihydro-5H-benzo[7]annulene-3-carboxylate

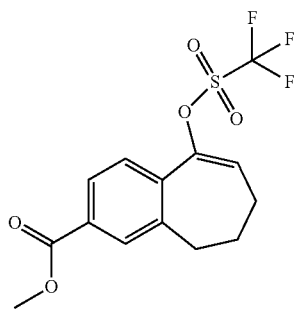 [SMILES: COC(=O)c1ccc2c(c1)CCCC=C2OS(=O)(=O)C(F)(F)F]

To a solution of methyl 5-oxo-6,7,8,9-tetrahydro-5H-benzo[7]annulene-2-carboxylate (A5) (18.19 g, 83.34 mmol) in DCM (500 ml) and anhydrous pyridine (11 ml, 130.56 mmol), cooled at 5° C. under argon, was added dropwise trifluoromethanesulfonic anhydride (30 ml, 176.54 mmol). The reaction mixture, a thick suspension, was stirred at room temperature for 24 hours, then ice was added and partitioned between water and DCM. The organic phase was dried over MgSO₄, filtered off and concentrated under reduced pressure to give 29 g (100%) of methyl 9-(trifluoromethanesulfonyloxy)-6,7-dihydro-5H-benzo[7]annulene-3-carboxylate (B3) as a yellow gum.

LC/MS (m/z, MH$^+$): 351

Intermediate (C3). methyl 9-(4-{[(3S)-1-(3-fluoropropyl)pyrrolidin-3-yl]oxy}phenyl)-6,7-dihydro-5H-benzo[7]annulene-3-carboxylate

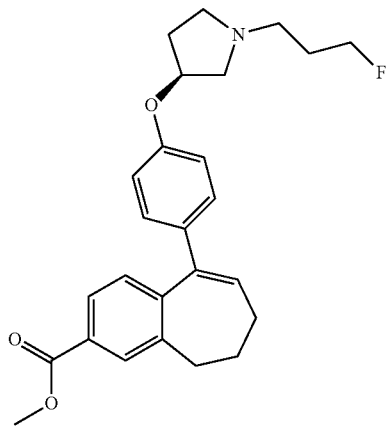 [SMILES: COC(=O)c1ccc2c(c1)CCCC=C2c1ccc(O[C@H]2CCN(CCCF)C2)cc1]

To a solution of methyl 9-(trifluoromethanesulfonyloxy)-6,7-dihydro-5H-benzo[7]annulene-3-carboxylate (B3) (29 g, 82.9 mmol), (3S)-1-(3-fluoropropyl)-3-[4-(tetramethyl-1,3,2-dioxaborolan-2-yl)phenoxy]pyrrolidine (1) (28.9 g, 82.9 mmol), in dioxane (225 ml) were added Pd(dppf)Cl₂ under argon, complex with DCM (3.73 g, 4.57 mmol) and Cs₂CO₃ 1.5 M aqueous solution (111.12 ml, 166.68 mmol). The reaction mixture was stirred at 60° C. for 1 hour.

After cooling to room temperature, the reaction mixture was poured into a mixture of water (500 ml) and AcOEt (400 ml). The organic phase was washed with brine, dried over MgSO₄, filtered on celite and concentrated under reduced pressure. The residue was purified by flash chromatography eluting with a gradient of DCM/MeOH from 100/0 to 95/05 to give 23 g (65%) of methyl 9-(4-{[(3S)-1-(3-fluoropropyl)pyrrolidin-3-yl]oxy}phenyl)-6,7-dihydro-5H-benzo[7]annulene-3-carboxylate (C3) as a brown gum.

LC/MS (m/z, MH$^+$): 424

Intermediate (D5). Methyl 8-bromo-9-(4-{[(3S)-1-(3-fluoropropyl)pyrrolidin-3-yl]oxy}phenyl)-6,7-dihydro-5H-benzo[7]annulene-3-carboxylate hydrobromide

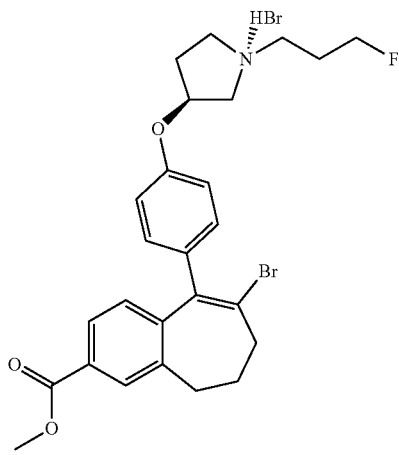

To a solution of methyl 9-(4-{[(3S)-1-(3-fluoropropyl)pyrrolidin-3-yl]oxy}phenyl)-6,7-dihydro-5H-benzo[7]annulene-3-carboxylate (C3) (13.93 g, 32.89 mmol), in DCM (150 ml) was added under argon pyridinium tribromide (15.78 g, 44.41 mmol). The reaction mixture was stirred for 1 hour at room temperature. Water (200 ml) was added, organic phase was then dried over MgSO₄, and concentrated under reduced pressure. The residue was purified by flash chromatography eluting with a gradient of DCM/MeOH from 100/0 to 95/05 to give 16.4 g (85%) of methyl 8-bromo-9-(4-{[(3S)-1-(3-fluoropropyl)pyrrolidin-3-yl]oxy}phenyl)-6,7-dihydro-5H-benzo[7]annulene-3-carboxylate hydrobromide (D5) as a yellow meringue.

LC/MS (m/z, MH$^+$): 502

Intermediate (C4). 9-(4-{[(3S)-1-(3-fluoropropyl)pyrrolidin-3-yl]oxy}phenyl)-6,7-dihydro-5H-benzo[7]annulen-3-ol

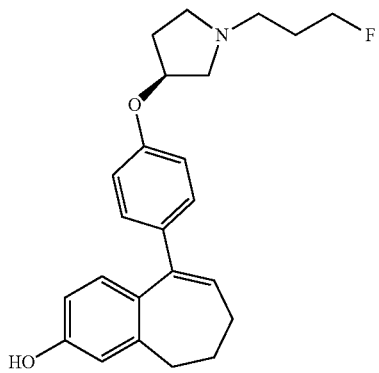 [SMILES: Oc1ccc2c(c1)CCCC=C2c1ccc(O[C@H]2CCN(CCCF)C2)cc1]

To a solution under argon of 9-(4-{[(3S)-1-(3-fluoropropyl)pyrrolidin-3-yl]oxy}phenyl)-6,7-dihydro-5H-benzo[7]annulen-3-yl-2,2-dimethylpropanoate (C2) (24.8 g, 53.26 mmol) in MeOH (300 ml), was added NaOH 5M (23 ml, 115.00 mmol). The reaction mixture was stirred for 2 hours at room temperature. pH was then adjusted to 7 by addition of 6N aqueous HCl solution. The MeOH was concentrated under reduced pressure, then DCM was added. The organic phase was dried over MgSO$_4$, and concentrated under reduced pressure. The residue was purified by flash chromatography eluting with a gradient of DCM/MeOH from 100/0 to 95/05 to give 18.8 g (93%) of 9-(4-{[(3S)-1-(3-fluoropropyl)pyrrolidin-3-yl]oxy}phenyl)-6,7-dihydro-5H-benzo[7]annulen-3-ol (C4) as a beige solid.

LC/MS (m/z, MH$^+$): 382

Intermediate (C5). 9-(4-{[(3S)-1-(3-fluoropropyl)pyrrolidin-3-yl]oxy}phenyl)-6,7-dihydro-5H-benzo[7]annulen-3-yl trifluoromethanesulfonate

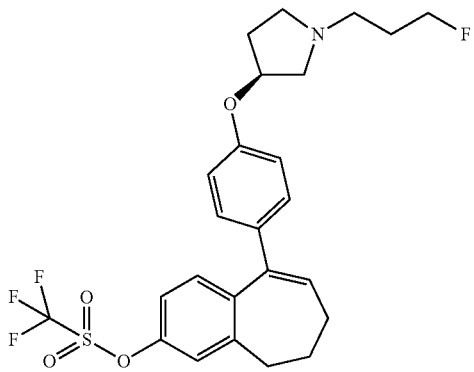 [SMILES: O=S(=O)(Oc1ccc2c(c1)CCCC=C2c1ccc(O[C@H]2CCN(CCCF)C2)cc1)C(F)(F)F]

To a solution of 9-(4-{[(3S)-1-(3-fluoropropyl)pyrrolidin-3-yl]oxy}phenyl)-6,7-dihydro-5H-benzo[7]annulen-3-ol (C4) (20.6 g, 54.00 mmol) in DCM (200 ml) and pyridine (6.55 ml, 81.00 mmol), cooled to 5° C. (ice bath), was added dropwise trifluoromethanesulfonic anhydride (18.93 ml, 108.00 mmol) under argon, and the reaction temperature was maintained <15° C. The ice bath was removed, and the brown suspension was stirred at room temperature for 2 hours. Ice (200 g) and DCM (200 ml) were added and the phases separated. The organic phase was dried over MgSO$_4$, and concentrated under reduced pressure. The residue was purified by flash chromatography eluting with a gradient of DCM/MeOH from 100/0 to 95/05 to give 24.7 g (89.1%) of 9-(4-{[(3S)-1-(3-fluoropropyl)pyrrolidin-3-yl]oxy}phenyl)-6,7-dihydro-5H-benzo[7]annulen-3-yl trifluoromethanesulfonate (C5) as a brown oil.

LC/MS (m/z, MH$^+$): 514

Intermediate (C3). Methyl 9-(4-{[(3S)-1-(3-fluoropropyl)pyrrolidin-3-yl]oxy}phenyl)-6,7-dihydro-5H-benzo[7]annulene-3-carboxylate

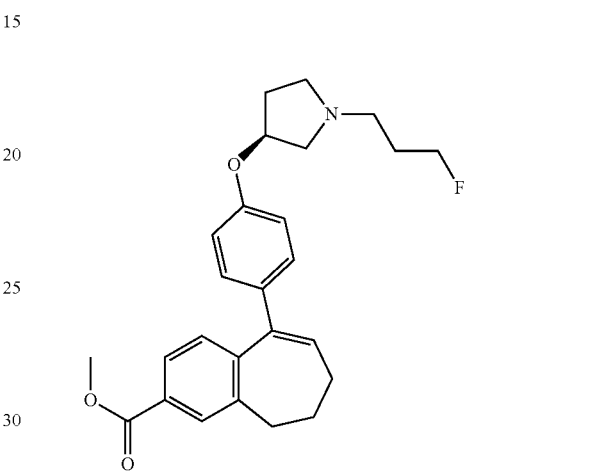

To a solution of 9-(4-{[(3S)-1-(3-fluoropropyl)pyrrolidin-3-yl]oxy}phenyl)-6,7-dihydro-5H-benzo[7]annulen-3-yl trifluoromethanesulfonate (C5) (10.1 g, 19.67 mmol) in DMF (66 ml) and MeOH (33 ml), were added Pd(dppf)Cl$_2$ (909 mg, 1.18 mmol) and diisopropylethylamine (7.21 ml). The black suspension was carbonylated in an autoclave at 70° C. under 5 bars of CO for 5 hours. The reaction mixture was filtered, then the filtrate was partially concentrated under reduced pressure. The residue was partitioned between AcOEt and water. The organic phase was washed with water (2×100 ml), dried over MgSO$_4$, and concentrated under reduced pressure. The residue was purified by flash chromatography eluting with a gradient of DCM/MeOH from 100/0 to 95/05 to give 7.13 g (86%) of methyl 9-(4-{[(3S)-1-(3-fluoropropyl)pyrrolidin-3-yl]oxy}phenyl)-6,7-dihydro-5H-benzo[7]annulene-3-carboxylate (C3) as a brown gum.

LC/MS (m/z, MH$^+$): 424

Intermediate (A6). 1-fluoro-2-methoxy-6,7,8,9-tetrahydro-5H-benzo[7]annulen-5-one

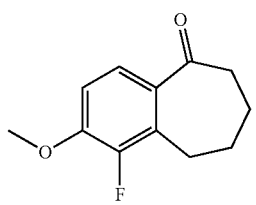

Step 1. Ethyl 5-(2-fluoro-3-methoxyphenyl)pent-4-enoate

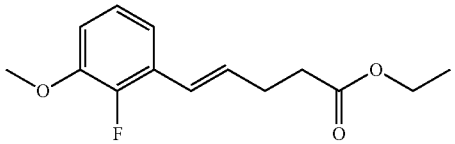 [SMILES: CCOC(=O)CC/C=C/c1cccc(OC)c1F]

To a solution of [3-(ethoxycarbonyl)propyl]triphenylphosphonium bromide (30 g, 65.5 mmol) in THF (300 ml) cooled at −78° C., was added potassium bis(trimethylsilyl) amide (16 g, 80.45 mmol) in 5 minutes. The orange suspension was stirred 1 hour at −78° C., and 2-fluoro-3-methoxybenzaldehyde (10 g, 65 mmol) was added. The reaction mixture was allowed to reach room temperature overnight under stirring. The solvent was concentrated under reduced pressure, the residue taken up in AcOEt (300 ml), washed twice with sodium bisulfite, 10% (w/v) aqueous solution (50 ml).

The organic phase was dried over anhydrous MgSO$_4$, filtered and concentrated under reduced pressure. The residue was purified by flash chromatography eluting with a mixture of AcOEt/cyclohexane 10/90 to give 9 g (55%) of (E)-ethyl 5-(2-fluoro-3-methoxyphenyl)pent-4-enoate as a yellow oil.

LC/MS (m/z, MH$^+$): 253 mixture of E/Z isomers 69/31%

Step 2. Ethyl 5-(2-fluoro-3-methoxyphenyl)pentanoate

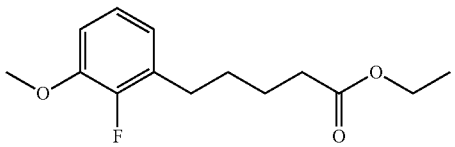 [SMILES: CCOC(=O)CCCCc1cccc(OC)c1F]

To a solution of (E)-ethyl 5-(2-fluoro-3-methoxyphenyl)pent-4-enoate (9 g, 35.67 mmol) in ethanol (100 ml), was added Pd/C 10% (100 mg). The black suspension was hydrogenated in an autoclave, at room temperature under 10 bars of hydrogen during 24 hours. The slurry was filtered then the filtrate was concentrated under reduced pressure to give 8.9 g (98%) of ethyl 5-(2-fluoro-3-ethoxyphenyl)pentanoate as a colorless oil.

LC/MS (m/z, MH$^+$): 255

Step 3. 5-(2-fluoro-3-methoxyphenyl)pentanoic acid

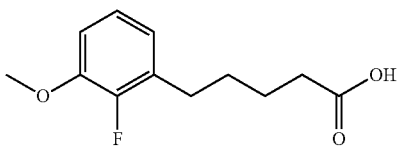 [SMILES: COc1cccc(CCCCC(=O)O)c1F]

To a solution of ethyl 5-(2-fluoro-3-methoxyphenyl)pentanoate (8.9 g, 35.00 mmol) in ethanol (60 ml), were added water (12 ml) and NaOH 32% (6 ml, 72 mmol). The white suspension was then stirred for 2 hours at 50° C. After cooling to room temperature, 100 g of ice were added and the reaction mixture was acidified with aqueous HCl to pH 3. The solid obtained was filtered off and dried to give 7.9 g (100%) of 5-(2-fluoro-3-methoxyphenyl)pentanoic acid as a white solid.

LC/MS (m/z, MH$^-$): 225

Step 4. 1-fluoro-2-methoxy-6,7,8,9-tetrahydro-5H-benzo[7]annulen-5-one (A6)

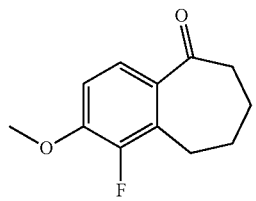

5-(2-fluoro-3-methoxyphenyl)pentanoic acid (4.8 g, 21.22 mmol) was added to trifluoromethane sulfonic acid (19 ml, 212 mmol) cooled at 5° C. The brown solution was stirred at 5° C. during 1 hour. Ice (100 g) and AcOEt (100 ml) were added, followed by an aqueous solution of NaHCO$_3$ until pH was 7. The organic phase was dried over MgSO$_4$, filtered off and concentrated under reduced pressure to give 4.4 g (99%) of 1-fluoro-2-methoxy-6,7,8,9-tetrahydro-5H-benzo[7]annulen-5-one (A6) as a brown oil.

LC/MS (m/z, MH$^+$): 209

Intermediate (A7). 1-fluoro-2-hydroxy-6,7,8,9-tetrahydro-5H-benzo[7]annulen-5-one

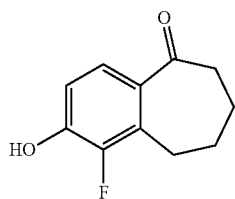 [SMILES: O=C1CCCCc2c1ccc(O)c2F]

To a solution of 1-fluoro-2-methoxy-6,7,8,9-tetrahydro-5H-benzo[7]annulen-5-one (A6) (6.2 g, 29.8 mmol) in toluene (100 ml) was added AlCl$_3$ (4.76 g, 35.7 mmol). The brown suspension was stirred for 1 hour at 90° C. After cooling to room temperature, the hot mixture was poured into 900 g of iced water. The solid obtained was filtered off, washed with water, aqueous HCl 0.1 N and dried to give 5.3 g (92%) of 1-fluoro-2-hydroxy-6,7,8,9-tetrahydro-5H-benzo[7]annulen-5-one (A7) as a beige solid.

LC/MS (m/z, MH$^+$): 195

Intermediate (A8). 1-fluoro-5-oxo-6,7,8,9-tetrahydro-5H-benzo[7]annulen-2-yl 2,2-dimethylpropanoate

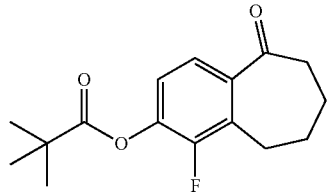 [SMILES: CC(C)(C)C(=O)Oc1ccc2c(c1F)CCCCC2=O]

To a solution of 1-fluoro-2-hydroxy-6,7,8,9-tetrahydro-5H-benzo[7]annulen-5-one (A7) (5.3 g, 27.3 mmol) in acetone (150 ml) were added $K_2CO_3$ (3.77 g, 27.29 mmol) and pivaloyl chloride (2.29 g/3.36 ml, 27.3 mmol). The orange suspension was stirred for 2 hours at room temperature. The solids were filtered off and then washed with acetone (10 ml). The filtrate was concentrated under reduced pressure. AcOEt (100 ml) and water were added to the residue obtained. The organic phase was dried over $MgSO_4$, filtered off and concentrated under reduced pressure to give 7.2 g (95%) of 1-fluoro-5-oxo-6,7,8,9-tetrahydro-5H-benzo[7]annulen-2-yl-2,2-dimethylpropanoate (A8) as a beige solid.

LC/MS (m/z, $MH^+$): 279

Intermediate (B4). 4-fluoro-9-(trifluoromethanesulfonyloxy)-6,7-dihydro-5H-benzo[7]annulen-3-yl 2,2-dimethylpropanoate

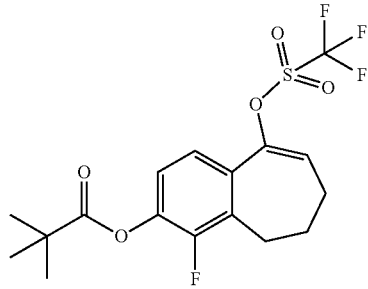 [SMILES: CC(C)(C)C(=O)Oc1ccc2c(c1F)CCCC=C2OS(=O)(=O)C(F)(F)F]

To a solution of 1-fluoro-5-oxo-6,7,8,9-tetrahydro-5H-benzo[7]annulen-2-yl-2,2-dimethylpropanoate (A8) (2.05 g, 7.37 mmol) in DCM (50 ml) was added under argon pyridine (0.93 ml, 11.05 mmol) and trifluoromethanesulfonic anhydride (2.5 ml, 14.73 mmol) dropwise. The reaction mixture was stirred at room temperature for 2 hours and ice (100 g) was added. The phases were separated, the aqueous phase was washed with DCM and the gathered organic phases were dried over $MgSO_4$, filtered and evaporated under pressure. The residue was purified by flash chromatography eluting with DCM to give 2.5 g (83%) of 4-fluoro-9-(trifluoromethanesulfonyloxy)-6,7-dihydro-5H-benzo[7]annulen-3-yl-2,2-dimethylpropanoate (B4) as a yellow oil.

LC/MS (m/z, $MH^+$): 411

Intermediate (C6). 4-fluoro-9-(4-{[(3S)-1-(3-fluoropropyl)pyrrolidin-3-yl]oxy}phenyl)-6,7-dihydro-5H-benzo[7]annulen-3-yl-2,2-dimethylpropanoate

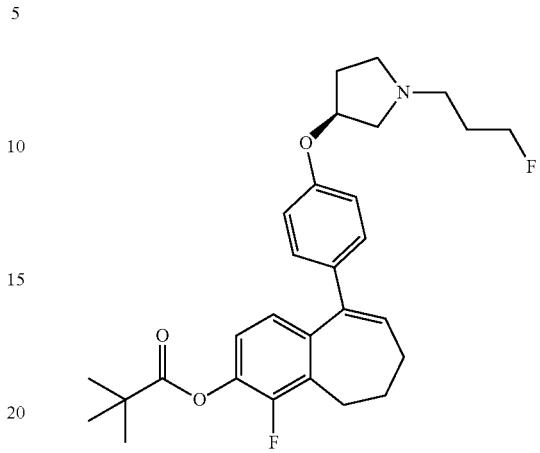

To a solution of 4-fluoro-9-(trifluoromethanesulfonyloxy)-6,7-dihydro-5H-benzo[7]annulen-3-yl-2,2-dimethylpropanoate (B4) (700 mg, 1.71 mmol) and (S)-1-(3-fluoropropyl)-3-(4-(4,4,5,5-tetramethyl-1,3,2-dioxaborolan-2-yl)phenoxy)pyrrolidine (1) (595.72 mg, 1.71 mmol) in dioxane (10 ml) and water (0.5 ml), were added $Cs_2CO_3$ (1.17 g, 3.58 mmol) and Pd(dppf)$Cl_2$ (139 mg, 0.171 mmol). The reaction mixture was stirred for 1 hour at room temperature and partitioned between water and AcOEt. The aqueous phase was washed with AcOEt and the gathered organic phases were dried over $MgSO_4$, filtered and concentrated under reduced pressure. The residue was purified by column chromatography eluting with DCM/MeOH/$NH_4OH$ 28% 93/6.3/0.07 to give 0.55 g (67%) of (4-fluoro-9-(4-{[(3S)-1-(3-fluoropropyl)pyrrolidin-3-yl]oxy}phenyl)-6,7-dihydro-5H-benzo[7]annulen-3-yl 2,2-dimethylpropanoate (C6).

LC/MS (m/z, $MH^+$): 484

Intermediate (D6). (8-bromo-4-fluoro-9-(4-{[(3S)-1-(3-fluoropropyl)pyrrolidin-3-yl]oxy}phenyl)-6,7-dihydro-5H-benzo[7]annulen-3-yl-2,2-dimethylpropanoate

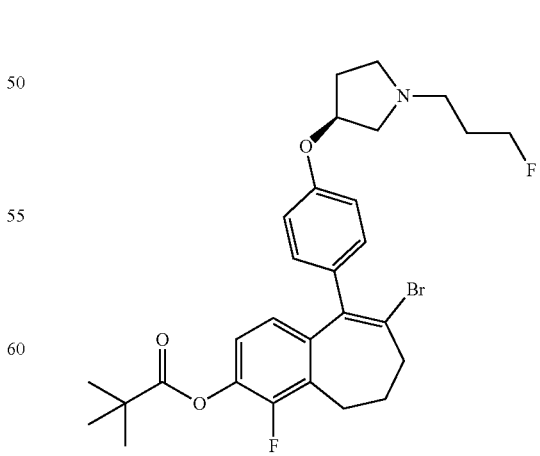

To a solution of (4-fluoro-9-(4-{[(3S)-1-(3-fluoropropyl)pyrrolidin-3-yl]oxy}phenyl)-6,7-dihydro-5H-benzo[7]annulen-3-yl-2,2-dimethylpropanoate (C6) (550 mg, 1.14 mmol) in THF (30 ml), was added pyridinium tribromide (404 mg, 1.14 mmol). The reaction mixture was stirred for 1 hour at room temperature. A solution of ammonium dihydrogen phosphate ($NH_4H_2PO_4$) and AcOEt was added. The aqueous phase was washed with AcOEt and the gathered organic phase dried over $MgSO_4$ and filtered. The organic phase was concentrated under reduced pressure to give 0.63 g (98%) of 8-bromo-4-fluoro-9-(4-{[(3S)-1-(3-fluoropropyl)pyrrolidin-3-yl]oxy}phenyl)-6,7-dihydro-5H-benzo[7]annulen-3-yl-2,2-dimethylpropanoate (D6).

LC/MS (m/z, $MH^+$): 562

Intermediate (D7). 8-bromo-4-fluoro-9-(4-{[(3S)-1-(3-fluoropropyl)pyrrolidin-3-yl]oxy}phenyl)-6,7-dihydro-5H-benzo[7]annulen-3-ol

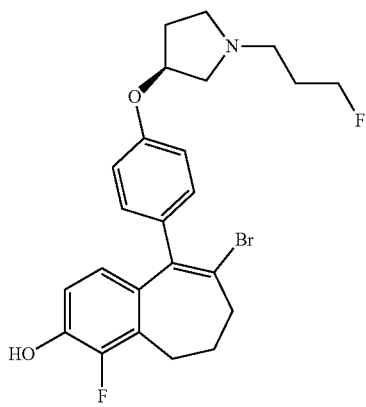 [SMILES: Oc1ccc2c(c1F)CCCC(Br)=C2c1ccc(O[C@H]2CCN(CCCF)C2)cc1]

To a solution of 8-bromo-4-fluoro-9-(4-{[(3S)-1-(3-fluoropropyl)pyrrolidin-3-yl]oxy}phenyl)-6,7-dihydro-5H-benzo[7]annulen-3-yl 2,2-dimethylpropanoate (D6) (640 mg, 1.14 mmol) in MeOH (15 ml), was added NaOH (2N, 2.84 ml, 5.69 mmol). The reaction mixture was stirred for 1 hour at room temperature and 2 ml of aqueous HCl 2N was added and the pH was adjusted to 5 with a solution of aqueous ammonium chloride ($NH_4Cl$). The solvent was removed under reduced pressure and the residue taken up into AcOEt. The phases were separated and the aqueous phase was washed with AcOEt. The organic phases were combined and dried over $MgSO_4$, filtered and concentrated under reduced pressure. The residue was purified by column chromatography eluting with DCM/MeOH: 95/05 to give 0.47 g (86%) of 8-bromo-4-fluoro-9-(4-{[(3S)-1-(3-fluoropropyl)pyrrolidin-3-yl]oxy}phenyl)-6,7-dihydro-5H-benzo[7]annulen-3-ol (D7) as a grey solid.

$^1$H NMR (400 MHz, DMSO-d6, δ ppm): 1.71 to 2.00 (m, 3H); 2.20 (m, 2H); 2.25 to 3.15 (m, 11H); 4.50 (td, J=6.1 and 47.5 Hz, 2H); 4.92 (m, 1H); 6.38 (d, J=8.5 Hz, 1H); 6.71 (t, J=8.5 Hz, 1H); 6.88 (d, J=8.8 Hz, 2H); 7.10 (d, J=8.8 Hz, 2H); 9.93 (s, 1H); 10.03 (m, 1H)

LC/MS (m/z, $MH^+$): 478

Intermediate (A9). 1-fluoro-5-oxo-6,7,8,9-tetrahydro-5H-benzo[7]annulen-2-yl trifluoromethane sulfonate

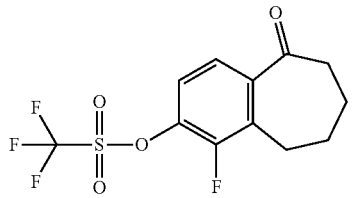 [SMILES: O=C1CCCCc2c1ccc(OS(=O)(=O)C(F)(F)F)c2F]

To a solution of 1-fluoro-2-hydroxy-6,7,8,9-tetrahydro-5H-benzo[7]annulen-5-one (A7) (5.5 g, 28.32 mmol), in DCM (35 ml) and lutidine (6.66 ml, 56.64 mmol), cooled at 5° C. under argon, was added dropwise trifluoromethanesulfonic anhydride (9.30 ml, 56.64 mmol) while keeping temperature between 10 and 20° C. The reaction mixture was stirred at 5° C. for 1 hour and then at room temperature for 1 hour.

Ice (50 g) was added and the slurry partitioned between water and DCM. The organic phase was washed with aqueous $NaHCO_3$ solution, dried over $MgSO_4$, filtered and concentrated under reduced pressure. The residue was purified by flash chromatography eluting with DCM to give 7.05 g (76%) of 1-fluoro-5-oxo-6,7,8,9-tetrahydro-5H-benzo[7]annulen-2-yl trifluoromethanesulfonate (A9) as a brown oil.

LC/MS (m/z, $MH^+$): 326

Intermediate (A10). Methyl 1-fluoro-5-oxo-6,7,8,9-tetrahydro-5H-benzo[7]annulene-2-carboxylate

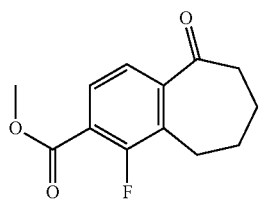 [SMILES: COC(=O)c1ccc2c(c1F)CCCCC2=O]

To a solution of 1-fluoro-5-oxo-6,7,8,9-tetrahydro-5H-benzo[7]annulen-2-yl trifluoromethanesulfonate (A9) (7 g, 21.46 mmol) in DMF (20 ml) and MeOH (40 ml), were added Pd(dppf)$Cl_2$ (991.51 mg, 1.29 mmol) and diisopropylethylamine (7.5 ml). The black suspension was carbonylated in an autoclave at 70° C. under 5 bars of CO for 18 hours. The reaction mixture was filtered, then the filtrate was partially concentrated under reduced pressure. AcOEt and water were added to the residue obtained. The organic phase was washed with water and aqueous HCl 0.5 N, dried over $MgSO_4$, filtered and concentrated under reduced pressure. The residue was purified by flash chromatography eluting with DCM to give 3.4 g (67%) of methyl 1-fluoro-5-oxo-6,7,8,9-tetrahydro-5H-benzo[7]annulene-2-carboxylate (A10) as a colorless oil.

LC/MS (m/z, $MH^+$): 237

Intermediate (B5). Methyl 4-fluoro-9-(trifluoromethanesulfonyloxy)-6,7-dihydro-5H-benzo[7]annulene-3-carboxylate

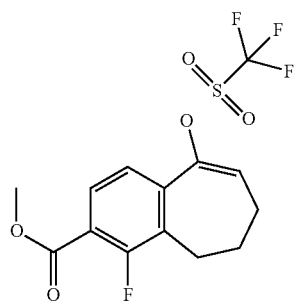

To a solution of methyl 1-fluoro-5-oxo-6,7,8,9-tetrahydro-5H-benzo[7]annulene-2-carboxylate (A10) (1.15 g, 4.87 mmol) in THF (25 ml) cooled at −10° C., was added dropwise potassium bis(trimethylsilyl)amide (1.94 g, 9.74 mmol), followed by N,N-bis(trifluoromethylsulfonyl)aniline (1.95 g, 5.35 mmol). The reaction mixture was stirred for 30 minutes at −10° C. and 20 hours at room temperature. The reaction mixture was cooled to 0° C. and water (500 ml) and AcOEt (200 ml) were added. The organic phase was dried over MgSO$_4$, filtered and concentrated under reduced pressure. The residue was purified by flash chromatography eluting with DCM to give 1.25 g (69%) of methyl 4-fluoro-9-(trifluoromethanesulfonyloxy)-6,7-dihydro-5H-benzo[7]annulene-3-carboxylate (B5) as an oil which was used as such in the following step.
LC/MS (m/z, MH$^+$): 369

Intermediate (C7). Methyl 4-fluoro-9-(4-{[(3S)-1-(3-fluoropropyl)pyrrolidin-3-yl]oxy}phenyl)-6,7-dihydro-5H-benzo[7]annulene-3-carboxylate

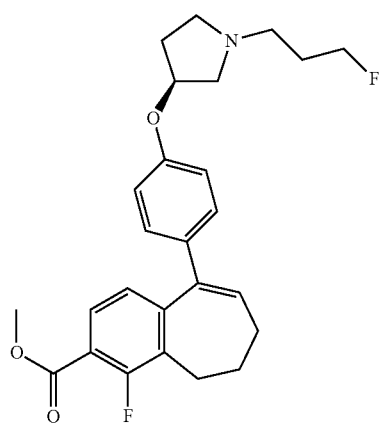 [SMILES: COC(=O)c1ccc2c(c1F)CCCC=C2c1ccc(O[C@H]2CCN(CCCF)C2)cc1]

To a solution under argon of methyl 4-fluoro-9-(trifluoromethanesulfonyloxy)-6,7-dihydro-5H-benzo[7]annulene-3-carboxylate (B5) (1.53 g, 4.15 mmol), (S)-1-(3-fluoropropyl)-3-(4-(4,4,5,5-tetramethyl-1,3,2-dioxaborolan-2-yl)phenoxy)pyrrolidine (1) (1.60 g, 4.57 mmol), in dioxane (10 ml) and water (0.5 ml) were added Pd(dppf)Cl$_2$, complex with DCM (191.98 mg, 0.25 mmol) and Cs$_2$CO$_3$ (2.85 g, 8.72 mmol). The reaction mixture was stirred at 80° C. for 1 hour. After cooling to room temperature, the reaction mixture was poured to a mixture of water (20 ml) and AcOEt (50 ml). The organic phase was washed with brine, dried over MgSO$_4$, filtered on celite and concentrated under reduced pressure. The residue was purified by flash chromatography eluting with isopropylether/MeOH 95/05 to give 0.7 g (39%) of methyl 4-fluoro-9-(4-{[(3S)-1-(3-fluoropropyl)pyrrolidin-3-yl]oxy}phenyl)-6,7-dihydro-5H-benzo[7]annulene-3-carboxylate (C7) as a yellow oil.
LC/MS (m/z, MH$^+$): 442

Intermediate (D8). Methyl 8-bromo-4-fluoro-9-(4-{[(3S)-1-(3-fluoropropyl)pyrrolidin-3-yl]oxy}phenyl)-6,7-dihydro-5H-benzo[7]annulene-3-carboxylate hydrobromide

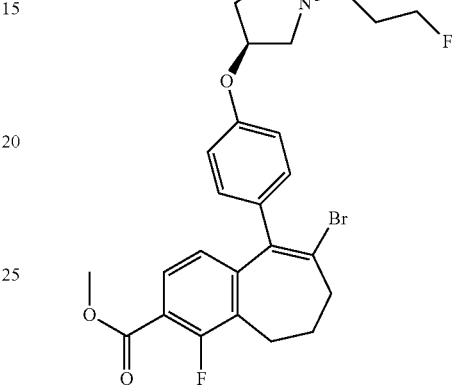

To a solution of methyl 4-fluoro-9-(4-{[(3S)-1-(3-fluoropropyl)pyrrolidin-3-yl]oxy}phenyl)-6,7-dihydro-5H-benzo[7]annulene-3-carboxylate (C7) (900 mg, 2.04 mmol), in DCM (30 ml) was added pyridinium tribromide (880.11 mg, 2.75 mmol). The reaction mixture was stirred under argon for 30 minutes at room temperature. Water (30 ml) was added then organic phase was dried over MgSO$_4$, and concentrated under reduced pressure. The obtained meringue was purified by flash chromatography eluting with a gradient of DCM/MeOH from 100/0 to 95/05 to give 0.8 g (63%) of methyl 8-bromo-4-fluoro-9-(4-{[(3S)-1-(3-fluoropropyl)pyrrolidin-3-yl]oxy}phenyl)-6,7-dihydro-5H-benzo[7]annulene-3-carboxylate hydrobromide (D8) as an orange meringue.
LC/MS (m/z, MH$^+$): 520

EXAMPLES

Example 1. 5-[4-[(3S)-1-(3-fluoropropyl)pyrrolidin-3-yl]oxyphenyl]-6-(4-hydroxyphenyl)-8,9-dihydro-7H-benzo[7]annulen-3-ol

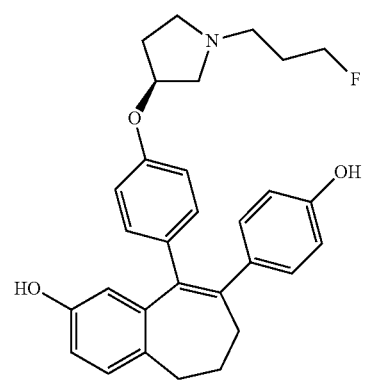 [SMILES: Oc1ccc(C2=C(c3ccc(O[C@H]4CCN(CCCF)C4)cc3)c3cc(O)ccc3CCC2)cc1]

Method A:

To a solution of 8-bromo-9-(4-{[(3S)-1-(3-fluoropropyl)pyrrolidin-3-yl]oxy}phenyl)-6,7-dihydro-5H-benzo[7]annulen-2-ol (D2) (80 mg, 173.8 µmol) in dioxane/water (80/20; V/V; 4 ml), were added 4-hydroxyphenyl-boronic acid (23.97 mg, 173.77 µmol), Cs₂CO₃(119.02 mg, 364.92 µmol), and Pd(dppf)Cl₂ (8.51 mg, 10.43 µmol). The reaction mixture was microwaved at 90° C. for 30 minutes, and purified by column chromatography eluting with a gradient of MeOH in DCM (0% to 10%) to give a solid which was further purified on strong cation exchange (SCX) column to give 58 mg (71%) of 5-[4-[(3S)-1-(3-fluoropropyl)pyrrolidin-3-yl]oxyphenyl]-6-(4-hydroxyphenyl)-8,9-dihydro-7H-benzo[7]annulen-3-ol.

Example 3. 5-[4-[(3S)-1-(3-fluoropropyl)pyrrolidin-3-yl]oxyphenyl]-6-(1H-indol-5-yl)-8,9-dihydro-7H-benzo[7]annulen-3-ol

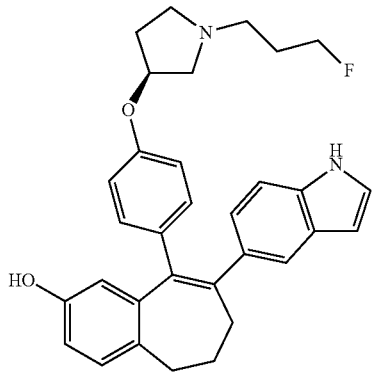 [SMILES: Oc1ccc2c(c1)C(c1ccc(O[C@H]3CCN(CCCF)C3)cc1)=C(c1ccc3[nH]ccc3c1)CCC2]

To a solution of 8-bromo-9-(4-{[(3S)-1-(3-fluoropropyl)pyrrolidin-3-yl]oxy}phenyl)-6,7-dihydro-5H-benzo[7]annulen-2-ol (D2) (80 mg, 173.8 µmol) in dioxane/water (80/20; V/V; 4 ml), were added 5-indolylboronic acid (30.77 mg, 191.15 µmol), Cs₂CO₃(119.02 mg, 364.92 µmol), and Pd(dppf)Cl₂ (8.51 mg, 10.43 µmol). The reaction mixture was microwaved at 90° C. for 30 minutes, and purified by column chromatography eluting with a gradient of MeOH in DCM (0% to 10%) to give a solid which was further purified on strong cation exchange (SCX) column to give 12 mg (14%) of 5-[4-[(3S)-1-(3-fluoropropyl)pyrrolidin-3-yl]oxyphenyl]-6-(1H-indol-5-yl)-8,9-dihydro-7H-benzo[7]annulen-3-01.

Example 4. 6-(2-chloro-4-fluoro-phenyl)-5-[4-[(3S)-1-(3-fluoropropyl)pyrrolidin-3-yl]oxyphenyl]-8,9-dihydro-7H-benzo[7]annulen-3-ol

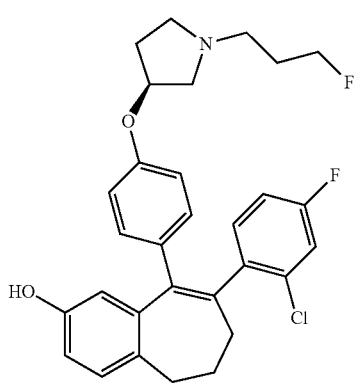 [SMILES: Oc1ccc2c(c1)C(c1ccc(O[C@H]3CCN(CCCF)C3)cc1)=C(c1ccc(F)cc1Cl)CCC2]

To a solution of 8-bromo-9-(4-{[(3S)-1-(3-fluoropropyl)pyrrolidin-3-yl]oxy}phenyl)-6,7-dihydro-5H-benzo[7]annulen-2-ol (D2) (80 mg, 173.8 µmol) in dioxane/water (80/20; V/V; 4 ml), were added 2-chloro-4-fluorophenylboronic acid (23.10 mg, 132.50 µmol), Cs₂CO₃ (119.02 mg, 364.92 µmol), and Pd(dppf)Cl₂ (8.51 mg, 10.43 µmol). The reaction mixture was microwaved at 90° C. for 30 minutes, and purified by column chromatography eluting with a gradient of MeOH in DCM (0% to 10%) to give a solid which was further purified on strong cation exchange (SCX) column to give 50 mg (74%) of 6-(2-chloro-4-fluoro-phenyl)-5-[4-[(3S)-1-(3-fluoropropyl)pyrrolidin-3-yl]oxyphenyl]-8,9-dihydro-7H-benzo[7]annulen-3-ol.

Example 5. 6-(2-chloro-4-fluoro-phenyl)-5-[4-[(3S)-1-(3-fluoropropyl)pyrrolidin-3-yl]oxyphenyl]-8,9-dihydro-7H-benzo[7]annulen-2-ol

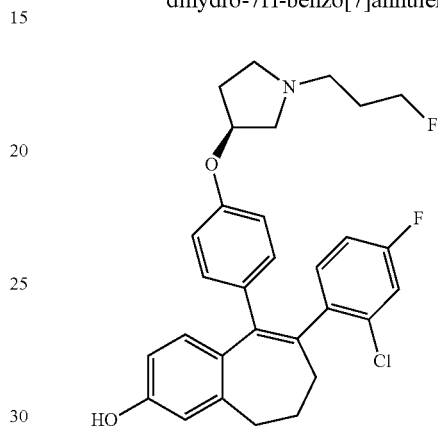

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (60 mg, 130.33 µmol) in dioxane/water (80/20; V/V; 3 ml), were added 2-chloro-4-fluorophenylboronic acid (23.43 mg, 130.33 µmol), Cs₂CO₃ (89.26 mg, 273.69 µmol), and Pd(dppf)Cl₂ (6.39 mg, 7.82 µmol). The reaction mixture was microwaved at 90° C. for 1 hour and purified by column chromatography eluting with a gradient of methanol in dichloromethane (0% to 10%) to give a solid which was further purified on strong cation exchange (SCX) column to give 52 mg (78.2%) of 6-(2-chloro-4-fluoro-phenyl)-5-[4-[(3S)-1-(3-fluoropropyl)pyrrolidin-3-yl]oxyphenyl]-8,9-dihydro-7H-benzo[7]annulen-2-ol.

Example 9. 6-(2-fluoro-4-methyl-phenyl)-5-[4-[(3S)-1-(3-fluoropropyl)pyrrolidin-3-yl]oxyphenyl]-8,9-dihydro-7H-benzo[7]annulen-2-ol

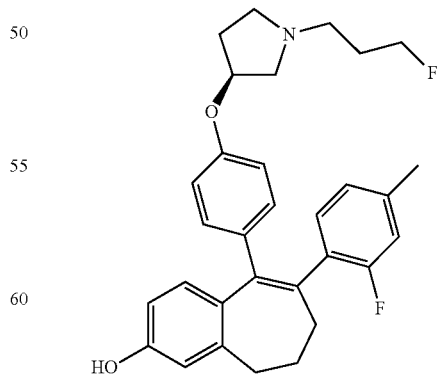

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (60 mg, 130.33 µmol) in dioxane/water (80/20; V/V; 3 ml), were added 2-fluoro-4-methylphenylboronic acid (22.99 mg, 143.36 µmol), Cs₂CO₃ (89.26 mg, 273.69 µmol), and Pd(dppf)Cl₂ (6.39 mg, 7.82 µmol). The reaction mixture was heated at 80° C. for 1 hour and purified by column chromatography eluting with a gradient of MeOH in DCM (0% to 10%) to give a solid which was further purified on strong cation exchange (SCX) column to give 52 mg (82%) of 6-(2-fluoro-4-methyl-phenyl)-5-[4-[(3S)-1-(3-fluoropropyl)pyrrolidin-3-yl]oxyphenyl]-8,9-dihydro-7H-benzo[7]annulen-2-ol.

Example 11. 5-[4-[(3S)-1-(3-fluoropropyl)pyrrolidin-3-yl]oxyphenyl]-6-(4-hydroxyphenyl)-8,9-dihydro-7H-benzo[7]annulen-2-ol

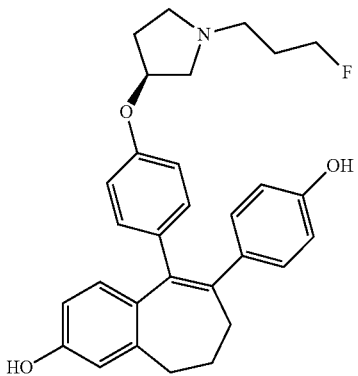 [SMILES: Oc1ccc(C2=C(c3ccc(O[C@H]4CCN(CCCF)C4)cc3)c3ccc(O)cc3CCC2)cc1]

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (60 mg, 130.33 µmol), in dioxane/water (80/20; V/V; 3 ml), were added (4-hydroxyphenyl)boronic acid (17.98 mg, 130.33 µmol), Cs₂CO₃ (89.26 mg, 273.69 µmol), and Pd(dppf)Cl₂ (6.39 mg, 7.82 µmol). The reaction mixture was microwaved at 90° C. for 40 minutes and poured in water. The aqueous phase was washed with DCM/MeOH solution (95/5; V/V) and the organic extracts dried over MgSO₄ and concentrated under reduced pressure. The residue was purified by column chromatography eluting with a gradient of MeOH in DCM (0% to 10%) to give a solid which was further purified on strong cation exchange (SCX) column to give 52 mg (41%) of 5-[4-[(3S)-1-(3-fluoropropyl)pyrrolidin-3-yl]oxyphenyl]-6-(4-hydroxyphenyl)-8,9-dihydro-7H-benzo[7]annulen-2-ol.

Example 21. 5-[4-[(3S)-1-(3-fluoropropyl)pyrrolidin-3-yl]oxyphenyl]-6-indolin-5-yl-8,9-dihydro-7H-benzo[7]annulen-2-ol

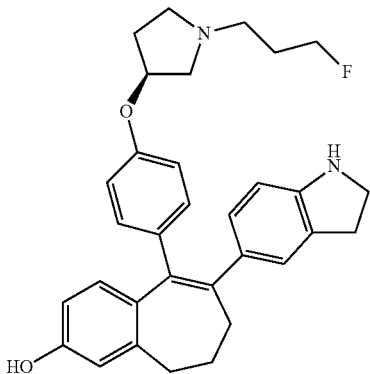 [SMILES: Oc1ccc2c(c1)CCCC(c1ccc3c(c1)CCN3)=C2c1ccc(O[C@H]2CCN(CCCF)C2)cc1]

To a solution of 8-bromo-9-(4-((3S)-1-(3-fluoropropyl)pyrrolidin-3-yl)oxy)phenyl)-6,7-dihydro-5H-benzo[7]annulen-3-ol (D4) (50 mg, 108.61 µmol), in dioxane/water (80/ 20; V/V; 3 ml), were added 5-(4,4,5,5-tetramethyl-1,3,2-dioxaborolan-2-yl)indoline (26.62 mg, 108.61 µmol), Cs₂CO₃ (74.39 mg, 228.07 µmol), and Pd(dppf)Cl₂ (5.32 mg, 6.52 µmol). The reaction mixture was microwaved at 90° C. for 45 minutes and concentrated under reduced pressure. The residue was purified by column chromatography eluting with a gradient of MeOH in DCM (0% to 10%) to give 32 mg (59%) of 5-[4-[(3S)-1-(3-fluoropropyl)pyrrolidin-3-yl]oxyphenyl]-6-indolin-5-yl-8,9-dihydro-7H-benzo[7]annulen-2-ol.

Example 25. 5-[4-[(3S)-1-(3-fluoropropyl)pyrrolidin-3-yl]oxyphenyl]-6-(1-methyl-3,6-dihydro-2H-pyridin-4-yl)-8,9-dihydro-7H-benzo[7]annulen-2-ol

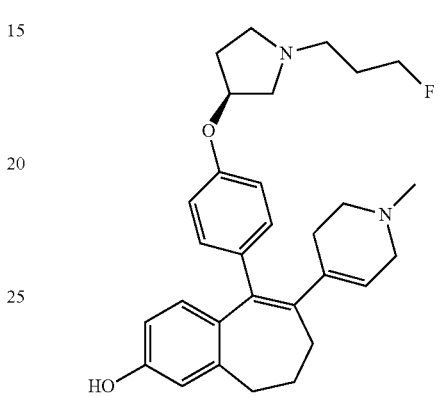

To a solution of 8-bromo-9-(4-((3S)-1-(3-fluoropropyl)pyrrolidin-3-yl)oxy)phenyl)-6,7-dihydro-5H-benzo[7]annulen-3-ol (D4) (139.3 mg, 302.58 µmol), in dioxane (2 ml) and water (1 ml), was added 1-methyl-4-(4,4,5,5-tetramethyl-1,3,2-dioxaborolan-2-yl)-1,2,3,6-tetrahydropyridine (81.01 mg, 363.09 µmol), Cs₂CO₃ (197.17 mg, 605.15 µmol), and Pd(dppf)Cl₂ (13.28 mg, 18.15 µmol). The reaction mixture was heated at 82° C. for 1.5 hours and partitioned between water and DCM. The aqueous phase was washed with DCM and the organic phase was concentrated under reduced pressure. The residue was purified by column chromatography eluting with a gradient of MeOH in DCM (0% to 10%) to give a solid which was further purified on strong cation exchange (SCX) column to give 63.7 mg (44.2%) of 5-[4-[(3S)-1-(3-fluoropropyl)pyrrolidin-3-yl]oxyphenyl]-6-(1-methyl-3,6-dihydro-2H-pyridin-4-yl)-8,9-dihydro-7H-benzo[7]annulen-2-ol.

Example 26. 5-[4-[(3S)-1-(3-fluoropropyl)pyrrolidin-3-yl]oxyphenyl]-6-(1,2,3,6-tetrahydropyridin-4-yl)-8,9-dihydro-7H-benzo[7]annulen-2-ol

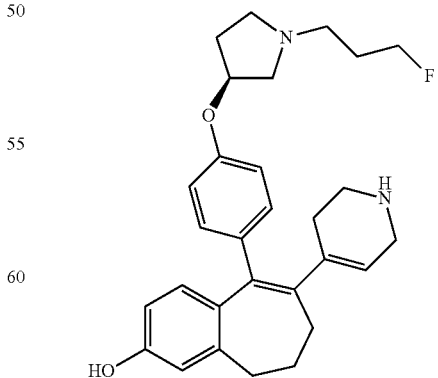

To a solution of 4-(5-{4-[(S)-1-(3-fluoro-propyl)-pyrrolidin-3-yloxy]-phenyl}-2-hydroxy-8,9-dihydro-7H-benzocyclohepten-6-yl)-3,6-dihydro-2H-pyridine-1-carboxylic acid tert-butyl ester (Example 24, 78.2 mg, 138.97 μmol), in MeOH (1.5 ml) was added HCl (120 μl, 4N dioxane solution). The reaction mixture was stirred at room temperature for 2.5 hours and concentrated under reduced pressure. The residue was purified by strong cation exchange (SCX) column to give 60.9 mg (94.7%) of 5-[4-[(3S)-1-(3-fluoropropyl)pyrrolidin-3-yl]oxyphenyl]-6-(1,2,3,6-tetrahydropyridin-4-yl)-8,9-dihydro-7H-benzo[7]annulen-2-ol.

Example 29. 6-(2-fluoro-4-methoxy-phenyl)-5-[4-[(3S)-1-(3-fluoropropyl)pyrrolidin-3-yl]oxyphenyl]-8,9-dihydro-7H-benzo[7]annulen-2-ol

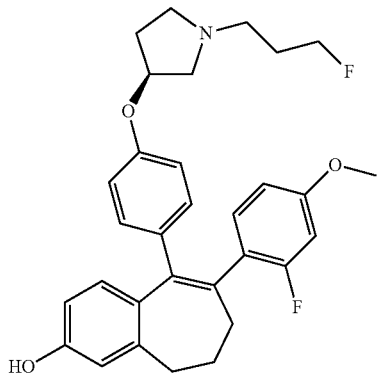 [SMILES: COc1ccc(C2=C(c3ccc(O[C@H]4CCN(CCCF)C4)cc3)c3ccc(O)cc3CCC2)c(F)c1]

To a solution of 8-bromo-9-(4-((3S)-1-(3-fluoropropyl)pyrrolidin-3-yl)oxy)phenyl)-6,7-dihydro-5H-benzo[7]annulen-3-ol (D4) (125.5 mg, 272.60 μmol), in dioxane (2 ml) and water (1 ml), were added 2-fluoro-4-methoxyphenylboronic acid (66.73 mg, 384.80 μmol), $Cs_2CO_3$ (177.64 mg, 545.20 μmol), and Pd(dppf)$Cl_2$ (11.97 mg, 16.36 μmol). The reaction mixture was heated at 90° C. for 1 hour and partitioned between water and DCM. The aqueous phase was washed with DCM and the organic phase concentrated under reduced pressure. The residue was purified by column chromatography eluting with a gradient of MeOH in diisopropyl ether (0% to 10%) to give a solid which was further purified on strong cation exchange (SCX) column to give 78 mg (56.6%) of 6-(2-fluoro-4-methoxy-phenyl)-5-[4-[(3S)-1-(3-fluoropropyl)pyrrolidin-3-yl]oxyphenyl]-8,9-dihydro-7H-benzo[7]annulen-2-ol.

Example 36. 5-[4-[(3S)-1-(1,1-dideuterio-3-fluoropropyl)pyrrolidin-3-yl]oxyphenyl]-6-(2-fluoro-4-methyl-phenyl)-8,9-dihydro-7H-benzo[7]annulen-2-ol Step 1. Tert-butyl (3S)-3-(4-{3-[(2,2-dimethylpropanoyl)oxy]-6,7-dihydro-5H-benzo[7]annulen-9-yl}phenoxy)pyrrolidine-1-carboxylate (E1)

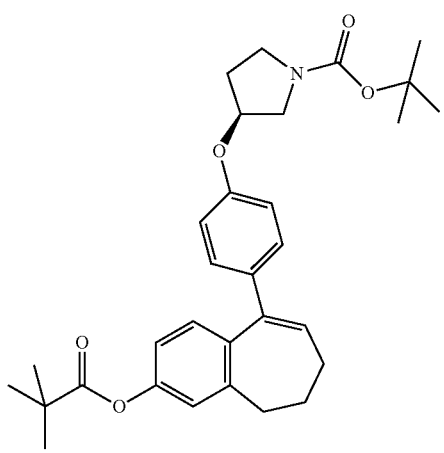 [SMILES: CC(C)(C)OC(=O)N1CC[C@H](Oc2ccc(C3=CCCCc4cc(OC(=O)C(C)(C)C)ccc43)cc2)C1]

To a solution of 9-(trifluoromethanesulfonyloxy)-6,7-dihydro-5H-benzo[7]annulen-3-yl-2,2-dimethylpropanoate (B2) (6.56 g, 16.72 mmol) in dioxane (45 ml), was added tert-butyl (3S)-3-[4-(4,4,5,5-tetramethyl-1,3,2-dioxaborolan-2-yl)phenoxy]pyrrolidine-1-carboxylate (c) (6.51 g, 16.72 mmol), $Cs_2CO_3$ (23 ml, 34.50 mmol), and Pd(dppf)$Cl_2$ (1.44 g, 1.67 mmol). The reaction mixture was stirred at room temperature for 24 hours, and partitioned between water and AcOEt. The aqueous phase was extracted with AcOEt and the organic phase dried over $MgSO_4$, filtered and concentrated under reduced pressure. The residue was purified by column chromatography, eluting with a mixture of heptane and DCM (60/40; V/V) to give 7.188 g (85%) of tert-butyl (3S)-3-(4-{3-[(2,2-dimethylpropanoyl)oxy]-6,7-dihydro-5H-benzo[7]annulen-9-yl}phenoxy)pyrrolidine-1-carboxylate (E1).

LC/MS (m/z, MH$^+$): 507

Step 2. Tert-butyl (3S)-3-(4-{8-bromo-3-[(2,2-dimethylpropanoyl)oxy]-6,7-dihydro-5H-benzo[7]annulen-9-yl}phenoxy)pyrrolidine-1-carboxylate (F1)

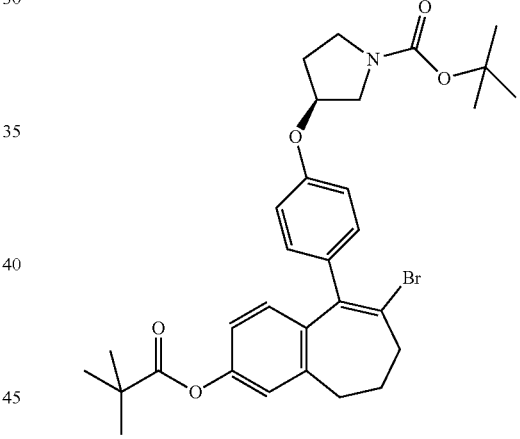

To a solution of tert-butyl (3S)-3(4-{3-[(2,2-dimethylpropanoyl)oxy]-6,7-dihydro-5H-benzo[7]annulen-9-yl}phenoxy)pyrrolidine-1-carboxylate (E1) (7.18 g, 14.20 mmol) in THF (60 ml), was added pyridinium tribromide (5.00 g, 15.62 mmol). The reaction mixture was stirred at room temperature for 1 hour, and partitioned between water and AcOEt. The aqueous phase was extracted with AcOEt and the organic phase dried over $MgSO_4$, filtered and concentrated under reduced pressure. The residue was purified by column chromatography, eluting with a mixture of DCM and MeOH (96/4; V/V) to give 3.43 g (41.3%) of tert-butyl (3S)-3-(4-{8-bromo-3-[(2,2-dimethylpropanoyl)oxy]-6,7-dihydro-5H-benzo[7]annulen-9-yl}phenoxy)pyrrolidine-1-carboxylate (F1).

LC/MS (m/z, MH+): 484 and 486 (M−BOC).

Step 3. Tert-butyl (3S)-3-(4-{3-[(2,2-dimethylpropanoyl)oxy]-8-(2-fluoro-4-methylphenyl)-6,7-dihydro-5H-benzo[7]annulen-9-yl}phenoxy)pyrrolidine-1-carboxylate (G1)

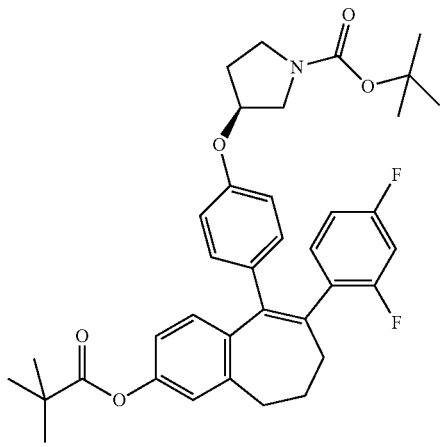 [SMILES: CC(C)(C)OC(=O)N1CC[C@H](Oc2ccc(C3=C(c4ccc(F)cc4F)CCCc4cc(OC(=O)C(C)(C)C)ccc43)cc2)C1]

To a solution of (3S)-3-(4-{8-bromo-3-[(2,2-dimethylpropanoyl)oxy]-6,7-dihydro-5H-benzo[7]annulen-9-yl}phenoxy)pyrrolidine-1-carboxylate (F1) (500 mg, 855.37 µmol) in dioxane (5 ml), was added 2-fluoro-4-methylphenylboronic acid (150.89 mg, 940.91 µmol), Cs₂CO₃ (2.5 ml, 3.75 mmol), and Pd(dppf)Cl₂ (65.88 mg, 85.54 µmol). The reaction mixture was heated at 80° C. for 2 hours, and partitioned between water and AcOEt. The aqueous phase was extracted with AcOEt and the organic phase dried over MgSO₄, filtered and concentrated under reduced pressure. The residue was purified by column chromatography, eluting with a mixture of heptane and DCM (50/50; V/V) to give 285 mg (54.3%) of tert-butyl (3S)-3-(4-{3-[(2,2-dimethylpropanoyl)oxy]-8-(2-fluoro-4-methylphenyl)-6,7-dihydro-5H-benzo[7]annulen-9-yl}phenoxy)pyrrolidine-1-carboxylate (G1).

LC/MS (m/z, MH+): 614

Step 4. 8-(2-fluoro-4-methylphenyl)-9-(4-{[(3S)-pyrrolidin-3-yl]oxy}phenyl)-6,7-dihydro-5H-benzo[7]annulen-3-yl 2,2-dimethylpropanoate hydrochloride salt (H1)

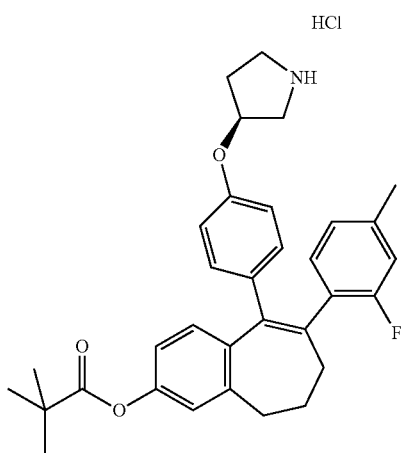 [SMILES: Cl ; Cc1ccc(C2=C(c3ccc(O[C@H]4CCNC4)cc3)c3ccc(OC(=O)C(C)(C)C)cc3CCC2)c(F)c1]

To a solution of tert-butyl (3S)-3-(4-{3-[(2,2-dimethylpropanoyl)oxy]-8-(2-fluoro-4-methylphenyl)-6,7-dihydro-5H-benzo[7]annulen-9-yl}phenoxy)pyrrolidine-1-carboxylate (G1) (295 mg, 480.65 µmol) in MeOH (5 ml), was added hydrochloric acid in (4N, 1.20 ml, 4.80 mmol). The reaction mixture was stirred at room temperature for 2 hours and concentrated under reduced pressure to give a solid which was triturated with diisopropyl ether, filtered and dried to give 221 mg (59.5%) of 8-(2-fluoro-4-methylphenyl)-9-(4-{[(3S)-pyrrolidin-3-yl]oxy}phenyl)-6,7-dihydro-5H-benzo[7]annulen-3-yl 2,2-dimethylpropanoate, as an hydrochloride salt (H1).

LC/MS (m/z, MH⁺): 514

Step 5. 8-(2-Fluoro-4-methylphenyl)-9-(4-{[(3S)-1-(3-fluoropropanoyl)pyrrolidin-3-yl]oxy}phenyl)-6,7-dihydro-5H-benzo[7]annulen-3-yl 2,2-dimethylpropanoate (J1)

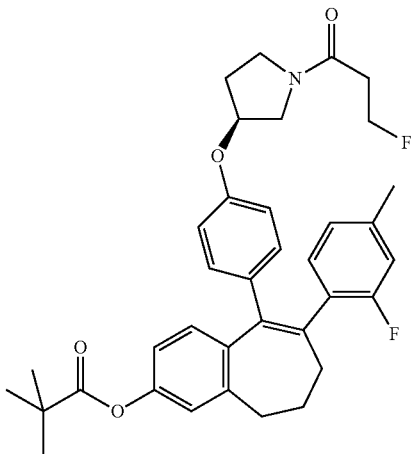 [SMILES: Cc1ccc(C2=C(c3ccc(O[C@H]4CCN(C(=O)CCF)C4)cc3)c3ccc(OC(=O)C(C)(C)C)cc3CCC2)c(F)c1]

To a solution of 8-(2-fluoro-4-methylphenyl)-9-(4-{[(3S)-pyrrolidin-3-yl]oxy}phenyl)-6,7-dihydro-5H-benzo[7]annulen-3-yl-2,2-dimethylpropanoate (H1) (163 mg, 317.34 µmol) in DMF (3 ml), was added 3-fluoropropanoic acid (30.76 mg, 317.34 µmol), 4-dimethylaminopyridine (121.15 mg, 952.02 µmol), and 1-(3-dimethylaminopropyl)-3-ethyl carbodiimide hydrochloride (76.84 mg, 380.81 µmol). The reaction mixture was stirred at room temperature for 2 hours, and partitioned between water and AcOEt. The aqueous phase was extracted with AcOEt and the organic phase dried over MgSO₄, filtered and concentrated under reduced pressure. The residue was purified by column chromatography, eluting with a mixture of DCM and MeOH (97/3; V/V) to give 180 mg (96.5%) of 8-(2-fluoro-4-methylphenyl)-9-(4-{[(3S)-1-(3-fluoropropanoyl)pyrrolidin-3-yl]oxy}phenyl)-6,7-dihydro-5H-benzo[7]annulen-3-yl 2,2-dimethylpropanoate (J1).

LC/MS (m/z, MH⁺): 588

Step 6. 5-[4-[(3S)-1-(1,1-dideuterio-3-fluoro-propyl) pyrrolidin-3-yl]oxyphenyl]-6-(2-fluoro-4-methyl-phenyl)-8,9-dihydro-7H-benzo[7]annulen-2-ol (Ic)

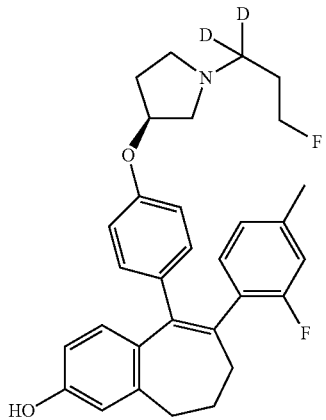 [SMILES: [2H]C([2H])(CCF)N1CC[C@H](Oc2ccc(C3=C(c4ccc(C)cc4F)CCCc4cc(O)ccc43)cc2)C1]

To a solution of 8-(2-fluoro-4-methylphenyl)-9-(4-{[(3S)-1-(3-fluoropropanoyl)pyrrolidin-3-yl]oxy}phenyl)-6,7-dihydro-5H-benzo[7]annulen-3-yl 2,2-dimethylpropanoate (J1) (180 mg, 306.28 μmol) in diethylether (5 ml), was added lithium aluminum deuteride (39.36 mg, 918.84 μmol). The reaction mixture was stirred at room temperature for 2 hours, diluted with DCM and a solution of sodium potassium bis-tartrate (1N) was added. The solid formed was filtered and the filtrate was dried over MgSO$_4$, filtered and concentrated under reduced pressure. The residue was purified by column chromatography, eluting with a mixture of DCM and MeOH (97/3; V/V) to give 36 mg (23.9%) of 5-[4-[(3S)-1-(1,1-dideuterio-3-fluoro-propyl)pyrrolidin-3-yl]oxyphenyl]-6-(2-fluoro-4-methyl-phenyl)-8,9-dihydro-7H-benzo[7]annulen-2-ol (Ic).

Example 39. 6-(3-chloro-2-fluoro-phenyl)-5-[4-[(3S)-1-(3-fluoropropyl)pyrrolidin-3-yl]oxyphenyl]-8,9-dihydro-7H-benzo[7]annulen-2-ol Step 1: 9-(4-{[(3S)-1-(3-fluoropropyl)pyrrolidin-3-yl]oxy}phenyl)-8-(4,4,5,5-tetramethyl-1,3,2-dioxaborolan-2-yl)-6,7-dihydro-5H-benzo[7]annulen-3-ol (D')

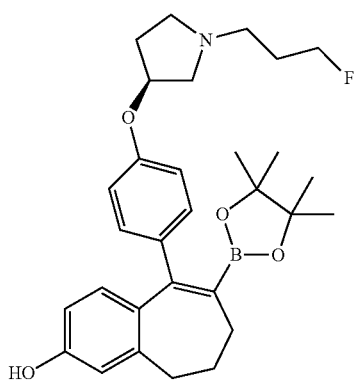 [SMILES: CC1(C)OB(C2=C(c3ccc(O[C@H]4CCN(CCCF)C4)cc3)c3ccc(O)cc3CCC2)OC1(C)C]

To a solution of 8-bromo-9-(4-{[(3S)-1-(3-fluoropropyl) pyrrolidin-3-yl]oxy}phenyl)-6,7-dihydro-5H-benzo[7]annulen-3-ol (D4) (2.03 g, 4.41 mmol), in dioxane (25 ml) and water (10 ml), was added 4,4,4',4',5,5,5',5'-octamethyl-2,2'-bi(1,3,2-dioxaborolane) (1.34 g, 5.29 mmol), Cs$_2$CO$_3$ (2.88 g, 8.82 mmol), and Pd(dppf)Cl$_2$ (203.77 mg, 264.56 μmol). The reaction mixture was heated at 70° C. for 45 minutes, and partitioned between DCM and water. The phases were separated and the organic phase concentrated under reduced pressure. The residue was first purified by column chromatography eluting with a gradient of MeOH in DCM (0% to 10%) to give a crude solid, which was further separated on chiralpak AD 20 μm, eluting with a mixture of heptane, ethanol and triethylamine (90/9.9/0.1; V/V/V) to give 967 mg (43%) of 5-{4-[(S)-1-(3-fluoro-propyl)-pyrrolidin-3-yloxy]-phenyl}-6-(4,4,5,5-tetramethyl-[1,3,2]dioxaborolan-2-yl)-8,9-dihydro-7H-benzocyclohepten-2-ol (D').

LC/MS (m/z, MH$^+$): 509

Step 2: 6-(3-chloro-2-fluoro-phenyl)-5-[4-[(3S)-1-(3-fluoropropyl)pyrrolidin-3-yl]oxyphenyl]-8,9-dihydro-7H-benzo[7]annulen-2-ol

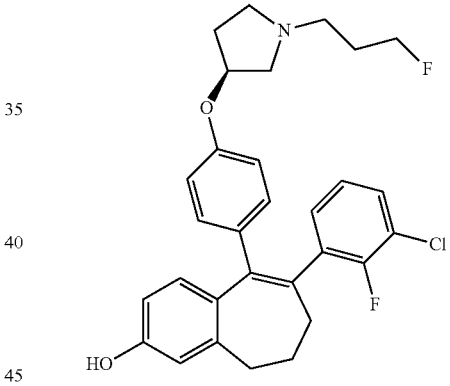

To a solution of 5-{4-[(S)-1-(3-fluoro-propyl)-pyrrolidin-3-yloxy]-phenyl}-6-(4,4,5,5-tetramethyl-[1,3,2]dioxaborolan-2-yl)-8,9-dihydro-7H-benzocyclohepten-2-ol (D') (100.3 mg, 197.66 μmol), in dioxane (1 ml) and water (0.5 ml), was added 3-chloro-2-fluoroiodobenzene (60.83 mg, 237.19 μmol), Cs$_2$CO$_3$ (128.93 mg, 395.31 μmol) and Pd(dppf)Cl$_2$ (9.68 mg, 11.86 μmol). The reaction mixture was heated at 70° C. for 6 hours, and partitioned between DCM and water. The aqueous phase was washed with DCM and organic phases were dried and concentrated under reduced pressure. The residue was purified by column chromatography eluting with a gradient of MeOH in DCM (0% to 10%) to give a solid which was further purified on strong cation exchange (SCX) column to give 18 mg (18%) of 6-(3-chloro-2-fluoro-phenyl)-5-[4-[(3S)-1-(3-fluoropropyl)pyrrolidin-3-yl]oxyphenyl]-8,9-dihydro-7H-benzo[7]annulen-2-ol.

223

Example 45. 1-fluoro-6-(2-fluoro-4-methyl-phenyl)-5-[4-[(3S)-1-(3-fluoropropyl)pyrrolidin-3-yl]oxyphenyl]-8,9-dihydro-7H-benzo[7]annulen-2-ol

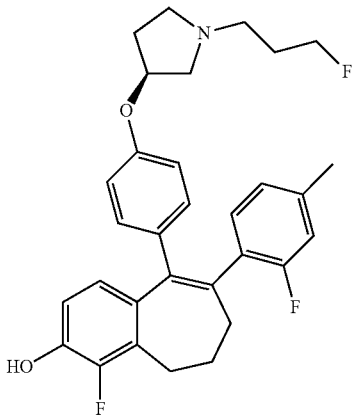 [SMILES: Cc1ccc(C2=C(c3ccc(O[C@H]4CCN(CCCF)C4)cc3)c3ccc(O)c(F)c3CCC2)c(F)c1]

To a solution of 8-bromo-4-fluoro-9-(4-{[(3S)-1-(3-fluoropropyl)pyrrolidin-3-yl]oxy}phenyl)-6,7-dihydro-5H-benzo[7]annulen-3-ol (D7) (60 mg, 125.43 µmol), in dioxane (1 ml) and water (0.5 ml), was added 2-fluoro-4-methylphenylboronic acid (22.12 mg, 137.97 µmol), $Cs_2CO_3$ (81.73 mg, 250.85 µmol), and Pd(dppf)$Cl_2$ (6.15 mg, 7.53 µmol). The reaction mixture was heated at 80° C. for 30 minutes and the solid formed, filtered and washed with dioxane. The filtrate was concentrated under reduced pressure and the residue was purified by column chromatography eluting with a gradient of MeOH in DCM (0% to 10%) to give 45 mg (71%) of 1-fluoro-6-(2-fluoro-4-methyl-phenyl)-5-[4-[(3S)-1-(3-fluoropropyl)pyrrolidin-3-yl]oxyphenyl]-8,9-dihydro-7H-benzo[7]annulen-2-ol.

Example 48. 6-(2-fluoro-4-methyl-phenyl)-5-[4-[(3S)-1-(3-fluoropropyl)pyrrolidin-3-yl]oxyphenyl]-8,9-dihydro-7H-benzo[7]annulene-2-carboxylic acid Method C Step 1. 8-(2-Fluoro-4-methylphenyl)-9-(4-{[(3S)-1-(3-fluoropropyl)pyrrolidin-3-yl]oxy}phenyl)-6,7-dihydro-5H-benzo[7]annulen-3-yl trifluoromethanesulfonate

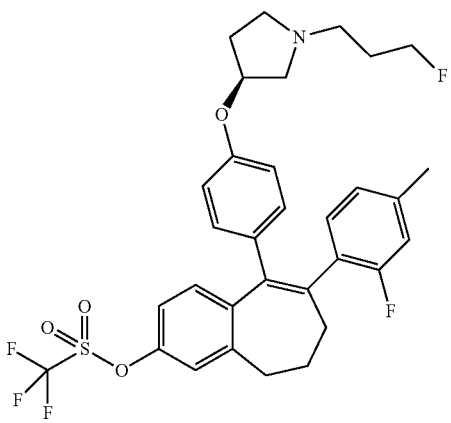 [SMILES: Cc1ccc(C2=C(c3ccc(O[C@H]4CCN(CCCF)C4)cc3)c3ccc(OS(=O)(=O)C(F)(F)F)cc3CCC2)c(F)c1]

224

To a solution of 8-(2-fluoro-4-methylphenyl)-9-(4-{[(3S)-1-(3-fluoropropyl)pyrrolidin-3-yl]oxy}phenyl)-6,7-dihydro-5H-benzo[7]annulen-3-ol (Example 9, 840 mg, 1.60 mmol), in DCM (30 ml), was added pyridine (387.4 µl, 4.79 mmol), and trifluoromethanesulfonic anhydride (839.5 µl, 4.79 mmol). The reaction mixture was stirred at room temperature for 16 hours, poured onto ice and partitioned between water and DCM. The aqueous phase was washed with DCM and the gathered organic phases, washed successively with a saturated solution of $NaHCO_3$, and brine. The organic phase was dried over $MgSO_4$, filtered, and the filtrate was concentrated under reduced pressure to give 860 mg (86.6%) of crude 8-(2-fluoro-4-methylphenyl)-9-(4-{[(3S)-1-(3-fluoropropyl)pyrrolidin-3-yl]oxy}phenyl)-6,7-dihydro-5H-benzo[7]annulen-3-yl trifluoromethanesulfonate.

LC/MS (m/z, MH$^+$): 622

Step 2. Methyl 8-(2-fluoro-4-methylphenyl)-9-(4-{[(3S)-1-(3-fluoropropyl)pyrrolidin-3-yl]oxy}phenyl)-6,7-dihydro-5H-benzo[7]annulen-3-carboxylate

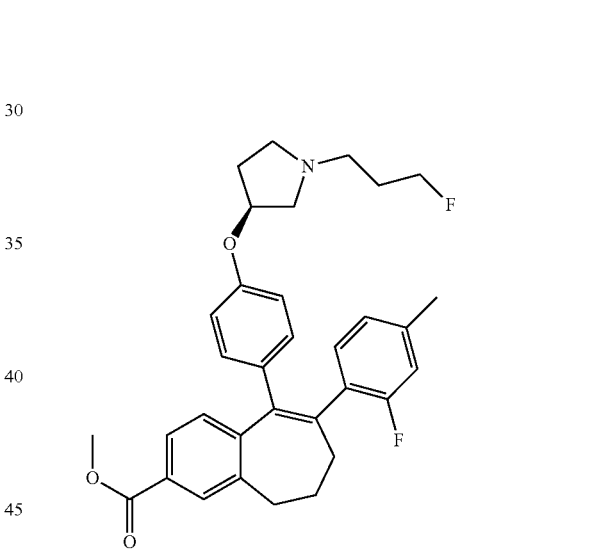

To a solution of 8-(2-fluoro-4-methylphenyl)-9-(4-{[(3S)-1-(3-fluoropropyl)pyrrolidin-3-yl]oxy}phenyl)-6,7-dihydro-5H-benzo[7]annulen-3-yl trifluoromethanesulfonate (860 mg, 1.35 mmol), in DMF (10 ml) and MeOH (5 ml), was added triethylamine (1 ml), Pd(OAc)$_2$ (60.52 mg, 269.54 µmol), and 1,3-bis(diphenylphosphino)propane (dppp) (115.80 mg, 269.54 µmol). The reaction mixture was heated at 40° C., under an atmosphere of CO (2 bars), for 16 hours, and concentrated under reduced pressure. The residue was purified by column chromatography eluting with a mixture of cyclohexane and AcOEt (80/20; V/V) to give 400 mg (55.8%) of methyl 8-(2-fluoro-4-methylphenyl)-9-(4-{[(3S)-1-(3-fluoropropyl)pyrrolidin-3-yl]oxy}phenyl)-6,7-dihydro-5H-benzo[7]annulen-3-carboxylate.

LC/MS (m/z, MH$^+$): 532

Step 3. 8-(2-Fluoro-4-methylphenyl)-9-(4-{[(3S)-1-(3-fluoropropyl)pyrrolidin-3-yl]oxy}phenyl)-6,7-dihydro-5H-benzo[7]annulene-3-carboxylic acid

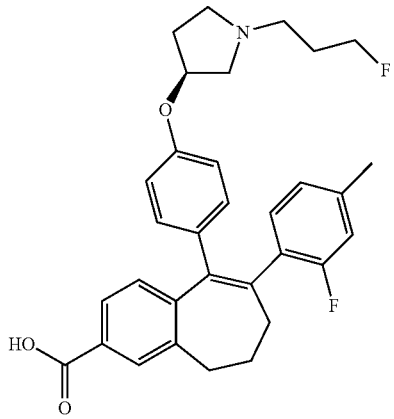 [SMILES: Cc1ccc(C2=C(c3ccc(O[C@H]4CCN(CCCF)C4)cc3)c3ccc(C(=O)O)cc3CCC2)c(F)c1]

To a solution of methyl 8-(2-fluoro-4-methylphenyl)-9-(4-{[(3S)-1-(3-fluoropropyl)pyrrolidin-3-yl]oxy}phenyl)-6,7-dihydro-5H-benzo[7]annulen-3-carboxylate (390 mg, 733.59 μmol), MeOH (20 ml), was added NaOH solution (5N, 1.5 ml). The reaction mixture was heated at 60° C., for 2 hours, and concentrated under reduced pressure. The residue was taken up into water (25 ml), and acidified with aqueous HCl (5N, 1.5 ml), and the solid formed was filtered, washed with water and dried under vacuum. The residue was purified by trituration in diisopropyl ether to give 180 mg (47.4%) of 8-(2-fluoro-4-methylphenyl)-9-(4-{[(3S)-1-(3-fluoropropyl)pyrrolidin-3-yl]oxy}phenyl)-6,7-dihydro-5H-benzo[7]annulene-3-carboxylic acid. Example 51. 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid
Method B:

Step 1: 6-(2,4-Dichloro-phenyl)-5-{4-[1-(3-fluoro-propyl)-pyrrolidin-3-yloxy]-phenyl}-8,9-dihydro-7H-benzocycloheptene-2-arboxylic acid methyl ester

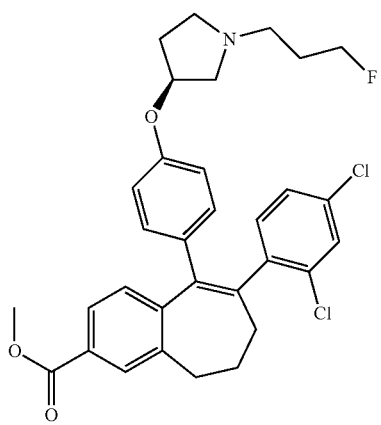 [SMILES: COC(=O)c1ccc2c(c1)CCCC(c1ccc(Cl)cc1Cl)=C2c1ccc(O[C@H]2CCN(CCCF)C2)cc1]

To a solution of methyl 8-bromo-9-(4-{[(3S)-1-(3-fluoropropyl)pyrrolidin-3-yl]oxy}phenyl)-6,7-dihydro-5H-benzo[7]annulene-3-carboxylate hydrobromide (D5) (150 mg, 298.56 μmol), in dioxane (12 ml) and water (2 ml), was added 2,4-dichlorophenyl-boronic acid (62.67 mg, 328.41 μmol), Cs₂CO₃ (204.48 mg, 626.97 μmol), and Pd(dppf)Cl₂ (14.63 mg, 17.91 μmol). The reaction mixture was heated at 90° C. for 3 hours, and partitioned between AcOEt and water. The phases were separated and the organic phase washed with brine, dried over MgSO₄ and concentrated under reduced pressure. The residue was purified by column chromatography eluting with a mixture of DCM, acetonitrile and MeOH (96/2/2; V/V/V) to give 80 mg (47%) of 6-(2,4-dichloro-phenyl)-5-{4-[1-(3-fluoro-propyl)-pyrrolidin-3-yloxy]-phenyl}-8,9-dihydro-7H-benzocycloheptene-2-arboxylic acid methyl ester.

LC/MS (m/z, MH⁺): 568

Step 2: 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid

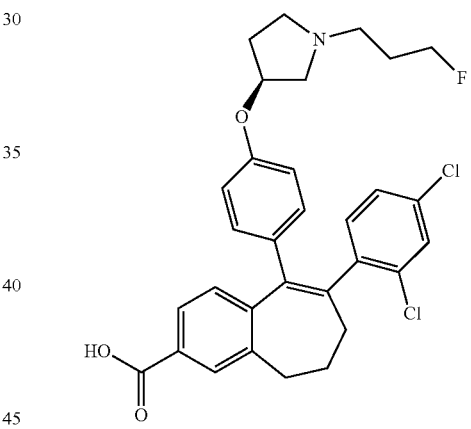

To a solution of 6-(2,4-dichloro-phenyl)-5-{4-[1-(3-fluoro-propyl)-pyrrolidin-3-yloxy]-phenyl}-8,9-dihydro-7H-benzocycloheptene-2-arboxylic acid methyl ester (80 mg, 140.72 μmol) in MeOH (5 ml) was added a solution of NaOH (562.88 μl, 5 M) and the reaction mixture was heated at 60° C. for 5 hours and the solvent removed under reduced pressure. The residue was taken up in water (10 ml) and aqueous HCl (5 M) added to pH 7. The slurry was extracted with DCM, dried over MgSO₄ and concentrated under reduced pressure. The solid was purified by column chromatography eluting with a mixture of DCM, acetonitrile and MeOH (90/5/5; V/V/V) to give 60 mg (77%) of 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid.

Example 63. 5-[4-[(3S)-1-(3-fluoropropyl)pyrrolidin-3-yl]oxyphenyl]-6-(4-methoxy-2-methyl-phenyl)-8,9-dihydro-7H-benzo[7]annulene-2-carboxylic acid hydrochloride Step 1: 6-(4-Methoxy-2-methyl-phenyl)-5-{4-[1-(3-fluoro-propyl)-pyrrolidin-3-yloxy]-phenyl}-8,9-dihydro-7H-benzocycloheptene-2-arboxylic acid methyl ester

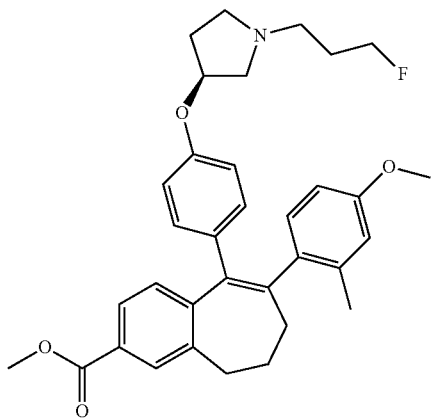

To a solution of methyl 8-bromo-9-(4-{[(3S)-1-(3-fluoropropyl)pyrrolidin-3-yl]oxy}phenyl)-6,7-dihydro-5H-benzo[7]annulene-3-carboxylate hydrobromide (D5) (250 mg, 497.60 µmol), in dioxane (12 ml) and water (2 ml), was added 4-methoxy-2-methylphenyl-boronic acid (90.85 mg, 547.36 µmol), Cs$_2$CO$_3$ (340.81 mg, 1.04 mmol), and Pd(dppf)Cl$_2$ (24.38 mg, 29.86 µmol). The reaction mixture was heated at 90° C. for 2 hours, and partitioned between AcOEt and water. The phases were separated and the organic phase washed with brine, dried over MgSO$_4$ and concentrated under reduced pressure. The residue was purified by column chromatography eluting with a mixture of DCM, acetonitrile and MeOH (96/2/2; V/V/V) to give 280 mg (100%) of crude 6-(4-methoxy-2-methyl-phenyl)-5-{4-[1-(3-fluoro-propyl)-pyrrolidin-3-yloxy]-phenyl}-8,9-dihydro-7H-benzocycloheptene-2-arboxylic acid methyl ester.
LC/MS (m/z, MH$^+$): 544

Step 2: 5-[4-[(3S)-1-(3-fluoropropyl)pyrrolidin-3-yl]oxyphenyl]-6-(4-methoxy-2-methyl-phenyl)-8,9-dihydro-7H-benzo[7]annulene-2-carboxylic acid hydrochloride

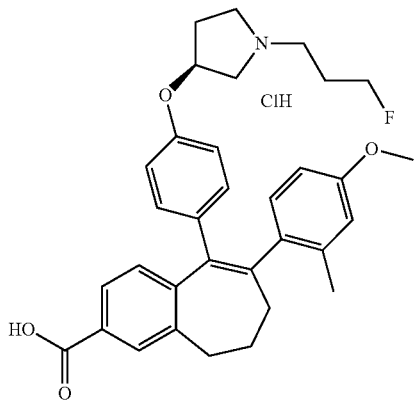 [SMILES: COc1ccc(C2=C(c3ccc(O[C@H]4CCN(CCCF)C4)cc3)c3ccc(C(=O)O)cc3CCC2)c(C)c1 ; Cl]

To a solution of 6-(4-methoxy-2-methyl-phenyl)-5-{4-[1-(3-fluoro-propyl)-pyrrolidin-3-yloxy]-phenyl}-8,9-dihydro-7H-benzocycloheptene-2-arboxylic acid methyl ester (280 mg, 543.668 µmol) in MeOH (10 ml) was added a solution of NaOH (5 M, 1.5 ml) and the reaction mixture was heated at 60° C. for 6 hours and the solvent removed under reduced pressure. The residue was taken up in water (25 ml) and aqueous HCl (5 M) was added to pH 7. The slurry was extracted with DCM, dried over MgSO$_4$ and concentrated under reduced pressure. The solid was purified by column chromatography eluting with a mixture of DCM, acetonitrile and MeOH (90/5/5; V/V/V) to give a solid. This solid was triturated in diisopropyl ether with anhydrous HCl (2 M in diethyl ether) to give a solid which was filtered and dried to give 134 mg (46%) of 5-[4-[(3S)-1-(3-fluoropropyl)pyrrolidin-3-yl]oxyphenyl]-6-(4-methoxy-2-methyl-phenyl)-8,9-dihydro-7H-benzo[7]annulene-2-carboxylic acid hydrochloride.

Example 70. 6-(2,2-dimethylindolin-5-yl)-5-[4-[(3S)-1-(3-fluoropropyl)pyrrolidin-3-yl]oxyphenyl]-8,9-dihydro-7H-benzo[7]annulen-2-ol Step 1: 1-[5-(5-{4-[(S)-1-(3-fluoro-propyl)-pyrrolidin-3-yloxy]-phenyl}-2-hydroxy-8,9-dihydro-7H-benzocyclohepten-6-yl)-2,2-dimethyl-2,3-dihydro-indol-1-yl]-ethanone

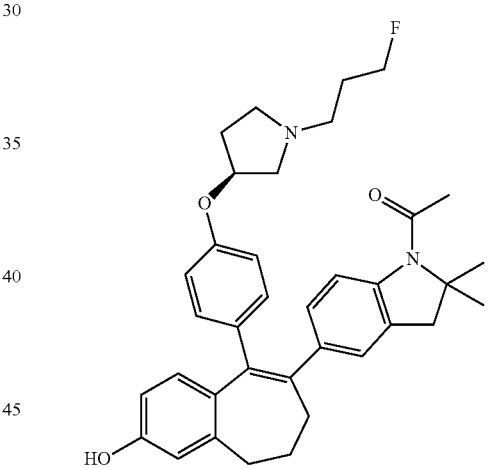

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (93.8 mg, 203.75 µmol), in dioxane (1 ml) and water (0.5 ml), was added 1-(2,2-dimethyl-5-(4,4,5,5-tetramethyl-1,3,2-dioxaborolan-2-yl)indolin-1-yl)ethanone (64.72 mg, 205.32 µmol), Cs$_2$CO$_3$ (132.90 mg, 407.49 µmol), and Pd(dppf)Cl$_2$ (9.98 mg, 12.22 µmol). The reaction mixture was heated at 72° C. for 45 minutes, and partitioned between DCM and water. The phases were separated on hydrophobic interaction column and the organic phase concentrated under reduced pressure. The residue was purified by column chromatography eluting with a gradient of MeOH in DCM (0% to 10%) to give a solid which was further purified on strong cation exchange (SCX) column to give 77 mg (67%) of 1-[5-(5-{4-[(S)-1-(3-Fluoro-propyl)-pyrrolidin-3-yloxy]-phenyl}-2-hydroxy-8, 9-dihydro-7H-benzocyclohepten-6-yl)-2,2-dimethyl-2,3-dihydro-indol-1-yl]-ethanone.
LC/MS (m/z, MH$^+$): 569

Step 2: 6-(2,2-dimethylindolin-5-yl)-5-[4-[(3S)-1-(3-fluoropropyl)pyrrolidin-3-yl]oxyphenyl]-8,9-dihydro-7H-benzo[7]annulen-2-ol

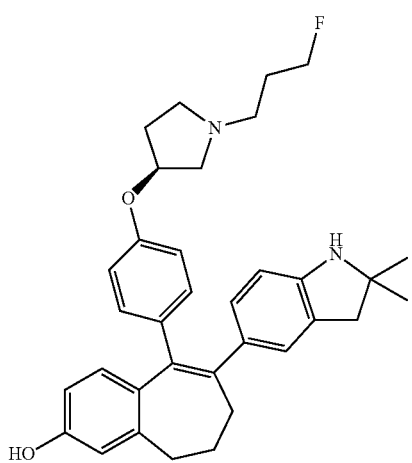 [SMILES: CC1(C)Cc2cc(C3=C(c4ccc(O[C@H]5CCN(CCCF)C5)cc4)c4ccc(O)cc4CCC3)ccc2N1]

To a solution of (S)-1-(5-(9-(4-((1-(3-fluoropropyl)pyrrolidin-3-yl)oxy)phenyl)-3-hydroxy-6,7-dihydro-5H-benzo[7]annulen-8-yl)-2,2-dimethylindolin-1-yl)ethanone (73 mg, 128.36 μmol) in dioxane (1.9 ml), was added aqueous HCl (1N, 1.5 ml) and the reaction mixture heated in a microwave oven at 120° C. for 2 hours. The reaction mixture was poured onto a saturated aqueous solution of NaHCO₃, and extracted with DCM. The phases were separated on hydrophobic interaction column and the organic phase concentrated under reduced pressure. The residue was purified by column chromatography eluting with a gradient of MeOH in DCM (0% to 10%) to give 39 mg (58%) of 6-(2,2-dimethylindolin-5-yl)-5-[4-[(3S)-1-(3-fluoropropyl)pyrrolidin-3-yl]oxyphenyl]-8,9-dihydro-7H-benzo[7]annulen-2-ol.

Example 73. 5-[4-[(3S)-1-(3-fluoropropyl)pyrrolidin-3-yl]oxyphenyl]-6-(1,2,3,4-tetrahydroquinolin-6-yl)-8,9-dihydro-7H-benzo[7]annulen-2-ol

Step 1: 6-(5-{4-[(S)-1-(3-Fluoro-propyl)-pyrrolidin-3-yloxy]-phenyl}-2-hydroxy-8,9-dihydro-7H-benzocyclohepten-6-yl)-3,4-dihydro-2H-quinoline-1-carboxylic acid tert-butyl ester

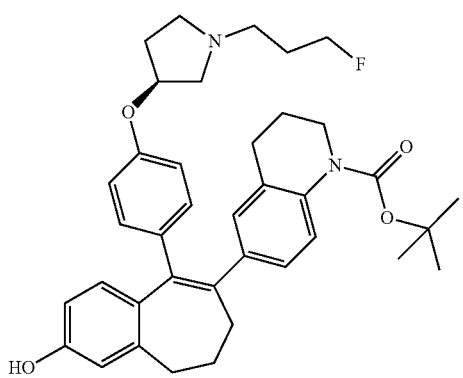 [SMILES: CC(C)(C)OC(=O)N1CCCc2cc(C3=C(c4ccc(O[C@H]5CCN(CCCF)C5)cc4)c4ccc(O)cc4CCC3)ccc21]

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (93.4 mg, 202.88 μmol), in dioxane (1 ml) and water (0.5 ml), was added tert-butyl 6-(4,4,5,5-tetramethyl-1,3,2-dioxaborolan-2-yl)-3,4-dihydroquinoline-1(2H)-carboxylate (85.18 mg, 237.09 μmol), Cs₂CO₃ (132.33 mg, 405.75 μmol), and Pd(dppf)Cl₂ (9 9.94 mg, 12.17 μmol). The reaction mixture was heated at 72° C. for 45 minutes, and partitioned between DCM and water. The phases were separated on hydrophobic interaction column and the organic phase concentrated under reduced pressure. The residue was purified by column chromatography eluting with a gradient of MeOH in DCM (0% to 10%) to give 75 mg (60.3%) of 6-(5-{4-[(S)-1-(3-fluoro-propyl)-pyrrolidin-3-yloxy]-phenyl}-2-hydroxy-8, 9-dihydro-7H-benzocyclohepten-6-yl)-3,4-dihydro-2H-quinoline-1-carboxylic acid tert-butyl ester.

LC/MS (m/z, MH⁺): 613

Step 2: 6-(2,2-dimethylindolin-5-yl)-5-[4-[(3S)-1-(3-fluoropropyl)pyrrolidin-3-yl]oxyphenyl]-8,9-dihydro-7H-benzo[7]annulen-2-ol

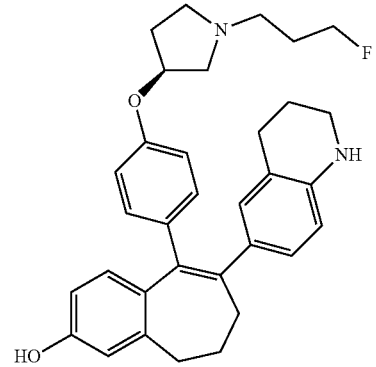

To a solution of 6-(5-{4-[(S)-1-(3-fluoro-propyl)-pyrrolidin-3-yloxy]-phenyl}-2-hydroxy-8,9-dihydro-7H-benzocyclohepten-6-yl)-3,4-dihydro-2H-quinoline-1-carboxylic acid tert-butyl ester in DCM (2.4 ml) was added HCl (1M in diethylether, 1.17 ml) and the reaction mixture stirred at room temperature for 18 hours. A saturated aqueous NaHCO₃ solution was added, and the aqueous phase was extracted with DCM. The phases were separated on hydrophobic interaction column and the organic phase concentrated under reduced pressure. The residue was purified by column chromatography eluting with a gradient of MeOH in DCM (0% to 10%) to give 57.3 mg (95.1%) of 6-(2,2-dimethylindolin-5-yl)-5-[4-[(3S)-1-(3-fluoropropyl)pyrrolidin-3-yl]oxyphenyl]-8,9-dihydro-7H-benzo[7]annulen-2-ol.

Example 75. 5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-ol

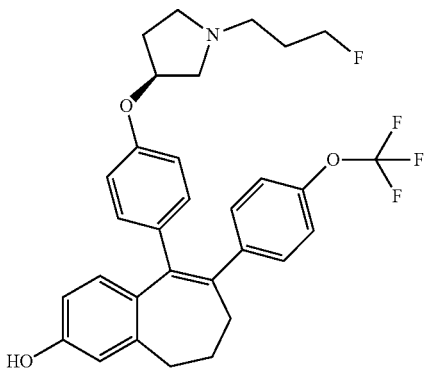

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (92.9 mg, 201.79 μmol), in dioxane (1 ml) and water (0.5 ml), was added 4-(trifluoromethoxy)phenylboronic acid (54.12 mg, 254.93 μmol), Cs$_2$CO$_3$ (131.63 mg, 403.58 μmol), and Pd(dppf)Cl$_2$ (9.89 mg, 12.11 μmol). The reaction mixture was heated at 72° C. for 45 minutes, and partitioned between DCM and water. The phases were separated on hydrophobic interaction column and the organic phase concentrated under reduced pressure. The residue was purified by column chromatography eluting with a gradient of MeOH in DCM (0% to 10%) to give 71.3 mg (61.4%) of 5-[4-[(3S)-1-(3-fluoropropyl)pyrrolidin-3-yl]oxyphenyl]-6-[4-trifluoromethoxy)phenyl]-8,9-dihydro-7H-benzo[7]annulen-2-ol.

Example 76. 5-[4-[(3S)-1-(3-fluoropropyl)pyrrolidin-3-yl]oxyphenyl]-6-(4-methoxyphenyl)-8,9-dihydro-7H-benzo[7]annulen-2-ol

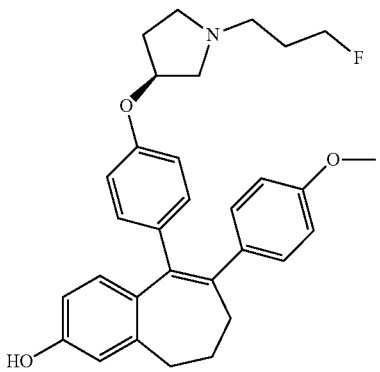

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (74.9 mg, 162.69 μmol), in dioxane (1 ml) and water (0.5 ml), was added 4-methoxyphenylboronic acid (34.49 mg, 222.45 μmol), Cs$_2$CO$_3$ (131.91 mg, 404.45 μmol), and Pd(dppf)Cl$_2$ (9.91 mg, 12.13 μmol). The reaction mixture was heated at 72° C. for 45 minutes, and partitioned between DCM and water. The phases were separated on hydrophobic interaction column and the organic phase concentrated under reduced pressure. The residue was purified by column chromatography eluting with a gradient of MeOH in DCM (0% to 10%) to give a solid which was further purified on strong cation exchange (SCX) column to give 63.9 mg (64.8%) of 5-[4-[(3S)-1-(3-fluoropropyl)pyrrolidin-3-yl]oxyphenyl]-6-(4-methoxyphenyl)-8,9-dihydro-7H-benzo[7]annulen-2-ol.

Example 82. 6-(6-ethoxy-2-fluoro-3-pyridyl)-1-fluoro-5-[4-[(3S)-1-(3-fluoropropyl)pyrrolidin-3-yl]oxyphenyl]-8,9-dihydro-7H-benzo[7]annulen-2-ol

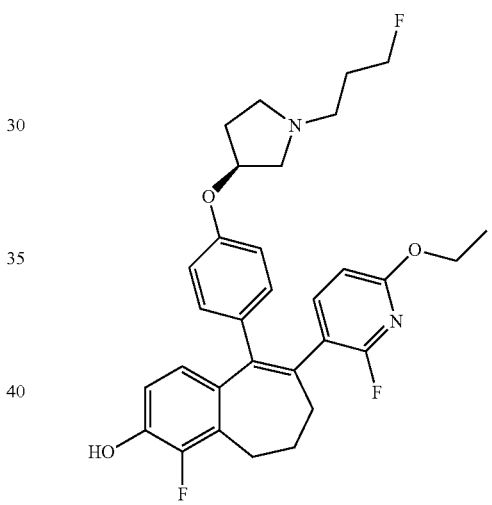

To a solution of 8-bromo-4-fluoro-9-(4-{[(3S)-1-(3-fluoropropyl)pyrrolidin-3-yl]oxy}phenyl)-6,7-dihydro-5H-benzo[7]annulen-3-ol (D7) (60 mg, 125.43 μmol), in dioxane (1 ml) and water (0.5 ml), was added 6-ethoxy-2-fluoropyridin-3-yl boronic acid (25.52 mg, 137.97 μmol), Cs$_2$CO$_3$ (171.05 mg, 525.0 μmol), and Pd(dppf)Cl$_2$ (9.66 mg, 12.54 μmol). The reaction mixture was heated at 60° C. for 1 hour and partitioned between water and AcOEt. The aqueous phase was washed with AcOEt and the organic extracts dried over MgSO$_4$, filtered and concentrated under reduced pressure. The residue was purified twice by column chromatography eluting first with a mixture of diisopropyl ether/MeOH (90/10; V/V) and with a mixture of DCM/MeOH (98/2) to give 38 mg (56.3%) of 6-(6-ethoxy-2-fluoro-3-pyridyl)-1-fluoro-5-[4-[(3S)-1-(3-fluoropropyl)pyrrolidin-3-yl]oxyphenyl]-8,9-dihydro-7H-benzo[7]annulen-2-ol.

Example 107. 6-(2-ethoxypyrimidin-5-yl)-5-[4-[(3S)-1-(3-fluoropropyl)pyrrolidin-3-yl]oxyphenyl]-8,9-dihydro-7H-benzo[7]annulen-2-ol

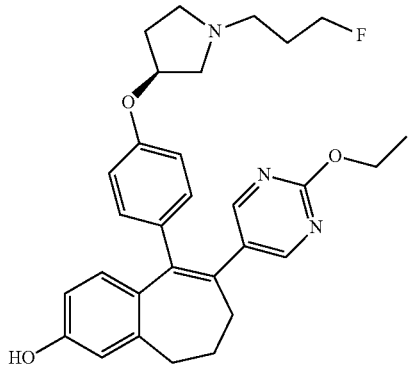 [SMILES: CCOc1ncc(C2=C(c3ccc(O[C@H]4CCN(CCCF)C4)cc3)c3ccc(O)cc3CCC2)cn1]

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (74.9 mg, 162.69 μmol), in dioxane (1 ml) and water (0.5 ml), was added 2-ethoxypyrimidin-5-yl boronic acid (30.06 mg, 178.96 μmol), $Cs_2CO_3$ (106.12 mg, 325.38 μmol), and $Pd(dppf)Cl_2$ (7.97 mg, 9.76 μmol). The reaction mixture was heated at 72° C. for 1 hour, partitioned between water and DCM and phases separated on hydrophobic partition column. The organic solvents were concentrated under reduced pressure and the residue was purified by column chromatography eluting with a gradient of MeOH in DCM (0% to 10%) to give a solid which was further purified on strong cation exchange (SCX) column to give 47.3 mg (57.7%) of 6-(2-ethoxypyrimidin-5-yl)-5-[4-[(3S)-1-(3-fluoropropyl)pyrrolidin-3-yl]oxyphenyl]-8,9-dihydro-7H-benzo[7]annulen-2-01.

Example 108. 5-[4-[(3S)-1-(3-fluoropropyl)pyrrolidin-3-yl]oxyphenyl]-6-(6-methoxy-3-pyridyl)-8,9-dihydro-7H-benzo[7]annulen-2-ol

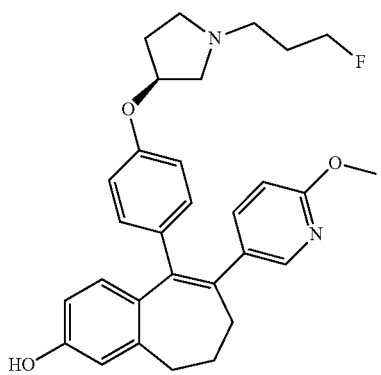 [SMILES: COc1ccc(C2=C(c3ccc(O[C@H]4CCN(CCCF)C4)cc3)c3ccc(O)cc3CCC2)cn1]

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (90 mg, 195.49 μmol), in dioxane/water (80/20; V/V; 4 ml), was added 2-methoxy-5-pyridineboronic acid (37.77 mg, 234.59 μmol), $Cs_2CO_3$ (133.89 mg, 410.53 μmol), and $Pd(dppf)Cl_2$ (9.58 mg, 11.73 μmol). The reaction mixture was heated in a microwave at 90° C. for 30 minutes, and concentrated under reduced pressure. The residue was purified by column chromatography eluting with a gradient of MeOH in DCM (0% to 4%) to give a solid which was further purified on strong cation exchange (SCX) column to give 59 mg (61.8%) of 5-[4-[(3S)-1-(3-fluoropropyl)pyrrolidin-3-yl]oxyphenyl]-6-(6-methoxy-3-pyridyl)-8,9-dihydro-7H-benzo[7]annulen-2-ol.

Example 109. 5-[4-[(3S)-1-(3-fluoropropyl)pyrrolidin-3-yl]oxyphenyl]-6-(2-methoxy-4-pyridyl)-8,9-dihydro-7H-benzo[7]annulen-2-ol

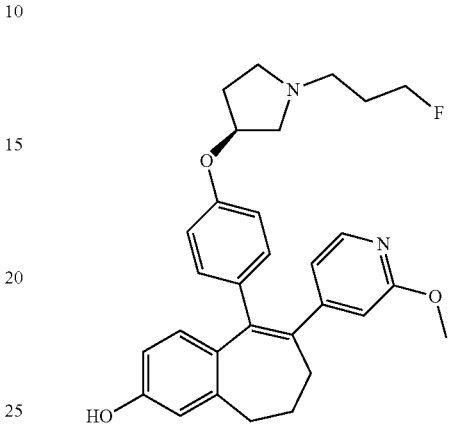

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (90 mg, 195.49 μmol), in dioxane/water (80/20; V/V; 4 ml), was added 2-methoxypyridine-4-boronic acid (36.99 mg, 234.59 μmol), $Cs_2CO_3$ (133.89 mg, 410.53 μmol), and $Pd(dppf)Cl_2$ (9.58 mg, 11.73 μmol). The reaction mixture was heated in a microwave at 90° C. for 30 minutes, and concentrated under reduced pressure. The residue was purified by column chromatography eluting with a gradient of MeOH in DCM (0% to 4%) to give a solid which was further purified on strong cation exchange (SCX) column to give 60 mg (62.8%) of 5-[4-[(3S)-1-(3-fluoropropyl)pyrrolidin-3-yl]oxyphenyl]-6-(2-methoxy-4-pyridyl)-8,9-dihydro-7H-benzo[7]annulen-2-ol.

Example 114. 1-fluoro-5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-ol

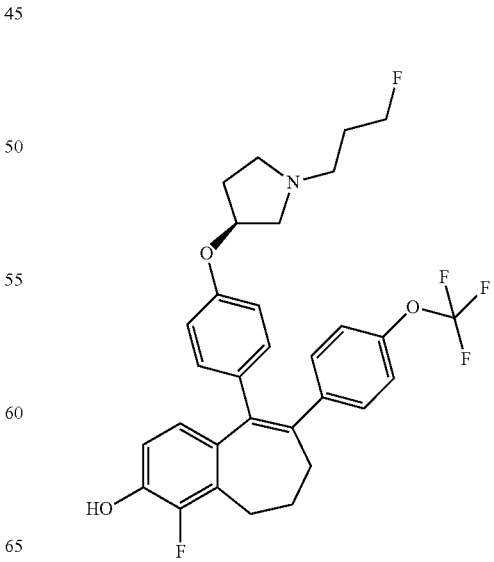

To a solution of 8-bromo-4-fluoro-9-(4-{[(3S)-1-(3-fluoropropyl)pyrrolidin-3-yl]oxy}phenyl)-6,7-dihydro-5H-benzo[7]annulen-3-ol (D7) (60 mg, 125.43 μmol), in dioxane (1 ml) and water (0.5 ml), was added 4-(trifluoromethoxy)phenylboronic acid (29 mg, 137.97 μmol), Cs₂CO₃ (81.73 mg, 250.85 μmol), and Pd(dppf)Cl₂ (6.15 mg, 7.53 μmol). The reaction mixture was heated at 80° C. for 30 minutes and the solid filtered and washed with dioxane. The filtrate was concentrated under educed pressure and the residue was purified by column chromatography eluting with a gradient of MeOH in DCM (0% to 10%) to give 45 mg (71%) of 1-fluoro-5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-ol.

Example 163. [5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-yl] dihydrogen phosphate Step 1: Diethyl 9-(4-{[(3S)-1-(3-fluoropropyl)pyrrolidin-3-yl]oxy}phenyl)-8-[4-(trifluoromethoxy)phenyl]-6,7-dihydro-5H-benzo[7]annulen-3-yl phosphate

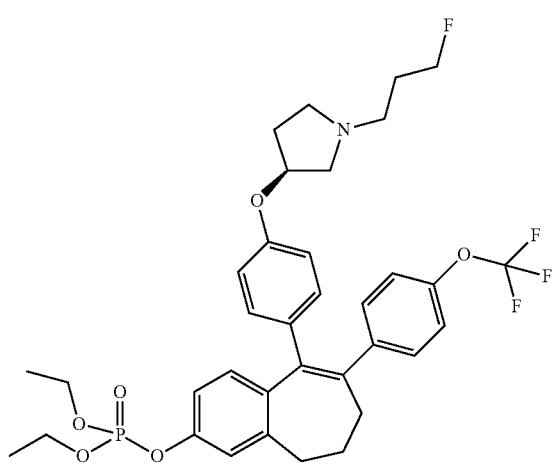 [SMILES: CCOP(=O)(OCC)Oc1ccc2c(c1)CCCC(c1ccc(OC(F)(F)F)cc1)=C2c1ccc(O[C@H]2CCN(CCCF)C2)cc1]

To a solution of 5-[4-[(3S)-1-(3-fluoropropyl)pyrrolidin-3-yl]oxyphenyl]-6-[4-trifluoromethoxy)phenyl]-8,9-dihydro-7H-benzo[7]annulen-2-ol (Example 75, 312 mg, 576.10 μmol), in acetonitrile (3 ml), was added triethylamine (353.1 μl, 2.54 mmol), and diethyl chlorophosphate (249.76 μl, 1.73 mmol). The reaction mixture was stirred at room temperature for 28 hours, and concentrated under reduced pressure. The residue was purified by strong cation exchange (SCX) column to give 256 mg (65.6%) of diethyl 9-(4-{[(3S)-1-(3-fluoropropyl)pyrrolidin-3-yl]oxy}phenyl)-8-[4-(trifluoromethoxy)phenyl]-6,7-dihydro-5H-benzo[7]annulen-3-yl phosphate.

LC/MS (m/z, MH⁺): 678

Step 2: [5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-yl] dihydrogen phosphate

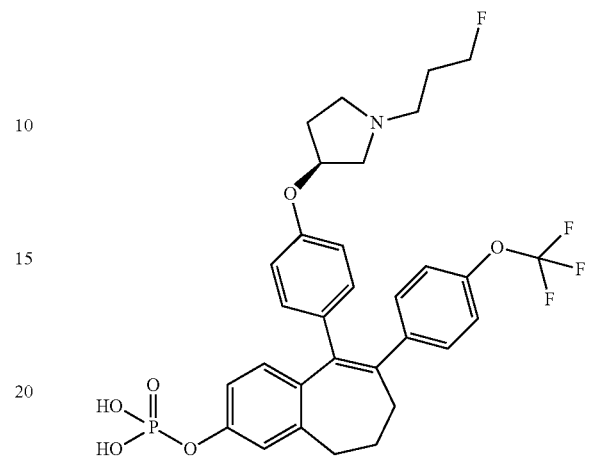

To a solution of diethyl 9-(4-{[(3S)-1-(3-fluoropropyl)pyrrolidin-3-yl]oxy}phenyl)-8-[4-(trifluoromethoxy)phenyl]-6,7-dihydro-5H-benzo[7]annulen-3-yl phosphate (256 mg, 377.77 μmol), in acetonitrile (6 ml), was added iodotrimethylsilane (277.12 μl, 1.89 mmol). The reaction mixture was stirred at room temperature for 1 hour, and concentrated under reduced pressure. The residue was purified by strong cation exchange (SCX) column and reverse phase column chromatography, eluting with a gradient of acetonitrile in water (20% to 80%) to give 167 mg (70.3%) of [5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-yl] dihydrogen phosphate.

Example 174. 6-(2,2-dimethylindolin-5-yl)-5-[4-[(3S)-1-(3-fluoropropyl)pyrrolidin-3-yl]oxyphenyl]-8,9-dihydro-7H-benzo[7]annulene-2-carboxylic acid hydrochloride Step 1: Methyl 8-(2,2-dimethyl-2,3-dihydro-1H-indol-5-yl)-9-(4-{[(3S)-1-(3-fluoropropyl)pyrrolidin-3-yl]oxy}phenyl)-6,7-dihydro-5H-benzo[7]annulene-3-carboxylate

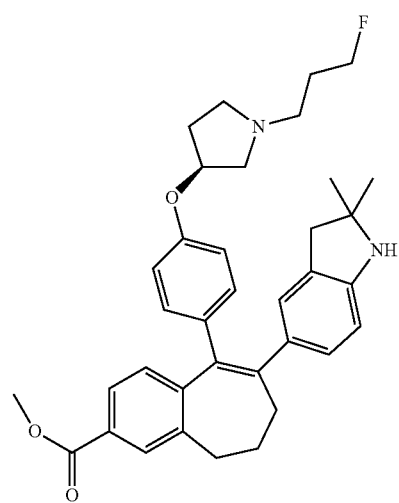 [SMILES: COC(=O)c1ccc2c(c1)CCCC(c1ccc3c(c1)CC(C)(C)N3)=C2c1ccc(O[C@H]2CCN(CCCF)C2)cc1]

To a solution of methyl 8-bromo-9-(4-{[(3S)-1-(3-fluoropropyl)pyrrolidin-3-yl]oxy}phenyl)-6,7-dihydro-5H-benzo[7]annulene-3-carboxylate hydrobromide (D5) (500 mg, 845.91 µmol), in dioxane (12 ml) and water (2 ml), was added 1-(2,2-dimethyl-5-(4,4,5,5-tetramethyl-1,3,2-dioxaborolan-2-yl)indolin-1-yl)ethanone (279.98 mg, 888.21 µmol), Cs$_2$CO$_3$ (744.91 mg, 2.28 mmol), and Pd(dppf)Cl$_2$ (41.45 mg, 50.75 µmol). The reaction mixture was heated in a microwave at 110° C. for 1 hour, DCM was added and the organic phase washed with saturated NH$_4$Cl solution. The organic phase was dried over MgSO$_4$, filtered and concentrated under reduced pressure. The residue was purified by column chromatography eluting with a mixture of DCM, acetonitrile and MeOH (96/2/2; V/V/V) to give 250 mg (48.4%) of methyl 8-(2,2-dimethyl-2,3-dihydro-1H-indol-5-yl)-9-(4-{[(3S)-1-(3-fluoropropyl)pyrrolidin-3-yl]oxy}phenyl)-6,7-dihydro-5H-benzo[7]annulene-3-carboxylate.

LC/MS (m/z, MH$^+$): 611

Step 2: 6-(2,2-dimethylindolin-5-yl)-5-[4-[(3S)-1-(3-fluoropropyl)pyrrolidin-3-yl]oxyphenyl]-8,9-dihydro-7H-benzo[7]annulene-2-carboxylic acid hydrochloride

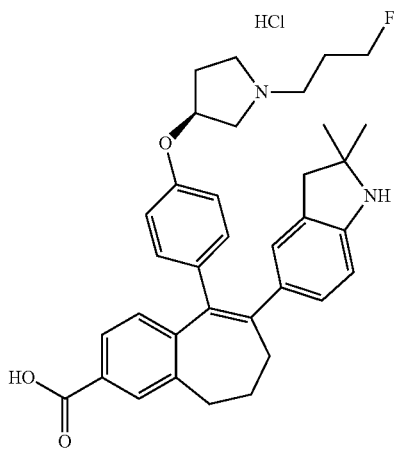 [SMILES: CC1(C)Cc2cc(C3=C(c4ccc(O[C@H]5CCN(CCCF)C5)cc4)c4ccc(C(=O)O)cc4CCC3)ccc2N1 ; Cl]

To a solution of methyl 8-(2,2-dimethyl-2,3-dihydro-1H-indol-5-yl)-9-(4-{[(3S)-1-(3-fluoropropyl)pyrrolidin-3-yl]oxy}phenyl)-6,7-dihydro-5H-benzo[7]annulene-3-carboxylate (240 mg, 392.95 µmol) in MeOH (20 ml) was added NaOH (15.72 mg, 392.95 µmol) and the reaction mixture was heated under reflux for 3 hours and the solvent removed under reduced pressure. The residue was taken up in water (15 ml), HCl (5 M, 1 ml) was added and the reaction mixture was heated under reflux for 2 hours. NaOH solution was added to pH 7, and the aqueous phase extracted with DCM. The organic phase was washed with brine, dried over MgSO$_4$, filtered and concentrated under reduced pressure. The residue was triturated with diisopropyl ether, filtered and dried to give 211 mg (90.8%) of 6-(2,2-dimethylindolin-5-yl)-5-[4-[(3S)-1-(3-fluoropropyl)pyrrolidin-3-yl]oxyphenyl]-8,9-dihydro-7H-benzo[7]annulene-2-carboxylic acid hydrochloride.

Example 189. 5-[4-[(3S)-1-(3-fluoropropyl)pyrrolidin-3-yl]oxyphenyl]-6-(1-oxidopyridin-1-ium-4-yl)-8,9-dihydro-7H-benzo[7]annulen-2-ol Step 1: 9-(4-{[(3S)-1-(3-fluoropropyl)pyrrolidin-3-yl]oxy}phenyl)-8-(4,4,5,5-tetramethyl-1,3,2-dioxaborolan-2-yl)-6,7-dihydro-5H-benzo[7]annulen-3-yl 2,2-dimethylpropanoate

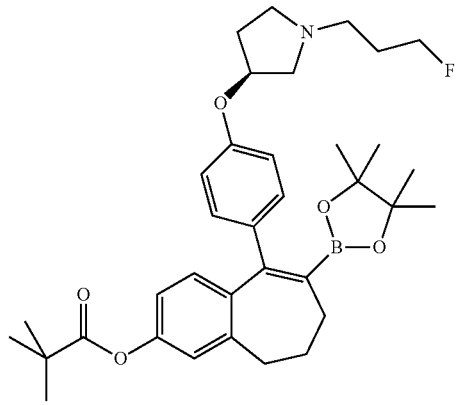 [SMILES: CC(C)(C)C(=O)Oc1ccc2c(c1)CCCC(B1OC(C)(C)C(C)(C)O1)=C2c1ccc(O[C@H]2CCN(CCCF)C2)cc1]

To a solution of 8-bromo-9-(4-{[(3S)-1-(3-fluoropropyl)pyrrolidin-3-yl]oxy}phenyl)-6,7-dihydro-5H-benzo[7]annulen-3-yl-2,2-dimethylpropanoate (D3) (1 g, 1.84 mmol), in dioxane (10 ml) and water (5 ml), was added 4,4,4',4',5,5,5',5'-octamethyl-2,2'-bi(1,3,2-dioxaborolane) (559.65 mg, 2.20 mmol), Cs$_2$CO$_3$ (1.20 g, 3.67 mmol), and Pd(dppf)Cl$_2$ (84.87 mg, 110.19 µmol). The reaction mixture was heated under reflux for 24 hours, and partitioned between DCM and water. The aqueous phase was washed with DCM and the gathered organic phase dried over hydrophobic partition column, and evaporated under reduced pressure. The residue was purified by column chromatography eluting with a mixture of DCM and MeOH (98/2; V/V) to give 426 mg (39.2%) of 9-(4-{[(3S)-1-(3-fluoropropyl)pyrrolidin-3-yl]oxy}phenyl)-8-(4,4,5,5-tetramethyl-1,3,2-dioxaborolan-2-yl)-6,7-dihydro-5H-benzo[7]annulen-3-yl 2,2-dimethylpropanoate.

LC/MS (m/z, MH$^+$): 592 (M+H).

Step 2: [9-(4-{[(3S)-1-(3-fluoropropyl)pyrrolidin-3-yl]oxy}phenyl)-3-hydroxy-6,7-dihydro-5H-benzo[7]annulen-8-yl]boronic acid

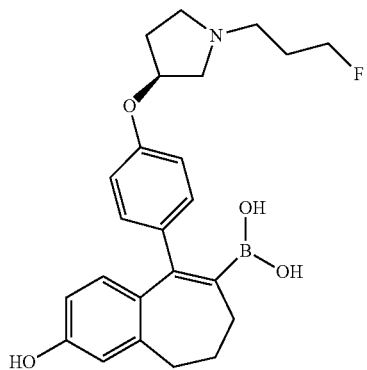 [SMILES: OB(O)C1=C(c2ccc(O[C@H]3CCN(CCCF)C3)cc2)c2ccc(O)cc2CCC1]

To a solution of 9-(4-{[(3S)-1-(3-fluoropropyl)pyrrolidin-3-yl]oxy}phenyl)-8-(4,4,5,5-tetramethyl-1,3,2-dioxaborolan-2-yl)-6,7-dihydro-5H-benzo[7]annulen-3-yl 2,2-dimethylpropanoate (426 mg, 720.13 µmol), in MeOH (10 ml), was added NaOH (2N, 2.16 ml, 4.32 mmol). The reaction mixture was stirred at room temperature for 1.5 hour, and HCl (2N, 2.2 ml) was added. The aqueous phases was washed with DCM, and evaporated under reduced pressure. The residue was triturated with a mixture of DCM and MeOH (95/5, V/V), filtered and concentrated under reduced pressure to give 100 mg (32.7%) of crude [9-(4-{[(3S)-1-(3-fluoropropyl)pyrrolidin-3-yl]oxy}phenyl)-3-hydroxy-6,7-dihydro-5H-benzo[7]annulen-8-yl]boronic acid.

LC/MS (m/z, MH+): 426 (M+H).

Step 3: 5-[4-[(3S)-1-(3-fluoropropyl)pyrrolidin-3-yl]oxyphenyl]-6-(1-oxidopyridin-1-ium-4-yl)-8,9-dihydro-7H-benzo[7]annulen-2-ol

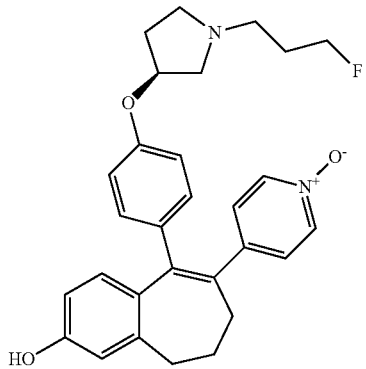 [SMILES: [O-][n+]1ccc(C2=C(c3ccc(O[C@H]4CCN(CCCF)C4)cc3)c3ccc(O)cc3CCC2)cc1]

To a solution of [9-(4-{[(3S)-1-(3-fluoropropyl)pyrrolidin-3-yl]oxy}phenyl)-3-hydroxy-6,7-dihydro-5H-benzo[7]annulen-8-yl]boronic acid (100 mg, 235.12 µmol), in dioxane (8 ml) and water (2 ml), 4-bromopyridine 1-oxide (57.28 mg, 329.17 µmol), Cs₂CO₃ (161.04 mg, 493.76 µmol) and Pd(dppf)Cl₂ (11.52 mg, 14.11 µmol). The reaction mixture was heated at 90° C. for 2 hours, and concentrated under reduced pressure. The residue was purified by column chromatography eluting with a gradient of MeOH in DCM (0% to 4%) to give a solid which was further purified on strong cation exchange (SCX) column to give 21 mg (18.8%) of 5-[4-[(3S)-1-(3-fluoropropyl)pyrrolidin-3-yl]oxyphenyl]-6-(1-oxidopyridin-1-ium-4-yl)-8,9-dihydro-7H-benzo[7]annulen-2-ol.

Example 203. 5-[4-[(3S)-1-(3-fluoropropyl)pyrrolidin-3-yl]oxyphenyl]-6-tetrahydropyran-4-yl-8,9-dihydro-7H-benzo[7]annulen-2-ol

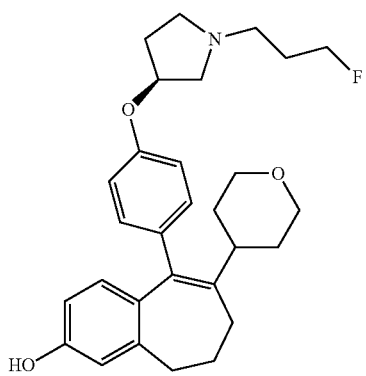 [SMILES: Oc1ccc2c(c1)CCCC(C1CCOCC1)=C2c1ccc(O[C@H]2CCN(CCCF)C2)cc1]

To a solution of 6-(3,6-dihydro-2H-pyran-4-yl)-5-{4-[(S)-1-(3-fluoro-propyl)-pyrrolidin-3-yloxy]-phenyl}-8,9-dihydro-7H-benzocyclohepten-2-ol (Example 202, 110 mg, 237.28 µmol) in AcOEt (3 ml) and ethanol (5 ml), was added palladium on carbon (10%, 2.53 mg, 23.73 µmol). The reaction mixture was stirred at 50° C. under hydrogen atmosphere (5 bars) for 2 hours. The reaction mixture was filtered on celite, washed with MeOH, and the filtrate was concentrated under reduced pressure. The residue was purified by column chromatography eluting with a mixture of DCM and MeOH (90/10; V/V)) to give 61 mg (55%) of 5-[4-[(3S)-1-(3-fluoropropyl)pyrrolidin-3-yl]oxyphenyl]-6-tetrahydropyran-4-yl-8,9-dihydro-7H-benzo[7]annulen-2-ol.

Example 204. 5-[4-[(3S)-1-(3-fluoropropyl)pyrrolidin-3-yl]oxyphenyl]-6-(4-hydroxycyclohexyl)-8,9-dihydro-7H-benzo[7]annulen-2-ol Step 1: 6-(1,4-Dioxa-spiro[4.5]dec-7-en-8-yl)-5-{4-[(S)-1-(3-fluoro-propyl)-pyrrolidin-3-yloxy]-phenyl}-8,9-dihydro-7H-benzocyclohepten-2-ol

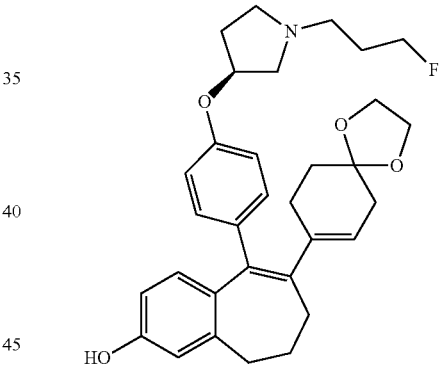

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (500 mg, 1.09 mmol), in dioxane/water (80/20; V/V, 25 ml), was added 1,4-dioxa-spiro[4,5]dec-7-en-8-boronic acid pinacoyl ester (412.93 mg, 1.52 mmol), Cs₂CO₃ (743.85 mg, 2.28 mmol), and Pd(dppf)Cl₂ (53.22 mg, 65.16 µmol). The reaction mixture was heated at 80° C. for 30 minutes, and concentrated under reduced pressure. The residue was purified by column chromatography eluting with a gradient of MeOH in DCM (0% to 4%) to give a solid which was further purified on strong cation exchange (SCX) column to give 485 mg (85.9%) of 6-(1,4-dioxa-spiro[4.5]dec-7-en-8-yl)-5-{4-[(S)-1-(3-fluoro-propyl)-pyrrolidin-3-yloxy]-phenyl}-8,9-dihydro-7H-benzocyclohepten-2-ol.

LC/MS (m/z, MH+): 520

Step 2: 6-(1,4-Dioxa-spiro[4.5]dec-8-yl)-5-{4-[(S)-1-(3-fluoro-propyl)-pyrrolidin-3-yloxy]-phenyl}-8,9-dihydro-7H-benzocyclohepten-2-ol

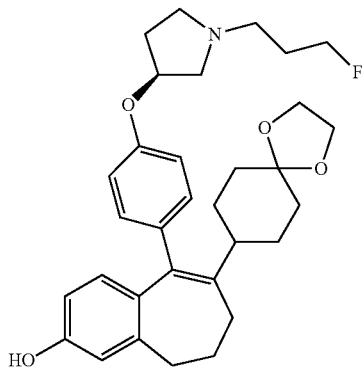 [SMILES: Oc1ccc2c(c1)CCCC(C1CCC3(CC1)OCCO3)=C2c1ccc(O[C@H]2CCN(CCCF)C2)cc1]

To a solution of 6-(1,4-dioxa-spiro[4.5]dec-7-en-8-yl)-5-{4-[(S)-1-(3-fluoro-propyl)-pyrrolidin-3-yloxy]-phenyl}-8,9-dihydro-7H-benzocyclohepten-2-ol (485 mg, 933.31 μmol), in AcOEt (10 ml) and ethanol (10 ml), was added palladium on carbon (10%, 9.93 mg, 93.33 μmol). The reaction mixture was stirred at 50° C. under hydrogen atmosphere (5 bars) for 24 hours. The reaction mixture was filtered over celite, rinsed with MeOH and the filtrate was concentrated under reduced pressure to give 487 mg (100%) of crude 6-(1,4-dioxa-spiro[4.5]dec-8-yl)-5-{4-[(S)-1-(3-fluoro-propyl)-pyrrolidin-3-yloxy]-phenyl}-8,9-dihydro-7H-benzocyclohepten-2-ol.
LC/MS (m/z, MH$^+$): 522

Step 3: 4-(5-{4-[(S)-1-(3-Fluoro-propyl)-pyrrolidin-3-yloxy]-phenyl}-2-hydroxy-8,9-dihydro-7H-benzocyclohepten-6-yl)-cyclohexanone

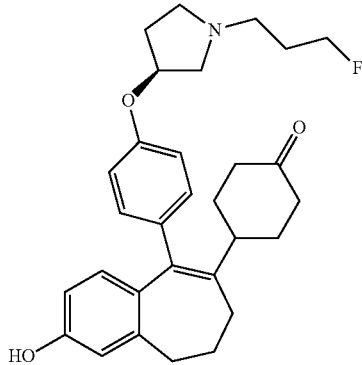 [SMILES: O=C1CCC(C2=C(c3ccc(O[C@H]4CCN(CCCF)C4)cc3)c3ccc(O)cc3CCC2)CC1]

To a solution of crude 6-(1,4-dioxa-spiro[4.5]dec-8-yl)-5-{4-[(S)-1-(3-fluoro-propyl)-pyrrolidin-3-yloxy]-phenyl}-8,9-dihydro-7H-benzocyclohepten-2-ol (487 mg, 933.53 μmol) in acetone (2 ml) was added concentrated aqueous HCl (1.4 ml) and the reaction mixture was stirred at room temperature for 4 days. A saturated aqueous solution of NaHCO$_3$ and DCM was added and the phases were separated on hydrophobic interaction column. The organic phase was concentrated under reduced pressure and the residue purified by column chromatography eluting with a mixture of MeOH in DCM (3/97; V/V) to give 390 mg (87.5%) of 4-(5-{4-[(S)-1-(3-Fluoro-propyl)-pyrrolidin-3-yloxy]-phenyl}-2-hydroxy-8,9-dihydro-7H-benzocyclohepten-6-yl)-cyclohexanone.
LC/MS (m/z, MH$^+$): 478.

Step 4: 5-[4-[(3S)-1-(3-fluoropropyl)pyrrolidin-3-yl]oxyphenyl]-6-(4-hydroxycyclohexyl)-8,9-dihydro-7H-benzo[7]annulen-2-ol

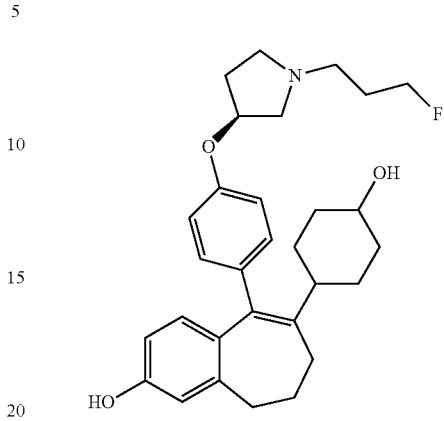

To a solution of 4-(5-{4-[(S)-1-(3-Fluoro-propyl)-pyrrolidin-3-yloxy]-phenyl}-2-hydroxy-8,9-dihydro-7H-benzocyclohepten-6-yl)-cyclohexanone (200 mg, 418.74 μmol), in MeOH (4 ml), was added sodium borohydride (147.3 mg, 3.89 mmol). The reaction mixture was stirred at room temperature for 4 days, and water was added. A solid forms which was filtered, rinsed with water and purified by column chromatography eluting with a gradient of MeOH in DCM (0% to 10%) to give 28 mg (14%) of 5-[4-[(3S)-1-(3-fluoropropyl)pyrrolidin-3-yl]oxyphenyl]-6-(4-hydroxycyclohexyl)-8,9-dihydro-7H-benzo[7]annulen-2-ol Example 207. 6-(4,4-difluorocyclohexen-1-yl)-5-[4-[(3S)-1-(3-fluoropropyl)pyrrolidin-3-yl]oxyphenyl]-8,9-dihydro-7H-benzo[7]annulen-2-ol

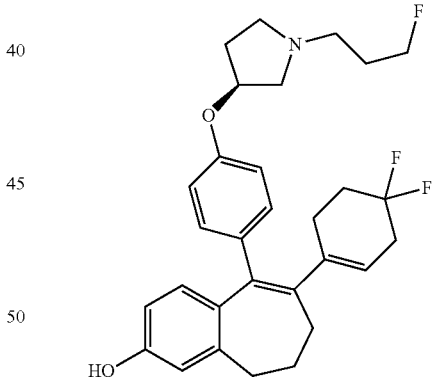

To a solution of 8-bromo-9-(4-{[(3S)-1-(3-fluoropropyl)pyrrolidin-3-yl]oxy}phenyl)-6,7-dihydro-5H-benzo[7]annulen-3-ol (D4) (200 mg, 434.42 μmol) in dioxane/water (80/20; V/V, 10 ml), was added 2-(4,4-difluorocyclohex-1-en-1-yl)-4,4,5,5-tetramethyl-1,3,2-dioxaborolane (127.24 mg, 521.30 μmol), Cs$_2$CO$_3$ (297.53 mg, 912.28 μmol), and Pd(dppf)Cl$_2$ (20.08 mg, 26.07 μmol). The reaction mixture was heated at 90° C. for 30 minutes, and the solvent was concentrated under reduced pressure. The residue was purified by column chromatography eluting with a gradient of MeOH in DCM (0% to 10%) to give a solid which was further purified on strong cation exchange (SCX) column to give 95 mg (44%) of 6-(4,4-difluorocyclohexen-1-yl)-5-[4-[(3S)-1-(3-fluoropropyl)pyrrolidin-3-yl]oxyphenyl]-8,9-dihydro-7H-benzo[7]annulen-2-ol.

Example 208. 6-(4,4-difluorocyclohexyl)-5-[4-[(3S)-1-(3-fluoropropyl)pyrrolidin-3-yl]oxyphenyl]-8,9-dihydro-7H-benzo[7]annulen-2-ol

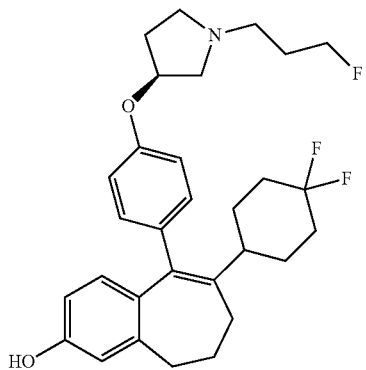 [SMILES: Oc1ccc2c(c1)CCCC(C1CCC(F)(F)CC1)=C2c1ccc(O[C@H]2CCN(CCCF)C2)cc1]

To a solution of 6-(4,4-difluorocyclohexen-1-yl)-5-[4-[(3S)-1-(3-fluoropropyl)pyrrolidin-3-yl]oxyphenyl]-8,9-dihydro-7H-benzo[7]annulen-2-ol (95 mg, 190.92 μmol), in AcOEt (3 ml) and ethanol (5 ml) was added palladium on carbon (10%, 2.03 mg, 19.09 μmol). The reaction mixture was stirred at 50° C. under hydrogen atmosphere (5 bars) for 2 hours and filtered on celite, rinsed with MeOH and the filtrate was concentrated under reduced pressure. The residue was purified by column chromatography eluting with a mixture of MeOH in DCM (3/97; V/V) to give 70 mg (73.4%) of 6-(4,4-difluorocyclohexyl)-5-[4-[(3S)-1-(3-fluoropropyl)pyrrolidin-3-yl]oxyphenyl]-8,9-dihydro-7H-benzo[7]annulen-2-ol.

Example 213. 6-(2-chloro-4-fluoro-phenyl)-1-fluoro-5-[4-[(3S)-1-(3-fluoropropyl)pyrrolidin-3-yl]oxyphenyl]-8,9-dihydro-7H-benzo[7]annulene-2-carboxylic acid Step 1: Methyl 8-(2-chloro-4-fluorophenyl)-4-fluoro-9-(4-{[(3S)-1-(3-fluoropropyl)pyrrolidin-3-yl]oxy}phenyl)-6,7-dihydro-5H-benzo[7]annulene-3-carboxylate

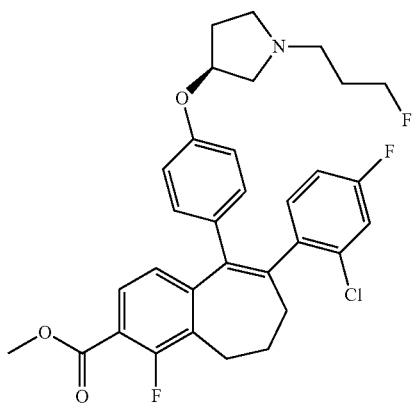 [SMILES: COC(=O)c1ccc2c(c1F)CCCC(c1ccc(F)cc1Cl)=C2c1ccc(O[C@H]2CCN(CCCF)C2)cc1]

To a solution of methyl 8-bromo-4-fluoro-9-(4-{[(3S)-1-(3-fluoropropyl)pyrrolidin-3-yl]oxy}phenyl)-6,7-dihydro-5H-benzo[7]annulene-3-carboxylate, hydrobromide (D8) (200 mg, 332.60 μmol) in dioxane (15 ml) was added 2-chloro-4-fluorophenyl boronic acid (69.59 mg, 399.12 μmol), Cs$_2$CO$_3$(465.64 μl, 698.46 μmol), and Pd(dppf)Cl$_2$ (15.37 mg, 19.96 μmol). The reaction mixture was heated at 70° C. for 1 hour, and concentrated under reduced pressure. The residue was purified by column chromatography eluting with a gradient of MeOH in DCM (0% to 5%), to give a solid which was further purified on strong cation exchange (SCX) column to give 170 mg (89.7%) of methyl 8-(2-chloro-4-fluorophenyl)-4-fluoro-9-(4-{[(3S)-1-(3-fluoropropyl)pyrrolidin-3-yl]oxy}phenyl)-6,7-dihydro-5H-benzo[7]annulene-3-carboxylate.

LC/MS (m/z, MH$^+$): 570

Step 2: 6-(2-chloro-4-fluoro-phenyl)-1-fluoro-5-[4-[(3S)-1-(3-fluoropropyl)pyrrolidin-3-yl]oxyphenyl]-8,9-dihydro-7H-benzo[7]annulene-2-carboxylic acid

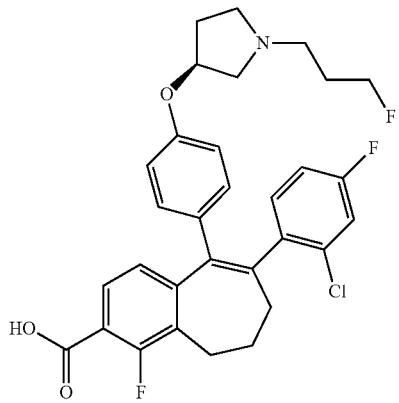 [SMILES: O=C(O)c1ccc2c(c1F)CCCC(c1ccc(F)cc1Cl)=C2c1ccc(O[C@H]2CCN(CCCF)C2)cc1]

To a solution of methyl 8-(2-chloro-4-fluorophenyl)-4-fluoro-9-(4-{[(3S)-1-(3-fluoropropyl)pyrrolidin-3-yl]oxy}phenyl)-6,7-dihydro-5H-benzo[7]annulene-3-carboxylate (170 mg, 298.22 μmol) in MeOH (150 ml), was added NaOH 5 M (238.58 μl, 1.19 mmol). The reaction mixture was heated at 90° C. for 2 hours, aqueous HCl (5 N) was added, and purified on strong cation exchange (SCX) column to give 65 mg (39.2%) of 6-(2-chloro-4-fluoro-phenyl)-1-fluoro-5-[4-[(3S)-1-(3-fluoropropyl)pyrrolidin-3-yl]oxyphenyl]-8,9-dihydro-7H-benzo[7]annulene-2-carboxylic acid.

Example 215. 5-[4-[(3S)-1-(3-fluoropropyl)pyrrolidin-3-yl]oxyphenyl]-6-(1H-indazol-5-yl)-8,9-dihydro-7H-benzo[7]annulen-2-ol

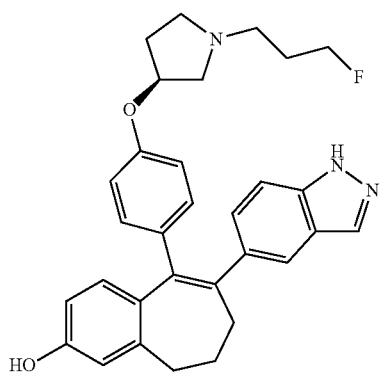 [SMILES: Oc1ccc2c(c1)CCCC(c1ccc3[nH]ncc3c1)=C2c1ccc(O[C@H]2CCN(CCCF)C2)cc1]

To a solution of 8-bromo-9-(4-((3S)-1-(3-fluoropropyl)pyrrolidin-3-yl)oxy)phenyl)-6,7-dihydro-5H-benzo[7]annulen-3-ol (D4) (306.6 mg, 665.97 µmol), in dioxane (4 mL) and water (0.5 ml), was added 5-(4,4,5,5-tetramethyl-1,3,2-dioxaborolan-2-yl)-1H-indazole (201 mg, 823.43 µmol), $Cs_2CO_3$ (557 mg, 1.71 mmol), and $Pd(dppf)Cl_2$ (70 mg, 85.72 µmol). The reaction mixture was heated at 72° C. for 4 hours and partitioned between water and DCM. The phases were separated on hydrophobic interaction column and the organic phase concentrated under reduced pressure. The residue was purified by column chromatography eluting with a gradient of MeOH in DCM (0% to 10%) to give 26 mg (8%) of 5-[4-[(3S)-1-(3-fluoropropyl)pyrrolidin-3-yl]oxyphenyl]-6-(1H-indazol-5-yl)-8,9-dihydro-7H-benzo[7]annulen-2-ol.

Some compounds of formula (I) were subjected to pharmacological tests for determining their antagonist and degradation effects on estrogen receptors.

Test A: Biochemical Antagonist Activity on Wild Type (WT) and Mutants Estrogen Receptors Test A involves measuring the in vitro antagonist activity of a compound of formula (I) on estrogen receptors.

The measurements of the antagonist activities were made using an estrogen receptor coactivator assay as described hereunder.

Antagonistic potency of compounds was evaluated using LanthaScreen® TR-FRET ERα Coactivator Assay (ThermoFisher) with modifications. It is a competition assay, where binding of a test compound to a complex comprised of (i) His6-ERα298-554 protein representing ERα ligand-binding domain, (ii) Tb-labeled His6 antibody, (iii) a fluorescein-labeled PGC1α coactivator peptide (EAEEPSLLK-KLLLAPANTQ), and (iv) estradiol, results in a decrease of the TR-FRET signal due to dissociation of the coactivator peptide. His6-ERα298-554 proteins were expressed as WT or D538G or Y537S mutants in *E. coli* and purified by affinity chromatography. The assay works in a homogeneous mix-and-read format. In a typical experiment, a 4 µL mixture of 0.5 nM His6-ERα298-554, 0.5 nM Tb-labeled His6 antibody, 250 nM PGC1a peptide, and 3 nM estradiol in 100 mM potassium phosphate, pH 7.4, 0.01% Tween-20, 0.02% $NaN_3$, 5 mM DTT, was added to 40 nL test compound in DMSO and incubated overnight at room temperature. The TR-FRET 520:495 nm emission ratio was calculated and used to determine the IC50 value from a dose response curve fit to the 4-parameter logistic equation.

The antagonist activity with respect to estrogen receptors in this test is given by the concentration which inhibits 50% of the estrogen receptor activity (or IC50) in nM.

The Table 2 below indicates the biochemical results of antagonist activity on WT and mutants estrogen receptors for compounds of formula (I), and demonstrates that the compounds tested have an antagonist activity regarding estrogen receptors.

TABLE 2

| Examples | Antagonism WT $IC_{50}$ (nM) | Antagonism D538G $IC_{50}$ (nM) | Antagonism Y537S $IC_{50}$ (nM) |
|---|---|---|---|
| Example 1 | 7 | 32 | 22 |
| Example 2 | 5 | 30 | 22 |
| Example 3 | 37 | 268 | 139 |
| Example 4 | 19 | 117 | 68 |
| Example 5 | 7 | 21 | 21 |
| Example 6 | 2 | 4 | 3 |
| Example 7 | 5 | 36 | 19 |
| Example 8 | 3 | 15 | 8 |
| Example 9 | 3 | 20 | 10 |
| Example 10 | 2 | 5 | 3 |
| Example 11 | 2 | 4 | 3 |
| Example 12 | 3 | 18 | 10 |
| Example 13 | 4 | 19 | 11 |
| Example 14 | 3 | 15 | 7 |
| Example 15 | 5 | 37 | 24 |
| Example 16 | 14 | 109 | 63 |
| Example 17 | 3 | 24 | 15 |
| Example 18 | 5 | 28 | 21 |
| Example 19 | 8 | 49 | 26 |
| Example 20 | 2 | 12 | 9 |
| Example 21 | 7 | 30 | 26 |
| Example 22 | 7 | 45 | 26 |
| Example 23 | 3 | 9 | 4 |
| Example 24 | 152 | 759 | 475 |
| Example 25 | 284 | 937 | 726 |
| Example 26 | 199 | 443 | 341 |
| Example 27 | 3 | 10 | 6 |
| Example 28 | 2 | 5 | 4 |
| Example 29 | 2 | 4 | 2 |
| Example 30 | 5 | 20 | 9 |
| Example 31 | 2 | 19 | 12 |
| Example 32 | 3 | 32 | 24 |
| Example 33 | 3 | 41 | 24 |
| Example 34 | 2 | 18 | 11 |
| Example 35 | 12 | 244 | 134 |
| Example 36 | 3 | 90 | 50 |
| Example 37 | 14 | 309 | 241 |
| Example 38 | 39 | 652 | 651 |
| Example 39 | 4 | 76 | 53 |
| Example 40 | 16 | 289 | 224 |
| Example 41 | 10 | 177 | 133 |
| Example 42 | 2 | 55 | 33 |
| Example 43 | 0.8 | 14 | 11 |
| Example 44 | 1 | 16 | 12 |
| Example 45 | 2 | 40 | 23 |
| Example 46 | 1 | 21 | 16 |
| Example 47 | 2 | 31 | 23 |
| Example 48 | 44 | 1119 | 549 |
| Example 49 | 1 | 11 | 6 |
| Example 50 | 10 | 208 | 113 |
| Example 51 | 15 | 389 | 221 |
| Example 52 | 2 | 49 | 29 |
| Example 53 | 244 | 3541 | 2857 |
| Example 54 | 1 | 8 | 5 |
| Example 55 | 23 | 635 | 338 |
| Example 56 | 15 | 389 | 204 |
| Example 57 | 3 | 56 | 39 |
| Example 58 | 2 | 37 | 24 |
| Example 59 | 2 | 57 | 34 |
| Example 60 | 3 | 68 | 39 |
| Example 61 | 10 | 178 | 99 |
| Example 62 | 20 | 337 | 178 |
| Example 63 | 6 | 132 | 72 |
| Example 64 | 6 | 149 | 88 |
| Example 65 | 2 | 38 | 25 |
| Example 66 | 12 | 217 | 127 |
| Example 67 | 5 | 145 | 85 |
| Example 68 | 12 | 184 | 109 |
| Example 69 | 5 | 172 | 90 |
| Example 70 | 2 | 36 | 22 |
| Example 71 | 1 | 28 | 18 |
| Example 72 | 31 | 895 | 498 |
| Example 73 | 4 | 59 | 40 |
| Example 74 | 2 | 28 | 26 |
| Example 75 | 56 | 1295 | 679 |
| Example 76 | 2 | 40 | 23 |
| Example 77 | 1 | 19 | 13 |
| Example 78 | 17 | 298 | 185 |
| Example 79 | 9 | 182 | 113 |
| Example 80 | 13 | 389 | 203 |
| Example 81 | 7 | 128 | 93 |
| Example 82 | 1 | 24 | 16 |
| Example 83 | 51 | 842 | 648 |

TABLE 2-continued

| Examples | Antagonism WT IC$_{50}$ (nM) | Antagonism D538G IC$_{50}$ (nM) | Antagonism Y537S IC$_{50}$ (nM) |
| --- | --- | --- | --- |
| Example 84 | 74 | 1464 | 964 |
| Example 85 | 58 | 1111 | 735 |
| Example 86 | 12 | 313 | 172 |
| Example 87 | 9 | 150 | 93 |
| Example 88 | 5 | 139 | 78 |
| Example 89 | 1 | 12 | 8 |
| Example 90 | 13 | 263 | 190 |
| Example 91 | 2 | 35 | 18 |
| Example 92 | 34 | 840 | 504 |
| Example 93 | 2 | 29 | 24 |
| Example 94 | 25 | 485 | 322 |
| Example 95 | 12 | 243 | 150 |
| Example 96 | 20 | 307 | 196 |
| Example 97 | 9 | 127 | 78 |
| Example 98 | 1 | 18 | 12 |
| Example 99 | 18 | 804 | 280 |
| Example 100 | 83 | 1329 | 1014 |
| Example 101 | 14 | 269 | 163 |
| Example 102 | 5 | 123 | 71 |
| Example 103 | 4 | 86 | 55 |
| Example 104 | 2 | 30 | 17 |
| Example 105 | 8 | 129 | 81 |
| Example 106 | 15 | 524 | 607 |
| Example 107 | 42 | 977 | 507 |
| Example 108 | 1 | 33 | 19 |
| Example 109 | 1 | 29 | 17 |
| Example 110 | 14 | 274 | 168 |
| Example 111 | 4 | 120 | 67 |
| Example 112 | 4 | 76 | 46 |
| Example 113 | 34 | 633 | 434 |
| Example 114 | 21 | 346 | 242 |
| Example 115 | 6 | 86 | 71 |
| Example 116 | 2 | 37 | 25 |
| Example 117 | 12 | 238 | 163 |
| Example 118 | 17 | 245 | 164 |
| Example 119 | 62 | 953 | 714 |
| Example 120 | 38 | 585 | 357 |
| Example 121 | 4 | 76 | 56 |
| Example 122 | 2 | 40 | 24 |
| Example 123 | 4 | 72 | 46 |
| Example 124 | 13 | 215 | 170 |
| Example 125 | 8 | 154 | 106 |
| Example 126 | 33 | 661 | 541 |
| Example 127 | 30 | 603 | 347 |
| Example 128 | 89 | 2046 | 1692 |
| Example 129 | 23 | 474 | 290 |
| Example 130 | 3 | 59 | 44 |
| Example 131 | 15 | 387 | 253 |
| Example 132 | 77 | 1371 | 1249 |
| Example 133 | 20 | 384 | 190 |
| Example 134 | 2 | 28 | 28 |
| Example 135 | 59 | 1077 | 1226 |
| Example 136 | 11 | 201 | 134 |
| Example 137 | 28 | 595 | 363 |
| Example 138 | 50 | 697 | 323 |
| Example 139 | 2 | 43 | 28 |
| Example 140 | 52 | 996 | 685 |
| Example 141 | 27 | 475 | 436 |
| Example 142 | 5 | 117 | 64 |
| Example 143 | 4 | 100 | 57 |
| Example 144 | 46 | 759 | 645 |
| Example 145 | 2 | 44 | 28 |
| Example 146 | 9 | 152 | 67 |
| Example 147 | 54 | 982 | 583 |
| Example 148 | 62 | 1037 | 916 |
| Example 149 | 5 | 114 | 72 |
| Example 150 | 91 | 1768 | 2148 |
| Example 151 | 122 | 1641 | >4000 |
| Example 152 | 8 | 268 | 132 |
| Example 153 | 4 | 74 | 47 |
| Example 154 | 10 | 191 | 117 |
| Example 155 | 11 | 231 | 141 |
| Example 156 | 90 | 885 | 1006 |
| Example 157 | 3 | 84 | 53 |
| Example 158 | 5 | 106 | 63 |
| Example 159 | 241 | 3816 | 2563 |
| Example 160 | 15 | 266 | 110 |
| Example 161 | 23 | 396 | 169 |
| Example 162 | 16 | 290 | 159 |
| Example 163 | N/A* | N/A* | N/A* |
| Example 164 | 8 | 191 | 121 |
| Example 165 | 2 | 47 | 27 |
| Example 166 | 13 | 560 | 299 |
| Example 167 | 3 | 42 | 33 |
| Example 168 | 228 | 3844 | >4000 |
| Example 169 | 46 | 868 | 787 |
| Example 170 | 6 | 143 | 89 |
| Example 171 | 2 | 33 | 20 |
| Example 172 | 95 | 1632 | 1072 |
| Example 173 | 154 | 2346 | 1495 |
| Example 174 | 31 | 707 | 429 |
| Example 175 | 1 | 20 | 14 |
| Example 176 | 33 | 873 | 435 |
| Example 177 | 289 | >4000 | 2911 |
| Example 178 | 2 | 52 | 29 |
| Example 179 | 46 | 755 | 538 |
| Example 180 | 7 | 133 | 78 |
| Example 181 | 14 | 260 | 187 |
| Example 182 | 10 | 176 | 120 |
| Example 183 | 9 | 180 | 125 |
| Example 184 | 49 | 991 | 459 |
| Example 185 | 67 | 1545 | 981 |
| Example 186 | 6 | 118 | 75 |
| Example 187 | 28 | 476 | 321 |
| Example 188 | 1 | 23 | 16 |
| Example 189 | 183 | 2973 | 2414 |
| Example 190 | 37 | 623 | 444 |
| Example 191 | 0 | 6 | 4 |
| Example 192 | 1 | 18 | 11 |
| Example 193 | 57 | 939 | 516 |
| Example 194 | 4 | 66 | 38 |
| Example 195 | 2 | 56 | 34 |
| Example 196 | 15 | 354 | 198 |
| Example 197 | 11 | 169 | 124 |
| Example 198 | 62 | 1039 | 586 |
| Example 199 | 1 | 21 | 15 |
| Example 200 | 195 | 3450 | 3097 |
| Example 201 | 6 | 125 | 74 |
| Example 202 | 5 | 94 | 67 |
| Example 203 | 3 | 69 | 48 |
| Example 204 | 2 | 50 | 29 |
| Example 205 | 12 | 331 | 187 |
| Example 206 | 27 | 606 | 374 |
| Example 207 | 3 | 58 | 39 |
| Example 208 | 1 | 32 | 19 |
| Example 209 | 33 | 703 | 543 |
| Example 210 | 11 | 283 | 162 |
| Example 211 | 30 | 618 | 443 |
| Example 212 | 84 | 2366 | 1111 |
| Example 213 | 22 | 529 | 334 |
| Example 214 | 2 | 39 | 23 |
| Example 215 | 4 | 88 | 57 |
| Example 216 | 31 | 743 | 431 |
| Example 217 | 39 | 960 | 632 |
| Example 218 | 61 | 1472 | 779 |
| Example 219 | 84 | 1595 | 1094 |

N/A*: Not available. Prodrug of example 75

Test B: Cell Proliferation/Viability Assay on MCF7 (Breast Tumor Cells) WT and Mutants Cell Lines Test B involves measuring the in vitro proliferation activity of a compound of formula (I) by analyzing the viability of the tumor cells.

The measurements of the viability were made using a breast cancer cell viability assay as described hereunder.

MCF7 cells expressing (and dependent) on mutants estrogen receptor Tyr 537 Ser or Asp 538 Gly were generated by transfection of MCF7 parental cells (ATCC) with expression vectors coding for different mutants of estrogen receptor Tyr 537 Ser or Asp 538 Gly. The cells were first selected by antibiotic (related to vector expression) and then selected for their growth dependence on estrogen receptor based on their ability to grow in vitro in absence of estradiol (parental cell line die in absence of estradiol).

MCF7 cells (ATCC) or MCF7 cells expressing (and dependent) on mutants estrogen receptor Tyr 537 Ser or Asp 538 Gly were seeded in 384 wells microplate at concentration of 1000 cells/30 µL per well in red phenol free MEM medium containing 5% charcoal dextran striped FBS. The following day, 9 points serial 1:5 dilution of each compound were added to the cells in 20 µL at final concentrations ranging from 3-0.000001 µM. After 7 days of compound exposure, 50 µL of CellTiter-Glo (Promega) was added to the cells and relative luminescence arbitrary units (RLUs) were determined in luminescence plate reader (Envision device). CellTiter-Glo was added to 50 µL medium without cells to determine the background signal.

The percent of viability of each sample was determined as follows: (RLU sample−RLU background/RLU untreated−RLU background)*100=% viability.

The viability activity with respect to estrogen receptors in this test is given by the concentration which inhibits 50% of the viability activity (or IC50) in nM.

The Table 3 below indicates the cell proliferation/viability assay results on MCF7 (breast tumor cells) WT and mutants cell lines, for compounds of formula (I), and demonstrates that the compounds tested have a significant antiproliferative activity regarding estrogen receptors.

TABLE 3

| Examples | proliferation MCF7 (WT) $IC_{50}$ (nM) | proliferation MCF7 (WT) $IC_{50}$ (nM) | proliferation MCF7 (WT) $IC_{50}$ (nM) |
|---|---|---|---|
| Example 1 | 0.6 | 0.1 | 3 |
| Example 2 | 1 | 0.1 | 6 |
| Example 3 | 9 | 0.2 | 17 |
| Example 4 | 5 | 0.2 | 11 |
| Example 5 | 0.3 | 0.2 | 2 |
| Example 6 | 3 | 0.1 | 3 |
| Example 7 | 0.2 | 0.3 | 1 |
| Example 8 | 4 | 0.1 | 6 |
| Example 9 | 0.4 | 1 | 5 |
| Example 10 | 7 | 0.4 | 15 |
| Example 11 | 3 | 0.2 | 7 |
| Example 12 | 28 | 2 | 35 |
| Example 13 | 0.5 | 0.4 | 5 |
| Example 14 | 2 | 0.1 | 2 |
| Example 15 | 0.2 | 0.4 | 4 |
| Example 16 | 3 | 0.4 | 7 |
| Example 17 | 0.2 | 0.3 | 2 |
| Example 18 | 0.7 | 1 | 5 |
| Example 19 | 5 | 0.4 | 19 |
| Example 20 | 5 | 0.1 | 14 |
| Example 21 | 23 | 2 | 36 |
| Example 22 | 6 | 30 | 306 |
| Example 23 | 0.2 | 1 | 4 |
| Example 24 | 63 | 7 | 71 |
| Example 25 | 48 | 5 | 67 |
| Example 26 | 25 | 4 | 31 |
| Example 27 | 0.2 | 1 | 8 |
| Example 28 | 0.2 | 1 | 7 |
| Example 29 | 0.5 | 1 | 3 |
| Example 30 | 36 | 2 | 39 |
| Example 31 | 4 | 0.3 | 6 |
| Example 32 | 0.3 | 1 | 3 |
| Example 33 | 0.3 | 1 | 3 |
| Example 34 | 0.2 | 0.4 | 2 |
| Example 35 | 0.2 | 1 | 5 |
| Example 36 | 0.3 | 0.4 | 4 |
| Example 37 | 0.5 | 1 | 7 |
| Example 38 | 0.6 | 1 | 9 |
| Example 39 | 0.2 | 1 | 4 |
| Example 40 | 0.2 | 0.4 | 4 |
| Example 41 | 0.2 | 1 | 4 |
| Example 42 | 0.4 | 1 | 6 |
| Example 43 | 0.4 | 1 | 5 |
| Example 44 | 0.2 | 1 | 3 |
| Example 45 | 0.7 | 2 | 14 |
| Example 46 | 0.6 | 1 | 8 |
| Example 47 | 0.3 | 0.3 | 3 |
| Example 48 | 0.7 | 2 | 13 |
| Example 49 | 0.4 | 1 | 5 |
| Example 50 | 0.2 | 0.3 | 4 |
| Example 51 | 0.4 | 1 | 10 |
| Example 52 | 0.3 | 1 | 5 |
| Example 53 | 10 | 21 | 112 |
| Example 54 | 0.1 | 0.2 | 2 |
| Example 55 | 2 | 4 | 39 |
| Example 56 | 0.5 | 2 | 10 |
| Example 57 | 0.2 | 0.3 | 3 |
| Example 58 | 0.3 | 1 | 4 |
| Example 59 | 0.1 | 0.5 | 3 |
| Example 60 | 0.4 | 0.3 | 5 |
| Example 61 | 0.3 | 1 | 4 |
| Example 62 | 0.4 | 1 | 7 |
| Example 63 | 0.4 | 1 | 5 |
| Example 64 | 0.3 | 0.4 | 4 |
| Example 65 | 0.1 | 1 | 2 |
| Example 66 | 0.4 | 1 | 6 |
| Example 67 | 0.2 | 0.4 | 3 |
| Example 68 | 0.2 | 0.3 | 2 |
| Example 69 | 0.3 | 1 | 5 |
| Example 70 | 0.2 | 1 | 8 |
| Example 71 | 0.2 | 0.4 | 4 |
| Example 72 | 0.6 | 1 | 14 |
| Example 73 | 0.9 | 2 | 15 |
| Example 74 | 0.1 | 0.3 | 2 |
| Example 75 | 0.5 | 1 | 7 |
| Example 76 | 0.2 | 0.3 | 3 |
| Example 77 | 0.1 | 0.3 | 2 |
| Example 78 | 0.4 | 0.4 | 6 |
| Example 79 | 6 | 0.6 | 12 |
| Example 80 | 0.5 | 1 | 11 |
| Example 81 | 0.2 | 0.2 | 4 |
| Example 82 | 0.8 | 1 | 8 |
| Example 83 | 1 | 1 | 14 |
| Example 84 | 0.7 | 1 | 13 |
| Example 85 | 0.8 | 1 | 9 |
| Example 86 | 0.4 | 1 | 5 |
| Example 87 | 0.1 | 0.4 | 2 |
| Example 88 | 0.2 | 0.3 | 4 |
| Example 89 | 0.2 | 0.3 | 3 |
| Example 90 | 0.4 | 0.3 | 6 |
| Example 91 | 0.1 | 0.2 | 1 |
| Example 92 | 0.5 | 1 | 8 |
| Example 93 | 0.2 | 1 | 4 |
| Example 94 | 0.7 | 1 | 7 |
| Example 95 | 0.5 | 1 | 10 |
| Example 96 | 0.8 | 1 | 5 |
| Example 97 | 0.2 | 0.1 | 1 |
| Example 98 | 0.4 | 0.3 | 2 |
| Example 99 | 0.4 | 1 | 3 |
| Example 100 | 1 | 2 | 15 |
| Example 101 | 0.8 | 1 | 6 |
| Example 102 | 0.1 | 0.3 | 1 |
| Example 103 | 0.5 | 1 | 5 |
| Example 104 | 0.1 | 0.1 | 1 |
| Example 105 | 0.3 | 0.3 | 4 |
| Example 106 | 1 | 3 | 54 |
| Example 107 | 0.5 | 1 | 12 |
| Example 108 | 0.2 | 0.1 | 1 |
| Example 109 | 0.2 | 0.1 | 2 |
| Example 110 | 0.4 | 1 | 9 |
| Example 111 | 0.2 | 0.2 | 3 |
| Example 112 | 0.2 | 0.2 | 4 |
| Example 113 | 0.6 | 2 | 11 |
| Example 114 | 0.4 | 1 | 5 |

TABLE 3-continued

| Examples | proliferation MCF7 (WT) IC$_{50}$ (nM) | proliferation MCF7 (WT) IC$_{50}$ (nM) | proliferation MCF7 (WT) IC$_{50}$ (nM) |
| --- | --- | --- | --- |
| Example 115 | 0.3 | 1 | 5 |
| Example 116 | 0.1 | 1 | 2 |
| Example 117 | 0.5 | 1 | 6 |
| Example 118 | 0.2 | 0.2 | 2 |
| Example 119 | 0.7 | 2 | 8 |
| Example 120 | 0.3 | 1 | 6 |
| Example 121 | 0.3 | 1 | 2 |
| Example 122 | 0.2 | 1 | 2 |
| Example 123 | 0.2 | 1 | 5 |
| Example 124 | 0.3 | 1 | 4 |
| Example 125 | 0.2 | 1 | 3 |
| Example 126 | 1 | 3 | 30 |
| Example 127 | 0.1 | 0.4 | 1 |
| Example 128 | 8 | 17 | 96 |
| Example 129 | 0.1 | 0.3 | 5 |
| Example 130 | 0.2 | 1 | 5 |
| Example 131 | 0.4 | 1 | 11 |
| Example 132 | 0.7 | 2 | 19 |
| Example 133 | 1 | 2 | 29 |
| Example 134 | 0.1 | 0.3 | 3 |
| Example 135 | 1 | 3 | 21 |
| Example 136 | 0.2 | 1 | 5 |
| Example 137 | 0.2 | 1 | 7 |
| Example 138 | 0.8 | 3 | 19 |
| Example 139 | 0.1 | 1 | 3 |
| Example 140 | 1 | 3 | 24 |
| Example 141 | 0.3 | 1 | 5 |
| Example 142 | 0.2 | 0.2 | 2 |
| Example 143 | 0.7 | 1 | 5 |
| Example 144 | 2 | 2 | 25 |
| Example 145 | 0.3 | 0.4 | 3 |
| Example 146 | 0.4 | 1 | 4 |
| Example 147 | 2 | 2 | 20 |
| Example 148 | 2 | 2 | 11 |
| Example 149 | 0.7 | 1 | 6 |
| Example 150 | 3 | 2 | 18 |
| Example 151 | 0.9 | 1 | 16 |
| Example 152 | 0.4 | 0.3 | 4 |
| Example 153 | 0.1 | 0.1 | 1 |
| Example 154 | 0.4 | 0.3 | 4 |
| Example 155 | 0.1 | 0.2 | 2 |
| Example 156 | 2 | 4 | 11 |
| Example 157 | 0.6 | 0.2 | 2 |
| Example 158 | 0.5 | 1 | 5 |
| Example 159 | 8 | 11 | 112 |
| Example 160 | 0.7 | 1 | 6 |
| Example 161 | 0.8 | 1 | 7 |
| Example 162 | 0.6 | 1 | 3 |
| Example 163 | N/A* | N/A* | N/A* |
| Example 164 | 2 | 0.2 | 2 |
| Example 165 | 0.4 | 0.3 | 4 |
| Example 166 | 0.8 | 1 | 12 |
| Example 167 | 0.4 | 1 | 3 |
| Example 168 | 4 | 5 | 33 |
| Example 169 | 10 | 1 | 1 |
| Example 170 | 3 | 0.3 | 0.3 |
| Example 171 | 0.9 | 0.1 | 0.1 |
| Example 172 | 30 | 2 | 4 |
| Example 173 | 5 | 11 | 177 |
| Example 174 | 1 | 3 | 40 |
| Example 175 | 0.2 | 1 | 10 |
| Example 176 | 5 | 12 | 108 |
| Example 177 | 11 | 18 | 187 |
| Example 178 | 0.5 | 2 | 15 |
| Example 179 | 1 | 3 | 35 |
| Example 180 | 2 | 3 | 39 |
| Example 181 | 2 | 4 | 52 |
| Example 182 | 0.3 | 1 | 15 |
| Example 183 | 1 | 1 | 9 |
| Example 184 | 1 | 2 | 36 |
| Example 185 | 41 | 77 | 1000 |
| Example 186 | 0.9 | 2 | 26 |
| Example 187 | 19 | 34 | 1000 |
| Example 188 | 0.1 | 0.1 | 3 |
| Example 189 | 12 | 27 | 246 |
| Example 190 | 7 | 15 | 148 |
| Example 191 | 0.5 | 2 | 19 |
| Example 192 | 0.6 | 2 | 17 |
| Example 193 | 0.6 | 1 | 20 |
| Example 194 | 0.3 | 1 | 8 |
| Example 195 | 0.2 | 0.2 | 4 |
| Example 196 | 1 | 5 | 43 |
| Example 197 | 0.2 | 1 | 6 |
| Example 198 | 3 | 11 | 79 |
| Example 199 | 0.2 | 1 | 2 |
| Example 200 | 78 | 108 | 1000 |
| Example 201 | 0.02 | 1 | 4 |
| Example 202 | 0.3 | 1 | 6 |
| Example 203 | 0.1 | 1 | 4 |
| Example 204 | 0.1 | 0.3 | 1 |
| Example 205 | 8 | 28 | 119 |
| Example 206 | 1 | 8 | 26 |
| Example 207 | 0.3 | 1 | 3 |
| Example 208 | 0.1 | 0.3 | 1 |
| Example 209 | 8 | 25 | 68 |
| Example 210 | 0.5 | 2 | 8 |
| Example 211 | 0.7 | 2 | 10 |
| Example 212 | 4 | 14 | 112 |
| Example 213 | 1 | 2 | 8 |
| Example 214 | 0.1 | 1 | 2 |
| Example 215 | 1 | 18 | 51 |
| Example 216 | 1 | 6 | 19 |
| Example 217 | 0.3 | 12 | 23 |
| Example 218 | 1 | 13 | 29 |
| Example 219 | 1 | 9 | 36 |

N/A*: Not available. Prodrug of example 75

Test C: Estrogen Receptor Degradation Activity

Test C involves measuring the in vitro degradation activity of a compound of formula (I).

The measurements of the degradation activities were made using a breast cancer cell ERα in cell western assay as described hereunder.

MCF7 cells (ATCC) were seeded in 384 wells microplate (collagen coated) at concentration of 10000 cells/30 μL per well in red phenol free MEM alpha medium (Invitrogen) containing 5% charcoal dextran striped FBS. The following day, 9 points serial 1:5 dilution of each compound were added to the cells in 2.5 μL at final concentrations ranging from 3-0.000018 μM or 0.1 μM for fulvestrant (using as positive control). At 4 hours post compounds addition the cells were fixed by adding 25 μL of formalin (final concentration 5% formalin containing 0.1% triton) for 10 minutes at room temperature and then washed twice with PBS. Then, 50 μL of LI-COR blocking buffer containing 0.1% Triton was added to plate for 30 minutes at room temperature. LI-COR blocking buffer was removed and cells were incubated overnight at cold room with 50 μL anti-ER rabbit monoclonal antibody (Thermo scientific MA1-39540) diluted at 1:1000 in LI-COR blocking buffer containing 0.1% tween-20. Wells which were treated with blocking but no antibody were used as background control. Wells were washed twice with PBS (0.1% tween-20) and incubated at 37° C. for 60 minutes in LI-COR (0.1% tween-20) containing goat anti-rabbit antibody Alexa 488 (1:1000) and Syto-64 a DNA dye (2 μM final concentration). Cells were then washed 3 times in PBS and scanned in ACUMEN explorer (TTP-Labtech). Integrated intensities in the green fluorescence and red fluoresence were measured to determine the levels of ERα and DNA respectively.

The degradation activity with respect to estrogen receptors in this test is given by the concentration which degrades 50% of the estrogen receptor (or IC50) in nM.

The % of ERα levels decrease were determined as follows: % inhibition=100*(1−(sample−fulvestrant: DMSO−fulvestrant)).

The Table 4 below indicates the estrogen receptor degradation activity results for compounds of formula (I), and demonstrates that compounds tested have a significant degradation activity on estrogen receptors.

TABLE 4

| Examples | Degradation IC$_{50}$ (nM) | % Degradation At 3 μM |
|---|---|---|
| Example 1 | 0.4 | 88 |
| Example 2 | 0.4 | 97 |
| Example 3 | 3 | 82 |
| Example 4 | 0.3 | 90 |
| Example 5 | 0.3 | 93 |
| Example 6 | 0.7 | 90 |
| Example 7 | 0.5 | 97 |
| Example 8 | 0.5 | 96 |
| Example 9 | 0.7 | 95 |
| Example 10 | 0.2 | 92 |
| Example 11 | 0.7 | 89 |
| Example 12 | 0.5 | 82 |
| Example 13 | 0.5 | 91 |
| Example 14 | 0.3 | 94 |
| Example 15 | 0.2 | 95 |
| Example 16 | 2 | 90 |
| Example 17 | 0.8 | 83 |
| Example 18 | 0.9 | 90 |
| Example 19 | 1 | 82 |
| Example 20 | 0.2 | 87 |
| Example 21 | 0.2 | 83 |
| Example 22 | 2 | 81 |
| Example 23 | 2 | 82 |
| Example 24 | 28 | 86 |
| Example 25 | 38 | 91 |
| Example 26 | 11 | 92 |
| Example 27 | 2 | 91 |
| Example 28 | 1 | 92 |
| Example 29 | 0.4 | 88 |
| Example 30 | 2 | 82 |
| Example 31 | 1 | 91 |
| Example 32 | 2 | 87 |
| Example 33 | 0.6 | 86 |
| Example 34 | 1 | 83 |
| Example 35 | 0.8 | 89 |
| Example 36 | 0.4 | 90 |
| Example 37 | 1 | 95 |
| Example 38 | 1 | 96 |
| Example 39 | 0.5 | 91 |
| Example 40 | 0.2 | 88 |
| Example 41 | 0.3 | 85 |
| Example 42 | 0.3 | 84 |
| Example 43 | 0.2 | 83 |
| Example 44 | 0.2 | 80 |
| Example 45 | 0.2 | 93 |
| Example 46 | 0.2 | 94 |
| Example 47 | 0.4 | 90 |
| Example 48 | 0.2 | 96 |
| Example 49 | 0.2 | 94 |
| Example 50 | 0.4 | 92 |
| Example 51 | 0.2 | 98 |
| Example 52 | 0.4 | 92 |
| Example 53 | 8 | 95 |
| Example 54 | 0.2 | 92 |
| Example 55 | 5 | 87 |
| Example 56 | 2 | 85 |
| Example 57 | 0.5 | 86 |
| Example 58 | 0.7 | 84 |
| Example 59 | 0.4 | 86 |
| Example 60 | 1 | 84 |
| Example 61 | 1 | 86 |
| Example 62 | 0.7 | 96 |
| Example 63 | 0.3 | 95 |
| Example 64 | 0.4 | 88 |
| Example 65 | 0.8 | 89 |
| Example 66 | 0.6 | 90 |
| Example 67 | 2 | 92 |
| Example 68 | 1 | 92 |
| Example 69 | 0.2 | 87 |
| Example 70 | 0.7 | 80 |
| Example 71 | 0.6 | 83 |
| Example 72 | 2 | 88 |
| Example 73 | 0.4 | 86 |
| Example 74 | 0.4 | 84 |
| Example 75 | 2 | 84 |
| Example 76 | 0.3 | 88 |
| Example 77 | 0.3 | 83 |
| Example 78 | 0.9 | 92 |
| Example 79 | 0.9 | 84 |
| Example 80 | 1 | 90 |
| Example 81 | 0.6 | 83 |
| Example 82 | 0.5 | 83 |
| Example 83 | 2 | 80 |
| Example 84 | 2 | 92 |
| Example 85 | 1 | 92 |
| Example 86 | 0.7 | 89 |
| Example 87 | 0.4 | 90 |
| Example 88 | 0.5 | 86 |
| Example 89 | 0.6 | 84 |
| Example 90 | 1 | 83 |
| Example 91 | 0.2 | 86 |
| Example 92 | 2 | 89 |
| Example 93 | 0.3 | 86 |
| Example 94 | 2 | 88 |
| Example 95 | 1 | 84 |
| Example 96 | 1 | 86 |
| Example 97 | 0.7 | 95 |
| Example 98 | 1 | 86 |
| Example 99 | 0.9 | 94 |
| Example 100 | 3 | 93 |
| Example 101 | 1 | 87 |
| Example 102 | 0.6 | 87 |
| Example 103 | 1 | 86 |
| Example 104 | 0.6 | 84 |
| Example 105 | 0.3 | 93 |
| Example 106 | 2 | 87 |
| Example 107 | 2 | 89 |
| Example 108 | 0.2 | 87 |
| Example 109 | 0.5 | 80 |
| Example 110 | 0.8 | 83 |
| Example 111 | 0.3 | 84 |
| Example 112 | 0.6 | 88 |
| Example 113 | 0.2 | 90 |
| Example 114 | 0.2 | 88 |
| Example 115 | 0.2 | 89 |
| Example 116 | 0.2 | 85 |
| Example 117 | 0.2 | 85 |
| Example 118 | 0.2 | 87 |
| Example 119 | 0.2 | 81 |
| Example 120 | 0.2 | 85 |
| Example 121 | 0.2 | 87 |
| Example 122 | 0.2 | 85 |
| Example 123 | 0.2 | 83 |
| Example 124 | 0.2 | 87 |
| Example 125 | 0.2 | 93 |
| Example 126 | 0.2 | 86 |
| Example 127 | 0.2 | 89 |
| Example 128 | 1 | 82 |
| Example 129 | 0.2 | 90 |
| Example 130 | 0.2 | 80 |
| Example 131 | 0.2 | 84 |
| Example 132 | 0.3 | 89 |
| Example 133 | 0.2 | 88 |
| Example 134 | 0.2 | 87 |
| Example 135 | 0.2 | 85 |
| Example 136 | 0.2 | 82 |
| Example 137 | 0.2 | 85 |
| Example 138 | 0.3 | 88 |
| Example 139 | 0.2 | 80 |
| Example 140 | 0.2 | 86 |
| Example 141 | 0.2 | 84 |
| Example 142 | 0.2 | 84 |
| Example 143 | 0.2 | 81 |
| Example 144 | 2 | 86 |

TABLE 4-continued

| Examples | Degradation IC$_{50}$ (nM) | % Degradation At 3 μM |
| --- | --- | --- |
| Example 145 | 0.2 | 83 |
| Example 146 | 0.2 | 83 |
| Example 147 | 0.2 | 88 |
| Example 148 | 0.2 | 83 |
| Example 149 | 0.2 | 82 |
| Example 150 | 1 | 82 |
| Example 151 | 1 | 81 |
| Example 152 | 0.2 | 80 |
| Example 153 | 0.2 | 91 |
| Example 154 | 0.2 | 87 |
| Example 155 | 0.2 | 89 |
| Example 156 | 0.2 | 85 |
| Example 157 | 0.2 | 81 |
| Example 158 | 0.2 | 82 |
| Example 159 | 0.7 | 84 |
| Example 160 | 0.2 | 83 |
| Example 161 | 0.2 | 81 |
| Example 162 | 0.2 | 82 |
| Example 163 | N/A* | N/A* |
| Example 164 | 0.2 | 88 |
| Example 165 | 0.2 | 82 |
| Example 166 | 0.5 | 86 |
| Example 167 | 0.2 | 81 |
| Example 168 | 0.6 | 91 |
| Example 169 | 1 | 87 |
| Example 170 | 0.5 | 82 |
| Example 171 | 0.3 | 83 |
| Example 172 | 2 | 80 |
| Example 173 | 9 | 85 |
| Example 174 | 0.7 | 92 |
| Example 175 | 0.2 | 88 |
| Example 176 | 2 | 81 |
| Example 177 | 8 | 92 |
| Example 178 | 0.2 | 94 |
| Example 179 | 0.9 | 94 |
| Example 180 | 3 | 91 |
| Example 181 | 3 | 94 |
| Example 182 | 0.2 | 93 |
| Example 183 | 0.7 | 98 |
| Example 184 | 2 | 95 |
| Example 185 | 9 | 80 |
| Example 186 | 0.9 | 87 |
| Example 187 | 15 | 90 |
| Example 188 | 0.2 | 91 |
| Example 189 | 22 | 90 |
| Example 190 | 7 | 80 |
| Example 191 | 0.5 | 89 |
| Example 192 | 0.3 | 88 |
| Example 193 | 0.2 | 88 |
| Example 194 | 0.8 | 90 |
| Example 195 | 0.2 | 87 |
| Example 196 | 8 | 86 |
| Example 197 | 0.6 | 92 |
| Example 198 | 3 | 81 |
| Example 199 | 0.2 | 95 |
| Example 200 | 15 | 85 |
| Example 201 | 0.3 | 90 |
| Example 202 | 0.2 | 84 |
| Example 203 | 0.2 | 81 |
| Example 204 | 0.2 | 82 |
| Example 205 | 4 | 88 |
| Example 206 | 1 | 85 |
| Example 207 | 0.2 | 86 |
| Example 208 | 0.2 | 94 |
| Example 209 | 8 | 91 |
| Example 210 | 1 | 91 |
| Example 211 | 0.3 | 95 |
| Example 212 | 2 | 94 |
| Example 213 | 0.2 | 96 |
| Example 214 | 0.5 | 92 |
| Example 215 | 1.5 | 80 |
| Example 216 | 3 | 90 |
| Example 217 | 2 | 90 |
| Example 218 | 3 | 92 |
| Example 219 | 1 | 89 |

N/A*: Not available. Prodrug of example 75

It is therefore apparent that the compounds of formula (I), or a pharmaceutically acceptable salt thereof, have antagonist and degradation activities for estrogen receptors, as well as antiproliferative activity. The compounds of formula (I), or a pharmaceutically acceptable salt thereof, can therefore be used for preparing medicaments, especially medicaments which are antagonists and degraders of estrogen receptors.

Accordingly, also provided are medicaments which comprise a compound of the formula (I), or a pharmaceutically acceptable salt thereof.

Another aspect is the compounds of formula (I) defined above, or a pharmaceutically acceptable salt thereof, for use in therapy, especially as inhibitors and degraders of estrogen receptors.

Another aspect is the compounds of formula (I) defined above, or a pharmaceutically acceptable salt thereof, for use in the treatment of ovulatory dysfunction, cancer, endometriosis, osteoporosis, benign prostatic hypertrophy or inflammation.

A particular aspect are the compounds of formula (I) defined above, or a pharmaceutically acceptable salt thereof, for use in the treatment of cancer.

In an embodiment, the cancer is a hormone dependent cancer.

In another embodiment, the cancer is an estrogen receptor dependent cancer, particularly the cancer is an estrogen receptor a dependent cancer.

In another embodiment, the cancer is a cancer with wild type estrogen receptors.

In another embodiment, the cancer is a cancer with deregulated function of estrogen receptors related to, but not limited to, at least one epigenetic and genetic alteration of estrogen receptors such us mutation, amplification, splice variant.

In another embodiment, the cancer is a cancer with mutated estrogen receptors.

In another embodiment, the mutations of estrogen receptors can include, but not limited to, new or known mutations such us Leu536Arg, Tyr537Ser, Tyr537Asn, Asp538Gly.

In another embodiment, the cancer is an estrogen-sensitive cancer.

In another embodiment, the cancer is selected from breast, ovarian, endometrial, prostate, uterine, cervical and lung cancer, or a metastasis thereof.

In another embodiment, the metastasis is a cerebral metastasis.

In another embodiment, the cancer is breast cancer. Particularly, the breast cancer is an estrogen receptor positive breast cancer (ERα positive breast cancer).

In another embodiment, the cancer is resistant to anti-hormonal treatment.

In a further embodiment, the anti-hormonal treatment is as single agent or in combination with other agents such as CDK4/6 or PI3K inhibitors.

In a further embodiment, the anti-hormonal treatment includes treatment with at least one agent selected from tamoxifen, fulvestrant, a steroidal aromatase inhibitor, and a non-steroidal aromatase inhibitor.

Another embodiment is a method of treating the pathological conditions indicated above, comprising administering to a subject in need thereof a therapeutically effective amount of a compound of formula (I), or a pharmaceutically acceptable salt thereof. In an embodiment of this method of treatment, the subject is a human.

Another aspect is the use of a compound of the formula (I), or a pharmaceutically acceptable salt thereof, for the manufacture of a medicament useful in treating any of the pathological conditions indicated above, more particularly the use in treating cancer.

Another aspect is a pharmaceutical composition comprising as active principle a compound of formula (I) or a pharmaceutically acceptable salt thereof. These pharmaceutical compositions comprise an effective dose of at least one compound of formula (I), or a pharmaceutically acceptable salt thereof, and also at least one pharmaceutically acceptable excipient.

The said excipients are selected, in accordance with the pharmaceutical form and method of administration desired, from the customary excipients, which are known to a person skilled in the art.

In the pharmaceutical compositions provided herein for oral, sublingual, subcutaneous, intramuscular, intravenous, topical, local, intra-tracheal, intranasal, transdermal or rectal administration, the active principle of formula (I) above, or its base, acid, zwitterion or salt thereof, may be administered in a unit administration form, in a mixture with conventional pharmaceutical excipients, to animals and to human beings for the treatment of the above disorders or diseases.

The unit administration forms appropriate include oral forms such as tablets, soft or hard gel capsules, powders, granules and oral solutions or suspensions, sublingual, buccal, intra-tracheal, intra-ocular and intra-nasal administration forms, forms for inhalative, topical, transdermal, subcutaneous, intra-muscular or intravenous administration, rectal administration forms and implants. For topical application it is possible to use the compounds of formula (I), or a pharmaceutically acceptable salt thereof, in creams, gels, ointments or lotions.

As an example, a unit administration form of a compound of formula (I) in tablet form may comprise the following components:

| | |
|---|---|
| Compound of formula (I) | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

There may be particular cases in which higher or lower dosages are appropriate. According to usual practice, the dosage that is appropriate for each patient is determined by the doctor according to the mode of administration and the weight and response of the said patient.

What is claimed is:

1. A compound of formula (I):

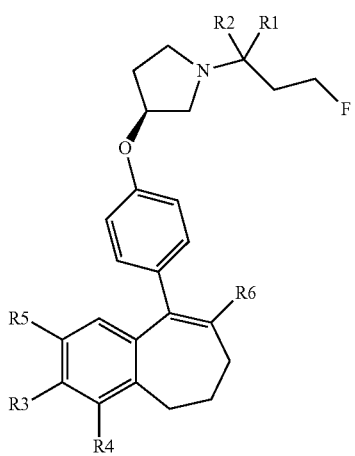

wherein:
R1 and R2 represent independently a hydrogen atom or a deuterium atom;
R3 represents a hydrogen atom, a —COOH group, a —OH group, or a —OPO(OH)$_2$ group;
R4 represents a hydrogen atom or a fluorine atom;
R5 represents a hydrogen atom or a —OH group;
wherein:
at least one of R3 or R5 is different from a hydrogen atom;
when R3 represents a —COOH group, a —OH group or a —OPO(OH)$_2$ group, then R5 represents a hydrogen atom; and
when R5 represents a —OH group, then R3 and R4 represent hydrogen atoms;
R6 is selected from the group consisting of
a phenyl group or a heteroaryl group comprising 3 to 9 carbon atoms and comprising from 1 to 3 heteroatoms independently selected from the group consisting of oxygen, nitrogen and sulphur, said phenyl and heteroaryl groups being unsubstituted or substituted with 1 to 3 substituents independently selected from the group consisting of a ($C_1$-$C_6$)-alkyl group unsubstituted or substituted with one or more fluorine atoms; a halogen atom; a —OH group; a ($C_1$-$C_6$)-alkoxy group unsubstituted or substituted with one or more fluorine atoms; a cyano group; a sulphur group substituted with 5 fluorine atoms or (C1-$C_6$)-alkyl groups substituted with two or more fluorine atoms; a sulfonyl-($C_1$-$C_6$)-alkyl group wherein said (C1-$C_6$)-alkyl group is unsubstituted or substituted with two or more fluorine atoms; a silane group substituted with 3 (C1-$C_6$)-alkyl groups; an amine group unsubstituted or substituted with one or more ($C_1$-$C_6$)-alkyl groups; an amide group unsubstituted or substituted with one or more (C1-$C_6$)-alkyl groups; a heterocycloalkyl group saturated or partially saturated, comprising 3 to 5 carbon atoms and comprising 1 or 2 heteroatoms independently selected from the group consisting of oxygen, nitrogen and sulphur; and a heteroaryl group comprising 2 to 4 carbon atoms and comprising 1 to 3 heteroatoms selected from the group consisting of oxygen, nitrogen and sulphur and being unsubstituted or substituted with an oxo group; and
a cycloalkyl group or a heterocycloalkyl group comprising 4 to 9 carbon atoms and comprising 1 or 2 heteroatoms independently selected from the group consisting of oxygen, nitrogen and sulphur, said cycloalkyl or heterocycloalkyl groups being saturated or partially saturated and being unsubstituted or substituted with 1 to 4 substituents independently selected from the group consisting of a fluorine atom; a —OH group; a (C1-$C_6$)-alkyl group; a —COOR7 group wherein R7 is an (C1-$C_6$)-alkyl group; and an oxo group;
or a pharmaceutically acceptable salt thereof.

2. The compound of formula (I) according to claim 1, wherein R6 is a phenyl group unsubstituted or substituted with 1 to 3 substituents independently selected from the group consisting of a ($C_1$-$C_6$)-alkyl group unsubstituted or substituted with one or more fluorine atoms; a halogen atom; a —OH group; a ($C_1$-$C_6$)-alkoxy group unsubstituted or substituted with one or more fluorine atoms; a cyano group;

a sulphur group substituted with 5 fluorine atoms or ($C_1$-$C_6$)-alkyl groups substituted with two or more fluorine atoms; a sulfonyl-($C_1$-$C_6$)-alkyl group wherein said ($C_1$-$C_6$)-alkyl group is unsubstituted or substituted with two or more fluorine atoms; a silane group substituted with 3 ($C_1$-$C_6$)-alkyl groups; an amine group unsubstituted or substituted with one or more ($C_1$-$C_6$)-alkyl groups; an amide group unsubstituted or substituted with one or more ($C_1$-$C_6$)-alkyl groups; a heterocycloalkyl group saturated or partially saturated, comprising 3 to 5 carbon atoms and comprising 1 or 2 heteroatoms independently selected from the group consisting of oxygen, nitrogen and sulphur; and a heteroaryl group comprising 2 to 4 carbon atoms and comprising 1 to 3 heteroatoms selected from the group consisting of oxygen, nitrogen and sulphur and being unsubstituted or substituted with an oxo group;

or a pharmaceutically acceptable salt thereof.

3. The compound of formula (I) according to claim 1, wherein R6 is a phenyl group unsubstituted or substituted with 1 to 3 substituents independently selected from the group consisting of a methyl group; an ethyl group; an isopropyl group; a tert-butyl group; a —$CHF_2$ group; a —$CF_3$ group; a —$CF_2CH_3$ group; a chlorine atom; a fluorine atom; a —OH group; a —$OCH_3$ group; a —$OCH_2CH_3$ group; a —$OCH_2CH_2F$ group; a —$OCHF_2$ group; a —$OCH_2CF_2$ group; a —$OCF_3$ group; a —$OCH_2CF_3$ group; a cyano group; a —$SCHF_2$ group; a —$SCF_3$ group; a —$SF_5$ group; a —$SO_2CH_3$ group; a —$SO_2CF_3$ group; a —Si($CH_3$)$_3$ group; an oxetane group; a piperidine group; a morpholine group; a pyrrolidine group; and a triazolone group;

or a pharmaceutically acceptable salt thereof.

4. The compound of formula (I) according to claim 1, wherein R3 is a —COOH group or a —OH group;

or a pharmaceutically acceptable salt thereof.

5. A compound 5-[4-[(3S)-1-(3-fluoropropyl)pyrrolidin-3-yl]oxyphenyl]-6-(1H-indol-5-yl)-8,9-dihydro-7H-benzo[7]annulen-3-ol; or a pharmaceutically acceptable salt thereof.

6. A compound 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid; or a pharmaceutically acceptable salt thereof.

7. A compound 5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-ol; or a pharmaceutically acceptable salt thereof.

8. A compound 6-(6-ethoxy-2-fluoro-3-pyridyl)-1-fluoro-5-[4-[(3S)-1-(3-fluoropropyl)pyrrolidin-3-yl]oxyphenyl]-8,9-dihydro-7H-benzo[7]annulen-2-ol; or a pharmaceutically acceptable salt thereof.

9. A compound 6-(2-ethoxypyrimidin-5-yl)-5-[4-[(3S)-1-(3-fluoropropyl)pyrrolidin-3-yl]oxyphenyl]-8,9-dihydro-7H-benzo[7]annulen-2-ol; or a pharmaceutically acceptable salt thereof.

10. A compound [5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-yl] dihydrogen phosphate; or a pharmaceutically acceptable salt thereof.

11. A pharmaceutical composition comprising a compound of formula (I) according to claim 1, or a pharmaceutically acceptable salt thereof, and at least one pharmaceutically acceptable excipient.

12. A pharmaceutical composition comprising 5-[4-[(3S)-1-(3-fluoropropyl)pyrrolidin-3-yl]oxyphenyl]-6-(1H-indol-5-yl)-8,9-dihydro-7H-benzo[7]annulen-3-ol, or a pharmaceutically acceptable salt thereof, and at least one pharmaceutically acceptable excipient.

13. A pharmaceutical composition comprising 6-(2,4-dichlorophenyl)-5-[4-[(3S)-1-(3-fluoropropyl)pyrrolidin-3-yl]oxyphenyl]-8,9-dihydro-7H-benzo[7]annulene-2-carboxylic acid, or a pharmaceutically acceptable salt thereof, and at least one pharmaceutically acceptable excipient.

14. A pharmaceutical composition comprising 5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-ol, or a pharmaceutically acceptable salt thereof, and at least one pharmaceutically acceptable excipient.

15. A pharmaceutical composition comprising 6-(6-ethoxy-2-fluoro-3-pyridyl)-1-fluoro-5-[4-[(3S)-1-(3-fluoropropyl)pyrrolidin-3-yl]oxyphenyl]-8,9-dihydro-7H-benzo[7]annulen-2-ol, or a pharmaceutically acceptable salt thereof, and at least one pharmaceutically acceptable excipient.

16. A pharmaceutical composition comprising 6-(2-ethoxypyrimidin-5-yl)-5-[4-[(3S)-1-(3-fluoropropyl)pyrrolidin-3-yl]oxyphenyl]-8,9-dihydro-7H-benzo[7]annulen-2-ol, or a pharmaceutically acceptable salt thereof, and at least one pharmaceutically acceptable excipient.

17. A pharmaceutical composition comprising [5-[4-[(3S)-1-(3-fluoropropyl)pyrrolidin-3-yl]oxyphenyl]-6-[4-(trifluoromethoxy)phenyl]-8,9-dihydro-7H-benzo[7]annulen-2-yl] dihydrogen phosphate, or a pharmaceutically acceptable salt thereof, and at least one pharmaceutically acceptable excipient.

* * * * *

UNITED STATES PATENT AND TRADEMARK OFFICE
CERTIFICATE OF CORRECTION

PATENT NO. : 9,714,221 B1  
APPLICATION NO. : 15/432470  
DATED : July 25, 2017  
INVENTOR(S) : Monsif Bouaboula et al.

Page 1 of 1

It is certified that error appears in the above-identified patent and that said Letters Patent is hereby corrected as shown below:

In the Specification

In Column 249, under TABLE 3, Line 33, delete "(WT) (WT) (WT)" and insert -- (WT) D538G Y537S --, therefor.

In Column 250, under TABLE 3-continued, Line 4, delete "(WT) (WT) (WT)" and insert -- (WT) D538G Y537S --, therefor.

In Column 251, under TABLE 3-continued, Line 4, delete "(WT) (WT) (WT)" and insert -- (WT) D538G Y537S --, therefor.

In Column 252, under TABLE 3-continued, Line 4, delete "(WT) (WT) (WT)" and insert -- (WT) D538G Y537S --, therefor.

Signed and Sealed this  
Twenty-second Day of September, 2020

Andrei Iancu  
*Director of the United States Patent and Trademark Office*